United States Patent
Cesaroni et al.

(10) Patent No.: US 11,578,124 B2
(45) Date of Patent: Feb. 14, 2023

(54) SAFE AND EFFECTIVE METHOD OF TREATING LUPUS WITH ANTI-IL12/IL23 ANTIBODY

(71) Applicant: Janssen Biotech, Inc., Horsham, PA (US)

(72) Inventors: Matteo Cesaroni, Philadelphia, PA (US); Matthew Loza, Paoli, PA (US); Jarrat Jordan, Norristown, PA (US); Loqmane Seridi, Horsham, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 16/415,231

(22) Filed: May 17, 2019

(65) Prior Publication Data
US 2019/0352388 A1 Nov. 21, 2019

Related U.S. Application Data

(60) Provisional application No. 62/673,426, filed on May 18, 2018.

(51) Int. Cl.
| | |
|---|---|
| C07K 16/24 | (2006.01) |
| A61K 9/00 | (2006.01) |
| A61P 37/06 | (2006.01) |
| G01N 29/44 | (2006.01) |
| G01N 33/483 | (2006.01) |
| G01N 33/564 | (2006.01) |
| C12Q 1/6883 | (2018.01) |
| A61K 39/00 | (2006.01) |

(52) U.S. Cl.
CPC .......... *C07K 16/244* (2013.01); *A61K 9/0019* (2013.01); *A61P 37/06* (2018.01); *C07K 16/249* (2013.01); *C12Q 1/6883* (2013.01); *G01N 29/4418* (2013.01); *G01N 33/483* (2013.01); *G01N 33/564* (2013.01); *A61K 2039/505* (2013.01); *A61K 2039/545* (2013.01); *C07K 2317/21* (2013.01); *C07K 2317/76* (2013.01); *C12Q 2600/106* (2013.01); *C12Q 2600/158* (2013.01); *G01N 2333/555* (2013.01)

(58) Field of Classification Search
None
See application file for complete search history.

(56) References Cited

U.S. PATENT DOCUMENTS

| | | | |
|---|---|---|---|
| 5,457,038 A | 10/1995 | Trinchieri | |
| 5,547,852 A | 8/1996 | Seiler | |
| 5,648,467 A | 7/1997 | Trinchieri | |
| 5,780,597 A | 7/1998 | Gately | |
| 5,811,523 A | 9/1998 | Trinchieri | |
| 5,891,680 A | 4/1999 | Lieschke | |
| 6,086,876 A | 7/2000 | Karp | |
| 6,225,117 B1 | 5/2001 | Gately | |
| 6,300,478 B1 | 10/2001 | Trinchieri | |
| 6,338,848 B1 | 1/2002 | Leonard | |
| 6,495,667 B1 | 12/2002 | Bazan | |
| 6,902,734 B2 | 6/2005 | Giles-Komar | |
| 6,914,128 B1 | 7/2005 | Salfeld | |
| 7,063,964 B2 | 6/2006 | Giles-Komar | |
| 7,166,285 B2 | 1/2007 | Giles-Komar | |
| 7,279,157 B2 | 10/2007 | Giles-Komar | |
| 7,560,247 B2 | 7/2009 | Giles-Komar | |
| 7,887,807 B2 | 2/2011 | Giles-Komar | |
| 8,084,233 B2 | 12/2011 | Giles-Komar | |
| 8,329,171 B2 | 12/2012 | Giles-Komar | |
| 8,703,141 B2 | 4/2014 | Giles-Komar | |
| 9,409,984 B2 | 8/2016 | Giles-Komar | |
| 9,676,848 B2 | 6/2017 | Giles-Komar | |
| 9,803,010 B2 | 10/2017 | Reichert | |
| 9,862,766 B2 | 1/2018 | Giles-Komar | |
| 10,259,867 B2 | 4/2019 | Giles-Komar | |
| 2005/0214293 A1 | 9/2005 | Giles-Komar | |
| 2009/0202549 A1 | 8/2009 | Giles-Komar | |
| 2014/0135225 A1 | 5/2014 | Crow | |
| 2015/0147337 A1 | 5/2015 | Reichert | |
| 2016/0115227 A1 | 4/2016 | Brod | |
| 2017/0002060 A1 | 1/2017 | Bolen | |
| 2017/0121417 A1 | 5/2017 | Jansson | |
| 2017/0266281 A1 | 9/2017 | Goldenberg | |
| 2017/0269075 A1 | 9/2017 | Ranger | |
| 2019/0092853 A1 | 3/2019 | Rose | |

(Continued)

FOREIGN PATENT DOCUMENTS

| | | |
|---|---|---|
| EP | 0640689 | 3/1995 |
| EP | 790255 | 8/1997 |
| EP | 433827 | 3/1998 |

(Continued)

OTHER PUBLICATIONS

Hidalgo et al (American Journal of Transplantation 2008; 8: 627-636) (Year: 2008).*
Samarajiwa et al (Nucleic Acids Res. Jan. 2009;37(Database issue):D852-7) (Year: 2009).*
The Interferome website (downloaded from http://www.interferome.org/interferome/site/dbStat.jspx on Jan. 17, 2021) (Year: 2021).*
Mayeux (NeuroRx. Apr. 2004;1(2):182-8) (Year: 2004).*

(Continued)

*Primary Examiner* — Brian Gangle
*Assistant Examiner* — Andrea K McCollum
(74) *Attorney, Agent, or Firm* — Riverside Law LLP

(57) ABSTRACT

Methods for selecting and treating patients with active Systemic Lupus Erythematosus (SLE) that are predicted to have an increased likelihood of having a positive response to a treatment with a safe and effective amount of an anti-IL-12/IL-23p40 antibody or an anti-IL-23 antibody, e.g., informs on what patients to treat with the anti-IL-12/IL-23p40 antibody ustekinumab.

30 Claims, 16 Drawing Sheets

Specification includes a Sequence Listing.

(56) References Cited

U.S. PATENT DOCUMENTS

| | | |
|---|---|---|
| 2019/0248884 A1 | 8/2019 | Giles-Komar |
| 2020/0062841 A1 | 2/2020 | Giles-Komar |

FOREIGN PATENT DOCUMENTS

| | | |
|---|---|---|
| EP | 804581 | 9/2001 |
| EP | 1137766 | 9/2005 |
| WO | 9005147 | 5/1990 |
| WO | 9205256 | 4/1992 |
| WO | 9633735 | 10/1996 |
| WO | 9715327 | 5/1997 |
| WO | 9937682 | 7/1999 |
| WO | 0034459 | 6/2000 |
| WO | 00/56772 | 9/2000 |
| WO | 0119373 | 3/2001 |
| WO | 2007070376 | 6/2007 |
| WO | 2009114040 | 9/2009 |
| WO | 2012074396 | 6/2012 |
| WO | 2013009535 | 1/2013 |
| WO | 2015175424 | 11/2015 |
| WO | 2017049035 | 3/2017 |
| WO | 2017172771 | 10/2017 |
| WO | 2017205536 | 11/2017 |
| WO | 2019058345 | 3/2019 |

OTHER PUBLICATIONS (Aetna Inc.) Ustekinumab (Stelara). Clinical Policy Bulletin [online]. Nov. 22, 2016 [retrieved on Feb. 14, 2020]. Retrieved from the Internet: <URL: http://www.aetna.com/cpb/medical/data/900_999/0912.html>: 32 pages.

A. U. Gubler et al. (Clonic and Expression of Cytotoxic Lymphocyte Maturation Factor (CLMF) A Heterodimeric Lymphokine That Potentiates NR. LAK NA D T-Cell Reponses) Abstracts Journal of celluar Biochemistry Supplement 15 F: 70 (1991) 1 page.

A. U. Gubler et. al (Coexpression of Two Distinct Genes is Required to Generate Secreted Bioactive Cytotoxic Lymphocyte Maturation Factor) Proc. Natl. acad. Sci. USA. vol. 88. pp. 4143-4147—(May 1991) Immunology.

Albrecht, et al., The CLASI (Cutaneous Lupus Erythematosus Disease Area and Severity Index): An Outcome Instrument for Cutaneous Lupus Erythematosus, Journal of Investigations in Dermatology, 125: 889-894 (2005).

Alvin S. Stern et al.—(Purification to Homogeneity and Partial Characterization of Cytotoxic Lymphocyte Maturation Factor From Human B-Lymphoblastoid Cells) (Jun. 11, 1990) F. Hoffmann La Roche Inc. Nutley NJ USA. Proc. National Acad. Sci. USA (vol. 87,pp. 6808-6812—Sep. 1990—Immunology).

Annalisa D'Andrea et al. (Production of Natural Killer Cell Stimulatory Factor (Interleukin 12) by Peripheral Blood Mononuclear Cell) J. Exp. Med. The Rockefeller university press—0022-1007/92/11/1387 vol. 176 Nov. 1992. pp: 1387-1398.

Anonymous, "Ustekinumab (Stelara)", Clinical Policy Bulletin, (Feb. 14, 2020), pp. 1-47, URL: http://www.aetna.com/cpb/medical/data/900_999/0912.html, (Nov. 22, 2016), XP055762398.

Banchereau R. et al., Personalized Immunomonitoring Uncovers Molecular Networks that Stratify Lupus Patients. Cell.165(3):551-65 (Apr. 21, 2016).

Bennett, et al., "Interferon and Granulopoiesis Signatures in Systemic Lupus Erythematosus Blood," The Journal of Experimental Medicine, 197 (6): 711-723 (2003).

Boedigheimer, M. J. et al., Safety, pharmacokinetics and pharmacodynamics of AMG 811, an anti-interferon-gamma monoclonal antibody, in SLE subjects without or with lupus nephritis. Lupus science & medicine 4, e000226 (2017). 9 pages.

Candia J, Tsang JS, eNetXplorer: an R package for the quantitative exploration of elastic net families for generalized linear models, BMC Bioinformatics 20:189 (2019). 11 pages.

Carter, et al., "Production and Characterization of Monoclonal Antibodies to Human Interleukin-12," Hybridoma, 16(4): 363-369 (1997).

Carvalho, B. S. & Irizarry, R. A. A Framework for Oligonucleotide Microarray Preprocessing. Bioinformatics 26, 2363-2367 (2010).

Casipit, et al., "Improving the binding affinity of an antibody using molecular modeling and site-directed mutagenesis," Protein Science, 7: 1671-1680 (1998).

Chen, et al., "Plasma IL-17 A Is Increased in New-Onset SLE Patients and Associated with Disease Activity," Journal of Clinical Immunology, 30: 221-225 (2010).

Core Curriculum on Tuberculosis What the Clinician Should Know, Department of Health and Human Services, Fourth Edition, 1-144 (2000).

Crispin, et al., "Expanded Double Negative T Cells in Patients with Systemic Lupus Erythematosus Produce IL-17 and Infiltrate the Kidneys," Journal of Immunology, 181:8761- 8766 (2008).

D. Wallace, "Evaluation of Treatment Success in Systemic Lupus Erythematosus Clinical Trials: Development of the British Isles Lupus Assessment Group-Based Composite Lupus Assessment Endpoint," Abstract 2265, ACR/ARHP Scientific Meeting, Nov. 4-9, 2011.

Dahl, et al., "Ustekinumab in the Treatment of Refractory Chronic Cutaneous Lupus Erythematosus: A Case Report," Acta Dermato-Venerologica, 93: 1-2 (2013).

De Souza, et al., "Successful Treatment of Subacute Lupus Erythematosus With Ustekinumab," Arch Dermatology, 147 (8): 896-898 (2011).

Diel, et al., Predictive Value of a whole Blood IFN-y Assay for the Development of Active Tuberculosis Disease after Recent Infection with *Mycobacterium tuberculosis*, American Journal of Respiratory and Critical Care Medicine, 177: 1164-1170 (2008).

Eduardo A. Padlan, "Anatomy of the Antibody Molecule," Molecular Immunology, 31(3): 169-217 (1994).

Ewer, et al., "Comparison of T-cell-based assay with tuberculin skin test for diagnosis of *Mycobacterium tuberculosis* infection in a school tuberculosis outbreak," Lancet, 261: 1168-1173 (2003).

Feagan, et al., "Ustekinumab as Induction and Maintenance Therapy for Crohn's Disease," The New England Journal of Medicine, 375: 1946-1960 (2016).

Felson, et al., "American College of Rheumatology Preliminary Definition of Improvement in Rheumatoid Arthritis," Arthritis & Rheumatism, 38 (6): 727-735 (1995).

Feng, Y et al., "Association between angiogenesis and cytotoxic signatures in the tumor microenvironment of gastric cancer", OncoTargets and Therapy, (May 10, 2018), vol. 11, pp. 2725-2733, XP055706651.

Ferrara, et al., "Routine Hospital Use of a New Commercial Whole Blood Interferon-y Assay for the Diagnosis of Tuberculosis Infection," American Journal of Respiratory and Critical Care Medicine, 117: 631-635 (2005).

Fine, et al., "A prospective study of protein excretion using short-interval timed urine collections in patients with lupus nephritis," Kidney International, 76: 1284-1288 (2009).

Furie R. et al., Anifrolumab, an Anti-Interferon-alpha Receptor Monoclonal Antibody, in Moderate-to-Severe Systemic Lupus Erythematosus. Arthritis Rheumatol 69, 376 (Feb. 2017). 11 pages.

Furie, et al., "Novel Evidence-Based systemic Lupus Erythematosus Responder Index," Arthritis & Rheumatism, 61 (9): 1143-1151 (2009).

G. Matulis, Detection of latent tuberculosis in immunosuppressed patients with autoimmune diseases: performance of a *Mycobacterium tuberculosis* antigen-specific interferon γ assay, Ann. Rheum. Dis., 67: 84-90 (2008).

Gautier, L., Cope, L., Bolstad, B. M. & Irizarry, R. A. affy—analysis of Affymetrix GeneChip data at the probe level. Bioinformatics 20, 307-315 (2004).

Gladman, et al., "Systemic Lupus Erythematosus Disease Activity Index 2000," The Journal of Rheumatology, 29 (2): 288-291 (2000).

Han, et al., "Genome-wide association study in a Chinese Han population identifies nine new susceptibility loci for systemic lupus erythematosus," Nature Genetics, 41 (11): 1234-1239 (2009).

Hänzelmann, S., Castelo, R. & Guinney, J. GSVA: gene set variation analysis for microarray and RNA-Seq data. BMC Bioinformatics 14, 7 (2013). 15 pages.

(56) References Cited

OTHER PUBLICATIONS

Harley, et al., "Genome-wide association scan in women with systemic lupus erythematosus identifies susceptibility variants in ITGAM, PXK, KIAA1542 and other loci," Nature Genetics, 40 (2): 24-210 (2008).
Hay, et al., "The BILAG index: a reliable and valid instrument for measuring clinical disease activity in systemic lupus erythematosus," Quarterly Journal of Medicine, 86: 447-458 (1993).
Higuchi, et al., "Use of QuantiFERON®-TB Gold to investigate tuberculosis contacts in a high school," Respirology, 12: 88-92 (2007).
Hong, et al., "IL-12, Independently of IFN-☐ Plays a Crucial Role in the Pathogenesis of a Murine Psoriasis-Like Skin Disorder," Journal of Immunology, 162: 7480-7491 (1999).
Huang, et al., "Dysregulated expression of interleukin-23 and interleukin-12 subunits in systemic lupus erythematosus patients," Modern Rheumatology, 17 (3): 220-223 (2007).
Huber et al. Orchestrating high-throughput genomic analysis with Bioconductor. Nat. Methods 12, 115-121 (2015).
Isenberg, et al., "BILAG 2004. Development and initial validation of an updated version of the British Isles Lupus Assessment Group's disease activity index for patients with systemic lupus erythematosus," Rheumatology, 44: 902-906 (2005).
John E. Ware Jr. Ph.D. "SF-36 Health Survey Update" SPINE 25 (24): 3130-3139 (2000).
Khamashta, M. et al., Sifalimumab, an anti-interferon-alpha monoclonal antibody, in moderate to severe systemic lupus erythematosus: a randomised, double-blind, placebo-controlled study. Annals of the rheumatic diseases 75, 1909 (Nov. 2016). 8 pages.
Kim, et al., "No association between interleukin 23 receptor gene polymorphisms and systemic lupus erythematosus," Rheumatology Int. 30: 33-38 (2009).
Kobashi, et al., "Clinical evaluation of QuantiFERON TG-2G test for immunocompromised patients," European Respiratory Journal, 30: 945-950 (2007).
Krupp, et al., The Fatigue Severity Scale Application to Patients with Multiple Sclerosis and Systemic Lupus Erythematosus, Arch. Neurol. 46: 1121-1123 (1989).
Liaw, A. & Wiener, M. Classification and Regression by random Forest. R News 2, 18-22 (2002).
Linker-Israeli, et al., "Elevated Levels of Endogenous IL-6 in Systemic Lupus Erythematosus," The Journal of Immunology, 147: 117-123 (1991).
Livak KJ, Schmittgen TD, Analysis of relative gene expression data using real-time quantitative PCR and the 2(-Delta Delta C(T)) Method. Methods. Dec. 2001;25(4):402-8.
M. Gately et. al. (Regulation of Human Lymphocyte Proliferation by a Heterodimeric Cytokine IL-12 (Cytotoxic Lymphocyte Maturation Factor) vol. 147-874-882 No. 3. (Aug. 1, 1991).(The Journal of Immunology).
Malfait, et al., "Blockade of IL-12 during the induction of collagen-induced arthritis (CIA) markedly attenuates the severity of the arthritis," Clinical and Experimental Immunology, 111:327-383 (1998).
Manzi, S., J. Merrill, J. Editorial: Lupus, the Chameleon: Many Disguises Difficult to Capture. Arthritis Rheumatol 69, 1921 (Oct. 2017). 4 pages.
Markus F. Neurath et. al. (Antibodies to Interleukin 12 Abrogate Established Experimental Colitis in Mice) The Journal of Experimental Medicine—vol. 182—Nov. 1995—pp. 1281-1290.
McHorney, et al., "The MOS 36-Item Short-Form Health Survey (SF-36): III. Tests of Data Quality, Scaling Assumptions, and Reliability Across Diverse Patient Groups," Medical Care, 32 (1): 40-66 (1994).
Michiko Kobayashi et al. I (Identification and Purification of Natural Killer Cell Stimulatory Factor (NKSF) A Cytokine With Multiple Biologic Efects on Human Lymphocytes) J. Exp. Med. The Rockefeller university Press—vol. 170—(Sep. 1989) pp. 827-845.

Mori, et al., "Specific Detection of Tuberculosis Infection And Interferon-γ-based Assay Using New Antigens," American Journal of Respiratory and Critical Care Medicine, 170: 59-64 (2004).
Navarra, et al., "Efficacy and safety of belimumab in patients with active systemic lupus erythematosus: a randomized, placebo-controlled, phase 3 trial," Lancet, 377: 721-731 (2011).
NCT02349061 (Pub date Aug. 3, 2016) , p. 1-7 (Year: 2016).
Nicolas M. Valiante et. al. (Role of the Production of Natural Killer Cell Stimulatory Factor (NKSF/IL-12) in the Ability of B Cell Lines to Stimulate T and NK Cell Proliferation). Cellunar Immunology 145, 187-198-(1992).
Niewold, et al., "High serum IFN-a activity if a heritable risk factor for systemic lupus erythematosus," Genes and Immunity, 8: 492-502 (2007).
Nikhil, Yawalkar et al.; "Expression of interleukin-12 is increased in psoriatic skin", Journal of Investigative Dermatology, Dec. 1998, pp. 1053-1057; vol. 111, No. 6; XP00800577; ISSN: 0022-202X, abstract.
Oh, et al., "Expression of interleukin-17 is correlated with interferon-a expression in cutaneous lesions of lupus erythematosus," Clinical and Experimental Dermatology, 36: 512-520 (2011).
PCT International Search Report PCT/US01/24720 dated Jul. 30, 2002, 9 pages.
Peter F. Barnes, M.D., "Diagnosing Latent Tuberculosis Infection Turning Glitter to Gold," American Journal of Respiratory and Critical Care Medicine, 170: 5-6 (2004).
Petri, et al., "Derivation and Validation of the Systemic Lupus International Collaborating Clinics Classification Criteria for Systemic Lupus Erythematosus," Arthritis & Rheumatism, 64 (8): 2677-2686 (2012).
Pfaffl MW, A new mathematical model for relative quantification in real-time RT-PCR. Nucleic Acids Res. May 1, 2001;29(9):e45. 6 pages.
Qiu, et al., "Glucocorticoid downregulates expression of IL-12 family cytokines in systemic lupus erythematosus patients," Lupus, 22: 1011-1016 (2013).
R. Chizzonite et. al. (IL-12 Monoclonal Antibodies Specific for the 40-KdA Subunit Block Receptor Binding and Biologic Activity on Activated Human Lymphoblasts.) vol. 147,1548-1556—No. 5, (Sep. 1, 1991) The Journal of Immunology.
R.W. Carter. et. al. (Production and Characterization of Monoclonal Antibodies to Human Interleukin-12) HYBRIIDONA 16: 363-369 (1997).
Rainer Duchmann et. al. (Tolerance Towards Resident Intestinal Flora in Mice is Abrogated in Experimental Colitis and Restores by Treatment With Intelukin-1 or Antibodies to Interleukin-12) European Journal of Immunology, 26: 394-938 (1996).
Romagnani, et al., "T cells and cytokines in Crohn's Disease," Current Opinion in Immunology, 9: 793-799 (1997).
Samsa, et al., "Determining Clinically Important Differences in Health Status Measures," Pharmaeconomics, 15 (2): 141-155 (1999).
Sanchez, et al., "Analysis of interleukin-23 receptor (IL23R) gene polymorphisms in systemic lupus erythematosus," Tissue Antigens, 70: 233-237 (2007).
Savage, LJ et al., Ustekinumab in the Treatment of Psoriasis and Psoriatic Arthritis. Rheumatology and Therapy, (Mar. 17, 2015), vol. 2, No. 1, pp. 1-16, XP055558345.
Schildbach, et al., "Modulation of antibody affinity by a non-contact residue," Protein Science, 2: 206-214 (1993).
Shah, et al., "Dysregulated balance of Th17 and Th1 cells in systemic lupus erythematosus," Arthritis Research & Therapy, 12: R53 (2010). 10 pages.
STELARA® (ustekinumab) administration instruction revised Sep. 2016., p. 1-37. (Year: 2016).
Stohl, W., Hilbert, D. M. The discovery and development of belimumab: the anti-BLyS-lupus connection. Nature biotechnology 30, 69 (Jan. 9, 2012). 20 pages.
Subramanian, A. et al. Gene set enrichment analysis: A knowledge-based approach for interpreting genome-wide expression profiles. Proc. Natl. Acad. Sci. 102, 15545-15550 (2005).
Susan H. Chan et. al. (Introduction of Interferon Production by Natural Killer Cell Stimulatory Factor Characterization of the

(56) References Cited

OTHER PUBLICATIONS

Responder Cells and Synergy With Other Inducers) (The Rockefeller University Press)—0022-1007/91/04/0869/—vol. 173 Apr. 1991—pp. 869-879.
Sylvie Trembleau et. al. (The Role of IL-12 in the Induction of Organ-Specific Autoimmune Diseases), Immunology Today, 16(8): 383-386 (1995).
Tanasescu, et al., "IL-17 in cutaneous lupus erythematosus," European Journal of Internal Medicine, 21: 202-207 (2010).
Touma, et al., "SLEDAI-2K for a 30-day window," Lupus, 19: 49-50 (2010).
Tuoma, et al., "Development and Initial Validation of the Systemic Lupus Erythematosus Disease Activity Index 2000 Responder Index 50," The Journal of Rheumatology, 38 (2): 275-284 (2011).
Tuoma, et al., "SLEDAI-2K 10 days versus SLEDAI-2K 30 days in a cross-sectional and longitudinal evaluation," Abstract P02.D.6, Lupus, 19: 1-185 (2010).
Tuoma, et al., "SLEDAI-2K Responder Index-50 (SRI-50)," Abstract P02.D.7, Lupus, 19: 1-185 (2010).
Van Vollenhoven, et al., "Belimumab in the treatment of systemic lupus erythematosus: high disease activity predictors of response," Ann. Rheum. Dis., 71: 1343-1349 (2012).
Vincent, et al., "Clinical associations of serum interleukin-17 in systemic lupus erythematosus," Arthritis Research & Therapy, 15: R97 (2013). 9 pages.
W. S. Cleveland, E. G. & Shyu, W. M. Local regression models. Chapter 8 Stat. Model. S eds J.M. Chambers T.J. Hast. Wadsworth Brooks/Cole (1992). 69 pages.
Ware, et al., "The MOS 36-Item Short-Form Health Survey (SF-36) Conceptual Framework and Item Selection," Medical Care, 30 (6): 473-483 (1992).
Werth, V. P. et al., Brief Report: Pharmacodynamics, Safety, and Clinical Efficacy of AMG 811, a Human Anti-Interferon-gamma Antibody, in Patients With Discoid Lupus Erythematosus. Arthritis Rheumatol 69, 1028 (May 2017). 7 pages.
Winchester, et al., "Response to ustekinumab I a patient with both severe psoriasis and hypertrophic cutaneous lupus," Lupus, 21: 1007-10 10 (2012).
Wong, et al., "Hyperproduction of IL-23 and IL-17 in patients with systemic lupus erythematosus: Implications for Th17-mediated inflammation in auto-immunity," Clinical Immunology, 127: 385-393 (2008).
Yabu, JM et al., "Immune Profiles to Predict Response to Desensitization Therapy in Highly HLA-Sensitized Kidney Transplant Candidates", PLoS One, (Apr. 14, 2016), vol. 11, No. 4, p. 5, XP055706650.
Yang, et al., "Th22, but not Th17 Might be a Good Index to Predict the Tissue Involvement of Systemic Lupus Erythematosus," Journal of Clinical Immunology, 33: 767-774 (2013).
Yao, Y. et al., Development of Potential Pharmacodynamic and Diagnostic Markers for Anti-IFN-alpha Monoclonal Antibody Trials in Systemic Lupus Erythematosus. Human genomics and proteomics: HGP 2009, (Nov. 17, 2009). 16 pages.
Yu, G., Wang, L.-G., Han, Y. & He, Q.-Y. clusterProfiler: an R package for comparing biological themes among gene clusters. Omi. A J. Integr. Biol. 16, 284-287 (2012).
Zhao, et al., "Increased serum interleukin 17 in patients with systemic lupus erythematosus," Mol. Biol. Rep., 37:81-85 (2010).
Anonymous: "A Multicenter. Randomized, Double-blind, Placebo-controlled, Proof-of-Concept Study of Ustekinumab in Subjects With Active Systemic Lupus Erythematosus". Janssen Research & Development* Clinical Protocol, approval date: Jan. 18, 2017, uploaded on: May 15, 2018. pages 1-148.
Anonymous: "NCT02349061: A Phase 2a. Efficacy and Safety Study of Ustekinumab in Systemic Lupus Erythematosus". Sep. 5, 2017 (Sep. 5 ,2017). XP055802677. Retrieved from the Internet: URL:https://clinicaltrials.gov/ct2/history/NCT02349061?V35= View#StudyPageTop [retrieved on May 10, 2021].
Klein Rachel et al: "Development of the CLASI as a Tool to Measure Disease Severity and Responsiveness to Therapy in Cutaneous Lupus Erythematosus", Archives of Dermatology, vol. 147, No. 2, Feb. 1, 2011 (Feb. 1, 2011), p. 203, XP055802684.
Laurie S. Davis et al: "Research and therapeutics-traditional and emerging therapies in systemic lupus erythematosus", Rheumatology, vol. 56, No. suppL 1, Mar. 27, 2017 (Mar. 27, 2017), pp. i100-i113, XP055476518.
Leng R X et al: "IL-23: A Promising Therapeutic Target for Systemic Lupus Erythematosus", Archives of Medical Research, Instituto Mexicano Del Seguro Social, Mexico, MX, vol. 41, No. 3, Apr. 1, 2010 (Apr. 1, 2010), pp. 221-225, XP027078888.
Merrill et al., "Efficacy and Safety of Rituximab in Moderately-to-Severely Active Systemic Lupus Erythematosus." Arthritis & Rheumatism, 62(1): 222-233 (2010).
Van Vollenhoven R et al: "Efficacy and safety of ustekinumab, an interleukin 12/23 inhibitor, in patients with active systemic lupus erythematosus: results of a phase 2, randomised placebo-controlled study (S7A:8)", Lupus Science and Medicine, Mar. 21, 2018 (Mar. 21, 2018), pp. A28-A29, XP055802467.
Van Vollenhoven Ronald F et al: "Efficacy and safety of ustekinumab, an IL-12 and IL-23 inhibitor, in patients with active systemic lupus erythematosus: results of a multicentre, double-blind. phase 2, randomised, controlled study". The Lancet. Elsevier. Amsterdam. NL. vol. 392. No. 10155. Sep. 21, 2018 (Sep. 21, 2018). pp. 1330-1339.
Brock, et al., "Comparison of Tuberculin Skin Test and New Specific Blood Test in Tuberculosis Contacts," American Journal of Respiratory and Critical Care Medicine, 170: 65-69 (2004).
Sestak, et al., "The genetics of systemic lupus erythematosus and implications for targeted therapy," Ann. Rheum. Dis., 70 (Supplement 1): i37-i43 (2011).
Anonymous, "History of Changes for Study NCT03517722" May 4, 2018, URL:https://clinicaltrials.gov/ct2/history/NCT03517722?V_2=View#StudyPageTop (5 pages).
Seridi et al., "Baseline cytotoxic gene expression associates with ustekinumab response in systemic lupus erythematosus", Journal of Clinical Rheumatology, vol. 20, No. 3, Suppl 1, Apr. 1, 2020 (3 pages).

\* cited by examiner

SEQUENCE LISTING

<160> NUMBER OF SEQ ID NOS: 1228

<210> SEQ ID NO 1
<211> LENGTH: 5
<212> TYPE: PRT
<213> ORGANISM: Homo sapiens

<400> SEQUENCE: 1

Thr Tyr Trp Leu Gly
1               5

<210> SEQ ID NO 2
<211> LENGTH: 17
<212> TYPE: PRT
<213> ORGANISM: Homo sapiens

<400> SEQUENCE: 2

Ile Met Ser Pro Val Asp Ser Asp Ile Arg Tyr Ser Pro Ser Phe Gln
1               5                   10                  15

Gly

<210> SEQ ID NO 3
<211> LENGTH: 10
<212> TYPE: PRT
<213> ORGANISM: Homo sapiens

<400> SEQUENCE: 3

Arg Arg Pro Gly Gln Gly Tyr Phe Asp Phe
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6

```
<211> LENGTH: 9
<212> TYPE: PRT
<213> ORGANISM: Homo sapiens

<400> SEQUENCE: 6

Gln Gln Tyr Asn Ile Tyr Pro Tyr Thr
1               5

<210> SEQ ID NO 7
<211> LENGTH: 119
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
                20                  25                  30

Trp Leu Gly Trp Val Arg Gln Met Pro Gly Lys Gly Leu Asp Trp Ile
            35                  40                  45

Gly Ile Met Ser Pro Val Asp Ser Asp Ile Arg Tyr Ser Pro Ser Phe
        50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
                100                 105                 110

Thr Leu Val Thr Val Ser Ser
            115

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg
                100                 105

<210> SEQ ID NO 9
<211> LENGTH: 503
<212> TYPE: PRT
<213> ORGANISM: Homo sapiens

<400> SEQUENCE: 9

Arg Asn Leu Pro Val Ala Thr Pro Asp Pro Gly Met Phe Pro Cys Leu
```

-continued

```
  1               5              10              15
His His Ser Gln Asn Leu Leu Arg Ala Val Ser Asn Met Leu Gln Lys
             20              25              30
Ala Arg Gln Thr Leu Glu Phe Tyr Pro Cys Thr Ser Glu Glu Ile Asp
             35              40              45
His Glu Asp Ile Thr Lys Asp Lys Thr Ser Thr Val Glu Ala Cys Leu
 50              55              60
Pro Leu Glu Leu Thr Lys Asn Glu Ser Cys Leu Asn Ser Arg Glu Thr
 65              70              75              80
Ser Phe Ile Thr Asn Gly Ser Cys Leu Ala Ser Arg Lys Thr Ser Phe
             85              90              95
Met Met Ala Leu Cys Leu Ser Ser Ile Tyr Glu Asp Leu Lys Met Tyr
            100             105             110
Gln Val Glu Phe Lys Thr Met Asn Ala Lys Leu Leu Met Asp Pro Lys
            115             120             125
Arg Gln Ile Phe Leu Asp Gln Asn Met Leu Ala Val Ile Asp Glu Leu
            130             135             140
Met Gln Ala Leu Asn Phe Asn Ser Glu Thr Val Pro Gln Lys Ser Ser
145             150             155             160
Leu Glu Glu Pro Asp Phe Tyr Lys Thr Lys Ile Lys Leu Cys Ile Leu
            165             170             175
Leu His Ala Phe Arg Ile Arg Ala Val Thr Ile Asp Arg Val Met Ser
            180             185             190
Tyr Leu Asn Ala Ser Ile Trp Glu Leu Lys Lys Asp Val Tyr Val Val
            195             200             205
Glu Leu Asp Trp Tyr Pro Asp Ala Pro Gly Glu Met Val Val Leu Thr
            210             215             220
Cys Asp Thr Pro Glu Glu Asp Gly Ile Thr Trp Thr Leu Asp Gln Ser
225             230             235             240
Ser Glu Val Leu Gly Ser Gly Lys Thr Leu Thr Ile Gln Val Lys Glu
            245             250             255
Phe Gly Asp Ala Gly Gln Tyr Thr Cys His Lys Gly Gly Glu Val Leu
            260             265             270
Ser His Ser Leu Leu Leu Leu His Lys Lys Glu Asp Gly Ile Trp Ser
            275             280             285
Thr Asp Ile Leu Lys Asp Gln Lys Glu Pro Lys Asn Lys Thr Phe Leu
            290             295             300
Arg Cys Glu Ala Lys Asn Tyr Ser Gly Arg Phe Thr Cys Trp Trp Leu
305             310             315             320
Thr Thr Ile Ser Thr Asp Leu Thr Phe Ser Val Lys Ser Ser Arg Gly
            325             330             335
Ser Ser Asp Pro Gln Gly Val Thr Cys Gly Ala Ala Thr Leu Ser Ala
            340             345             350
Glu Arg Val Arg Gly Asp Asn Lys Glu Tyr Glu Tyr Ser Val Glu Cys
            355             360             365
Gln Glu Asp Ser Ala Cys Pro Ala Ala Glu Glu Ser Leu Pro Ile Glu
            370             375             380
Val Met Val Asp Ala Val His Lys Leu Lys Tyr Glu Asn Tyr Thr Ser
385             390             395             400
Ser Phe Phe Ile Arg Asp Ile Ile Lys Pro Asp Pro Lys Asn Leu
            405             410             415
Gln Leu Lys Pro Leu Lys Asn Ser Arg Gln Val Glu Val Ser Trp Glu
            420             425             430
```

```
Tyr Pro Asp Thr Trp Ser Thr Pro His Ser Tyr Phe Ser Leu Thr Phe
            435                 440                 445

Cys Val Gln Val Gln Gly Lys Ser Lys Arg Glu Lys Asp Arg Val
450                 455                 460

Phe Thr Asp Lys Thr Ser Ala Thr Val Ile Cys Arg Lys Asn Ala Ser
465                 470                 475                 480

Ile Ser Val Arg Ala Gln Asp Arg Tyr Tyr Ser Ser Ser Trp Ser Glu
                485                 490                 495

Trp Ala Ser Val Pro Cys Ser
                500

<210> SEQ ID NO 10
<211> LENGTH: 449
<212> TYPE: PRT
<213> ORGANISM: Homo sapiens

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
              290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 11
<211> LENGTH: 214
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 12
<211> LENGTH: 25
<212> TYPE: DNA
<213> ORGANISM: Homo sapiens

<400> SEQUENCE: 12
taagcctgag gcacacacgt caggg        25

<210> SEQ ID NO 13
<211> LENGTH: 25
<212> TYPE: DNA
<213> ORGANISM: Homo sapiens

<400> SEQUENCE: 13
gcagcaccgg ccctattata agcct        25

<210> SEQ ID NO 14
<211> LENGTH: 25
<212> TYPE: DNA
<213> ORGANISM: Homo sapiens

<400> SEQUENCE: 14
agatgagttc gctgcctctc agccg        25

<210> SEQ ID NO 15
<211> LENGTH: 25
<212> TYPE: DNA
<213> ORGANISM: Homo sapiens

<400> SEQUENCE: 15
tactggcaaa gatgagttcg ctgcc        25

<210> SEQ ID NO 16
<211> LENGTH: 25
<212> TYPE: DNA
<213> ORGANISM: Homo sapiens

<400> SEQUENCE: 16
tcctgtactg gcaaagatga gttcg        25

<210> SEQ ID NO 17
<211> LENGTH: 25
<212> TYPE: DNA
<213> ORGANISM: Homo sapiens

<400> SEQUENCE: 17
tgtgggccac ggcacaagct cctgt        25

<210> SEQ ID NO 18
<211> LENGTH: 25
<212> TYPE: DNA
<213> ORGANISM: Homo sapiens

<400> SEQUENCE: 18
acacctggaa ttcgttgccc gccag        25

<210> SEQ ID NO 19
<211> LENGTH: 25
<212> TYPE: DNA
<213> ORGANISM: Homo sapiens

<400> SEQUENCE: 19
tgacaccgac atggagctgc tcagg                                             25

<210> SEQ ID NO 20
<211> LENGTH: 25
<212> TYPE: DNA
<213> ORGANISM: Homo sapiens

<400> SEQUENCE: 20
gcgtgcacgc cgatcttctg ggtga                                             25

<210> SEQ ID NO 21
<211> LENGTH: 25
<212> TYPE: DNA
<213> ORGANISM: Homo sapiens

<400> SEQUENCE: 21
tcagaggttc gtcgcatttg tccac                                             25

<210> SEQ ID NO 22
<211> LENGTH: 25
<212> TYPE: DNA
<213> ORGANISM: Homo sapiens

<400> SEQUENCE: 22
tgcggccctt gttattcctc accag                                             25

<210> SEQ ID NO 23
<211> LENGTH: 25
<212> TYPE: DNA
<213> ORGANISM: Homo sapiens

<400> SEQUENCE: 23
tgcgtcagcc gtacctcgta ggtgc                                             25

<210> SEQ ID NO 24
<211> LENGTH: 25
<212> TYPE: DNA
<213> ORGANISM: Homo sapiens

<400> SEQUENCE: 24
ccctcgaagg tcagccagaa caggt                                             25

<210> SEQ ID NO 25
<211> LENGTH: 25
<212> TYPE: DNA
<213> ORGANISM: Homo sapiens

<400> SEQUENCE: 25
gcaggcgcag attcatgaac acggt                                             25

<210> SEQ ID NO 26
<211> LENGTH: 25
<212> TYPE: DNA
<213> ORGANISM: Homo sapiens

<400> SEQUENCE: 26
tccggccctt gatcctgctc ggatg                                             25

<210> SEQ ID NO 27
<211> LENGTH: 25
<212> TYPE: DNA
<213> ORGANISM: Homo sapiens

<400> SEQUENCE: 27
ttccggccct tgatcctgct cggat                                          25

<210> SEQ ID NO 28
<211> LENGTH: 25
<212> TYPE: DNA
<213> ORGANISM: Homo sapiens

<400> SEQUENCE: 28
tttccggccc ttgatcctgc tcgga                                          25

<210> SEQ ID NO 29
<211> LENGTH: 25
<212> TYPE: DNA
<213> ORGANISM: Homo sapiens

<400> SEQUENCE: 29
atttccggcc cttgatcctg ctcgg                                          25

<210> SEQ ID NO 30
<211> LENGTH: 25
<212> TYPE: DNA
<213> ORGANISM: Homo sapiens

<400> SEQUENCE: 30
tatttccggc ccttgatcct gctcg                                          25

<210> SEQ ID NO 31
<211> LENGTH: 25
<212> TYPE: DNA
<213> ORGANISM: Homo sapiens

<400> SEQUENCE: 31
ttatttccgg cccttgatcc tgctc                                          25

<210> SEQ ID NO 32
<211> LENGTH: 25
<212> TYPE: DNA
<213> ORGANISM: Homo sapiens

<400> SEQUENCE: 32
cagcctttat ttccggccct tgatc                                          25

<210> SEQ ID NO 33
<211> LENGTH: 25
<212> TYPE: DNA
<213> ORGANISM: Homo sapiens

<400> SEQUENCE: 33
acagccttta tttccggccc ttgat                                          25

<210> SEQ ID NO 34
<211> LENGTH: 25
<212> TYPE: DNA
<213> ORGANISM: Homo sapiens

<400> SEQUENCE: 34
tccgagtgtt cagggagcaa ggtcc                                          25

<210> SEQ ID NO 35
<211> LENGTH: 25
<212> TYPE: DNA
<213> ORGANISM: Homo sapiens

```
<400> SEQUENCE: 35
aaggtcgtca cttccaacca acagg                                              25

<210> SEQ ID NO 36
<211> LENGTH: 25
<212> TYPE: DNA
<213> ORGANISM: Homo sapiens

<400> SEQUENCE: 36
tctggccagc tgattggaga cgtcc                                              25

<210> SEQ ID NO 37
<211> LENGTH: 25
<212> TYPE: DNA
<213> ORGANISM: Homo sapiens

<400> SEQUENCE: 37
tagatgggaa tacaagcctg gcttc                                              25

<210> SEQ ID NO 38
<211> LENGTH: 25
<212> TYPE: DNA
<213> ORGANISM: Homo sapiens

<400> SEQUENCE: 38
gaaagttcct cctagtgcag tggca                                              25

<210> SEQ ID NO 39
<211> LENGTH: 25
<212> TYPE: DNA
<213> ORGANISM: Homo sapiens

<400> SEQUENCE: 39
gaactggctt cagctggaca tacca                                              25

<210> SEQ ID NO 40
<211> LENGTH: 25
<212> TYPE: DNA
<213> ORGANISM: Homo sapiens

<400> SEQUENCE: 40
gctgcatcat tgtaggaagt tcctc                                              25

<210> SEQ ID NO 41
<211> LENGTH: 25
<212> TYPE: DNA
<213> ORGANISM: Homo sapiens

<400> SEQUENCE: 41
tgttggacca gcaaaagaaa cgcca                                              25

<210> SEQ ID NO 42
<211> LENGTH: 25
<212> TYPE: DNA
<213> ORGANISM: Homo sapiens

<400> SEQUENCE: 42
tatgaagatt ctacccggtg ctggg                                              25

<210> SEQ ID NO 43
<211> LENGTH: 25
<212> TYPE: DNA
```

```
<213> ORGANISM: Homo sapiens

<400> SEQUENCE: 43
cccttgtgta cagaggtttt gggag                                          25

<210> SEQ ID NO 44
<211> LENGTH: 25
<212> TYPE: DNA
<213> ORGANISM: Homo sapiens

<400> SEQUENCE: 44
cagacagcca cccttgtgta cagag                                          25

<210> SEQ ID NO 45
<211> LENGTH: 25
<212> TYPE: DNA
<213> ORGANISM: Homo sapiens

<400> SEQUENCE: 45
ggtggatgcc tccttcattg ctgaa                                          25

<210> SEQ ID NO 46
<211> LENGTH: 25
<212> TYPE: DNA
<213> ORGANISM: Homo sapiens

<400> SEQUENCE: 46
ttgtcttcaa cttcgttcag ctgca                                          25

<210> SEQ ID NO 47
<211> LENGTH: 25
<212> TYPE: DNA
<213> ORGANISM: Homo sapiens

<400> SEQUENCE: 47
tcctctatcg ttctctttcc aacag                                          25

<210> SEQ ID NO 48
<211> LENGTH: 25
<212> TYPE: DNA
<213> ORGANISM: Homo sapiens

<400> SEQUENCE: 48
gcagcacagc cgtccagagc agcat                                          25

<210> SEQ ID NO 49
<211> LENGTH: 25
<212> TYPE: DNA
<213> ORGANISM: Homo sapiens

<400> SEQUENCE: 49
gaatatacat cacctgccca gagca                                          25

<210> SEQ ID NO 50
<211> LENGTH: 25
<212> TYPE: DNA
<213> ORGANISM: Homo sapiens

<400> SEQUENCE: 50
gaccccgatg ggaggcagtt tcatc                                          25

<210> SEQ ID NO 51
<211> LENGTH: 25
```

```
<212> TYPE: DNA
<213> ORGANISM: Homo sapiens

<400> SEQUENCE: 51
agggtcacca ggctaccctc tcggg                                           25

<210> SEQ ID NO 52
<211> LENGTH: 25
<212> TYPE: DNA
<213> ORGANISM: Homo sapiens

<400> SEQUENCE: 52
ccctgtcctg caaggtgtgg ccgtc                                           25

<210> SEQ ID NO 53
<211> LENGTH: 25
<212> TYPE: DNA
<213> ORGANISM: Homo sapiens

<400> SEQUENCE: 53
gagtagttcc cagcatcctg ttctg                                           25

<210> SEQ ID NO 54
<211> LENGTH: 25
<212> TYPE: DNA
<213> ORGANISM: Homo sapiens

<400> SEQUENCE: 54
ttgctggcgg gagtgaacaa gactt                                           25

<210> SEQ ID NO 55
<211> LENGTH: 25
<212> TYPE: DNA
<213> ORGANISM: Homo sapiens

<400> SEQUENCE: 55
ggatctcaca taaaccagaa gtgca                                           25

<210> SEQ ID NO 56
<211> LENGTH: 25
<212> TYPE: DNA
<213> ORGANISM: Homo sapiens

<400> SEQUENCE: 56
ttggcatata gtgggcactg ctctc                                           25

<210> SEQ ID NO 57
<211> LENGTH: 25
<212> TYPE: DNA
<213> ORGANISM: Homo sapiens

<400> SEQUENCE: 57
cgttggcata tagtgggcac tgctc                                           25

<210> SEQ ID NO 58
<211> LENGTH: 25
<212> TYPE: DNA
<213> ORGANISM: Homo sapiens

<400> SEQUENCE: 58
gagtagacaa caccttcatc tttcc                                           25

<210> SEQ ID NO 59
```

```
<211> LENGTH: 25
<212> TYPE: DNA
<213> ORGANISM: Homo sapiens

<400> SEQUENCE: 59
gaggttctat gcaccacaga gtaga                                              25

<210> SEQ ID NO 60
<211> LENGTH: 25
<212> TYPE: DNA
<213> ORGANISM: Homo sapiens

<400> SEQUENCE: 60
ttctccccac ggtgaactca gcaga                                              25

<210> SEQ ID NO 61
<211> LENGTH: 25
<212> TYPE: DNA
<213> ORGANISM: Homo sapiens

<400> SEQUENCE: 61
tttctcccca cggtgaactc agcag                                              25

<210> SEQ ID NO 62
<211> LENGTH: 25
<212> TYPE: DNA
<213> ORGANISM: Homo sapiens

<400> SEQUENCE: 62
tctcacctcc gcacagatga tagaa                                              25

<210> SEQ ID NO 63
<211> LENGTH: 25
<212> TYPE: DNA
<213> ORGANISM: Homo sapiens

<400> SEQUENCE: 63
ggcatctcac ctccgcacag atgat                                              25

<210> SEQ ID NO 64
<211> LENGTH: 25
<212> TYPE: DNA
<213> ORGANISM: Homo sapiens

<400> SEQUENCE: 64
tatttgtata tgactagcgg cgctg                                              25

<210> SEQ ID NO 65
<211> LENGTH: 25
<212> TYPE: DNA
<213> ORGANISM: Homo sapiens

<400> SEQUENCE: 65
tgtttccctt cagctgacgt tacaa                                              25

<210> SEQ ID NO 66
<211> LENGTH: 25
<212> TYPE: DNA
<213> ORGANISM: Homo sapiens

<400> SEQUENCE: 66
tatatataca agtggcctct ggttc                                              25
```

```
<210> SEQ ID NO 67
<211> LENGTH: 25
<212> TYPE: DNA
<213> ORGANISM: Homo sapiens

<400> SEQUENCE: 67
gacctatata tacaagtggc ctctg                                  25

<210> SEQ ID NO 68
<211> LENGTH: 25
<212> TYPE: DNA
<213> ORGANISM: Homo sapiens

<400> SEQUENCE: 68
gaagagacct atatatacaa gtggc                                  25

<210> SEQ ID NO 69
<211> LENGTH: 25
<212> TYPE: DNA
<213> ORGANISM: Homo sapiens

<400> SEQUENCE: 69
gcaattctca gctgttcggc agggc                                  25

<210> SEQ ID NO 70
<211> LENGTH: 25
<212> TYPE: DNA
<213> ORGANISM: Homo sapiens

<400> SEQUENCE: 70
tgcaattctc agctgttcgg caggg                                  25

<210> SEQ ID NO 71
<211> LENGTH: 25
<212> TYPE: DNA
<213> ORGANISM: Homo sapiens

<400> SEQUENCE: 71
ggttgcagtg caattctcag ctgtt                                  25

<210> SEQ ID NO 72
<211> LENGTH: 25
<212> TYPE: DNA
<213> ORGANISM: Homo sapiens

<400> SEQUENCE: 72
ctttagatag gccagtaggt tgcac                                  25

<210> SEQ ID NO 73
<211> LENGTH: 25
<212> TYPE: DNA
<213> ORGANISM: Homo sapiens

<400> SEQUENCE: 73
tggaagactt ttgccctata gcagc                                  25

<210> SEQ ID NO 74
<211> LENGTH: 25
<212> TYPE: DNA
<213> ORGANISM: Homo sapiens

<400> SEQUENCE: 74
tgaaagttgc cataccgcag atgga                                  25
```

<210> SEQ ID NO 75
<211> LENGTH: 25
<212> TYPE: DNA
<213> ORGANISM: Homo sapiens

<400> SEQUENCE: 75
tcctgaagga atgccaagac atgca                                    25

<210> SEQ ID NO 76
<211> LENGTH: 25
<212> TYPE: DNA
<213> ORGANISM: Homo sapiens

<400> SEQUENCE: 76
ccaacttggt ggaggaattt cagct                                    25

<210> SEQ ID NO 77
<211> LENGTH: 25
<212> TYPE: DNA
<213> ORGANISM: Homo sapiens

<400> SEQUENCE: 77
tctcaagacc cagcaattca ggtgt                                    25

<210> SEQ ID NO 78
<211> LENGTH: 25
<212> TYPE: DNA
<213> ORGANISM: Homo sapiens

<400> SEQUENCE: 78
taacctctat gggatgcaaa atgac                                    25

<210> SEQ ID NO 79
<211> LENGTH: 25
<212> TYPE: DNA
<213> ORGANISM: Homo sapiens

<400> SEQUENCE: 79
cctatttaga ctttggtccg ccagc                                    25

<210> SEQ ID NO 80
<211> LENGTH: 25
<212> TYPE: DNA
<213> ORGANISM: Homo sapiens

<400> SEQUENCE: 80
aacattttcc aacccagagt gtggc                                    25

<210> SEQ ID NO 81
<211> LENGTH: 25
<212> TYPE: DNA
<213> ORGANISM: Homo sapiens

<400> SEQUENCE: 81
gattatgata gtagaccagt cgagg                                    25

<210> SEQ ID NO 82
<211> LENGTH: 25
<212> TYPE: DNA
<213> ORGANISM: Homo sapiens

<400> SEQUENCE: 82
gaagccctgg actcttaaag ctgag                                    25

```
<210> SEQ ID NO 83
<211> LENGTH: 25
<212> TYPE: DNA
<213> ORGANISM: Homo sapiens

<400> SEQUENCE: 83
tgttcacgta ggtcaatggt agcag                                          25

<210> SEQ ID NO 84
<211> LENGTH: 25
<212> TYPE: DNA
<213> ORGANISM: Homo sapiens

<400> SEQUENCE: 84
gcatcagctg atgttttctc cgttt                                          25

<210> SEQ ID NO 85
<211> LENGTH: 25
<212> TYPE: DNA
<213> ORGANISM: Homo sapiens

<400> SEQUENCE: 85
tcctgtctgc ctcaagtaaa tactg                                          25

<210> SEQ ID NO 86
<211> LENGTH: 25
<212> TYPE: DNA
<213> ORGANISM: Homo sapiens

<400> SEQUENCE: 86
tctgctgttc cgaaaagctg gtgac                                          25

<210> SEQ ID NO 87
<211> LENGTH: 25
<212> TYPE: DNA
<213> ORGANISM: Homo sapiens

<400> SEQUENCE: 87
cccagggtgc tgttaggtct gtgct                                          25

<210> SEQ ID NO 88
<211> LENGTH: 25
<212> TYPE: DNA
<213> ORGANISM: Homo sapiens

<400> SEQUENCE: 88
tgaagaggtt tccacccagg gtgct                                          25

<210> SEQ ID NO 89
<211> LENGTH: 25
<212> TYPE: DNA
<213> ORGANISM: Homo sapiens

<400> SEQUENCE: 89
ccaagcaaat gctgaagagg tttcc                                          25

<210> SEQ ID NO 90
<211> LENGTH: 25
<212> TYPE: DNA
<213> ORGANISM: Homo sapiens

<400> SEQUENCE: 90
```
gtttttagct tactgattcc aagca                                          25

<210> SEQ ID NO 91
<211> LENGTH: 25
<212> TYPE: DNA
<213> ORGANISM: Homo sapiens

<400> SEQUENCE: 91
aaatggcatt tcagctgtgg aagga                                          25

<210> SEQ ID NO 92
<211> LENGTH: 25
<212> TYPE: DNA
<213> ORGANISM: Homo sapiens

<400> SEQUENCE: 92
tctagatccc ttgagacact gtctt                                          25

<210> SEQ ID NO 93
<211> LENGTH: 25
<212> TYPE: DNA
<213> ORGANISM: Homo sapiens

<400> SEQUENCE: 93
ccatctaggt gttttatgta ggcca                                          25

<210> SEQ ID NO 94
<211> LENGTH: 25
<212> TYPE: DNA
<213> ORGANISM: Homo sapiens

<400> SEQUENCE: 94
cctcacagtc aagttcagaa tactc                                          25

<210> SEQ ID NO 95
<211> LENGTH: 25
<212> TYPE: DNA
<213> ORGANISM: Homo sapiens

<400> SEQUENCE: 95
atttcttcca cacttcagtt gtgtc                                          25

<210> SEQ ID NO 96
<211> LENGTH: 25
<212> TYPE: DNA
<213> ORGANISM: Homo sapiens

<400> SEQUENCE: 96
cccaatctgg tgatagaggt agcca                                          25

<210> SEQ ID NO 97
<211> LENGTH: 25
<212> TYPE: DNA
<213> ORGANISM: Homo sapiens

<400> SEQUENCE: 97
gaaaatactg cctatgcctg aaggg                                          25

<210> SEQ ID NO 98
<211> LENGTH: 25
<212> TYPE: DNA
<213> ORGANISM: Homo sapiens

<400> SEQUENCE: 98

```
cagtgattag ttgtaagacc ttcgg                                              25

<210> SEQ ID NO 99
<211> LENGTH: 25
<212> TYPE: DNA
<213> ORGANISM: Homo sapiens

<400> SEQUENCE: 99
gaactaatca gcatcatgtg ggcct                                              25

<210> SEQ ID NO 100
<211> LENGTH: 25
<212> TYPE: DNA
<213> ORGANISM: Homo sapiens

<400> SEQUENCE: 100
caaattttgt tgttaggcag tcacc                                              25

<210> SEQ ID NO 101
<211> LENGTH: 25
<212> TYPE: DNA
<213> ORGANISM: Homo sapiens

<400> SEQUENCE: 101
tacatgcctg aagctataag tgaga                                              25

<210> SEQ ID NO 102
<211> LENGTH: 25
<212> TYPE: DNA
<213> ORGANISM: Homo sapiens

<400> SEQUENCE: 102
ccaagacagt gttatataag ggagc                                              25

<210> SEQ ID NO 103
<211> LENGTH: 25
<212> TYPE: DNA
<213> ORGANISM: Homo sapiens

<400> SEQUENCE: 103
gagatctggc tattctgtct tgtgg                                              25

<210> SEQ ID NO 104
<211> LENGTH: 25
<212> TYPE: DNA
<213> ORGANISM: Homo sapiens

<400> SEQUENCE: 104
tgctgtaaat taggcagccg ttctg                                              25

<210> SEQ ID NO 105
<211> LENGTH: 25
<212> TYPE: DNA
<213> ORGANISM: Homo sapiens

<400> SEQUENCE: 105
caacataaga gggttaaggc ttcaa                                              25

<210> SEQ ID NO 106
<211> LENGTH: 25
<212> TYPE: DNA
<213> ORGANISM: Homo sapiens
```

```
<400> SEQUENCE: 106
gcctttcctc agtggcacag agaga                                              25

<210> SEQ ID NO 107
<211> LENGTH: 25
<212> TYPE: DNA
<213> ORGANISM: Homo sapiens

<400> SEQUENCE: 107
gaagtcctag atgaaggtga caacc                                              25

<210> SEQ ID NO 108
<211> LENGTH: 25
<212> TYPE: DNA
<213> ORGANISM: Homo sapiens

<400> SEQUENCE: 108
tatccttgac ctgatgatca tcacc                                              25

<210> SEQ ID NO 109
<211> LENGTH: 25
<212> TYPE: DNA
<213> ORGANISM: Homo sapiens

<400> SEQUENCE: 109
tcgtcatcaa tggataactc ccatg                                              25

<210> SEQ ID NO 110
<211> LENGTH: 25
<212> TYPE: DNA
<213> ORGANISM: Homo sapiens

<400> SEQUENCE: 110
taaagccatc caggcgatag gcaga                                              25

<210> SEQ ID NO 111
<211> LENGTH: 25
<212> TYPE: DNA
<213> ORGANISM: Homo sapiens

<400> SEQUENCE: 111
tggatttaag cggacagcct gcctt                                              25

<210> SEQ ID NO 112
<211> LENGTH: 25
<212> TYPE: DNA
<213> ORGANISM: Homo sapiens

<400> SEQUENCE: 112
tttgtagacg aacccaagga ggctc                                              25

<210> SEQ ID NO 113
<211> LENGTH: 25
<212> TYPE: DNA
<213> ORGANISM: Homo sapiens

<400> SEQUENCE: 113
gaaatgtgaa agtggctgat atctg                                              25

<210> SEQ ID NO 114
<211> LENGTH: 25
<212> TYPE: DNA
<213> ORGANISM: Homo sapiens
```

```
<400> SEQUENCE: 114
tactacatag cactcataca aatga                                          25

<210> SEQ ID NO 115
<211> LENGTH: 25
<212> TYPE: DNA
<213> ORGANISM: Homo sapiens

<400> SEQUENCE: 115
caaagaagac agagcagctg gagct                                          25

<210> SEQ ID NO 116
<211> LENGTH: 25
<212> TYPE: DNA
<213> ORGANISM: Homo sapiens

<400> SEQUENCE: 116
gctttgccac accatagagg gctca                                          25

<210> SEQ ID NO 117
<211> LENGTH: 25
<212> TYPE: DNA
<213> ORGANISM: Homo sapiens

<400> SEQUENCE: 117
tgtgatctgt gtagctgtga ctgca                                          25

<210> SEQ ID NO 118
<211> LENGTH: 25
<212> TYPE: DNA
<213> ORGANISM: Homo sapiens

<400> SEQUENCE: 118
gattagcgtg taaacccagc cacct                                          25

<210> SEQ ID NO 119
<211> LENGTH: 25
<212> TYPE: DNA
<213> ORGANISM: Homo sapiens

<400> SEQUENCE: 119
tgggaatacg aagacagccc tggct                                          25

<210> SEQ ID NO 120
<211> LENGTH: 25
<212> TYPE: DNA
<213> ORGANISM: Homo sapiens

<400> SEQUENCE: 120
tccaagcata ctggtccttt ccaag                                          25

<210> SEQ ID NO 121
<211> LENGTH: 25
<212> TYPE: DNA
<213> ORGANISM: Homo sapiens

<400> SEQUENCE: 121
catgatagcg gaattttagg tggcc                                          25

<210> SEQ ID NO 122
<211> LENGTH: 25
<212> TYPE: DNA
```

<213> ORGANISM: Homo sapiens

<400> SEQUENCE: 122
tcatgggaac cagacttggg agcct                                         25

<210> SEQ ID NO 123
<211> LENGTH: 25
<212> TYPE: DNA
<213> ORGANISM: Homo sapiens

<400> SEQUENCE: 123
tgttattgtc ccacacggtg ctcgt                                         25

<210> SEQ ID NO 124
<211> LENGTH: 25
<212> TYPE: DNA
<213> ORGANISM: Homo sapiens

<400> SEQUENCE: 124
gaagagcttc acataggcat ccgtg                                         25

<210> SEQ ID NO 125
<211> LENGTH: 25
<212> TYPE: DNA
<213> ORGANISM: Homo sapiens

<400> SEQUENCE: 125
taatggaggt gtgatggccg ccaac                                         25

<210> SEQ ID NO 126
<211> LENGTH: 25
<212> TYPE: DNA
<213> ORGANISM: Homo sapiens

<400> SEQUENCE: 126
cagtgagggc cgatatgcgg ccacc                                         25

<210> SEQ ID NO 127
<211> LENGTH: 25
<212> TYPE: DNA
<213> ORGANISM: Homo sapiens

<400> SEQUENCE: 127
gtgagggccg atatgcggcc accca                                         25

<210> SEQ ID NO 128
<211> LENGTH: 25
<212> TYPE: DNA
<213> ORGANISM: Homo sapiens

<400> SEQUENCE: 128
tgagggccga tatgcggcca cccag                                         25

<210> SEQ ID NO 129
<211> LENGTH: 25
<212> TYPE: DNA
<213> ORGANISM: Homo sapiens

<400> SEQUENCE: 129
cagctccaca gcccggatga agtgg                                         25

<210> SEQ ID NO 130
<211> LENGTH: 25

```
<212> TYPE: DNA
<213> ORGANISM: Homo sapiens

<400> SEQUENCE: 130
gtgccgtagt tggagataag cctga                                              25

<210> SEQ ID NO 131
<211> LENGTH: 25
<212> TYPE: DNA
<213> ORGANISM: Homo sapiens

<400> SEQUENCE: 131
gaacctttgt gtgtccactg ggaag                                              25

<210> SEQ ID NO 132
<211> LENGTH: 25
<212> TYPE: DNA
<213> ORGANISM: Homo sapiens

<400> SEQUENCE: 132
catgcaccag gcacgaactt gtggc                                              25

<210> SEQ ID NO 133
<211> LENGTH: 25
<212> TYPE: DNA
<213> ORGANISM: Homo sapiens

<400> SEQUENCE: 133
ctggaatccc gtatagagaa gcggc                                              25

<210> SEQ ID NO 134
<211> LENGTH: 25
<212> TYPE: DNA
<213> ORGANISM: Homo sapiens

<400> SEQUENCE: 134
tggaatcccg tatagagaag cggct                                              25

<210> SEQ ID NO 135
<211> LENGTH: 25
<212> TYPE: DNA
<213> ORGANISM: Homo sapiens

<400> SEQUENCE: 135
gaatcccgta tagagaagcg gctac                                              25

<210> SEQ ID NO 136
<211> LENGTH: 25
<212> TYPE: DNA
<213> ORGANISM: Homo sapiens

<400> SEQUENCE: 136
gaagcggcta cacagatgga tatcc                                              25

<210> SEQ ID NO 137
<211> LENGTH: 25
<212> TYPE: DNA
<213> ORGANISM: Homo sapiens

<400> SEQUENCE: 137
tcttcaccga ggctcctgga atggt                                              25

<210> SEQ ID NO 138
```

```
<211> LENGTH: 25
<212> TYPE: DNA
<213> ORGANISM: Homo sapiens

<400> SEQUENCE: 138
tcagacgaga ctgggcatgt tcagg                                              25

<210> SEQ ID NO 139
<211> LENGTH: 25
<212> TYPE: DNA
<213> ORGANISM: Homo sapiens

<400> SEQUENCE: 139
atcagacgag actgggcatg ttcag                                              25

<210> SEQ ID NO 140
<211> LENGTH: 25
<212> TYPE: DNA
<213> ORGANISM: Homo sapiens

<400> SEQUENCE: 140
gatcagacga gactgggcat gttca                                              25

<210> SEQ ID NO 141
<211> LENGTH: 25
<212> TYPE: DNA
<213> ORGANISM: Homo sapiens

<400> SEQUENCE: 141
agatcagacg agactgggca tgttc                                              25

<210> SEQ ID NO 142
<211> LENGTH: 25
<212> TYPE: DNA
<213> ORGANISM: Homo sapiens

<400> SEQUENCE: 142
gagatcagac gagactgggc atgtt                                              25

<210> SEQ ID NO 143
<211> LENGTH: 25
<212> TYPE: DNA
<213> ORGANISM: Homo sapiens

<400> SEQUENCE: 143
cgagatcaga cgagactggg catgt                                              25

<210> SEQ ID NO 144
<211> LENGTH: 25
<212> TYPE: DNA
<213> ORGANISM: Homo sapiens

<400> SEQUENCE: 144
cttttattta gactgggcgg ccgcg                                              25

<210> SEQ ID NO 145
<211> LENGTH: 25
<212> TYPE: DNA
<213> ORGANISM: Homo sapiens

<400> SEQUENCE: 145
ttctggagtt ctcattagac tgggt                                              25
```

```
<210> SEQ ID NO 146
<211> LENGTH: 25
<212> TYPE: DNA
<213> ORGANISM: Homo sapiens

<400> SEQUENCE: 146
tccataagga agcactcgat gtcgt                                         25

<210> SEQ ID NO 147
<211> LENGTH: 25
<212> TYPE: DNA
<213> ORGANISM: Homo sapiens

<400> SEQUENCE: 147
tcatagaggc tgttggcgct ggaca                                         25

<210> SEQ ID NO 148
<211> LENGTH: 25
<212> TYPE: DNA
<213> ORGANISM: Homo sapiens

<400> SEQUENCE: 148
cccgaagccc aggtagatgg tatag                                         25

<210> SEQ ID NO 149
<211> LENGTH: 25
<212> TYPE: DNA
<213> ORGANISM: Homo sapiens

<400> SEQUENCE: 149
gaagcccagg tagatggtat agcgt                                         25

<210> SEQ ID NO 150
<211> LENGTH: 25
<212> TYPE: DNA
<213> ORGANISM: Homo sapiens

<400> SEQUENCE: 150
tgtcacagtt ccgaggcagc aggca                                         25

<210> SEQ ID NO 151
<211> LENGTH: 25
<212> TYPE: DNA
<213> ORGANISM: Homo sapiens

<400> SEQUENCE: 151
tataggaacg tgcagctcgg gtgtc                                         25

<210> SEQ ID NO 152
<211> LENGTH: 25
<212> TYPE: DNA
<213> ORGANISM: Homo sapiens

<400> SEQUENCE: 152
gagggtgaca ggtacggctc tgcct                                         25

<210> SEQ ID NO 153
<211> LENGTH: 25
<212> TYPE: DNA
<213> ORGANISM: Homo sapiens

<400> SEQUENCE: 153
tgacaggtac ggctctgcct ggtgc                                         25
```

```
<210> SEQ ID NO 154
<211> LENGTH: 25
<212> TYPE: DNA
<213> ORGANISM: Homo sapiens

<400> SEQUENCE: 154
ctgcatccgg aagggaatcc tgtgc                                    25

<210> SEQ ID NO 155
<211> LENGTH: 25
<212> TYPE: DNA
<213> ORGANISM: Homo sapiens

<400> SEQUENCE: 155
catccggaag ggaatcctgt gctgg                                    25

<210> SEQ ID NO 156
<211> LENGTH: 25
<212> TYPE: DNA
<213> ORGANISM: Homo sapiens

<400> SEQUENCE: 156
cttctaaagt gtccgtccag gtgca                                    25

<210> SEQ ID NO 157
<211> LENGTH: 25
<212> TYPE: DNA
<213> ORGANISM: Homo sapiens

<400> SEQUENCE: 157
tgacgctgtc agcagatggt ctgcc                                    25

<210> SEQ ID NO 158
<211> LENGTH: 25
<212> TYPE: DNA
<213> ORGANISM: Homo sapiens

<400> SEQUENCE: 158
agtccagcat gtgtgtgtgc cagga                                    25

<210> SEQ ID NO 159
<211> LENGTH: 25
<212> TYPE: DNA
<213> ORGANISM: Homo sapiens

<400> SEQUENCE: 159
aagtcagggt gaacgtaagc agctc                                    25

<210> SEQ ID NO 160
<211> LENGTH: 25
<212> TYPE: DNA
<213> ORGANISM: Homo sapiens

<400> SEQUENCE: 160
agtcagggtg aacgtaagca gctcc                                    25

<210> SEQ ID NO 161
<211> LENGTH: 25
<212> TYPE: DNA
<213> ORGANISM: Homo sapiens

<400> SEQUENCE: 161
cggctgagcg cgtacacctt gtgcg                                    25
```

```
<210> SEQ ID NO 162
<211> LENGTH: 25
<212> TYPE: DNA
<213> ORGANISM: Homo sapiens

<400> SEQUENCE: 162
tgagcgcgta caccttgtgc gggtc                                          25

<210> SEQ ID NO 163
<211> LENGTH: 25
<212> TYPE: DNA
<213> ORGANISM: Homo sapiens

<400> SEQUENCE: 163
cagtgcgcag cggaagttgg ttttc                                          25

<210> SEQ ID NO 164
<211> LENGTH: 25
<212> TYPE: DNA
<213> ORGANISM: Homo sapiens

<400> SEQUENCE: 164
aagttggttt tccagccggc gcgct                                          25

<210> SEQ ID NO 165
<211> LENGTH: 25
<212> TYPE: DNA
<213> ORGANISM: Homo sapiens

<400> SEQUENCE: 165
gacagaacac gtgtgccggg cccgc                                          25

<210> SEQ ID NO 166
<211> LENGTH: 25
<212> TYPE: DNA
<213> ORGANISM: Homo sapiens

<400> SEQUENCE: 166
tccttgcgcg cgaagtgctt ccagg                                          25

<210> SEQ ID NO 167
<211> LENGTH: 25
<212> TYPE: DNA
<213> ORGANISM: Homo sapiens

<400> SEQUENCE: 167
taggtggcgg tcaggtgtta taaca                                          25

<210> SEQ ID NO 168
<211> LENGTH: 25
<212> TYPE: DNA
<213> ORGANISM: Homo sapiens

<400> SEQUENCE: 168
gactgagggc ttgtagccac cgacg                                          25

<210> SEQ ID NO 169
<211> LENGTH: 25
<212> TYPE: DNA
<213> ORGANISM: Homo sapiens

<400> SEQUENCE: 169
```
tgttgaacca gtgtccaggc ctggc    25

<210> SEQ ID NO 170
<211> LENGTH: 25
<212> TYPE: DNA
<213> ORGANISM: Homo sapiens

<400> SEQUENCE: 170
gaaagcgaaa cctaaacagt ggcgc    25

<210> SEQ ID NO 171
<211> LENGTH: 25
<212> TYPE: DNA
<213> ORGANISM: Homo sapiens

<400> SEQUENCE: 171
gaaacctaaa cagtggcgct tcgca    25

<210> SEQ ID NO 172
<211> LENGTH: 25
<212> TYPE: DNA
<213> ORGANISM: Homo sapiens

<400> SEQUENCE: 172
agcgctacca ctccgggatc ttgaa    25

<210> SEQ ID NO 173
<211> LENGTH: 25
<212> TYPE: DNA
<213> ORGANISM: Homo sapiens

<400> SEQUENCE: 173
tctctacaga gagcctaggc ctggc    25

<210> SEQ ID NO 174
<211> LENGTH: 25
<212> TYPE: DNA
<213> ORGANISM: Homo sapiens

<400> SEQUENCE: 174
gatgacaccc aacagggagc acgtt    25

<210> SEQ ID NO 175
<211> LENGTH: 25
<212> TYPE: DNA
<213> ORGANISM: Homo sapiens

<400> SEQUENCE: 175
caccccaggg tgtatactga caggg    25

<210> SEQ ID NO 176
<211> LENGTH: 25
<212> TYPE: DNA
<213> ORGANISM: Homo sapiens

<400> SEQUENCE: 176 aacttttgc ccatccgctc atgga    25

<210> SEQ ID NO 177
<211> LENGTH: 25
<212> TYPE: DNA
<213> ORGANISM: Homo sapiens

<400> SEQUENCE: 177
ggtacttaga gacacatcgg tccag                                              25

<210> SEQ ID NO 178
<211> LENGTH: 25
<212> TYPE: DNA
<213> ORGANISM: Homo sapiens

<400> SEQUENCE: 178
tagtgaggag gcacacactt ccggt                                              25

<210> SEQ ID NO 179
<211> LENGTH: 25
<212> TYPE: DNA
<213> ORGANISM: Homo sapiens

<400> SEQUENCE: 179
ctgttgtaca tatcggccat catct                                              25

<210> SEQ ID NO 180
<211> LENGTH: 25
<212> TYPE: DNA
<213> ORGANISM: Homo sapiens

<400> SEQUENCE: 180
tgttgtacat atcggccatc atctc                                              25

<210> SEQ ID NO 181
<211> LENGTH: 25
<212> TYPE: DNA
<213> ORGANISM: Homo sapiens

<400> SEQUENCE: 181
agctgttggg ccctgagagg atcca                                              25

<210> SEQ ID NO 182
<211> LENGTH: 25
<212> TYPE: DNA
<213> ORGANISM: Homo sapiens

<400> SEQUENCE: 182
gctgttgggc cctgagagga tccat                                              25

<210> SEQ ID NO 183
<211> LENGTH: 25
<212> TYPE: DNA
<213> ORGANISM: Homo sapiens

<400> SEQUENCE: 183
ctcagcctag caccgtggaa gggat                                              25

<210> SEQ ID NO 184
<211> LENGTH: 25
<212> TYPE: DNA
<213> ORGANISM: Homo sapiens

<400> SEQUENCE: 184
cctagcaccg tggaagggat ctcct                                              25

<210> SEQ ID NO 185
<211> LENGTH: 25
<212> TYPE: DNA
<213> ORGANISM: Homo sapiens

<400> SEQUENCE: 185
ctagcaccgt ggaagggatc tcctt                                          25

<210> SEQ ID NO 186
<211> LENGTH: 25
<212> TYPE: DNA
<213> ORGANISM: Homo sapiens

<400> SEQUENCE: 186
aagggatctc cttctggcct cctaa                                          25

<210> SEQ ID NO 187
<211> LENGTH: 25
<212> TYPE: DNA
<213> ORGANISM: Homo sapiens

<400> SEQUENCE: 187
ctgggagcag acatcaccat cagca                                          25

<210> SEQ ID NO 188
<211> LENGTH: 25
<212> TYPE: DNA
<213> ORGANISM: Homo sapiens

<400> SEQUENCE: 188
tgggagcaga catcaccatc agcac                                          25

<210> SEQ ID NO 189
<211> LENGTH: 25
<212> TYPE: DNA
<213> ORGANISM: Homo sapiens

<400> SEQUENCE: 189
cactgcctgg gacggatcac aatgc                                          25

<210> SEQ ID NO 190
<211> LENGTH: 25
<212> TYPE: DNA
<213> ORGANISM: Homo sapiens

<400> SEQUENCE: 190
ctgcctggga cggatcacaa tgccc                                          25

<210> SEQ ID NO 191
<211> LENGTH: 25
<212> TYPE: DNA
<213> ORGANISM: Homo sapiens

<400> SEQUENCE: 191
caacttctga caaatactat aacgt                                          25

<210> SEQ ID NO 192
<211> LENGTH: 25
<212> TYPE: DNA
<213> ORGANISM: Homo sapiens

<400> SEQUENCE: 192
tgacaaatac tataacgtta cccgc                                          25

<210> SEQ ID NO 193
<211> LENGTH: 25
<212> TYPE: DNA
<213> ORGANISM: Homo sapiens

```
<400> SEQUENCE: 193
gctccagcgg aagcacgtgg gttac                                            25

<210> SEQ ID NO 194
<211> LENGTH: 25
<212> TYPE: DNA
<213> ORGANISM: Homo sapiens

<400> SEQUENCE: 194
tccagcggaa gcacgtgggt tactt                                            25

<210> SEQ ID NO 195
<211> LENGTH: 25
<212> TYPE: DNA
<213> ORGANISM: Homo sapiens

<400> SEQUENCE: 195
ccagcggaag cacgtgggtt acttc                                            25

<210> SEQ ID NO 196
<211> LENGTH: 25
<212> TYPE: DNA
<213> ORGANISM: Homo sapiens

<400> SEQUENCE: 196
gaaagtcccg cctcttcttt gattc                                            25

<210> SEQ ID NO 197
<211> LENGTH: 25
<212> TYPE: DNA
<213> ORGANISM: Homo sapiens

<400> SEQUENCE: 197
catgaactcg aggaagtggc cgaac                                            25

<210> SEQ ID NO 198
<211> LENGTH: 25
<212> TYPE: DNA
<213> ORGANISM: Homo sapiens

<400> SEQUENCE: 198
tctaagggcc tttcctgcac tgaca                                            25

<210> SEQ ID NO 199
<211> LENGTH: 25
<212> TYPE: DNA
<213> ORGANISM: Homo sapiens

<400> SEQUENCE: 199
tagtggagcc tctgtaatgt tccgg                                            25

<210> SEQ ID NO 200
<211> LENGTH: 25
<212> TYPE: DNA
<213> ORGANISM: Homo sapiens

<400> SEQUENCE: 200
ttctgaagag tgtccagctt gggct                                            25

<210> SEQ ID NO 201
<211> LENGTH: 25
<212> TYPE: DNA
```

```
<213> ORGANISM: Homo sapiens

<400> SEQUENCE: 201
cagcagttct tcatagccgt ggtac                                  25

<210> SEQ ID NO 202
<211> LENGTH: 25
<212> TYPE: DNA
<213> ORGANISM: Homo sapiens

<400> SEQUENCE: 202
ggacagggtc tcttcactat gcaca                                  25

<210> SEQ ID NO 203
<211> LENGTH: 25
<212> TYPE: DNA
<213> ORGANISM: Homo sapiens

<400> SEQUENCE: 203
gagtgagcag ctctacagcc aggtt                                  25

<210> SEQ ID NO 204
<211> LENGTH: 25
<212> TYPE: DNA
<213> ORGANISM: Homo sapiens

<400> SEQUENCE: 204
taagtggatt cccagtcgct cctgg                                  25

<210> SEQ ID NO 205
<211> LENGTH: 25
<212> TYPE: DNA
<213> ORGANISM: Homo sapiens

<400> SEQUENCE: 205
tcgtgtatgg gccaccagag ggttg                                  25

<210> SEQ ID NO 206
<211> LENGTH: 25
<212> TYPE: DNA
<213> ORGANISM: Homo sapiens

<400> SEQUENCE: 206
tgaaagacga actcgcagag agatg                                  25

<210> SEQ ID NO 207
<211> LENGTH: 25
<212> TYPE: DNA
<213> ORGANISM: Homo sapiens

<400> SEQUENCE: 207
taggccaggc taaggtatct cagct                                  25

<210> SEQ ID NO 208
<211> LENGTH: 25
<212> TYPE: DNA
<213> ORGANISM: Homo sapiens

<400> SEQUENCE: 208
tccagggtaa gatgaaaaca caacc                                  25

<210> SEQ ID NO 209
<211> LENGTH: 25
```

```
<212> TYPE: DNA
<213> ORGANISM: Homo sapiens

<400> SEQUENCE: 209
tgattgatgc ctagagcacc cagga                                            25

<210> SEQ ID NO 210
<211> LENGTH: 25
<212> TYPE: DNA
<213> ORGANISM: Homo sapiens

<400> SEQUENCE: 210
ggtcaacatc cttttcatg ggcag                                             25

<210> SEQ ID NO 211
<211> LENGTH: 25
<212> TYPE: DNA
<213> ORGANISM: Homo sapiens

<400> SEQUENCE: 211
gttggagagt ctgttgtcat ccagc                                            25

<210> SEQ ID NO 212
<211> LENGTH: 25
<212> TYPE: DNA
<213> ORGANISM: Homo sapiens

<400> SEQUENCE: 212
ggatgtacct cttgcttgtc agcga                                            25

<210> SEQ ID NO 213
<211> LENGTH: 25
<212> TYPE: DNA
<213> ORGANISM: Homo sapiens

<400> SEQUENCE: 213
ttagggctgg aaacgtgtga aatgc                                            25

<210> SEQ ID NO 214
<211> LENGTH: 25
<212> TYPE: DNA
<213> ORGANISM: Homo sapiens

<400> SEQUENCE: 214
tctttaatga tatgctccta tcaag                                            25

<210> SEQ ID NO 215
<211> LENGTH: 25
<212> TYPE: DNA
<213> ORGANISM: Homo sapiens

<400> SEQUENCE: 215
tctggaggtg caagagacaa accac                                            25

<210> SEQ ID NO 216
<211> LENGTH: 25
<212> TYPE: DNA
<213> ORGANISM: Homo sapiens

<400> SEQUENCE: 216
ccaggatatg tccaggaagg tccac                                            25

<210> SEQ ID NO 217
```

```
<211> LENGTH: 25
<212> TYPE: DNA
<213> ORGANISM: Homo sapiens

<400> SEQUENCE: 217
tccggcacgc gaagcagatt tctgg                                             25

<210> SEQ ID NO 218
<211> LENGTH: 25
<212> TYPE: DNA
<213> ORGANISM: Homo sapiens

<400> SEQUENCE: 218
gatctttgac tttgggaatg gcccc                                             25

<210> SEQ ID NO 219
<211> LENGTH: 25
<212> TYPE: DNA
<213> ORGANISM: Homo sapiens

<400> SEQUENCE: 219
ttagtaactg cgacgcgacg gcaga                                             25

<210> SEQ ID NO 220
<211> LENGTH: 25
<212> TYPE: DNA
<213> ORGANISM: Homo sapiens

<400> SEQUENCE: 220
tactgggaag agatagaaac gtctt                                             25

<210> SEQ ID NO 221
<211> LENGTH: 25
<212> TYPE: DNA
<213> ORGANISM: Homo sapiens

<400> SEQUENCE: 221
cgaagtaact ctttcagtgc tgggc                                             25

<210> SEQ ID NO 222
<211> LENGTH: 25
<212> TYPE: DNA
<213> ORGANISM: Homo sapiens

<400> SEQUENCE: 222
ggaaggaagt actatttgag aatct                                             25

<210> SEQ ID NO 223
<211> LENGTH: 25
<212> TYPE: DNA
<213> ORGANISM: Homo sapiens

<400> SEQUENCE: 223
ggaagtacta tttgagaatc ttgtg                                             25

<210> SEQ ID NO 224
<211> LENGTH: 25
<212> TYPE: DNA
<213> ORGANISM: Homo sapiens

<400> SEQUENCE: 224
gaagtactat ttgagaatct tgtgt                                             25
```

```
<210> SEQ ID NO 225
<211> LENGTH: 25
<212> TYPE: DNA
<213> ORGANISM: Homo sapiens

<400> SEQUENCE: 225
gtagtaaggt gatttccaga tgttg                                   25

<210> SEQ ID NO 226
<211> LENGTH: 25
<212> TYPE: DNA
<213> ORGANISM: Homo sapiens

<400> SEQUENCE: 226
gagccccttt ccgaataaca gagtc                                   25

<210> SEQ ID NO 227
<211> LENGTH: 25
<212> TYPE: DNA
<213> ORGANISM: Homo sapiens

<400> SEQUENCE: 227
aacagagtca agcaaagctc gggcc                                   25

<210> SEQ ID NO 228
<211> LENGTH: 25
<212> TYPE: DNA
<213> ORGANISM: Homo sapiens

<400> SEQUENCE: 228
tgtctccaat aattcaccca gtaag                                   25

<210> SEQ ID NO 229
<211> LENGTH: 25
<212> TYPE: DNA
<213> ORGANISM: Homo sapiens

<400> SEQUENCE: 229
ttattgtacc ttcgcccact gaacg                                   25

<210> SEQ ID NO 230
<211> LENGTH: 25
<212> TYPE: DNA
<213> ORGANISM: Homo sapiens

<400> SEQUENCE: 230
tcgcccactg aacggataaa ctgct                                   25

<210> SEQ ID NO 231
<211> LENGTH: 25
<212> TYPE: DNA
<213> ORGANISM: Homo sapiens

<400> SEQUENCE: 231
gcccactgaa cggataaact gcttt                                   25

<210> SEQ ID NO 232
<211> LENGTH: 25
<212> TYPE: DNA
<213> ORGANISM: Homo sapiens

<400> SEQUENCE: 232
agtcgagact cgaagcttcc acgcg                                   25
```

```
<210> SEQ ID NO 233
<211> LENGTH: 25
<212> TYPE: DNA
<213> ORGANISM: Homo sapiens

<400> SEQUENCE: 233
tgtcgttaag aaagccagga cgcac                                           25

<210> SEQ ID NO 234
<211> LENGTH: 25
<212> TYPE: DNA
<213> ORGANISM: Homo sapiens

<400> SEQUENCE: 234
ccaaagcttt cattgtggga aaact                                           25

<210> SEQ ID NO 235
<211> LENGTH: 25
<212> TYPE: DNA
<213> ORGANISM: Homo sapiens

<400> SEQUENCE: 235
tctgggccca aagctttcat tgtgg                                           25

<210> SEQ ID NO 236
<211> LENGTH: 25
<212> TYPE: DNA
<213> ORGANISM: Homo sapiens

<400> SEQUENCE: 236
tgtaagtaca ctctcccaat ttggt                                           25

<210> SEQ ID NO 237
<211> LENGTH: 25
<212> TYPE: DNA
<213> ORGANISM: Homo sapiens

<400> SEQUENCE: 237
aaagaaaact tcgtgctcag gtgac                                           25

<210> SEQ ID NO 238
<211> LENGTH: 25
<212> TYPE: DNA
<213> ORGANISM: Homo sapiens

<400> SEQUENCE: 238
cttcagctaa gatctttcac atgca                                           25

<210> SEQ ID NO 239
<211> LENGTH: 25
<212> TYPE: DNA
<213> ORGANISM: Homo sapiens

<400> SEQUENCE: 239
gccgtaggca actctaacat ggaat                                           25

<210> SEQ ID NO 240
<211> LENGTH: 25
<212> TYPE: DNA
<213> ORGANISM: Homo sapiens

<400> SEQUENCE: 240
catagtcatt ctgggcttgg gttgc                                           25
```

<210> SEQ ID NO 241
<211> LENGTH: 25
<212> TYPE: DNA
<213> ORGANISM: Homo sapiens

<400> SEQUENCE: 241
tctcagggct ctatgtaaaa atggc                                25

<210> SEQ ID NO 242
<211> LENGTH: 25
<212> TYPE: DNA
<213> ORGANISM: Homo sapiens

<400> SEQUENCE: 242
tagtgggaac tgagatccag gccat                                25

<210> SEQ ID NO 243
<211> LENGTH: 25
<212> TYPE: DNA
<213> ORGANISM: Homo sapiens

<400> SEQUENCE: 243
gaaagtcagg gaaggatatc gcatc                                25

<210> SEQ ID NO 244
<211> LENGTH: 25
<212> TYPE: DNA
<213> ORGANISM: Homo sapiens

<400> SEQUENCE: 244
gaagaactgc agtcagaagc cccaa                                25

<210> SEQ ID NO 245
<211> LENGTH: 25
<212> TYPE: DNA
<213> ORGANISM: Homo sapiens

<400> SEQUENCE: 245
cacaggatcc actggtatag cagca                                25

<210> SEQ ID NO 246
<211> LENGTH: 25
<212> TYPE: DNA
<213> ORGANISM: Homo sapiens

<400> SEQUENCE: 246
gacagctggc acaagtggag tagtt                                25

<210> SEQ ID NO 247
<211> LENGTH: 25
<212> TYPE: DNA
<213> ORGANISM: Homo sapiens

<400> SEQUENCE: 247
tctgggcagc taggacagct ggcac                                25

<210> SEQ ID NO 248
<211> LENGTH: 25
<212> TYPE: DNA
<213> ORGANISM: Homo sapiens

<400> SEQUENCE: 248

```
tgagtctctg gctaggcaga attcc                                          25

<210> SEQ ID NO 249
<211> LENGTH: 25
<212> TYPE: DNA
<213> ORGANISM: Homo sapiens

<400> SEQUENCE: 249
gattgtccgt tatcacaagg aggtg                                          25

<210> SEQ ID NO 250
<211> LENGTH: 25
<212> TYPE: DNA
<213> ORGANISM: Homo sapiens

<400> SEQUENCE: 250
tcactgagga aaacttggag caggc                                          25

<210> SEQ ID NO 251
<211> LENGTH: 25
<212> TYPE: DNA
<213> ORGANISM: Homo sapiens

<400> SEQUENCE: 251
cagccagaat tgttcctcag accaa                                          25

<210> SEQ ID NO 252
<211> LENGTH: 25
<212> TYPE: DNA
<213> ORGANISM: Homo sapiens

<400> SEQUENCE: 252
tttgttgatg gcaccgcatg tctgc                                          25

<210> SEQ ID NO 253
<211> LENGTH: 25
<212> TYPE: DNA
<213> ORGANISM: Homo sapiens

<400> SEQUENCE: 253
taaaggaact tcacagcttg aggct                                          25

<210> SEQ ID NO 254
<211> LENGTH: 25
<212> TYPE: DNA
<213> ORGANISM: Homo sapiens

<400> SEQUENCE: 254
caaagagaat ccatcagtta ggcat                                          25

<210> SEQ ID NO 255
<211> LENGTH: 25
<212> TYPE: DNA
<213> ORGANISM: Homo sapiens

<400> SEQUENCE: 255
taccatcagg gatcagtaat gtaca                                          25

<210> SEQ ID NO 256
<211> LENGTH: 25
<212> TYPE: DNA
<213> ORGANISM: Homo sapiens

<400> SEQUENCE: 256
```

```
aataaagctt gatctgcaaa gggac                                              25

<210> SEQ ID NO 257
<211> LENGTH: 25
<212> TYPE: DNA
<213> ORGANISM: Homo sapiens

<400> SEQUENCE: 257
gaataaagct tgatctgcaa aggga                                              25

<210> SEQ ID NO 258
<211> LENGTH: 25
<212> TYPE: DNA
<213> ORGANISM: Homo sapiens

<400> SEQUENCE: 258
gaaaatgcct tatcgaattg actgc                                              25

<210> SEQ ID NO 259
<211> LENGTH: 25
<212> TYPE: DNA
<213> ORGANISM: Homo sapiens

<400> SEQUENCE: 259
tgtatgtcca aactctactg aggag                                              25

<210> SEQ ID NO 260
<211> LENGTH: 25
<212> TYPE: DNA
<213> ORGANISM: Homo sapiens

<400> SEQUENCE: 260
gaagtgccaa atccaatcca gcctg                                              25

<210> SEQ ID NO 261
<211> LENGTH: 25
<212> TYPE: DNA
<213> ORGANISM: Homo sapiens

<400> SEQUENCE: 261
gagtctcttg aacttgatga gctga                                              25

<210> SEQ ID NO 262
<211> LENGTH: 25
<212> TYPE: DNA
<213> ORGANISM: Homo sapiens

<400> SEQUENCE: 262
cacaagcctc tgaagtgttc cagga                                              25

<210> SEQ ID NO 263
<211> LENGTH: 25
<212> TYPE: DNA
<213> ORGANISM: Homo sapiens

<400> SEQUENCE: 263
gaatcatcta ttggtgagac atgta                                              25

<210> SEQ ID NO 264
<211> LENGTH: 25
<212> TYPE: DNA
<213> ORGANISM: Homo sapiens
```

<400> SEQUENCE: 264
ggcacgatgt gtacttttc agaaa                                            25

<210> SEQ ID NO 265
<211> LENGTH: 25
<212> TYPE: DNA
<213> ORGANISM: Homo sapiens

<400> SEQUENCE: 265
gaaattatgt tccaagagcg aagta                                            25

<210> SEQ ID NO 266
<211> LENGTH: 25
<212> TYPE: DNA
<213> ORGANISM: Homo sapiens

<400> SEQUENCE: 266
ggtaacaact ttgaggcctg gcttc                                            25

<210> SEQ ID NO 267
<211> LENGTH: 25
<212> TYPE: DNA
<213> ORGANISM: Homo sapiens

<400> SEQUENCE: 267
cagaaactag tgacggagaa tccac                                            25

<210> SEQ ID NO 268
<211> LENGTH: 25
<212> TYPE: DNA
<213> ORGANISM: Homo sapiens

<400> SEQUENCE: 268
cagaaattaa cctccacaga gtggt                                            25

<210> SEQ ID NO 269
<211> LENGTH: 25
<212> TYPE: DNA
<213> ORGANISM: Homo sapiens

<400> SEQUENCE: 269
ttatggagac ttgcttagaa aaact                                            25

<210> SEQ ID NO 270
<211> LENGTH: 25
<212> TYPE: DNA
<213> ORGANISM: Homo sapiens

<400> SEQUENCE: 270 tattcacat tagcaagatg aagcc                                             25

<210> SEQ ID NO 271
<211> LENGTH: 25
<212> TYPE: DNA
<213> ORGANISM: Homo sapiens

<400> SEQUENCE: 271
ggtcctggag taaatgctgg ctcaa                                            25

<210> SEQ ID NO 272
<211> LENGTH: 25
<212> TYPE: DNA
<213> ORGANISM: Homo sapiens

```
<400> SEQUENCE: 272
ctttctggag ttctatgttg ggtcc                                              25

<210> SEQ ID NO 273
<211> LENGTH: 25
<212> TYPE: DNA
<213> ORGANISM: Homo sapiens

<400> SEQUENCE: 273
gaagtaacag ttgcaccggt accca                                              25

<210> SEQ ID NO 274
<211> LENGTH: 25
<212> TYPE: DNA
<213> ORGANISM: Homo sapiens

<400> SEQUENCE: 274
cagagatgcc gactttcgtt ccaag                                              25

<210> SEQ ID NO 275
<211> LENGTH: 25
<212> TYPE: DNA
<213> ORGANISM: Homo sapiens

<400> SEQUENCE: 275
gagtccaatc cagtaaaatt gttga                                              25

<210> SEQ ID NO 276
<211> LENGTH: 25
<212> TYPE: DNA
<213> ORGANISM: Homo sapiens

<400> SEQUENCE: 276
tgtaagagag tccaatccag taaaa                                              25

<210> SEQ ID NO 277
<211> LENGTH: 25
<212> TYPE: DNA
<213> ORGANISM: Homo sapiens

<400> SEQUENCE: 277
tactgggaga gtgcagagcc attct                                              25

<210> SEQ ID NO 278
<211> LENGTH: 25
<212> TYPE: DNA
<213> ORGANISM: Homo sapiens

<400> SEQUENCE: 278
gatactggga gagtgcagag ccatt                                              25

<210> SEQ ID NO 279
<211> LENGTH: 25
<212> TYPE: DNA
<213> ORGANISM: Homo sapiens

<400> SEQUENCE: 279
tccatttgga ttatacgcta tgcag                                              25

<210> SEQ ID NO 280
<211> LENGTH: 25
<212> TYPE: DNA
```

<213> ORGANISM: Homo sapiens

<400> SEQUENCE: 280
catagtgaca tggtgcctgc agtcc 25

<210> SEQ ID NO 281
<211> LENGTH: 25
<212> TYPE: DNA
<213> ORGANISM: Homo sapiens

<400> SEQUENCE: 281
tctggcgcgg ccttcggatt tctgg 25

<210> SEQ ID NO 282
<211> LENGTH: 25
<212> TYPE: DNA
<213> ORGANISM: Homo sapiens

<400> SEQUENCE: 282
cttgacagtt ttcagcaccc gcggg 25

<210> SEQ ID NO 283
<211> LENGTH: 25
<212> TYPE: DNA
<213> ORGANISM: Homo sapiens

<400> SEQUENCE: 283
caagatctac ggatgtcagg cggaa 25

<210> SEQ ID NO 284
<211> LENGTH: 25
<212> TYPE: DNA
<213> ORGANISM: Homo sapiens

<400> SEQUENCE: 284
cctggaatgg tctaggaacc cctca 25

<210> SEQ ID NO 285
<211> LENGTH: 25
<212> TYPE: DNA
<213> ORGANISM: Homo sapiens

<400> SEQUENCE: 285
tccaggcagt ggctgaggga aactc 25

<210> SEQ ID NO 286
<211> LENGTH: 25
<212> TYPE: DNA
<213> ORGANISM: Homo sapiens

<400> SEQUENCE: 286
tgtctggaga aaccttcca agtgg 25

<210> SEQ ID NO 287
<211> LENGTH: 25
<212> TYPE: DNA
<213> ORGANISM: Homo sapiens

<400> SEQUENCE: 287
cctggcagga tagggaaaga cttct 25

<210> SEQ ID NO 288
<211> LENGTH: 25

```
<212> TYPE: DNA
<213> ORGANISM: Homo sapiens

<400> SEQUENCE: 288
tgacagtcca gaaaacacac aggtg                                          25

<210> SEQ ID NO 289
<211> LENGTH: 25
<212> TYPE: DNA
<213> ORGANISM: Homo sapiens

<400> SEQUENCE: 289
gactcttgag gccttgtgaa cacag                                          25

<210> SEQ ID NO 290
<211> LENGTH: 25
<212> TYPE: DNA
<213> ORGANISM: Homo sapiens

<400> SEQUENCE: 290
aagaacagct cagatcaggg accct                                          25

<210> SEQ ID NO 291
<211> LENGTH: 25
<212> TYPE: DNA
<213> ORGANISM: Homo sapiens

<400> SEQUENCE: 291
tctcatcaag gatctctgcg cggcg                                          25

<210> SEQ ID NO 292
<211> LENGTH: 25
<212> TYPE: DNA
<213> ORGANISM: Homo sapiens

<400> SEQUENCE: 292
caggttcttc agcttgacag ggcga                                          25

<210> SEQ ID NO 293
<211> LENGTH: 25
<212> TYPE: DNA
<213> ORGANISM: Homo sapiens

<400> SEQUENCE: 293
tgttgaaaca atcctgcctg cagcc                                          25

<210> SEQ ID NO 294
<211> LENGTH: 25
<212> TYPE: DNA
<213> ORGANISM: Homo sapiens

<400> SEQUENCE: 294
tatcaacggc cttgttcacc tgggc                                          25

<210> SEQ ID NO 295
<211> LENGTH: 25
<212> TYPE: DNA
<213> ORGANISM: Homo sapiens

<400> SEQUENCE: 295
tgttgccctg ctcagtgaac tggct                                          25

<210> SEQ ID NO 296
```

```
<211> LENGTH: 25
<212> TYPE: DNA
<213> ORGANISM: Homo sapiens

<400> SEQUENCE: 296
ttcaaacttg acctcgaact gccgc                                              25

<210> SEQ ID NO 297
<211> LENGTH: 25
<212> TYPE: DNA
<213> ORGANISM: Homo sapiens

<400> SEQUENCE: 297
gaagtcccgt tgtagctctg tgaag                                              25

<210> SEQ ID NO 298
<211> LENGTH: 25
<212> TYPE: DNA
<213> ORGANISM: Homo sapiens

<400> SEQUENCE: 298
tgcggaagcc ctcagccatg ttgaa                                              25

<210> SEQ ID NO 299
<211> LENGTH: 25
<212> TYPE: DNA
<213> ORGANISM: Homo sapiens

<400> SEQUENCE: 299
gctcctatac actacagggc aggta                                              25

<210> SEQ ID NO 300
<211> LENGTH: 25
<212> TYPE: DNA
<213> ORGANISM: Homo sapiens

<400> SEQUENCE: 300
cagtcaagtc tttccatccg agggt                                              25

<210> SEQ ID NO 301
<211> LENGTH: 25
<212> TYPE: DNA
<213> ORGANISM: Homo sapiens

<400> SEQUENCE: 301
tattttccaa tcataacggt ctgca                                              25

<210> SEQ ID NO 302
<211> LENGTH: 25
<212> TYPE: DNA
<213> ORGANISM: Homo sapiens

<400> SEQUENCE: 302
tcaaactata tagagaggga aaagt                                              25

<210> SEQ ID NO 303
<211> LENGTH: 25
<212> TYPE: DNA
<213> ORGANISM: Homo sapiens

<400> SEQUENCE: 303
aacatcatct agttaaaaat aggga                                              25
```

<210> SEQ ID NO 304
<211> LENGTH: 25
<212> TYPE: DNA
<213> ORGANISM: Homo sapiens

<400> SEQUENCE: 304
cacaagctaa atggtacatg agcac                               25

<210> SEQ ID NO 305
<211> LENGTH: 25
<212> TYPE: DNA
<213> ORGANISM: Homo sapiens

<400> SEQUENCE: 305
gctaaatggt acatgagcac tcagg                               25

<210> SEQ ID NO 306
<211> LENGTH: 25
<212> TYPE: DNA
<213> ORGANISM: Homo sapiens

<400> SEQUENCE: 306
tgatgcactg caagctcaag cgctt                               25

<210> SEQ ID NO 307
<211> LENGTH: 25
<212> TYPE: DNA
<213> ORGANISM: Homo sapiens

<400> SEQUENCE: 307
gatgcactgc aagctcaagc gcttt                               25

<210> SEQ ID NO 308
<211> LENGTH: 25
<212> TYPE: DNA
<213> ORGANISM: Homo sapiens

<400> SEQUENCE: 308
tgcactgcaa gctcaagcgc tttaa                               25

<210> SEQ ID NO 309
<211> LENGTH: 25
<212> TYPE: DNA
<213> ORGANISM: Homo sapiens

<400> SEQUENCE: 309
gcactgcaag ctcaagcgct ttaat                               25

<210> SEQ ID NO 310
<211> LENGTH: 25
<212> TYPE: DNA
<213> ORGANISM: Homo sapiens

<400> SEQUENCE: 310
cacactggtc tgatataagt ccacg                               25

<210> SEQ ID NO 311
<211> LENGTH: 25
<212> TYPE: DNA
<213> ORGANISM: Homo sapiens

<400> SEQUENCE: 311
ggtctgatat aagtccacgt acatg                               25

```
<210> SEQ ID NO 312
<211> LENGTH: 25
<212> TYPE: DNA
<213> ORGANISM: Homo sapiens

<400> SEQUENCE: 312
tccacgtaca tgtagcattg cacag                                              25

<210> SEQ ID NO 313
<211> LENGTH: 25
<212> TYPE: DNA
<213> ORGANISM: Homo sapiens

<400> SEQUENCE: 313
aaagcagact agaagagttc tttga                                              25

<210> SEQ ID NO 314
<211> LENGTH: 25
<212> TYPE: DNA
<213> ORGANISM: Homo sapiens

<400> SEQUENCE: 314
aagcagacta gaagagttct ttgaa                                              25

<210> SEQ ID NO 315
<211> LENGTH: 25
<212> TYPE: DNA
<213> ORGANISM: Homo sapiens

<400> SEQUENCE: 315
cacgtctggc ctgggataac tcatt                                              25

<210> SEQ ID NO 316
<211> LENGTH: 25
<212> TYPE: DNA
<213> ORGANISM: Homo sapiens

<400> SEQUENCE: 316
tgtaaaactg gtgaagacct gggac                                              25

<210> SEQ ID NO 317
<211> LENGTH: 25
<212> TYPE: DNA
<213> ORGANISM: Homo sapiens

<400> SEQUENCE: 317
cagaaatgta cagagaagtc tccca                                              25

<210> SEQ ID NO 318
<211> LENGTH: 25
<212> TYPE: DNA
<213> ORGANISM: Homo sapiens

<400> SEQUENCE: 318
tcttcgagag gatgagagtg tcact                                              25

<210> SEQ ID NO 319
<211> LENGTH: 25
<212> TYPE: DNA
<213> ORGANISM: Homo sapiens

<400> SEQUENCE: 319
tatttggcta aggagcacct gctgc                                              25
```

```
<210> SEQ ID NO 320
<211> LENGTH: 25
<212> TYPE: DNA
<213> ORGANISM: Homo sapiens

<400> SEQUENCE: 320
actgtcaagt ggatgtctcg tgccc                                          25

<210> SEQ ID NO 321
<211> LENGTH: 25
<212> TYPE: DNA
<213> ORGANISM: Homo sapiens

<400> SEQUENCE: 321
gaatttgtcc aagttcacgg agccc                                          25

<210> SEQ ID NO 322
<211> LENGTH: 25
<212> TYPE: DNA
<213> ORGANISM: Homo sapiens

<400> SEQUENCE: 322
tgcagctggc ccttaaacgg tgact                                          25

<210> SEQ ID NO 323
<211> LENGTH: 25
<212> TYPE: DNA
<213> ORGANISM: Homo sapiens

<400> SEQUENCE: 323
cttgacagcc cagagaggag ccatt                                          25

<210> SEQ ID NO 324
<211> LENGTH: 25
<212> TYPE: DNA
<213> ORGANISM: Homo sapiens

<400> SEQUENCE: 324
tgggaggccc tctgagcaac gatgt                                          25

<210> SEQ ID NO 325
<211> LENGTH: 25
<212> TYPE: DNA
<213> ORGANISM: Homo sapiens

<400> SEQUENCE: 325
tctgtaccct tctgccacgt tgagg                                          25

<210> SEQ ID NO 326
<211> LENGTH: 25
<212> TYPE: DNA
<213> ORGANISM: Homo sapiens

<400> SEQUENCE: 326
ggtgaagcct tcgtccaaca tgaaa                                          25

<210> SEQ ID NO 327
<211> LENGTH: 25
<212> TYPE: DNA
<213> ORGANISM: Homo sapiens

<400> SEQUENCE: 327
```

```
gcttagttgg ccgatgtttc acgaa                                           25

<210> SEQ ID NO 328
<211> LENGTH: 25
<212> TYPE: DNA
<213> ORGANISM: Homo sapiens

<400> SEQUENCE: 328
tgggcagaaa tttccaggac caccg                                           25

<210> SEQ ID NO 329
<211> LENGTH: 25
<212> TYPE: DNA
<213> ORGANISM: Homo sapiens

<400> SEQUENCE: 329
tctgtaggca ggcacaatgg tgacc                                           25

<210> SEQ ID NO 330
<211> LENGTH: 25
<212> TYPE: DNA
<213> ORGANISM: Homo sapiens

<400> SEQUENCE: 330
cccctggtct ggatggtgaa gacga                                           25

<210> SEQ ID NO 331
<211> LENGTH: 25
<212> TYPE: DNA
<213> ORGANISM: Homo sapiens

<400> SEQUENCE: 331
tggtgctcct gagaaccgtg ccatt                                           25

<210> SEQ ID NO 332
<211> LENGTH: 25
<212> TYPE: DNA
<213> ORGANISM: Homo sapiens

<400> SEQUENCE: 332
actgagccac gaaggagtcc agcct                                           25

<210> SEQ ID NO 333
<211> LENGTH: 25
<212> TYPE: DNA
<213> ORGANISM: Homo sapiens

<400> SEQUENCE: 333
gctggtgtgc tatacagttc ctgca                                           25

<210> SEQ ID NO 334
<211> LENGTH: 25
<212> TYPE: DNA
<213> ORGANISM: Homo sapiens

<400> SEQUENCE: 334
tgggcagata tatagccagg ctcct                                           25

<210> SEQ ID NO 335
<211> LENGTH: 25
<212> TYPE: DNA
<213> ORGANISM: Homo sapiens

<400> SEQUENCE: 335
```
aaaccaggtg tgacgggctg actcc                                   25

<210> SEQ ID NO 336
<211> LENGTH: 25
<212> TYPE: DNA
<213> ORGANISM: Homo sapiens

<400> SEQUENCE: 336
cttggagaca cccttgctgc agtag                                   25

<210> SEQ ID NO 337
<211> LENGTH: 25
<212> TYPE: DNA
<213> ORGANISM: Homo sapiens

<400> SEQUENCE: 337
cattctgctg ctatgagcga ggaga                                   25

<210> SEQ ID NO 338
<211> LENGTH: 25
<212> TYPE: DNA
<213> ORGANISM: Homo sapiens

<400> SEQUENCE: 338
gctttagctc atggttggca tctga                                   25

<210> SEQ ID NO 339
<211> LENGTH: 25
<212> TYPE: DNA
<213> ORGANISM: Homo sapiens

<400> SEQUENCE: 339
taactcaggg tttcctagcg agaag                                   25

<210> SEQ ID NO 340
<211> LENGTH: 25
<212> TYPE: DNA
<213> ORGANISM: Homo sapiens

<400> SEQUENCE: 340
gggccatgaa ggtgttcccg ccatt                                   25

<210> SEQ ID NO 341
<211> LENGTH: 25
<212> TYPE: DNA
<213> ORGANISM: Homo sapiens

<400> SEQUENCE: 341
catgaaggtg ttcccgccat tgaga                                   25

<210> SEQ ID NO 342
<211> LENGTH: 25
<212> TYPE: DNA
<213> ORGANISM: Homo sapiens

<400> SEQUENCE: 342
cagctctgga gagtcattcc attcc                                   25

<210> SEQ ID NO 343
<211> LENGTH: 25
<212> TYPE: DNA
<213> ORGANISM: Homo sapiens

<400> SEQUENCE: 343
tgccaccatg acacggaaca gcttt                                             25

<210> SEQ ID NO 344
<211> LENGTH: 25
<212> TYPE: DNA
<213> ORGANISM: Homo sapiens

<400> SEQUENCE: 344
gaactttcag gctctcctaa tggct                                             25

<210> SEQ ID NO 345
<211> LENGTH: 25
<212> TYPE: DNA
<213> ORGANISM: Homo sapiens

<400> SEQUENCE: 345
gatacctaga aggtttgccc ctcag                                             25

<210> SEQ ID NO 346
<211> LENGTH: 25
<212> TYPE: DNA
<213> ORGANISM: Homo sapiens

<400> SEQUENCE: 346
tgtatccagg ctccaggtgc ataga                                             25

<210> SEQ ID NO 347
<211> LENGTH: 25
<212> TYPE: DNA
<213> ORGANISM: Homo sapiens

<400> SEQUENCE: 347
tgaagattcc tgaaggccct ggtcc                                             25

<210> SEQ ID NO 348
<211> LENGTH: 25
<212> TYPE: DNA
<213> ORGANISM: Homo sapiens

<400> SEQUENCE: 348
ccctggtcct aggtcatagt tgttc                                             25

<210> SEQ ID NO 349
<211> LENGTH: 25
<212> TYPE: DNA
<213> ORGANISM: Homo sapiens

<400> SEQUENCE: 349
ttgagttaca gggaccgaag cagct                                             25

<210> SEQ ID NO 350
<211> LENGTH: 25
<212> TYPE: DNA
<213> ORGANISM: Homo sapiens

<400> SEQUENCE: 350
tggattcaga tctgggcgat accgc                                             25

<210> SEQ ID NO 351
<211> LENGTH: 25
<212> TYPE: DNA
<213> ORGANISM: Homo sapiens

```
<400> SEQUENCE: 351
aacgtggttt taggatgtga gtctc                                           25

<210> SEQ ID NO 352
<211> LENGTH: 25
<212> TYPE: DNA
<213> ORGANISM: Homo sapiens

<400> SEQUENCE: 352
ctatggttca aatgtgggat ctcac                                           25

<210> SEQ ID NO 353
<211> LENGTH: 25
<212> TYPE: DNA
<213> ORGANISM: Homo sapiens

<400> SEQUENCE: 353
gacgtggttt catcttgcaa ttcga                                           25

<210> SEQ ID NO 354
<211> LENGTH: 25
<212> TYPE: DNA
<213> ORGANISM: Homo sapiens

<400> SEQUENCE: 354
aggtcctgcc cgctaacaga gagag                                           25

<210> SEQ ID NO 355
<211> LENGTH: 25
<212> TYPE: DNA
<213> ORGANISM: Homo sapiens

<400> SEQUENCE: 355
tggatgaagc cccttagtcc tcaat                                           25

<210> SEQ ID NO 356
<211> LENGTH: 25
<212> TYPE: DNA
<213> ORGANISM: Homo sapiens

<400> SEQUENCE: 356
gcagtgcttc agtcaaggtg atcaa                                           25

<210> SEQ ID NO 357
<211> LENGTH: 25
<212> TYPE: DNA
<213> ORGANISM: Homo sapiens

<400> SEQUENCE: 357
cacctgtgaa actgtccctg taaac                                           25

<210> SEQ ID NO 358
<211> LENGTH: 25
<212> TYPE: DNA
<213> ORGANISM: Homo sapiens

<400> SEQUENCE: 358
cgcttagcat tcaccatgag ggaag                                           25

<210> SEQ ID NO 359
<211> LENGTH: 25
<212> TYPE: DNA
```

```
<213> ORGANISM: Homo sapiens

<400> SEQUENCE: 359
tcgattagag agtgtgctgc ggcaa                                            25

<210> SEQ ID NO 360
<211> LENGTH: 25
<212> TYPE: DNA
<213> ORGANISM: Homo sapiens

<400> SEQUENCE: 360
caactcctgg ttgcatgctg gaaaa                                            25

<210> SEQ ID NO 361
<211> LENGTH: 25
<212> TYPE: DNA
<213> ORGANISM: Homo sapiens

<400> SEQUENCE: 361
agtgaggcac accaagcata gacgc                                            25

<210> SEQ ID NO 362
<211> LENGTH: 25
<212> TYPE: DNA
<213> ORGANISM: Homo sapiens

<400> SEQUENCE: 362
gaaagacaag cctgtagcac ccata                                            25

<210> SEQ ID NO 363
<211> LENGTH: 25
<212> TYPE: DNA
<213> ORGANISM: Homo sapiens

<400> SEQUENCE: 363
aacctgaaag catcaagtga ctccc                                            25

<210> SEQ ID NO 364
<211> LENGTH: 25
<212> TYPE: DNA
<213> ORGANISM: Homo sapiens

<400> SEQUENCE: 364
taatgtagca tttccctggc agtag                                            25

<210> SEQ ID NO 365
<211> LENGTH: 25
<212> TYPE: DNA
<213> ORGANISM: Homo sapiens

<400> SEQUENCE: 365
gcataaatga ggacaaggag aagcc                                            25

<210> SEQ ID NO 366
<211> LENGTH: 25
<212> TYPE: DNA
<213> ORGANISM: Homo sapiens

<400> SEQUENCE: 366
taggtgcctc gaaaaaacta ataga                                            25

<210> SEQ ID NO 367
<211> LENGTH: 25
```

```
<212> TYPE: DNA
<213> ORGANISM: Homo sapiens

<400> SEQUENCE: 367
ggtgcctcga aaaactaat agaga                                      25

<210> SEQ ID NO 368
<211> LENGTH: 25
<212> TYPE: DNA
<213> ORGANISM: Homo sapiens

<400> SEQUENCE: 368
cagattgctc gaggccacct ggttg                                     25

<210> SEQ ID NO 369
<211> LENGTH: 25
<212> TYPE: DNA
<213> ORGANISM: Homo sapiens

<400> SEQUENCE: 369
ggagtcggtc cagaaaagca ttatt                                     25

<210> SEQ ID NO 370
<211> LENGTH: 25
<212> TYPE: DNA
<213> ORGANISM: Homo sapiens

<400> SEQUENCE: 370
ggtggatttt ggctctttct tgctc                                     25

<210> SEQ ID NO 371
<211> LENGTH: 25
<212> TYPE: DNA
<213> ORGANISM: Homo sapiens

<400> SEQUENCE: 371
tgccgtttca gttccagtaa ttcac                                     25

<210> SEQ ID NO 372
<211> LENGTH: 25
<212> TYPE: DNA
<213> ORGANISM: Homo sapiens

<400> SEQUENCE: 372
cagctgtgat ccctaggcag gatag                                     25

<210> SEQ ID NO 373
<211> LENGTH: 25
<212> TYPE: DNA
<213> ORGANISM: Homo sapiens

<400> SEQUENCE: 373
ctgtgatccc taggcaggat aggaa                                     25

<210> SEQ ID NO 374
<211> LENGTH: 25
<212> TYPE: DNA
<213> ORGANISM: Homo sapiens

<400> SEQUENCE: 374
ccatgttgag gattgtgggc cacaa                                     25

<210> SEQ ID NO 375
```

```
<211> LENGTH: 25
<212> TYPE: DNA
<213> ORGANISM: Homo sapiens

<400> SEQUENCE: 375
gtttgctcaa gaactcagcg gtttt                                        25

<210> SEQ ID NO 376
<211> LENGTH: 25
<212> TYPE: DNA
<213> ORGANISM: Homo sapiens

<400> SEQUENCE: 376
tttgctcaag aactcagcgg ttttg                                        25

<210> SEQ ID NO 377
<211> LENGTH: 25
<212> TYPE: DNA
<213> ORGANISM: Homo sapiens

<400> SEQUENCE: 377
ccgtctgggc accaggtgaa ccggt                                        25

<210> SEQ ID NO 378
<211> LENGTH: 25
<212> TYPE: DNA
<213> ORGANISM: Homo sapiens

<400> SEQUENCE: 378
taagccaggc gagaaatatc aaatc                                        25

<210> SEQ ID NO 379
<211> LENGTH: 25
<212> TYPE: DNA
<213> ORGANISM: Homo sapiens

<400> SEQUENCE: 379
caagagtcag cacagagggt tcgaa                                        25

<210> SEQ ID NO 380
<211> LENGTH: 25
<212> TYPE: DNA
<213> ORGANISM: Homo sapiens

<400> SEQUENCE: 380
tgctacaggt ggagaccctt gctct                                        25

<210> SEQ ID NO 381
<211> LENGTH: 25
<212> TYPE: DNA
<213> ORGANISM: Homo sapiens

<400> SEQUENCE: 381
ggtttcaggc actccagacc actgt                                        25

<210> SEQ ID NO 382
<211> LENGTH: 25
<212> TYPE: DNA
<213> ORGANISM: Homo sapiens

<400> SEQUENCE: 382
tagtccctgc atggctgtga ttgtc                                        25
```

```
<210> SEQ ID NO 383
<211> LENGTH: 25
<212> TYPE: DNA
<213> ORGANISM: Homo sapiens

<400> SEQUENCE: 383
caaaaacgag taagatgtgg tccct                                  25

<210> SEQ ID NO 384
<211> LENGTH: 25
<212> TYPE: DNA
<213> ORGANISM: Homo sapiens

<400> SEQUENCE: 384
catttctccg gtttatattt ggtgc                                  25

<210> SEQ ID NO 385
<211> LENGTH: 25
<212> TYPE: DNA
<213> ORGANISM: Homo sapiens

<400> SEQUENCE: 385
tatttggtgc tatcaaggtg tatgc                                  25

<210> SEQ ID NO 386
<211> LENGTH: 25
<212> TYPE: DNA
<213> ORGANISM: Homo sapiens

<400> SEQUENCE: 386
taagaggcta gtttatctgc gagtc                                  25

<210> SEQ ID NO 387
<211> LENGTH: 25
<212> TYPE: DNA
<213> ORGANISM: Homo sapiens

<400> SEQUENCE: 387
tcttgctggg acgtaggctt gctcc                                  25

<210> SEQ ID NO 388
<211> LENGTH: 25
<212> TYPE: DNA
<213> ORGANISM: Homo sapiens

<400> SEQUENCE: 388
tcttgttgac ccttacctgt tagtg                                  25

<210> SEQ ID NO 389
<211> LENGTH: 25
<212> TYPE: DNA
<213> ORGANISM: Homo sapiens

<400> SEQUENCE: 389
gtgcacgacg ctctcccgcg aaggg                                  25

<210> SEQ ID NO 390
<211> LENGTH: 25
<212> TYPE: DNA
<213> ORGANISM: Homo sapiens

<400> SEQUENCE: 390
ggagttcacc actctattgc gggtg                                  25
```

```
<210> SEQ ID NO 391
<211> LENGTH: 25
<212> TYPE: DNA
<213> ORGANISM: Homo sapiens

<400> SEQUENCE: 391
cggctgggac gcttagcgag tctca                                       25

<210> SEQ ID NO 392
<211> LENGTH: 25
<212> TYPE: DNA
<213> ORGANISM: Homo sapiens

<400> SEQUENCE: 392
tagcgagtct caagatggga ttcca                                       25

<210> SEQ ID NO 393
<211> LENGTH: 25
<212> TYPE: DNA
<213> ORGANISM: Homo sapiens

<400> SEQUENCE: 393
tacaccagag atccatttat tacag                                       25

<210> SEQ ID NO 394
<211> LENGTH: 25
<212> TYPE: DNA
<213> ORGANISM: Homo sapiens

<400> SEQUENCE: 394
tattacagtc ctgcaacccc gactg                                       25

<210> SEQ ID NO 395
<211> LENGTH: 25
<212> TYPE: DNA
<213> ORGANISM: Homo sapiens

<400> SEQUENCE: 395
caggcccaga ggaaggttag tctca                                       25

<210> SEQ ID NO 396
<211> LENGTH: 25
<212> TYPE: DNA
<213> ORGANISM: Homo sapiens

<400> SEQUENCE: 396
gcccagagga aggttagtct catgc                                       25

<210> SEQ ID NO 397
<211> LENGTH: 25
<212> TYPE: DNA
<213> ORGANISM: Homo sapiens

<400> SEQUENCE: 397
gaggaaggtt agtctcatgc ctgct                                       25

<210> SEQ ID NO 398
<211> LENGTH: 25
<212> TYPE: DNA
<213> ORGANISM: Homo sapiens

<400> SEQUENCE: 398
gcaggaagtg tgagaccttg atgta                                       25
```

```
<210> SEQ ID NO 399
<211> LENGTH: 25
<212> TYPE: DNA
<213> ORGANISM: Homo sapiens

<400> SEQUENCE: 399
ttttgtttcc ataggagaga atacc                                      25

<210> SEQ ID NO 400
<211> LENGTH: 25
<212> TYPE: DNA
<213> ORGANISM: Homo sapiens

<400> SEQUENCE: 400
tttccatagg agagaatacc ttggg                                      25

<210> SEQ ID NO 401
<211> LENGTH: 25
<212> TYPE: DNA
<213> ORGANISM: Homo sapiens

<400> SEQUENCE: 401
gaaaccggtc tgtgtcttct ttgga                                      25

<210> SEQ ID NO 402
<211> LENGTH: 25
<212> TYPE: DNA
<213> ORGANISM: Homo sapiens

<400> SEQUENCE: 402
tggaagagac gttcacactg gcagt                                      25

<210> SEQ ID NO 403
<211> LENGTH: 25
<212> TYPE: DNA
<213> ORGANISM: Homo sapiens

<400> SEQUENCE: 403
agtgctcatt gagacataac cccag                                      25

<210> SEQ ID NO 404
<211> LENGTH: 25
<212> TYPE: DNA
<213> ORGANISM: Homo sapiens

<400> SEQUENCE: 404
cagagctgtt ggtgttgact ccttc                                      25

<210> SEQ ID NO 405
<211> LENGTH: 25
<212> TYPE: DNA
<213> ORGANISM: Homo sapiens

<400> SEQUENCE: 405
gagctgttgg tgttgactcc ttcca                                      25

<210> SEQ ID NO 406
<211> LENGTH: 25
<212> TYPE: DNA
<213> ORGANISM: Homo sapiens

<400> SEQUENCE: 406
```

```
ctgcataacc tgtgctacca ccatt                                              25

<210> SEQ ID NO 407
<211> LENGTH: 25
<212> TYPE: DNA
<213> ORGANISM: Homo sapiens

<400> SEQUENCE: 407
tgcataacct gtgctaccac cattc                                              25

<210> SEQ ID NO 408
<211> LENGTH: 25
<212> TYPE: DNA
<213> ORGANISM: Homo sapiens

<400> SEQUENCE: 408
taacctgtgc taccaccatt ccaat                                              25

<210> SEQ ID NO 409
<211> LENGTH: 25
<212> TYPE: DNA
<213> ORGANISM: Homo sapiens

<400> SEQUENCE: 409
caccattcca attaatacca gagac                                              25

<210> SEQ ID NO 410
<211> LENGTH: 25
<212> TYPE: DNA
<213> ORGANISM: Homo sapiens

<400> SEQUENCE: 410
accattccaa ttaataccag agacc                                              25

<210> SEQ ID NO 411
<211> LENGTH: 25
<212> TYPE: DNA
<213> ORGANISM: Homo sapiens

<400> SEQUENCE: 411
ccattccaat taataccaga gaccc                                              25

<210> SEQ ID NO 412
<211> LENGTH: 25
<212> TYPE: DNA
<213> ORGANISM: Homo sapiens

<400> SEQUENCE: 412
gacccagctc atgccataat catca                                              25

<210> SEQ ID NO 413
<211> LENGTH: 25
<212> TYPE: DNA
<213> ORGANISM: Homo sapiens

<400> SEQUENCE: 413
ccagctcatg ccataatcat caaag                                              25

<210> SEQ ID NO 414
<211> LENGTH: 25
<212> TYPE: DNA
<213> ORGANISM: Homo sapiens

<400> SEQUENCE: 414
```
gaaagttata tctctgtgta catcc                                    25

<210> SEQ ID NO 415
<211> LENGTH: 25
<212> TYPE: DNA
<213> ORGANISM: Homo sapiens

<400> SEQUENCE: 415
gaatccagca cgtgtactcc taagt                                    25

<210> SEQ ID NO 416
<211> LENGTH: 25
<212> TYPE: DNA
<213> ORGANISM: Homo sapiens

<400> SEQUENCE: 416
taatgagaga atccagcacg tgtac                                    25

<210> SEQ ID NO 417
<211> LENGTH: 25
<212> TYPE: DNA
<213> ORGANISM: Homo sapiens

<400> SEQUENCE: 417
tgattctgga tagttgactc atgaa                                    25

<210> SEQ ID NO 418
<211> LENGTH: 25
<212> TYPE: DNA
<213> ORGANISM: Homo sapiens

<400> SEQUENCE: 418
ccacaccgct tgaataataa ctatg                                    25

<210> SEQ ID NO 419
<211> LENGTH: 25
<212> TYPE: DNA
<213> ORGANISM: Homo sapiens

<400> SEQUENCE: 419
gccatggcat caaatctcct tttaa                                    25

<210> SEQ ID NO 420
<211> LENGTH: 25
<212> TYPE: DNA
<213> ORGANISM: Homo sapiens

<400> SEQUENCE: 420
ctaagtcagt gaggtttgcc atggc                                    25

<210> SEQ ID NO 421
<211> LENGTH: 25
<212> TYPE: DNA
<213> ORGANISM: Homo sapiens

<400> SEQUENCE: 421
gaagaacagt ctaagtcagt gaggt                                    25

<210> SEQ ID NO 422
<211> LENGTH: 25
<212> TYPE: DNA
<213> ORGANISM: Homo sapiens

<400> SEQUENCE: 422
gaagccatat gtgtttcagc cactt 25

<210> SEQ ID NO 423
<211> LENGTH: 25
<212> TYPE: DNA
<213> ORGANISM: Homo sapiens

<400> SEQUENCE: 423
tgaagccata tgtgtttcag ccact 25

<210> SEQ ID NO 424
<211> LENGTH: 25
<212> TYPE: DNA
<213> ORGANISM: Homo sapiens

<400> SEQUENCE: 424
tcttgacaca ctgaagccat atgtg 25

<210> SEQ ID NO 425
<211> LENGTH: 25
<212> TYPE: DNA
<213> ORGANISM: Homo sapiens

<400> SEQUENCE: 425
tcaggtcttc ttgacacact gaagc 25

<210> SEQ ID NO 426
<211> LENGTH: 25
<212> TYPE: DNA
<213> ORGANISM: Homo sapiens

<400> SEQUENCE: 426
gccaccgtgc ttgccagtaa tgaat 25

<210> SEQ ID NO 427
<211> LENGTH: 25
<212> TYPE: DNA
<213> ORGANISM: Homo sapiens

<400> SEQUENCE: 427
ttcaagatca aactaggcca tggag 25

<210> SEQ ID NO 428
<211> LENGTH: 25
<212> TYPE: DNA
<213> ORGANISM: Homo sapiens

<400> SEQUENCE: 428
caaagagtaa tgtcaatccg ctgga 25

<210> SEQ ID NO 429
<211> LENGTH: 25
<212> TYPE: DNA
<213> ORGANISM: Homo sapiens

<400> SEQUENCE: 429
caagagtcag ccaatatagt gcaca 25

<210> SEQ ID NO 430
<211> LENGTH: 25
<212> TYPE: DNA
<213> ORGANISM: Homo sapiens

```
<400> SEQUENCE: 430
ccaatacgag gagagtgtca ctgac                                              25

<210> SEQ ID NO 431
<211> LENGTH: 25
<212> TYPE: DNA
<213> ORGANISM: Homo sapiens

<400> SEQUENCE: 431
tgaacctctt ggtgacccgg aatga                                              25

<210> SEQ ID NO 432
<211> LENGTH: 25
<212> TYPE: DNA
<213> ORGANISM: Homo sapiens

<400> SEQUENCE: 432
tcccaatgtc tagcgtagtg cccag                                              25

<210> SEQ ID NO 433
<211> LENGTH: 25
<212> TYPE: DNA
<213> ORGANISM: Homo sapiens

<400> SEQUENCE: 433
tattctgatt gcaacagtag gcagc                                              25

<210> SEQ ID NO 434
<211> LENGTH: 25
<212> TYPE: DNA
<213> ORGANISM: Homo sapiens

<400> SEQUENCE: 434
caggcaccca gtctgagctt gtctg                                              25

<210> SEQ ID NO 435
<211> LENGTH: 25
<212> TYPE: DNA
<213> ORGANISM: Homo sapiens

<400> SEQUENCE: 435
agaggcttaa cctgccagcc ctggt                                              25

<210> SEQ ID NO 436
<211> LENGTH: 25
<212> TYPE: DNA
<213> ORGANISM: Homo sapiens

<400> SEQUENCE: 436
ggcggctgga ccacctttca ggatc                                              25

<210> SEQ ID NO 437
<211> LENGTH: 25
<212> TYPE: DNA
<213> ORGANISM: Homo sapiens

<400> SEQUENCE: 437
tgctgtccag cccttgtttg ggtac                                              25

<210> SEQ ID NO 438
<211> LENGTH: 25
<212> TYPE: DNA
```

```
<213> ORGANISM: Homo sapiens

<400> SEQUENCE: 438
ctgctgtcca gcccttgttt gggta                                       25

<210> SEQ ID NO 439
<211> LENGTH: 25
<212> TYPE: DNA
<213> ORGANISM: Homo sapiens

<400> SEQUENCE: 439
acagagactt tgaagctggg ccacc                                       25

<210> SEQ ID NO 440
<211> LENGTH: 25
<212> TYPE: DNA
<213> ORGANISM: Homo sapiens

<400> SEQUENCE: 440
gacggagtca ctcttggaag tcacc                                       25

<210> SEQ ID NO 441
<211> LENGTH: 25
<212> TYPE: DNA
<213> ORGANISM: Homo sapiens

<400> SEQUENCE: 441
ttcctccgac ggagtcactc ttgga                                       25

<210> SEQ ID NO 442
<211> LENGTH: 25
<212> TYPE: DNA
<213> ORGANISM: Homo sapiens

<400> SEQUENCE: 442
gcaggaacag tgtcgtctgc agcag                                       25

<210> SEQ ID NO 443
<211> LENGTH: 25
<212> TYPE: DNA
<213> ORGANISM: Homo sapiens

<400> SEQUENCE: 443
cagactcagc aggaacagtg tcgtc                                       25

<210> SEQ ID NO 444
<211> LENGTH: 25
<212> TYPE: DNA
<213> ORGANISM: Homo sapiens

<400> SEQUENCE: 444
gaagcgaaag tcttccctgt ggccc                                       25

<210> SEQ ID NO 445
<211> LENGTH: 25
<212> TYPE: DNA
<213> ORGANISM: Homo sapiens

<400> SEQUENCE: 445
tgcagaagcg aaagtcttcc ctgtg                                       25

<210> SEQ ID NO 446
<211> LENGTH: 25
```

```
<212> TYPE: DNA
<213> ORGANISM: Homo sapiens

<400> SEQUENCE: 446
cagcatgtcg gttccagtag aggca                                         25

<210> SEQ ID NO 447
<211> LENGTH: 25
<212> TYPE: DNA
<213> ORGANISM: Homo sapiens

<400> SEQUENCE: 447
tttgtcactc agcaagaagt cacgc                                         25

<210> SEQ ID NO 448
<211> LENGTH: 25
<212> TYPE: DNA
<213> ORGANISM: Homo sapiens

<400> SEQUENCE: 448
ccaccgaggc attgtgagcg gccgt                                         25

<210> SEQ ID NO 449
<211> LENGTH: 25
<212> TYPE: DNA
<213> ORGANISM: Homo sapiens

<400> SEQUENCE: 449
tccaccgagg cattgtgagc ggccg                                         25

<210> SEQ ID NO 450
<211> LENGTH: 25
<212> TYPE: DNA
<213> ORGANISM: Homo sapiens

<400> SEQUENCE: 450
tggaggtccc ttttgagctc gcaca                                         25

<210> SEQ ID NO 451
<211> LENGTH: 25
<212> TYPE: DNA
<213> ORGANISM: Homo sapiens

<400> SEQUENCE: 451
gctggaggtc ccttttgagc tcgca                                         25

<210> SEQ ID NO 452
<211> LENGTH: 25
<212> TYPE: DNA
<213> ORGANISM: Homo sapiens

<400> SEQUENCE: 452
cagaggtcag tttcgactcc aggct                                         25

<210> SEQ ID NO 453
<211> LENGTH: 25
<212> TYPE: DNA
<213> ORGANISM: Homo sapiens

<400> SEQUENCE: 453
ggtgttctgt accacaatcc ccaag                                         25

<210> SEQ ID NO 454
```

```
<211> LENGTH: 25
<212> TYPE: DNA
<213> ORGANISM: Homo sapiens

<400> SEQUENCE: 454
gggtttctct cctgacggtc tcaca                                              25

<210> SEQ ID NO 455
<211> LENGTH: 25
<212> TYPE: DNA
<213> ORGANISM: Homo sapiens

<400> SEQUENCE: 455
tcaggtagtg cttgtgcacg gcgtc                                              25

<210> SEQ ID NO 456
<211> LENGTH: 25
<212> TYPE: DNA
<213> ORGANISM: Homo sapiens

<400> SEQUENCE: 456
caccacgagt cggtagaggt tgtac                                              25

<210> SEQ ID NO 457
<211> LENGTH: 25
<212> TYPE: DNA
<213> ORGANISM: Homo sapiens

<400> SEQUENCE: 457
tagccaggga cataggtgcc aaaga                                              25

<210> SEQ ID NO 458
<211> LENGTH: 25
<212> TYPE: DNA
<213> ORGANISM: Homo sapiens

<400> SEQUENCE: 458
atagttgtcc acatccacca gggcc                                              25

<210> SEQ ID NO 459
<211> LENGTH: 25
<212> TYPE: DNA
<213> ORGANISM: Homo sapiens

<400> SEQUENCE: 459
ggagtcctat gcacagccaa gatga                                              25

<210> SEQ ID NO 460
<211> LENGTH: 25
<212> TYPE: DNA
<213> ORGANISM: Homo sapiens

<400> SEQUENCE: 460
aaaaggtaga ggacgacaag ctgga                                              25

<210> SEQ ID NO 461
<211> LENGTH: 25
<212> TYPE: DNA
<213> ORGANISM: Homo sapiens

<400> SEQUENCE: 461
ggcgctgtct gagttgctct tcaga                                              25
```

```
<210> SEQ ID NO 462
<211> LENGTH: 25
<212> TYPE: DNA
<213> ORGANISM: Homo sapiens

<400> SEQUENCE: 462
gaattaacca tgatgggcgg ccgag                                      25

<210> SEQ ID NO 463
<211> LENGTH: 25
<212> TYPE: DNA
<213> ORGANISM: Homo sapiens

<400> SEQUENCE: 463
tgttaggcag ggcttccaaa aatga                                      25

<210> SEQ ID NO 464
<211> LENGTH: 25
<212> TYPE: DNA
<213> ORGANISM: Homo sapiens

<400> SEQUENCE: 464
tgtgtgttag gcagggcttc caaaa                                      25

<210> SEQ ID NO 465
<211> LENGTH: 25
<212> TYPE: DNA
<213> ORGANISM: Homo sapiens

<400> SEQUENCE: 465
ctgtgtgtta ggcagggctt ccaaa                                      25

<210> SEQ ID NO 466
<211> LENGTH: 25
<212> TYPE: DNA
<213> ORGANISM: Homo sapiens

<400> SEQUENCE: 466
tacagtgcag ctgtgtgtta ggcag                                      25

<210> SEQ ID NO 467
<211> LENGTH: 25
<212> TYPE: DNA
<213> ORGANISM: Homo sapiens

<400> SEQUENCE: 467
gaactgggat gtacagtgca gctgt                                      25

<210> SEQ ID NO 468
<211> LENGTH: 25
<212> TYPE: DNA
<213> ORGANISM: Homo sapiens

<400> SEQUENCE: 468
tttctgcaga caagagcagc cctgg                                      25

<210> SEQ ID NO 469
<211> LENGTH: 25
<212> TYPE: DNA
<213> ORGANISM: Homo sapiens

<400> SEQUENCE: 469
tgcatgtacc ctggaaggtc tcccg                                      25
```

<210> SEQ ID NO 470
<211> LENGTH: 25
<212> TYPE: DNA
<213> ORGANISM: Homo sapiens

<400> SEQUENCE: 470
gatgctgttc ctccatacca ggcgg                                    25

<210> SEQ ID NO 471
<211> LENGTH: 25
<212> TYPE: DNA
<213> ORGANISM: Homo sapiens

<400> SEQUENCE: 471
tcaagcagct cgtcggagat acagt                                    25

<210> SEQ ID NO 472
<211> LENGTH: 25
<212> TYPE: DNA
<213> ORGANISM: Homo sapiens

<400> SEQUENCE: 472
gactcatggt tgttgttgaa ttcac                                    25

<210> SEQ ID NO 473
<211> LENGTH: 25
<212> TYPE: DNA
<213> ORGANISM: Homo sapiens

<400> SEQUENCE: 473
caaggaaagc ccagattttg aagta                                    25

<210> SEQ ID NO 474
<211> LENGTH: 25
<212> TYPE: DNA
<213> ORGANISM: Homo sapiens

<400> SEQUENCE: 474
ttctgactct tcaggatccg ctcca                                    25

<210> SEQ ID NO 475
<211> LENGTH: 25
<212> TYPE: DNA
<213> ORGANISM: Homo sapiens

<400> SEQUENCE: 475
ttgaatacac gcagggcaca ctgcc                                    25

<210> SEQ ID NO 476
<211> LENGTH: 25
<212> TYPE: DNA
<213> ORGANISM: Homo sapiens

<400> SEQUENCE: 476
ggtcttgtcc tcttcattcg tctca                                    25

<210> SEQ ID NO 477
<211> LENGTH: 25
<212> TYPE: DNA
<213> ORGANISM: Homo sapiens

<400> SEQUENCE: 477
tacttcctgt aaatttcctg caggg                                    25

<210> SEQ ID NO 478
<211> LENGTH: 25
<212> TYPE: DNA
<213> ORGANISM: Homo sapiens

<400> SEQUENCE: 478
aatagctaag ctctgattcg atcag                                          25

<210> SEQ ID NO 479
<211> LENGTH: 25
<212> TYPE: DNA
<213> ORGANISM: Homo sapiens

<400> SEQUENCE: 479
tacatcacag agtaaacgat gacaa                                          25

<210> SEQ ID NO 480
<211> LENGTH: 25
<212> TYPE: DNA
<213> ORGANISM: Homo sapiens

<400> SEQUENCE: 480
cggcagtgcc caagtgtagt tctaa                                          25

<210> SEQ ID NO 481
<211> LENGTH: 25
<212> TYPE: DNA
<213> ORGANISM: Homo sapiens

<400> SEQUENCE: 481
tcaggtcatg ggcagtctca gcctt                                          25

<210> SEQ ID NO 482
<211> LENGTH: 25
<212> TYPE: DNA
<213> ORGANISM: Homo sapiens

<400> SEQUENCE: 482
tagcgcttta aagccacctg gagcc                                          25

<210> SEQ ID NO 483
<211> LENGTH: 25
<212> TYPE: DNA
<213> ORGANISM: Homo sapiens

<400> SEQUENCE: 483
taggtctgga ctaagctctg gccct                                          25

<210> SEQ ID NO 484
<211> LENGTH: 25
<212> TYPE: DNA
<213> ORGANISM: Homo sapiens

<400> SEQUENCE: 484
ttcccattgc gggagcctaa gccag                                          25

<210> SEQ ID NO 485
<211> LENGTH: 25
<212> TYPE: DNA
<213> ORGANISM: Homo sapiens

<400> SEQUENCE: 485

```
tccagggaga ggtccgacaa gttct                                          25

<210> SEQ ID NO 486
<211> LENGTH: 25
<212> TYPE: DNA
<213> ORGANISM: Homo sapiens

<400> SEQUENCE: 486
cacgcgggac cacttttggg cctgg                                          25

<210> SEQ ID NO 487
<211> LENGTH: 25
<212> TYPE: DNA
<213> ORGANISM: Homo sapiens

<400> SEQUENCE: 487
cacattgaca tggtgggtgc cctcc                                          25

<210> SEQ ID NO 488
<211> LENGTH: 25
<212> TYPE: DNA
<213> ORGANISM: Homo sapiens

<400> SEQUENCE: 488
gctgcacgtg ctccactggg aactg                                          25

<210> SEQ ID NO 489
<211> LENGTH: 25
<212> TYPE: DNA
<213> ORGANISM: Homo sapiens

<400> SEQUENCE: 489
tactcggcct ggtccatttt ctgca                                          25

<210> SEQ ID NO 490
<211> LENGTH: 25
<212> TYPE: DNA
<213> ORGANISM: Homo sapiens

<400> SEQUENCE: 490
caaacgcgta tacactctga tcggc                                          25

<210> SEQ ID NO 491
<211> LENGTH: 25
<212> TYPE: DNA
<213> ORGANISM: Homo sapiens

<400> SEQUENCE: 491
tcgtggccac cagaaggttc agggt                                          25

<210> SEQ ID NO 492
<211> LENGTH: 25
<212> TYPE: DNA
<213> ORGANISM: Homo sapiens

<400> SEQUENCE: 492
ccaatcagta gctgggcccg gatgt                                          25

<210> SEQ ID NO 493
<211> LENGTH: 25
<212> TYPE: DNA
<213> ORGANISM: Homo sapiens

<400> SEQUENCE: 493
```

```
ccatgagttg ccaagtgggc cagct                                    25

<210> SEQ ID NO 494
<211> LENGTH: 25
<212> TYPE: DNA
<213> ORGANISM: Homo sapiens

<400> SEQUENCE: 494
gatctgggtt ttagtgacgt gctcc                                    25

<210> SEQ ID NO 495
<211> LENGTH: 25
<212> TYPE: DNA
<213> ORGANISM: Homo sapiens

<400> SEQUENCE: 495
tgtgatagaa atcctgcagc gcagc                                    25

<210> SEQ ID NO 496
<211> LENGTH: 25
<212> TYPE: DNA
<213> ORGANISM: Homo sapiens

<400> SEQUENCE: 496
tgtactgttt gcaaggctgt tggct                                    25

<210> SEQ ID NO 497
<211> LENGTH: 25
<212> TYPE: DNA
<213> ORGANISM: Homo sapiens

<400> SEQUENCE: 497
gggtgacatg atgcaccacg tgtcc                                    25

<210> SEQ ID NO 498
<211> LENGTH: 25
<212> TYPE: DNA
<213> ORGANISM: Homo sapiens

<400> SEQUENCE: 498
catctgcaga agctctgctg tgcag                                    25

<210> SEQ ID NO 499
<211> LENGTH: 25
<212> TYPE: DNA
<213> ORGANISM: Homo sapiens

<400> SEQUENCE: 499
agggttgtca cggtccagcg tccat                                    25

<210> SEQ ID NO 500
<211> LENGTH: 25
<212> TYPE: DNA
<213> ORGANISM: Homo sapiens

<400> SEQUENCE: 500
tcccattggt aggaccgaag ctcca                                    25

<210> SEQ ID NO 501
<211> LENGTH: 25
<212> TYPE: DNA
<213> ORGANISM: Homo sapiens
```

```
<400> SEQUENCE: 501
tctagtaggt aggtctgccc agggc                                          25

<210> SEQ ID NO 502
<211> LENGTH: 25
<212> TYPE: DNA
<213> ORGANISM: Homo sapiens

<400> SEQUENCE: 502
gcagtcccac ttaactcagc ctggt                                          25

<210> SEQ ID NO 503
<211> LENGTH: 25
<212> TYPE: DNA
<213> ORGANISM: Homo sapiens

<400> SEQUENCE: 503
ggagccagct gagccgactt aggaa                                          25

<210> SEQ ID NO 504
<211> LENGTH: 25
<212> TYPE: DNA
<213> ORGANISM: Homo sapiens

<400> SEQUENCE: 504
gccagctgag ccgacttagg aatct                                          25

<210> SEQ ID NO 505
<211> LENGTH: 25
<212> TYPE: DNA
<213> ORGANISM: Homo sapiens

<400> SEQUENCE: 505
tccggttaag tactgctgct gcgcc                                          25

<210> SEQ ID NO 506
<211> LENGTH: 25
<212> TYPE: DNA
<213> ORGANISM: Homo sapiens

<400> SEQUENCE: 506
tgtgctcagc gcagagagca gaaat                                          25

<210> SEQ ID NO 507
<211> LENGTH: 25
<212> TYPE: DNA
<213> ORGANISM: Homo sapiens

<400> SEQUENCE: 507
tcagcgcaga gagcagaaat cagaa                                          25

<210> SEQ ID NO 508
<211> LENGTH: 25
<212> TYPE: DNA
<213> ORGANISM: Homo sapiens

<400> SEQUENCE: 508
tccaagttga tagtctgcat gccgt                                          25

<210> SEQ ID NO 509
<211> LENGTH: 25
<212> TYPE: DNA
<213> ORGANISM: Homo sapiens
```

```
<400> SEQUENCE: 509
tgtaccattg catggcttcc acgtg                                          25

<210> SEQ ID NO 510
<211> LENGTH: 25
<212> TYPE: DNA
<213> ORGANISM: Homo sapiens

<400> SEQUENCE: 510
cgtgagtcgt ttacaaggag tttgc                                          25

<210> SEQ ID NO 511
<211> LENGTH: 25
<212> TYPE: DNA
<213> ORGANISM: Homo sapiens

<400> SEQUENCE: 511
gcattacgtt tgcaactgtg cttgt                                          25

<210> SEQ ID NO 512
<211> LENGTH: 25
<212> TYPE: DNA
<213> ORGANISM: Homo sapiens

<400> SEQUENCE: 512
ggcttcgtcc atctcaatct tcagt                                          25

<210> SEQ ID NO 513
<211> LENGTH: 25
<212> TYPE: DNA
<213> ORGANISM: Homo sapiens

<400> SEQUENCE: 513
tcgttagttg ggtctgaagc cggct                                          25

<210> SEQ ID NO 514
<211> LENGTH: 25
<212> TYPE: DNA
<213> ORGANISM: Homo sapiens

<400> SEQUENCE: 514
cgttagttgg gtctgaagcc ggctc                                          25

<210> SEQ ID NO 515
<211> LENGTH: 25
<212> TYPE: DNA
<213> ORGANISM: Homo sapiens

<400> SEQUENCE: 515
tagttgggtc tgaagccggc tctga                                          25

<210> SEQ ID NO 516
<211> LENGTH: 25
<212> TYPE: DNA
<213> ORGANISM: Homo sapiens

<400> SEQUENCE: 516
tattttttgg agctcaaaga cccca                                          25

<210> SEQ ID NO 517
<211> LENGTH: 25
<212> TYPE: DNA
```

```
<213> ORGANISM: Homo sapiens

<400> SEQUENCE: 517
actcattgtc cggagggagg ctctg                                 25

<210> SEQ ID NO 518
<211> LENGTH: 25
<212> TYPE: DNA
<213> ORGANISM: Homo sapiens

<400> SEQUENCE: 518
catgacccgc tcagaactga tgaga                                 25

<210> SEQ ID NO 519
<211> LENGTH: 25
<212> TYPE: DNA
<213> ORGANISM: Homo sapiens

<400> SEQUENCE: 519
caagggaatg ttcaagcgaa aagcc                                 25

<210> SEQ ID NO 520
<211> LENGTH: 25
<212> TYPE: DNA
<213> ORGANISM: Homo sapiens

<400> SEQUENCE: 520
tagtacttct tgtccgcgat tctca                                 25

<210> SEQ ID NO 521
<211> LENGTH: 25
<212> TYPE: DNA
<213> ORGANISM: Homo sapiens

<400> SEQUENCE: 521
gcgattctca cgcttaagac ctggt                                 25

<210> SEQ ID NO 522
<211> LENGTH: 25
<212> TYPE: DNA
<213> ORGANISM: Homo sapiens

<400> SEQUENCE: 522
cgattctcac gcttaagacc tggtt                                 25

<210> SEQ ID NO 523
<211> LENGTH: 25
<212> TYPE: DNA
<213> ORGANISM: Homo sapiens

<400> SEQUENCE: 523
gattctcacg cttaagacct ggttt                                 25

<210> SEQ ID NO 524
<211> LENGTH: 25
<212> TYPE: DNA
<213> ORGANISM: Homo sapiens

<400> SEQUENCE: 524
tctgcagacg cgtcctgaag cttat                                 25

<210> SEQ ID NO 525
<211> LENGTH: 25
```

```
<212> TYPE: DNA
<213> ORGANISM: Homo sapiens

<400> SEQUENCE: 525
tgcagacgcg tcctgaagct tatgg                                          25

<210> SEQ ID NO 526
<211> LENGTH: 25
<212> TYPE: DNA
<213> ORGANISM: Homo sapiens

<400> SEQUENCE: 526
gcagacgcgt cctgaagctt atggt                                          25

<210> SEQ ID NO 527
<211> LENGTH: 25
<212> TYPE: DNA
<213> ORGANISM: Homo sapiens

<400> SEQUENCE: 527
gacgcgtcct gaagcttatg gttta                                          25

<210> SEQ ID NO 528
<211> LENGTH: 25
<212> TYPE: DNA
<213> ORGANISM: Homo sapiens

<400> SEQUENCE: 528
tggtgaagat aatcaagggc acccc                                          25

<210> SEQ ID NO 529
<211> LENGTH: 25
<212> TYPE: DNA
<213> ORGANISM: Homo sapiens

<400> SEQUENCE: 529
tatccccagc agaagcttac agcgc                                          25

<210> SEQ ID NO 530
<211> LENGTH: 25
<212> TYPE: DNA
<213> ORGANISM: Homo sapiens

<400> SEQUENCE: 530
tgggcactct gcaatagtca tacga                                          25

<210> SEQ ID NO 531
<211> LENGTH: 25
<212> TYPE: DNA
<213> ORGANISM: Homo sapiens

<400> SEQUENCE: 531
tgctggaatc ttctacgggc caccc                                          25

<210> SEQ ID NO 532
<211> LENGTH: 25
<212> TYPE: DNA
<213> ORGANISM: Homo sapiens

<400> SEQUENCE: 532
gggcagatgt gggaccagac tttcc                                          25

<210> SEQ ID NO 533
```

```
<211> LENGTH: 25
<212> TYPE: DNA
<213> ORGANISM: Homo sapiens

<400> SEQUENCE: 533
cagatgtggg accagacttt cccga                                         25

<210> SEQ ID NO 534
<211> LENGTH: 25
<212> TYPE: DNA
<213> ORGANISM: Homo sapiens

<400> SEQUENCE: 534
gaggctccag atgaggcctt tggaa                                         25

<210> SEQ ID NO 535
<211> LENGTH: 25
<212> TYPE: DNA
<213> ORGANISM: Homo sapiens

<400> SEQUENCE: 535
tggaatacaa cgctcaaaac tcatc                                         25

<210> SEQ ID NO 536
<211> LENGTH: 25
<212> TYPE: DNA
<213> ORGANISM: Homo sapiens

<400> SEQUENCE: 536
tcacaaggtt tcatagccag gacgg                                         25

<210> SEQ ID NO 537
<211> LENGTH: 25
<212> TYPE: DNA
<213> ORGANISM: Homo sapiens

<400> SEQUENCE: 537
gtttcatagc caggacgggg accgc                                         25

<210> SEQ ID NO 538
<211> LENGTH: 25
<212> TYPE: DNA
<213> ORGANISM: Homo sapiens

<400> SEQUENCE: 538
tttcatagcc aggacgggga ccgcc                                         25

<210> SEQ ID NO 539
<211> LENGTH: 25
<212> TYPE: DNA
<213> ORGANISM: Homo sapiens

<400> SEQUENCE: 539
acagtgagca cccaggctca gggca                                         25

<210> SEQ ID NO 540
<211> LENGTH: 25
<212> TYPE: DNA
<213> ORGANISM: Homo sapiens

<400> SEQUENCE: 540
agcaagagga tagctgagac ccagc                                         25
```

```
<210> SEQ ID NO 541
<211> LENGTH: 25
<212> TYPE: DNA
<213> ORGANISM: Homo sapiens

<400> SEQUENCE: 541
gcaagaggat agctgagacc cagcc                                         25

<210> SEQ ID NO 542
<211> LENGTH: 25
<212> TYPE: DNA
<213> ORGANISM: Homo sapiens

<400> SEQUENCE: 542
caagaggata gctgagaccc agccc                                         25

<210> SEQ ID NO 543
<211> LENGTH: 25
<212> TYPE: DNA
<213> ORGANISM: Homo sapiens

<400> SEQUENCE: 543
aggctggtcc caccgctcgc tggtg                                         25

<210> SEQ ID NO 544
<211> LENGTH: 25
<212> TYPE: DNA
<213> ORGANISM: Homo sapiens

<400> SEQUENCE: 544
tcgctggtgt acaccgccat ggcca                                         25

<210> SEQ ID NO 545
<211> LENGTH: 25
<212> TYPE: DNA
<213> ORGANISM: Homo sapiens

<400> SEQUENCE: 545
cagggcccac agaacagcca taatg                                         25

<210> SEQ ID NO 546
<211> LENGTH: 25
<212> TYPE: DNA
<213> ORGANISM: Homo sapiens

<400> SEQUENCE: 546
gccataatgc tgaaggtctg cgtca                                         25

<210> SEQ ID NO 547
<211> LENGTH: 25
<212> TYPE: DNA
<213> ORGANISM: Homo sapiens

<400> SEQUENCE: 547
ctgatatgat gtccccatgc cctgt                                         25

<210> SEQ ID NO 548
<211> LENGTH: 25
<212> TYPE: DNA
<213> ORGANISM: Homo sapiens

<400> SEQUENCE: 548
tatgatgtcc ccatgccctg ttggc                                         25
```

```
<210> SEQ ID NO 549
<211> LENGTH: 25
<212> TYPE: DNA
<213> ORGANISM: Homo sapiens

<400> SEQUENCE: 549
cacagcctca aaccagaaat cggtg                                      25

<210> SEQ ID NO 550
<211> LENGTH: 25
<212> TYPE: DNA
<213> ORGANISM: Homo sapiens

<400> SEQUENCE: 550
aaatcggtgc tcaaagcaat caggc                                      25

<210> SEQ ID NO 551
<211> LENGTH: 25
<212> TYPE: DNA
<213> ORGANISM: Homo sapiens

<400> SEQUENCE: 551
gaggctgctg atcagactct tgaat                                      25

<210> SEQ ID NO 552
<211> LENGTH: 25
<212> TYPE: DNA
<213> ORGANISM: Homo sapiens

<400> SEQUENCE: 552
gactcttgaa tctcagagag aagga                                      25

<210> SEQ ID NO 553
<211> LENGTH: 25
<212> TYPE: DNA
<213> ORGANISM: Homo sapiens

<400> SEQUENCE: 553
aaggaggctg tgcacccaga ctcct                                      25

<210> SEQ ID NO 554
<211> LENGTH: 25
<212> TYPE: DNA
<213> ORGANISM: Homo sapiens

<400> SEQUENCE: 554
gactcctggg tccttagagc ccaag                                      25

<210> SEQ ID NO 555
<211> LENGTH: 25
<212> TYPE: DNA
<213> ORGANISM: Homo sapiens

<400> SEQUENCE: 555
gagcgccggc cgtttatcgc gcaca                                      25

<210> SEQ ID NO 556
<211> LENGTH: 25
<212> TYPE: DNA
<213> ORGANISM: Homo sapiens

<400> SEQUENCE: 556
gggcctcatt cggtgtcagc cccgg                                      25
```

```
<210> SEQ ID NO 557
<211> LENGTH: 25
<212> TYPE: DNA
<213> ORGANISM: Homo sapiens

<400> SEQUENCE: 557
taagtgttca gttagggtta gctcc                                    25

<210> SEQ ID NO 558
<211> LENGTH: 25
<212> TYPE: DNA
<213> ORGANISM: Homo sapiens

<400> SEQUENCE: 558
gagtcctagt agctgaactt ccaga                                    25

<210> SEQ ID NO 559
<211> LENGTH: 25
<212> TYPE: DNA
<213> ORGANISM: Homo sapiens

<400> SEQUENCE: 559
caggacacac cttctttgac taaca                                    25

<210> SEQ ID NO 560
<211> LENGTH: 25
<212> TYPE: DNA
<213> ORGANISM: Homo sapiens

<400> SEQUENCE: 560
tatagggatg gaaatcagca gtctc                                    25

<210> SEQ ID NO 561
<211> LENGTH: 25
<212> TYPE: DNA
<213> ORGANISM: Homo sapiens

<400> SEQUENCE: 561
agagcagtct ctgtatgcca gggac                                    25

<210> SEQ ID NO 562
<211> LENGTH: 25
<212> TYPE: DNA
<213> ORGANISM: Homo sapiens

<400> SEQUENCE: 562
ggttgcctga acacactcaa gagct                                    25

<210> SEQ ID NO 563
<211> LENGTH: 25
<212> TYPE: DNA
<213> ORGANISM: Homo sapiens

<400> SEQUENCE: 563
tgtgtggaaa cagaagccgc atttg                                    25

<210> SEQ ID NO 564
<211> LENGTH: 25
<212> TYPE: DNA
<213> ORGANISM: Homo sapiens

<400> SEQUENCE: 564
```
gaaggtactc taggaaagac aggaa                                          25

<210> SEQ ID NO 565
<211> LENGTH: 25
<212> TYPE: DNA
<213> ORGANISM: Homo sapiens

<400> SEQUENCE: 565
aaattcatca gggtgcacat ccaga                                          25

<210> SEQ ID NO 566
<211> LENGTH: 25
<212> TYPE: DNA
<213> ORGANISM: Homo sapiens

<400> SEQUENCE: 566
ggctctccac ctgaaaagtt gatct                                          25

<210> SEQ ID NO 567
<211> LENGTH: 25
<212> TYPE: DNA
<213> ORGANISM: Homo sapiens

<400> SEQUENCE: 567
gctgggcagc cgcaactcta ctttg                                          25

<210> SEQ ID NO 568
<211> LENGTH: 25
<212> TYPE: DNA
<213> ORGANISM: Homo sapiens

<400> SEQUENCE: 568
gatcaggctt ccattgctca cgatg                                          25

<210> SEQ ID NO 569
<211> LENGTH: 25
<212> TYPE: DNA
<213> ORGANISM: Homo sapiens

<400> SEQUENCE: 569
taatgccgtg cacagcttga aaagc                                          25

<210> SEQ ID NO 570
<211> LENGTH: 25
<212> TYPE: DNA
<213> ORGANISM: Homo sapiens

<400> SEQUENCE: 570
gccaaacttg tttactgaga gccct                                          25

<210> SEQ ID NO 571
<211> LENGTH: 25
<212> TYPE: DNA
<213> ORGANISM: Homo sapiens

<400> SEQUENCE: 571
tcacaggaga tagcgagaat gtcca                                          25

<210> SEQ ID NO 572
<211> LENGTH: 25
<212> TYPE: DNA
<213> ORGANISM: Homo sapiens

<400> SEQUENCE: 572

```
ttggccacgg ccaataagga cattg                                    25
```

<210> SEQ ID NO 573
<211> LENGTH: 25
<212> TYPE: DNA
<213> ORGANISM: Homo sapiens

<400> SEQUENCE: 573

```
tttccagcgg acagggttta gtgct                                    25
```

<210> SEQ ID NO 574
<211> LENGTH: 25
<212> TYPE: DNA
<213> ORGANISM: Homo sapiens

<400> SEQUENCE: 574

```
tttgtggcgc tccaagaatc tttca                                    25
```

<210> SEQ ID NO 575
<211> LENGTH: 25
<212> TYPE: DNA
<213> ORGANISM: Homo sapiens

<400> SEQUENCE: 575

```
tagattcagg caccaagcag gacac                                    25
```

<210> SEQ ID NO 576
<211> LENGTH: 25
<212> TYPE: DNA
<213> ORGANISM: Homo sapiens

<400> SEQUENCE: 576

```
ccagaataag gtaggagtct ttcat                                    25
```

<210> SEQ ID NO 577
<211> LENGTH: 25
<212> TYPE: DNA
<213> ORGANISM: Homo sapiens

<400> SEQUENCE: 577

```
ttcatccaga ataaggtagg agtct                                    25
```

<210> SEQ ID NO 578
<211> LENGTH: 25
<212> TYPE: DNA
<213> ORGANISM: Homo sapiens

<400> SEQUENCE: 578

```
cttccgtccc tttctacagt tcaga                                    25
```

<210> SEQ ID NO 579
<211> LENGTH: 25
<212> TYPE: DNA
<213> ORGANISM: Homo sapiens

<400> SEQUENCE: 579

```
gcttcttcta caccaacatc cagga                                    25
```

<210> SEQ ID NO 580
<211> LENGTH: 25
<212> TYPE: DNA
<213> ORGANISM: Homo sapiens

```
<400> SEQUENCE: 580
ttcagatcag ccttactcca tatgt                                              25

<210> SEQ ID NO 581
<211> LENGTH: 25
<212> TYPE: DNA
<213> ORGANISM: Homo sapiens

<400> SEQUENCE: 581
tgaccacagg taatcagatg ccacg                                              25

<210> SEQ ID NO 582
<211> LENGTH: 25
<212> TYPE: DNA
<213> ORGANISM: Homo sapiens

<400> SEQUENCE: 582
gcattcatgg aacagccacc gtggg                                              25

<210> SEQ ID NO 583
<211> LENGTH: 25
<212> TYPE: DNA
<213> ORGANISM: Homo sapiens

<400> SEQUENCE: 583
ttccagctgg actcccttag gctga                                              25

<210> SEQ ID NO 584
<211> LENGTH: 25
<212> TYPE: DNA
<213> ORGANISM: Homo sapiens

<400> SEQUENCE: 584
ttccttccag ctggactccc ttagg                                              25

<210> SEQ ID NO 585
<211> LENGTH: 25
<212> TYPE: DNA
<213> ORGANISM: Homo sapiens

<400> SEQUENCE: 585
gcagggagcc tgcagcttaa tcttt                                              25

<210> SEQ ID NO 586
<211> LENGTH: 25
<212> TYPE: DNA
<213> ORGANISM: Homo sapiens

<400> SEQUENCE: 586
cagtgtggcc agtagagtta ggacc                                              25

<210> SEQ ID NO 587
<211> LENGTH: 25
<212> TYPE: DNA
<213> ORGANISM: Homo sapiens

<400> SEQUENCE: 587
tggccttcac cacgcagatg cggag                                              25

<210> SEQ ID NO 588
<211> LENGTH: 25
<212> TYPE: DNA
<213> ORGANISM: Homo sapiens
```

```
<400> SEQUENCE: 588
gaggaaacgc agatccaccg atgag                                          25

<210> SEQ ID NO 589
<211> LENGTH: 25
<212> TYPE: DNA
<213> ORGANISM: Homo sapiens

<400> SEQUENCE: 589
actctccctt ccagaagtgt tcttg                                          25

<210> SEQ ID NO 590
<211> LENGTH: 25
<212> TYPE: DNA
<213> ORGANISM: Homo sapiens

<400> SEQUENCE: 590
cactctccct tccagaagtg ttctt                                          25

<210> SEQ ID NO 591
<211> LENGTH: 25
<212> TYPE: DNA
<213> ORGANISM: Homo sapiens

<400> SEQUENCE: 591
cacgttcctt ctagaaagcc aggag                                          25

<210> SEQ ID NO 592
<211> LENGTH: 25
<212> TYPE: DNA
<213> ORGANISM: Homo sapiens

<400> SEQUENCE: 592
cactctcagc acaaacacgt gttct                                          25

<210> SEQ ID NO 593
<211> LENGTH: 25
<212> TYPE: DNA
<213> ORGANISM: Homo sapiens

<400> SEQUENCE: 593
aggagaggga aagcccgttc tcctg                                          25

<210> SEQ ID NO 594
<211> LENGTH: 25
<212> TYPE: DNA
<213> ORGANISM: Homo sapiens

<400> SEQUENCE: 594
caggtcgtag tactcagggc tcaga                                          25

<210> SEQ ID NO 595
<211> LENGTH: 25
<212> TYPE: DNA
<213> ORGANISM: Homo sapiens

<400> SEQUENCE: 595
gatttctcct catcacgcag gtggg                                          25

<210> SEQ ID NO 596
<211> LENGTH: 25
<212> TYPE: DNA
```

```
<213> ORGANISM: Homo sapiens

<400> SEQUENCE: 596
ccagctcctg tgttttggtc aacag                                 25

<210> SEQ ID NO 597
<211> LENGTH: 25
<212> TYPE: DNA
<213> ORGANISM: Homo sapiens

<400> SEQUENCE: 597
gactatcgtc agacaggtcc tgtag                                 25

<210> SEQ ID NO 598
<211> LENGTH: 25
<212> TYPE: DNA
<213> ORGANISM: Homo sapiens

<400> SEQUENCE: 598
ccaggatcac tgtgcaaggt gcccc                                 25

<210> SEQ ID NO 599
<211> LENGTH: 25
<212> TYPE: DNA
<213> ORGANISM: Homo sapiens

<400> SEQUENCE: 599
tatccagggc taagtgcgag cctgc                                 25

<210> SEQ ID NO 600
<211> LENGTH: 25
<212> TYPE: DNA
<213> ORGANISM: Homo sapiens

<400> SEQUENCE: 600
ccttctgtgt ggagaatggt gccca                                 25

<210> SEQ ID NO 601
<211> LENGTH: 25
<212> TYPE: DNA
<213> ORGANISM: Homo sapiens

<400> SEQUENCE: 601
tgaaatttct gcagacgtcg cgcca                                 25

<210> SEQ ID NO 602
<211> LENGTH: 25
<212> TYPE: DNA
<213> ORGANISM: Homo sapiens

<400> SEQUENCE: 602
ggccctgggt aactctagac tgata                                 25

<210> SEQ ID NO 603
<211> LENGTH: 25
<212> TYPE: DNA
<213> ORGANISM: Homo sapiens

<400> SEQUENCE: 603
ccagtcggca gcctgagcag gttgt                                 25

<210> SEQ ID NO 604
<211> LENGTH: 25
```

```
<212> TYPE: DNA
<213> ORGANISM: Homo sapiens

<400> SEQUENCE: 604
gcttcttcca caggacaagg tgaga                                              25

<210> SEQ ID NO 605
<211> LENGTH: 25
<212> TYPE: DNA
<213> ORGANISM: Homo sapiens

<400> SEQUENCE: 605
caagttacac atgggcatcg tgggc                                              25

<210> SEQ ID NO 606
<211> LENGTH: 25
<212> TYPE: DNA
<213> ORGANISM: Homo sapiens

<400> SEQUENCE: 606
gaaaatgaac tttgctccct cagca                                              25

<210> SEQ ID NO 607
<211> LENGTH: 25
<212> TYPE: DNA
<213> ORGANISM: Homo sapiens

<400> SEQUENCE: 607
cacaatccgc acgtgttgca agaga                                              25

<210> SEQ ID NO 608
<211> LENGTH: 25
<212> TYPE: DNA
<213> ORGANISM: Homo sapiens

<400> SEQUENCE: 608
gaagaatccc agtacagctt ccgca                                              25

<210> SEQ ID NO 609
<211> LENGTH: 25
<212> TYPE: DNA
<213> ORGANISM: Homo sapiens

<400> SEQUENCE: 609
ggactggatt ccttcactga cacaa                                              25

<210> SEQ ID NO 610
<211> LENGTH: 25
<212> TYPE: DNA
<213> ORGANISM: Homo sapiens

<400> SEQUENCE: 610
aatcaaagac tgcaacggtg tggcc                                              25

<210> SEQ ID NO 611
<211> LENGTH: 25
<212> TYPE: DNA
<213> ORGANISM: Homo sapiens

<400> SEQUENCE: 611
gaatccacag caatgttcct gaaag                                              25

<210> SEQ ID NO 612
```

```
<211> LENGTH: 25
<212> TYPE: DNA
<213> ORGANISM: Homo sapiens

<400> SEQUENCE: 612
cactgagatg tttggcactc cctcc                                              25

<210> SEQ ID NO 613
<211> LENGTH: 25
<212> TYPE: DNA
<213> ORGANISM: Homo sapiens

<400> SEQUENCE: 613
tcttttcccg agtttcccat gaggc                                              25

<210> SEQ ID NO 614
<211> LENGTH: 25
<212> TYPE: DNA
<213> ORGANISM: Homo sapiens

<400> SEQUENCE: 614 tcccttttg tgaaactgcc cagtg                                               25

<210> SEQ ID NO 615
<211> LENGTH: 25
<212> TYPE: DNA
<213> ORGANISM: Homo sapiens

<400> SEQUENCE: 615
ggtttcctcg tgctccaaat caggg                                              25

<210> SEQ ID NO 616
<211> LENGTH: 25
<212> TYPE: DNA
<213> ORGANISM: Homo sapiens

<400> SEQUENCE: 616
caaatcgctt tctgacttgc ttgtc                                              25

<210> SEQ ID NO 617
<211> LENGTH: 25
<212> TYPE: DNA
<213> ORGANISM: Homo sapiens

<400> SEQUENCE: 617
ttcacatgag tattgagttc agcca                                              25

<210> SEQ ID NO 618
<211> LENGTH: 25
<212> TYPE: DNA
<213> ORGANISM: Homo sapiens

<400> SEQUENCE: 618
gattctaacc gcgatccctt ggaga                                              25

<210> SEQ ID NO 619
<211> LENGTH: 25
<212> TYPE: DNA
<213> ORGANISM: Homo sapiens

<400> SEQUENCE: 619
tgccaatcct cgatcagcac catgg                                              25
```

```
<210> SEQ ID NO 620
<211> LENGTH: 25
<212> TYPE: DNA
<213> ORGANISM: Homo sapiens

<400> SEQUENCE: 620
caaactgttg gagcaccagg actat                                        25

<210> SEQ ID NO 621
<211> LENGTH: 25
<212> TYPE: DNA
<213> ORGANISM: Homo sapiens

<400> SEQUENCE: 621
ttctcacgag ggataagggc tggtt                                        25

<210> SEQ ID NO 622
<211> LENGTH: 25
<212> TYPE: DNA
<213> ORGANISM: Homo sapiens

<400> SEQUENCE: 622
cttgggttac aaggctgctc agctg                                        25

<210> SEQ ID NO 623
<211> LENGTH: 25
<212> TYPE: DNA
<213> ORGANISM: Homo sapiens

<400> SEQUENCE: 623
tatctagtta gagaaacggt gcagc                                        25

<210> SEQ ID NO 624
<211> LENGTH: 25
<212> TYPE: DNA
<213> ORGANISM: Homo sapiens

<400> SEQUENCE: 624
ccatttctgc cattaatgaa acttc                                        25

<210> SEQ ID NO 625
<211> LENGTH: 25
<212> TYPE: DNA
<213> ORGANISM: Homo sapiens

<400> SEQUENCE: 625
cggttttaag ttggcaggtg tcagt                                        25

<210> SEQ ID NO 626
<211> LENGTH: 25
<212> TYPE: DNA
<213> ORGANISM: Homo sapiens

<400> SEQUENCE: 626
tcttctcagc actgggttag gtgcc                                        25

<210> SEQ ID NO 627
<211> LENGTH: 25
<212> TYPE: DNA
<213> ORGANISM: Homo sapiens

<400> SEQUENCE: 627
taatttctgc cctgagttcg gccag                                        25
```

<210> SEQ ID NO 628
<211> LENGTH: 25
<212> TYPE: DNA
<213> ORGANISM: Homo sapiens

<400> SEQUENCE: 628
gcaggaaccc catgattaca gaaat                                    25

<210> SEQ ID NO 629
<211> LENGTH: 25
<212> TYPE: DNA
<213> ORGANISM: Homo sapiens

<400> SEQUENCE: 629
cttgttggcc ggcatggtct ggtga                                    25

<210> SEQ ID NO 630
<211> LENGTH: 25
<212> TYPE: DNA
<213> ORGANISM: Homo sapiens

<400> SEQUENCE: 630
tcacagccgg gactgagaga actgc                                    25

<210> SEQ ID NO 631
<211> LENGTH: 25
<212> TYPE: DNA
<213> ORGANISM: Homo sapiens

<400> SEQUENCE: 631
tttaggaaaa gaactgcgca ggccc                                    25

<210> SEQ ID NO 632
<211> LENGTH: 25
<212> TYPE: DNA
<213> ORGANISM: Homo sapiens

<400> SEQUENCE: 632
cattccaggc cttgactcga gtgtg                                    25

<210> SEQ ID NO 633
<211> LENGTH: 25
<212> TYPE: DNA
<213> ORGANISM: Homo sapiens

<400> SEQUENCE: 633
tcatgacgag tgcaaccaga tgtgg                                    25

<210> SEQ ID NO 634
<211> LENGTH: 25
<212> TYPE: DNA
<213> ORGANISM: Homo sapiens

<400> SEQUENCE: 634
cactggaaca tgatgagagg gacct                                    25

<210> SEQ ID NO 635
<211> LENGTH: 25
<212> TYPE: DNA
<213> ORGANISM: Homo sapiens

<400> SEQUENCE: 635
aatctagtta gacgtggcac ctggc                                    25

<210> SEQ ID NO 636
<211> LENGTH: 25
<212> TYPE: DNA
<213> ORGANISM: Homo sapiens

<400> SEQUENCE: 636
tacggttcac taaaactatt ctgga                                          25

<210> SEQ ID NO 637
<211> LENGTH: 25
<212> TYPE: DNA
<213> ORGANISM: Homo sapiens

<400> SEQUENCE: 637
ttaggcttaa taccgtctgc aggac                                          25

<210> SEQ ID NO 638
<211> LENGTH: 25
<212> TYPE: DNA
<213> ORGANISM: Homo sapiens

<400> SEQUENCE: 638
caggattctc catccgctgg tagga                                          25

<210> SEQ ID NO 639
<211> LENGTH: 25
<212> TYPE: DNA
<213> ORGANISM: Homo sapiens

<400> SEQUENCE: 639
cacacgggaa gcatctaata ggtag                                          25

<210> SEQ ID NO 640
<211> LENGTH: 25
<212> TYPE: DNA
<213> ORGANISM: Homo sapiens

<400> SEQUENCE: 640
agataacaat gctgcagccc tgtgg                                          25

<210> SEQ ID NO 641
<211> LENGTH: 25
<212> TYPE: DNA
<213> ORGANISM: Homo sapiens

<400> SEQUENCE: 641
caatcctaaa gccagtgcca gtggt                                          25

<210> SEQ ID NO 642
<211> LENGTH: 25
<212> TYPE: DNA
<213> ORGANISM: Homo sapiens

<400> SEQUENCE: 642
caggtttgag caggtcctct ggcca                                          25

<210> SEQ ID NO 643
<211> LENGTH: 25
<212> TYPE: DNA
<213> ORGANISM: Homo sapiens

<400> SEQUENCE: 643

-continued gattctttag ctatttcgga ggcca                                   25

<210> SEQ ID NO 644
<211> LENGTH: 25
<212> TYPE: DNA
<213> ORGANISM: Homo sapiens

<400> SEQUENCE: 644
ctccactggc caatgcaaga gggtg                                   25

<210> SEQ ID NO 645
<211> LENGTH: 25
<212> TYPE: DNA
<213> ORGANISM: Homo sapiens

<400> SEQUENCE: 645
gaggacagcc ttaagtgaat ctgcc                                   25

<210> SEQ ID NO 646
<211> LENGTH: 25
<212> TYPE: DNA
<213> ORGANISM: Homo sapiens

<400> SEQUENCE: 646
tcgatggcaa caacctggaa ctttc                                   25

<210> SEQ ID NO 647
<211> LENGTH: 25
<212> TYPE: DNA
<213> ORGANISM: Homo sapiens

<400> SEQUENCE: 647
tctgttttgg gcactggtcg accag                                   25

<210> SEQ ID NO 648
<211> LENGTH: 25
<212> TYPE: DNA
<213> ORGANISM: Homo sapiens

<400> SEQUENCE: 648
ttgcgctctt aactgctcca caacg                                   25

<210> SEQ ID NO 649
<211> LENGTH: 25
<212> TYPE: DNA
<213> ORGANISM: Homo sapiens

<400> SEQUENCE: 649
caacgctgtc ccgtaagctt ggaaa                                   25

<210> SEQ ID NO 650
<211> LENGTH: 25
<212> TYPE: DNA
<213> ORGANISM: Homo sapiens

<400> SEQUENCE: 650
ggaaaatatt cccaagatcc atggg                                   25

<210> SEQ ID NO 651
<211> LENGTH: 25
<212> TYPE: DNA
<213> ORGANISM: Homo sapiens

<400> SEQUENCE: 651
acggaactgg gcaagtctgg cacca 25

<210> SEQ ID NO 652
<211> LENGTH: 25
<212> TYPE: DNA
<213> ORGANISM: Homo sapiens

<400> SEQUENCE: 652
gcttgccggg tgtcagggtc atcca 25

<210> SEQ ID NO 653
<211> LENGTH: 25
<212> TYPE: DNA
<213> ORGANISM: Homo sapiens

<400> SEQUENCE: 653
tgcagtcggg aagctccagg acgaa 25

<210> SEQ ID NO 654
<211> LENGTH: 25
<212> TYPE: DNA
<213> ORGANISM: Homo sapiens

<400> SEQUENCE: 654
gactctccaa ctgggaagtg tcgcc 25

<210> SEQ ID NO 655
<211> LENGTH: 25
<212> TYPE: DNA
<213> ORGANISM: Homo sapiens

<400> SEQUENCE: 655
gaagtgtgtc aggatagcac cctct 25

<210> SEQ ID NO 656
<211> LENGTH: 25
<212> TYPE: DNA
<213> ORGANISM: Homo sapiens

<400> SEQUENCE: 656
tgttgctgcc taacagtgta actgc 25

<210> SEQ ID NO 657
<211> LENGTH: 25
<212> TYPE: DNA
<213> ORGANISM: Homo sapiens

<400> SEQUENCE: 657
catgaagagt ggacgctggg ctcct 25

<210> SEQ ID NO 658
<211> LENGTH: 25
<212> TYPE: DNA
<213> ORGANISM: Homo sapiens

<400> SEQUENCE: 658
aaccagatga agctcgtgtc gggcc 25

<210> SEQ ID NO 659
<211> LENGTH: 25
<212> TYPE: DNA
<213> ORGANISM: Homo sapiens

<400> SEQUENCE: 659
tcatcgttct cattgcgggc cagga                                    25

<210> SEQ ID NO 660
<211> LENGTH: 25
<212> TYPE: DNA
<213> ORGANISM: Homo sapiens

<400> SEQUENCE: 660
aagtggtccg catcccagat ctgca                                    25

<210> SEQ ID NO 661
<211> LENGTH: 25
<212> TYPE: DNA
<213> ORGANISM: Homo sapiens

<400> SEQUENCE: 661
cttccgaggt gagatgtcca gaggc                                    25

<210> SEQ ID NO 662
<211> LENGTH: 25
<212> TYPE: DNA
<213> ORGANISM: Homo sapiens

<400> SEQUENCE: 662
cacatgctcg tctgtgggct tcctc                                    25

<210> SEQ ID NO 663
<211> LENGTH: 25
<212> TYPE: DNA
<213> ORGANISM: Homo sapiens

<400> SEQUENCE: 663
ggtcccgcca gatattgtag ccatg                                    25

<210> SEQ ID NO 664
<211> LENGTH: 25
<212> TYPE: DNA
<213> ORGANISM: Homo sapiens

<400> SEQUENCE: 664
gaaggaggcc tcgatgtcaa aggac                                    25

<210> SEQ ID NO 665
<211> LENGTH: 25
<212> TYPE: DNA
<213> ORGANISM: Homo sapiens

<400> SEQUENCE: 665
gatgtcagtc ttgcctagcc ggatg                                    25

<210> SEQ ID NO 666
<211> LENGTH: 25
<212> TYPE: DNA
<213> ORGANISM: Homo sapiens

<400> SEQUENCE: 666
gcactttgta cacgcagagg gagcc                                    25

<210> SEQ ID NO 667
<211> LENGTH: 25
<212> TYPE: DNA
<213> ORGANISM: Homo sapiens

```
<400> SEQUENCE: 667
tcaatggagg caaagtactt ggacc                                          25

<210> SEQ ID NO 668
<211> LENGTH: 25
<212> TYPE: DNA
<213> ORGANISM: Homo sapiens

<400> SEQUENCE: 668
gtttggacac acaatcaagc tcagc                                          25

<210> SEQ ID NO 669
<211> LENGTH: 25
<212> TYPE: DNA
<213> ORGANISM: Homo sapiens

<400> SEQUENCE: 669
tttcttgatg ggtacctctg gctcc                                          25

<210> SEQ ID NO 670
<211> LENGTH: 25
<212> TYPE: DNA
<213> ORGANISM: Homo sapiens

<400> SEQUENCE: 670
acagcacacg gcagcgccgg agaag                                          25

<210> SEQ ID NO 671
<211> LENGTH: 25
<212> TYPE: DNA
<213> ORGANISM: Homo sapiens

<400> SEQUENCE: 671
tccaccacac ggatgttcaa gggcg                                          25

<210> SEQ ID NO 672
<211> LENGTH: 25
<212> TYPE: DNA
<213> ORGANISM: Homo sapiens

<400> SEQUENCE: 672
taattgtgga tcagggacga ctgca                                          25

<210> SEQ ID NO 673
<211> LENGTH: 25
<212> TYPE: DNA
<213> ORGANISM: Homo sapiens

<400> SEQUENCE: 673
ggtccggccc atgaagtcag ctttg                                          25

<210> SEQ ID NO 674
<211> LENGTH: 25
<212> TYPE: DNA
<213> ORGANISM: Homo sapiens

<400> SEQUENCE: 674
catagagctc caggttgtcg aacac                                          25

<210> SEQ ID NO 675
<211> LENGTH: 25
<212> TYPE: DNA
```

```
<213> ORGANISM: Homo sapiens

<400> SEQUENCE: 675
cctggtacat gtgcgctcgg agctg                                          25

<210> SEQ ID NO 676
<211> LENGTH: 25
<212> TYPE: DNA
<213> ORGANISM: Homo sapiens

<400> SEQUENCE: 676
tccacgatgg agaagagcag gtcct                                          25

<210> SEQ ID NO 677
<211> LENGTH: 25
<212> TYPE: DNA
<213> ORGANISM: Homo sapiens

<400> SEQUENCE: 677
tgcaggaagt tctggcacag cctca                                          25

<210> SEQ ID NO 678
<211> LENGTH: 25
<212> TYPE: DNA
<213> ORGANISM: Homo sapiens

<400> SEQUENCE: 678
gatgagtggc cctggtcctt gtcag                                          25

<210> SEQ ID NO 679
<211> LENGTH: 25
<212> TYPE: DNA
<213> ORGANISM: Homo sapiens

<400> SEQUENCE: 679
gacgctcagg gtaggacttc tccgt                                          25

<210> SEQ ID NO 680
<211> LENGTH: 25
<212> TYPE: DNA
<213> ORGANISM: Homo sapiens

<400> SEQUENCE: 680
caaatgcctc ctccctgttg atcag                                          25

<210> SEQ ID NO 681
<211> LENGTH: 25
<212> TYPE: DNA
<213> ORGANISM: Homo sapiens

<400> SEQUENCE: 681
tgatctggga gctctcgcta gggcc                                          25

<210> SEQ ID NO 682
<211> LENGTH: 25
<212> TYPE: DNA
<213> ORGANISM: Homo sapiens

<400> SEQUENCE: 682
gaagtcatca atttcccagg ttctg                                          25

<210> SEQ ID NO 683
<211> LENGTH: 25
```

```
<212> TYPE: DNA
<213> ORGANISM: Homo sapiens

<400> SEQUENCE: 683
tagatgcagg gctttcgctc caggt                                              25

<210> SEQ ID NO 684
<211> LENGTH: 25
<212> TYPE: DNA
<213> ORGANISM: Homo sapiens

<400> SEQUENCE: 684
ggcctcgtca tcacttgcgt tctga                                              25

<210> SEQ ID NO 685
<211> LENGTH: 25
<212> TYPE: DNA
<213> ORGANISM: Homo sapiens

<400> SEQUENCE: 685
tccggtcgat cattgaggcc tccag                                              25

<210> SEQ ID NO 686
<211> LENGTH: 25
<212> TYPE: DNA
<213> ORGANISM: Homo sapiens

<400> SEQUENCE: 686
tgtggagccg tacatgttca cccag                                              25

<210> SEQ ID NO 687
<211> LENGTH: 25
<212> TYPE: DNA
<213> ORGANISM: Homo sapiens

<400> SEQUENCE: 687
ttttcacata gaaccgggcc cactg                                              25

<210> SEQ ID NO 688
<211> LENGTH: 25
<212> TYPE: DNA
<213> ORGANISM: Homo sapiens

<400> SEQUENCE: 688
caggatggcc cacttgtgat ggaac                                              25

<210> SEQ ID NO 689
<211> LENGTH: 25
<212> TYPE: DNA
<213> ORGANISM: Homo sapiens

<400> SEQUENCE: 689 ccatttgaa ggagcccacc agggt                                               25

<210> SEQ ID NO 690
<211> LENGTH: 25
<212> TYPE: DNA
<213> ORGANISM: Homo sapiens

<400> SEQUENCE: 690
tgacatccgg agagacatgg aagtc                                              25

<210> SEQ ID NO 691
```

```
<211> LENGTH: 25
<212> TYPE: DNA
<213> ORGANISM: Homo sapiens

<400> SEQUENCE: 691
acagggtcca tgttcaagcc cacca                                              25

<210> SEQ ID NO 692
<211> LENGTH: 25
<212> TYPE: DNA
<213> ORGANISM: Homo sapiens

<400> SEQUENCE: 692
gctccatctt aatgtctggc ttaga                                              25

<210> SEQ ID NO 693
<211> LENGTH: 25
<212> TYPE: DNA
<213> ORGANISM: Homo sapiens

<400> SEQUENCE: 693
aatggccaga tggtcaaggt cttcc                                              25

<210> SEQ ID NO 694
<211> LENGTH: 25
<212> TYPE: DNA
<213> ORGANISM: Homo sapiens

<400> SEQUENCE: 694
tgggagcagt ccatccgtct cttgg                                              25

<210> SEQ ID NO 695
<211> LENGTH: 25
<212> TYPE: DNA
<213> ORGANISM: Homo sapiens

<400> SEQUENCE: 695
cgtcagtggc ctgataccgg acctc                                              25

<210> SEQ ID NO 696
<211> LENGTH: 25
<212> TYPE: DNA
<213> ORGANISM: Homo sapiens

<400> SEQUENCE: 696
ttctgcagca ccatgcggaa ggtcc                                              25

<210> SEQ ID NO 697
<211> LENGTH: 25
<212> TYPE: DNA
<213> ORGANISM: Homo sapiens

<400> SEQUENCE: 697
tcatttctgt cgatgctgct ggcca                                              25

<210> SEQ ID NO 698
<211> LENGTH: 25
<212> TYPE: DNA
<213> ORGANISM: Homo sapiens

<400> SEQUENCE: 698
tccaggaccc gagagtagaa ggatt                                              25
```

```
<210> SEQ ID NO 699
<211> LENGTH: 25
<212> TYPE: DNA
<213> ORGANISM: Homo sapiens

<400> SEQUENCE: 699
gaaagtcact ttggcgatcc ggtcg                                    25

<210> SEQ ID NO 700
<211> LENGTH: 25
<212> TYPE: DNA
<213> ORGANISM: Homo sapiens

<400> SEQUENCE: 700
gctagccggt ggagcacggc tcaca                                    25

<210> SEQ ID NO 701
<211> LENGTH: 25
<212> TYPE: DNA
<213> ORGANISM: Homo sapiens

<400> SEQUENCE: 701
tatgggatgc atcatggaag cctcc                                    25

<210> SEQ ID NO 702
<211> LENGTH: 25
<212> TYPE: DNA
<213> ORGANISM: Homo sapiens

<400> SEQUENCE: 702
gaaactgcag acattgaggc ctgga                                    25

<210> SEQ ID NO 703
<211> LENGTH: 25
<212> TYPE: DNA
<213> ORGANISM: Homo sapiens

<400> SEQUENCE: 703
aaattcttaa gtcacatcag gaggg                                    25

<210> SEQ ID NO 704
<211> LENGTH: 25
<212> TYPE: DNA
<213> ORGANISM: Homo sapiens

<400> SEQUENCE: 704
ccaccttggg tgatgctaaa ttgaa                                    25

<210> SEQ ID NO 705
<211> LENGTH: 25
<212> TYPE: DNA
<213> ORGANISM: Homo sapiens

<400> SEQUENCE: 705
tgaatacatt aatgccgtcc ctggg                                    25

<210> SEQ ID NO 706
<211> LENGTH: 25
<212> TYPE: DNA
<213> ORGANISM: Homo sapiens

<400> SEQUENCE: 706
catatagttg gaaggcccac tgggc                                    25
```

<210> SEQ ID NO 707
<211> LENGTH: 25
<212> TYPE: DNA
<213> ORGANISM: Homo sapiens

<400> SEQUENCE: 707
tcttccacac agtcaaggtc cttag                                  25

<210> SEQ ID NO 708
<211> LENGTH: 25
<212> TYPE: DNA
<213> ORGANISM: Homo sapiens

<400> SEQUENCE: 708
cagatgtgtt aggtcgatcc tcagg                                  25

<210> SEQ ID NO 709
<211> LENGTH: 25
<212> TYPE: DNA
<213> ORGANISM: Homo sapiens

<400> SEQUENCE: 709
tatatctgag atgatgccat cccgt                                  25

<210> SEQ ID NO 710
<211> LENGTH: 25
<212> TYPE: DNA
<213> ORGANISM: Homo sapiens

<400> SEQUENCE: 710
gatgccatcc cgtaggtctg tgaaa                                  25

<210> SEQ ID NO 711
<211> LENGTH: 25
<212> TYPE: DNA
<213> ORGANISM: Homo sapiens

<400> SEQUENCE: 711
gaattagccc caaagcgtag aggtc                                  25

<210> SEQ ID NO 712
<211> LENGTH: 25
<212> TYPE: DNA
<213> ORGANISM: Homo sapiens

<400> SEQUENCE: 712
taccgccgaa tagctgaatc ctctg                                  25

<210> SEQ ID NO 713
<211> LENGTH: 25
<212> TYPE: DNA
<213> ORGANISM: Homo sapiens

<400> SEQUENCE: 713
tctgggctca tgtatcgcaa agttc                                  25

<210> SEQ ID NO 714
<211> LENGTH: 25
<212> TYPE: DNA
<213> ORGANISM: Homo sapiens

<400> SEQUENCE: 714
tatcgcaaag ttcccttact ccttg                                  25

```
<210> SEQ ID NO 715
<211> LENGTH: 25
<212> TYPE: DNA
<213> ORGANISM: Homo sapiens

<400> SEQUENCE: 715
tccatttgga tgaaaaggca cttag                                   25

<210> SEQ ID NO 716
<211> LENGTH: 25
<212> TYPE: DNA
<213> ORGANISM: Homo sapiens

<400> SEQUENCE: 716
gccaatgctt ttacttcacg ctccg                                   25

<210> SEQ ID NO 717
<211> LENGTH: 25
<212> TYPE: DNA
<213> ORGANISM: Homo sapiens

<400> SEQUENCE: 717
gtaagtcttt ccgtcaattc tgtgt                                   25

<210> SEQ ID NO 718
<211> LENGTH: 25
<212> TYPE: DNA
<213> ORGANISM: Homo sapiens

<400> SEQUENCE: 718
gaaaacttgg ccaaatccac ctgag                                   25

<210> SEQ ID NO 719
<211> LENGTH: 25
<212> TYPE: DNA
<213> ORGANISM: Homo sapiens

<400> SEQUENCE: 719
tcaggaaggt caaatctggg tgcca                                   25

<210> SEQ ID NO 720
<211> LENGTH: 25
<212> TYPE: DNA
<213> ORGANISM: Homo sapiens

<400> SEQUENCE: 720
tgtagcatgt gcacatagtc aaaga                                   25

<210> SEQ ID NO 721
<211> LENGTH: 25
<212> TYPE: DNA
<213> ORGANISM: Homo sapiens

<400> SEQUENCE: 721
gaaactctgc tcaaataagg gtgta                                   25

<210> SEQ ID NO 722
<211> LENGTH: 25
<212> TYPE: DNA
<213> ORGANISM: Homo sapiens

<400> SEQUENCE: 722
```

```
gccttcctttgattatttctgagac                                              25

<210> SEQ ID NO 723
<211> LENGTH: 25
<212> TYPE: DNA
<213> ORGANISM: Homo sapiens

<400> SEQUENCE: 723
ccttcctttg attatttctg agacc                                            25

<210> SEQ ID NO 724
<211> LENGTH: 25
<212> TYPE: DNA
<213> ORGANISM: Homo sapiens

<400> SEQUENCE: 724
cgaagaactg tttaaactgt cactg                                            25

<210> SEQ ID NO 725
<211> LENGTH: 25
<212> TYPE: DNA
<213> ORGANISM: Homo sapiens

<400> SEQUENCE: 725
tgatgtatct gctgagaagt cacct                                            25

<210> SEQ ID NO 726
<211> LENGTH: 25
<212> TYPE: DNA
<213> ORGANISM: Homo sapiens

<400> SEQUENCE: 726
tgtgctggtc actaaagagt tgctt                                            25

<210> SEQ ID NO 727
<211> LENGTH: 25
<212> TYPE: DNA
<213> ORGANISM: Homo sapiens

<400> SEQUENCE: 727
gaagatatgc aagtttagcg gccaa                                            25

<210> SEQ ID NO 728
<211> LENGTH: 25
<212> TYPE: DNA
<213> ORGANISM: Homo sapiens

<400> SEQUENCE: 728
tcctgtttag tagaacctgt accaa                                            25

<210> SEQ ID NO 729
<211> LENGTH: 25
<212> TYPE: DNA
<213> ORGANISM: Homo sapiens

<400> SEQUENCE: 729
gataaggcct atgtaattcc ccatg                                            25

<210> SEQ ID NO 730
<211> LENGTH: 25
<212> TYPE: DNA
<213> ORGANISM: Homo sapiens

<400> SEQUENCE: 730
```
ccttctgaag aattcgttgt tgtca    25

<210> SEQ ID NO 731
<211> LENGTH: 25
<212> TYPE: DNA
<213> ORGANISM: Homo sapiens

<400> SEQUENCE: 731
tctcaacagc taatttggct gcggc    25

<210> SEQ ID NO 732
<211> LENGTH: 25
<212> TYPE: DNA
<213> ORGANISM: Homo sapiens

<400> SEQUENCE: 732
catgtggagg tcctgaatta ggcag    25

<210> SEQ ID NO 733
<211> LENGTH: 25
<212> TYPE: DNA
<213> ORGANISM: Homo sapiens

<400> SEQUENCE: 733
tgaagaaacc tgctgaaaga tcacc    25

<210> SEQ ID NO 734
<211> LENGTH: 25
<212> TYPE: DNA
<213> ORGANISM: Homo sapiens

<400> SEQUENCE: 734
cacgcagata atcacggaag tgtgg    25

<210> SEQ ID NO 735
<211> LENGTH: 25
<212> TYPE: DNA
<213> ORGANISM: Homo sapiens

<400> SEQUENCE: 735
ctgagtcaga tggaagaact gctaa    25

<210> SEQ ID NO 736
<211> LENGTH: 25
<212> TYPE: DNA
<213> ORGANISM: Homo sapiens

<400> SEQUENCE: 736
ggtcattaca atttacaaat ccagg    25

<210> SEQ ID NO 737
<211> LENGTH: 25
<212> TYPE: DNA
<213> ORGANISM: Homo sapiens

<400> SEQUENCE: 737
tattgggatg gacctcgatg cctcg    25

<210> SEQ ID NO 738
<211> LENGTH: 25
<212> TYPE: DNA
<213> ORGANISM: Homo sapiens

```
<400> SEQUENCE: 738
gagctgaatg ccactgtgac cgcaa                                         25

<210> SEQ ID NO 739
<211> LENGTH: 25
<212> TYPE: DNA
<213> ORGANISM: Homo sapiens

<400> SEQUENCE: 739
caagccctcg tctgctacgg gattg                                         25

<210> SEQ ID NO 740
<211> LENGTH: 25
<212> TYPE: DNA
<213> ORGANISM: Homo sapiens

<400> SEQUENCE: 740
aagccctcgt ctgctacggg attgg                                         25

<210> SEQ ID NO 741
<211> LENGTH: 25
<212> TYPE: DNA
<213> ORGANISM: Homo sapiens

<400> SEQUENCE: 741
tactctgatg acagtaatac gttgc                                         25

<210> SEQ ID NO 742
<211> LENGTH: 25
<212> TYPE: DNA
<213> ORGANISM: Homo sapiens

<400> SEQUENCE: 742
tgacagtaat acgttgcagc atctt                                         25

<210> SEQ ID NO 743
<211> LENGTH: 25
<212> TYPE: DNA
<213> ORGANISM: Homo sapiens

<400> SEQUENCE: 743
gacagtaata cgttgcagca tcttc                                         25

<210> SEQ ID NO 744
<211> LENGTH: 25
<212> TYPE: DNA
<213> ORGANISM: Homo sapiens

<400> SEQUENCE: 744
cgttgcagca tcttcagctt ccagg                                         25

<210> SEQ ID NO 745
<211> LENGTH: 25
<212> TYPE: DNA
<213> ORGANISM: Homo sapiens

<400> SEQUENCE: 745
gacccctgag aaggactggg aagca                                         25

<210> SEQ ID NO 746
<211> LENGTH: 25
<212> TYPE: DNA
<213> ORGANISM: Homo sapiens
```

-continued

<400> SEQUENCE: 746 ccccctgagaa ggactgggaa gcata                                    25

<210> SEQ ID NO 747
<211> LENGTH: 25
<212> TYPE: DNA
<213> ORGANISM: Homo sapiens

<400> SEQUENCE: 747
ccctgagaag gactgggaag catac                                     25

<210> SEQ ID NO 748
<211> LENGTH: 25
<212> TYPE: DNA
<213> ORGANISM: Homo sapiens

<400> SEQUENCE: 748
cctgagaagg actgggaagc atact                                     25

<210> SEQ ID NO 749
<211> LENGTH: 25
<212> TYPE: DNA
<213> ORGANISM: Homo sapiens

<400> SEQUENCE: 749
aggactggga agcatacttg atgag                                     25

<210> SEQ ID NO 750
<211> LENGTH: 25
<212> TYPE: DNA
<213> ORGANISM: Homo sapiens

<400> SEQUENCE: 750
agaaacccaa tgagttgtga tggca                                     25

<210> SEQ ID NO 751
<211> LENGTH: 25
<212> TYPE: DNA
<213> ORGANISM: Homo sapiens

<400> SEQUENCE: 751
gaaacccaat gagttgtgat ggcaa                                     25

<210> SEQ ID NO 752
<211> LENGTH: 25
<212> TYPE: DNA
<213> ORGANISM: Homo sapiens

<400> SEQUENCE: 752
aaacccaatg agttgtgatg gcaac                                     25

<210> SEQ ID NO 753
<211> LENGTH: 25
<212> TYPE: DNA
<213> ORGANISM: Homo sapiens

<400> SEQUENCE: 753
aacccaatga gttgtgatgg caaca                                     25

<210> SEQ ID NO 754
<211> LENGTH: 25
<212> TYPE: DNA

<213> ORGANISM: Homo sapiens

<400> SEQUENCE: 754
acccaatgag ttgtgatggc aacat                                        25

<210> SEQ ID NO 755
<211> LENGTH: 25
<212> TYPE: DNA
<213> ORGANISM: Homo sapiens

<400> SEQUENCE: 755
gatgggaccc ctgattgcaa agtgg                                        25

<210> SEQ ID NO 756
<211> LENGTH: 25
<212> TYPE: DNA
<213> ORGANISM: Homo sapiens

<400> SEQUENCE: 756 atgggaccccc tgattgcaaa gtgga                                       25

<210> SEQ ID NO 757
<211> LENGTH: 25
<212> TYPE: DNA
<213> ORGANISM: Homo sapiens

<400> SEQUENCE: 757
tgggacccct gattgcaaag tggat                                        25

<210> SEQ ID NO 758
<211> LENGTH: 25
<212> TYPE: DNA
<213> ORGANISM: Homo sapiens

<400> SEQUENCE: 758
gggacccctg attgcaaagt ggatg                                        25

<210> SEQ ID NO 759
<211> LENGTH: 25
<212> TYPE: DNA
<213> ORGANISM: Homo sapiens

<400> SEQUENCE: 759
ctgtgtcctg actgagagag acttc                                        25

<210> SEQ ID NO 760
<211> LENGTH: 25
<212> TYPE: DNA
<213> ORGANISM: Homo sapiens

<400> SEQUENCE: 760
tgtcctgact gagagagact tctgc                                        25

<210> SEQ ID NO 761
<211> LENGTH: 25
<212> TYPE: DNA
<213> ORGANISM: Homo sapiens

<400> SEQUENCE: 761
gtcctgactg agagagactt ctgca                                        25

<210> SEQ ID NO 762
<211> LENGTH: 25

<212> TYPE: DNA
<213> ORGANISM: Homo sapiens

<400> SEQUENCE: 762
tcctgactga gagagacttc tgcac                                               25

<210> SEQ ID NO 763
<211> LENGTH: 25
<212> TYPE: DNA
<213> ORGANISM: Homo sapiens

<400> SEQUENCE: 763
tgagacaaaa catggcctgc tggtg                                               25

<210> SEQ ID NO 764
<211> LENGTH: 25
<212> TYPE: DNA
<213> ORGANISM: Homo sapiens

<400> SEQUENCE: 764
aagtgtgact tggagccctg gccta                                               25

<210> SEQ ID NO 765
<211> LENGTH: 25
<212> TYPE: DNA
<213> ORGANISM: Homo sapiens

<400> SEQUENCE: 765
tgaaaagcca tctccaccga attct                                               25

<210> SEQ ID NO 766
<211> LENGTH: 25
<212> TYPE: DNA
<213> ORGANISM: Homo sapiens

<400> SEQUENCE: 766
caagagcgtg ggaacctcat ggaga                                               25

<210> SEQ ID NO 767
<211> LENGTH: 25
<212> TYPE: DNA
<213> ORGANISM: Homo sapiens

<400> SEQUENCE: 767
caatcagttt agagtcgaca ggcaa                                               25

<210> SEQ ID NO 768
<211> LENGTH: 25
<212> TYPE: DNA
<213> ORGANISM: Homo sapiens

<400> SEQUENCE: 768
gctgggcttt tgtgcagagt ggcct                                               25

<210> SEQ ID NO 769
<211> LENGTH: 25
<212> TYPE: DNA
<213> ORGANISM: Homo sapiens

<400> SEQUENCE: 769
gaacagatgt attccccttg gtcgc                                               25

<210> SEQ ID NO 770

```
<211> LENGTH: 25
<212> TYPE: DNA
<213> ORGANISM: Homo sapiens

<400> SEQUENCE: 770
ccatgcaaag gtggagttgc ccaca                                              25

<210> SEQ ID NO 771
<211> LENGTH: 25
<212> TYPE: DNA
<213> ORGANISM: Homo sapiens

<400> SEQUENCE: 771
cgcccgatgg tgctgattga gccca                                              25

<210> SEQ ID NO 772
<211> LENGTH: 25
<212> TYPE: DNA
<213> ORGANISM: Homo sapiens

<400> SEQUENCE: 772
caacgaccgt tgtggtacca agtat                                              25

<210> SEQ ID NO 773
<211> LENGTH: 25
<212> TYPE: DNA
<213> ORGANISM: Homo sapiens

<400> SEQUENCE: 773
tagaaaccct catccctggg ctgtg                                              25

<210> SEQ ID NO 774
<211> LENGTH: 25
<212> TYPE: DNA
<213> ORGANISM: Homo sapiens

<400> SEQUENCE: 774
cacacaaggc aggtcaggtt cacca                                              25

<210> SEQ ID NO 775
<211> LENGTH: 25
<212> TYPE: DNA
<213> ORGANISM: Homo sapiens

<400> SEQUENCE: 775
ttgagcgtcg aagtcagctg aggcc                                              25

<210> SEQ ID NO 776
<211> LENGTH: 25
<212> TYPE: DNA
<213> ORGANISM: Homo sapiens

<400> SEQUENCE: 776
tgataggccc cagcttgtgt caaag                                              25

<210> SEQ ID NO 777
<211> LENGTH: 25
<212> TYPE: DNA
<213> ORGANISM: Homo sapiens

<400> SEQUENCE: 777
taaagggcag catcagttct ggcca                                              25
```

```
<210> SEQ ID NO 778
<211> LENGTH: 25
<212> TYPE: DNA
<213> ORGANISM: Homo sapiens

<400> SEQUENCE: 778
caacacggtc cttgtggagc agctg                                    25

<210> SEQ ID NO 779
<211> LENGTH: 25
<212> TYPE: DNA
<213> ORGANISM: Homo sapiens

<400> SEQUENCE: 779
gaagcagggc tccattcagg tacca                                    25

<210> SEQ ID NO 780
<211> LENGTH: 25
<212> TYPE: DNA
<213> ORGANISM: Homo sapiens

<400> SEQUENCE: 780
gaagcgtggg ctgtgatcac tgtcc                                    25

<210> SEQ ID NO 781
<211> LENGTH: 25
<212> TYPE: DNA
<213> ORGANISM: Homo sapiens

<400> SEQUENCE: 781
tatcagccct agtggccaag tgcag                                    25

<210> SEQ ID NO 782
<211> LENGTH: 25
<212> TYPE: DNA
<213> ORGANISM: Homo sapiens

<400> SEQUENCE: 782
tggaggtgaa tctcgctctg agccc                                    25

<210> SEQ ID NO 783
<211> LENGTH: 25
<212> TYPE: DNA
<213> ORGANISM: Homo sapiens

<400> SEQUENCE: 783
tctcgaagcg gaagttgtag gaacc                                    25

<210> SEQ ID NO 784
<211> LENGTH: 25
<212> TYPE: DNA
<213> ORGANISM: Homo sapiens

<400> SEQUENCE: 784
ccatgatgga aggtaactcc aggca                                    25

<210> SEQ ID NO 785
<211> LENGTH: 25
<212> TYPE: DNA
<213> ORGANISM: Homo sapiens

<400> SEQUENCE: 785
tactcctggc catcaaaaga cctgg                                    25
```

```
<210> SEQ ID NO 786
<211> LENGTH: 25
<212> TYPE: DNA
<213> ORGANISM: Homo sapiens

<400> SEQUENCE: 786
tcaaacaaga cgctaaggaa tgcag                                    25

<210> SEQ ID NO 787
<211> LENGTH: 25
<212> TYPE: DNA
<213> ORGANISM: Homo sapiens

<400> SEQUENCE: 787
tgtccaagcc ccacgtgagg ctgtg                                    25

<210> SEQ ID NO 788
<211> LENGTH: 25
<212> TYPE: DNA
<213> ORGANISM: Homo sapiens

<400> SEQUENCE: 788
gtttccaaga gtcatagttt ccagc                                    25

<210> SEQ ID NO 789
<211> LENGTH: 25
<212> TYPE: DNA
<213> ORGANISM: Homo sapiens

<400> SEQUENCE: 789
gatgggctga ccaatgtctc gagga                                    25

<210> SEQ ID NO 790
<211> LENGTH: 25
<212> TYPE: DNA
<213> ORGANISM: Homo sapiens

<400> SEQUENCE: 790
cataagtgca acacagagtg attcc                                    25

<210> SEQ ID NO 791
<211> LENGTH: 25
<212> TYPE: DNA
<213> ORGANISM: Homo sapiens

<400> SEQUENCE: 791
gatcaccaat ctacatgccg ttaag                                    25

<210> SEQ ID NO 792
<211> LENGTH: 25
<212> TYPE: DNA
<213> ORGANISM: Homo sapiens

<400> SEQUENCE: 792
cgatggtggc gtcctcgaga aagca                                    25

<210> SEQ ID NO 793
<211> LENGTH: 25
<212> TYPE: DNA
<213> ORGANISM: Homo sapiens

<400> SEQUENCE: 793
ttcaaacgaa gcttctgggc cggca                                    25
```

```
<210> SEQ ID NO 794
<211> LENGTH: 25
<212> TYPE: DNA
<213> ORGANISM: Homo sapiens

<400> SEQUENCE: 794
ctcgtgctgt tgtgctgtct gggaa                                  25

<210> SEQ ID NO 795
<211> LENGTH: 25
<212> TYPE: DNA
<213> ORGANISM: Homo sapiens

<400> SEQUENCE: 795
gctgcacccg tctcagtatg gactg                                  25

<210> SEQ ID NO 796
<211> LENGTH: 25
<212> TYPE: DNA
<213> ORGANISM: Homo sapiens

<400> SEQUENCE: 796
gaatcacctg gtgccattga aggga                                  25

<210> SEQ ID NO 797
<211> LENGTH: 25
<212> TYPE: DNA
<213> ORGANISM: Homo sapiens

<400> SEQUENCE: 797
cagagtacag ggaaatcagg agagc                                  25

<210> SEQ ID NO 798
<211> LENGTH: 25
<212> TYPE: DNA
<213> ORGANISM: Homo sapiens

<400> SEQUENCE: 798
ctcaggacgg ccgtaaaggt ggact                                  25

<210> SEQ ID NO 799
<211> LENGTH: 25
<212> TYPE: DNA
<213> ORGANISM: Homo sapiens

<400> SEQUENCE: 799
agaggatccg gtggctcccc accga                                  25

<210> SEQ ID NO 800
<211> LENGTH: 25
<212> TYPE: DNA
<213> ORGANISM: Homo sapiens

<400> SEQUENCE: 800
aggatccggt ggctccccac cgagg                                  25

<210> SEQ ID NO 801
<211> LENGTH: 25
<212> TYPE: DNA
<213> ORGANISM: Homo sapiens

<400> SEQUENCE: 801
```

```
tcggagtttg caatggaaat ccagc                                              25

<210> SEQ ID NO 802
<211> LENGTH: 25
<212> TYPE: DNA
<213> ORGANISM: Homo sapiens

<400> SEQUENCE: 802
ggcggtaaat cgtccatgct ttgga                                              25

<210> SEQ ID NO 803
<211> LENGTH: 25
<212> TYPE: DNA
<213> ORGANISM: Homo sapiens

<400> SEQUENCE: 803
tgctcatcca tgtccagaag gtgcc                                              25

<210> SEQ ID NO 804
<211> LENGTH: 25
<212> TYPE: DNA
<213> ORGANISM: Homo sapiens

<400> SEQUENCE: 804
agtagtccta gggtttgcat ctgcc                                              25

<210> SEQ ID NO 805
<211> LENGTH: 25
<212> TYPE: DNA
<213> ORGANISM: Homo sapiens

<400> SEQUENCE: 805
tagtcctagg gtttgcatct gcccc                                              25

<210> SEQ ID NO 806
<211> LENGTH: 25
<212> TYPE: DNA
<213> ORGANISM: Homo sapiens

<400> SEQUENCE: 806
ccgttgttgg ctgaactgag ggcca                                              25

<210> SEQ ID NO 807
<211> LENGTH: 25
<212> TYPE: DNA
<213> ORGANISM: Homo sapiens

<400> SEQUENCE: 807
gggtctctgg aattgtagct gcatg                                              25

<210> SEQ ID NO 808
<211> LENGTH: 25
<212> TYPE: DNA
<213> ORGANISM: Homo sapiens

<400> SEQUENCE: 808
tgggtgaacc ccaaaacagt gcctg                                              25

<210> SEQ ID NO 809
<211> LENGTH: 25
<212> TYPE: DNA
<213> ORGANISM: Homo sapiens

<400> SEQUENCE: 809
```
aaacctgtga gctcccatgt ggcag                                          25

<210> SEQ ID NO 810
<211> LENGTH: 25
<212> TYPE: DNA
<213> ORGANISM: Homo sapiens

<400> SEQUENCE: 810
cattcggtag aggacttggt tgagc                                          25

<210> SEQ ID NO 811
<211> LENGTH: 25
<212> TYPE: DNA
<213> ORGANISM: Homo sapiens

<400> SEQUENCE: 811
tcaccagctg ggcaagtttc accgg                                          25

<210> SEQ ID NO 812
<211> LENGTH: 25
<212> TYPE: DNA
<213> ORGANISM: Homo sapiens

<400> SEQUENCE: 812
taggtacagt gataggctcc ccgtt                                          25

<210> SEQ ID NO 813
<211> LENGTH: 25
<212> TYPE: DNA
<213> ORGANISM: Homo sapiens

<400> SEQUENCE: 813
ttaatgagga ctaagcagga cccca                                          25

<210> SEQ ID NO 814
<211> LENGTH: 25
<212> TYPE: DNA
<213> ORGANISM: Homo sapiens

<400> SEQUENCE: 814
cgggagctac cgctggtcct tggaa                                          25

<210> SEQ ID NO 815
<211> LENGTH: 25
<212> TYPE: DNA
<213> ORGANISM: Homo sapiens

<400> SEQUENCE: 815
gagctaccgc tggtccttgg aagga                                          25

<210> SEQ ID NO 816
<211> LENGTH: 25
<212> TYPE: DNA
<213> ORGANISM: Homo sapiens

<400> SEQUENCE: 816
tacagcccgg aaatagatgc ctagc                                          25

<210> SEQ ID NO 817
<211> LENGTH: 25
<212> TYPE: DNA
<213> ORGANISM: Homo sapiens

<400> SEQUENCE: 817
cggccagatt cggtttcagg agaaa				25

<210> SEQ ID NO 818
<211> LENGTH: 25
<212> TYPE: DNA
<213> ORGANISM: Homo sapiens

<400> SEQUENCE: 818
tggaaagcga aacttacagc ggcct				25

<210> SEQ ID NO 819
<211> LENGTH: 25
<212> TYPE: DNA
<213> ORGANISM: Homo sapiens

<400> SEQUENCE: 819
tccgctgctg agttccacgt cggga				25

<210> SEQ ID NO 820
<211> LENGTH: 25
<212> TYPE: DNA
<213> ORGANISM: Homo sapiens

<400> SEQUENCE: 820
atgtgagcca ggcacgatgg aatct				25

<210> SEQ ID NO 821
<211> LENGTH: 25
<212> TYPE: DNA
<213> ORGANISM: Homo sapiens

<400> SEQUENCE: 821
gaagcgctta tgtgagccag gcacg				25

<210> SEQ ID NO 822
<211> LENGTH: 25
<212> TYPE: DNA
<213> ORGANISM: Homo sapiens

<400> SEQUENCE: 822
tgcctggccc gcgttcagga cagca				25

<210> SEQ ID NO 823
<211> LENGTH: 25
<212> TYPE: DNA
<213> ORGANISM: Homo sapiens

<400> SEQUENCE: 823
tcaggagccc aaacgccttg ctcat				25

<210> SEQ ID NO 824
<211> LENGTH: 25
<212> TYPE: DNA
<213> ORGANISM: Homo sapiens

<400> SEQUENCE: 824
gacagatttg cctcaggagc ccaaa				25

<210> SEQ ID NO 825
<211> LENGTH: 25
<212> TYPE: DNA
<213> ORGANISM: Homo sapiens

```
<400> SEQUENCE: 825
tgacagattt gcctcaggag cccaa                                  25

<210> SEQ ID NO 826
<211> LENGTH: 25
<212> TYPE: DNA
<213> ORGANISM: Homo sapiens

<400> SEQUENCE: 826
gactcagcca ggatggactg acaga                                  25

<210> SEQ ID NO 827
<211> LENGTH: 25
<212> TYPE: DNA
<213> ORGANISM: Homo sapiens

<400> SEQUENCE: 827
ttggacaggt acaggcccca ttcca                                  25

<210> SEQ ID NO 828
<211> LENGTH: 25
<212> TYPE: DNA
<213> ORGANISM: Homo sapiens

<400> SEQUENCE: 828
gagcccaatg cagggacgct tctca                                  25

<210> SEQ ID NO 829
<211> LENGTH: 25
<212> TYPE: DNA
<213> ORGANISM: Homo sapiens

<400> SEQUENCE: 829
aagagcccaa tgcagggacg cttct                                  25

<210> SEQ ID NO 830
<211> LENGTH: 25
<212> TYPE: DNA
<213> ORGANISM: Homo sapiens

<400> SEQUENCE: 830
caagagccca atgcagggac gcttc                                  25

<210> SEQ ID NO 831
<211> LENGTH: 25
<212> TYPE: DNA
<213> ORGANISM: Homo sapiens

<400> SEQUENCE: 831
ccaagagccc aatgcaggga cgctt                                  25

<210> SEQ ID NO 832
<211> LENGTH: 25
<212> TYPE: DNA
<213> ORGANISM: Homo sapiens

<400> SEQUENCE: 832
tcatgtccaa gacgggtccc caaga                                  25

<210> SEQ ID NO 833
<211> LENGTH: 25
<212> TYPE: DNA
```

<213> ORGANISM: Homo sapiens

<400> SEQUENCE: 833
tcgctatcat catagacgac cagca                                      25

<210> SEQ ID NO 834
<211> LENGTH: 25
<212> TYPE: DNA
<213> ORGANISM: Homo sapiens

<400> SEQUENCE: 834
gccggtcgct atcatcatag acgac                                      25

<210> SEQ ID NO 835
<211> LENGTH: 25
<212> TYPE: DNA
<213> ORGANISM: Homo sapiens

<400> SEQUENCE: 835
ggccggtcgc tatcatcata gacga                                      25

<210> SEQ ID NO 836
<211> LENGTH: 25
<212> TYPE: DNA
<213> ORGANISM: Homo sapiens

<400> SEQUENCE: 836
gggccggtcg ctatcatcat agacg                                      25

<210> SEQ ID NO 837
<211> LENGTH: 25
<212> TYPE: DNA
<213> ORGANISM: Homo sapiens

<400> SEQUENCE: 837
agggccggtc gctatcatca tagac                                      25

<210> SEQ ID NO 838
<211> LENGTH: 25
<212> TYPE: DNA
<213> ORGANISM: Homo sapiens

<400> SEQUENCE: 838
gagggccggt cgctatcatc ataga                                      25

<210> SEQ ID NO 839
<211> LENGTH: 25
<212> TYPE: DNA
<213> ORGANISM: Homo sapiens

<400> SEQUENCE: 839
cttctgagat cagggcgtgt tcagg                                      25

<210> SEQ ID NO 840
<211> LENGTH: 25
<212> TYPE: DNA
<213> ORGANISM: Homo sapiens

<400> SEQUENCE: 840
gcttctgaga tcagggcgtg ttcag                                      25

<210> SEQ ID NO 841
<211> LENGTH: 25

```
<212> TYPE: DNA
<213> ORGANISM: Homo sapiens

<400> SEQUENCE: 841
agcttctgag atcagggcgt gttca                                    25

<210> SEQ ID NO 842
<211> LENGTH: 25
<212> TYPE: DNA
<213> ORGANISM: Homo sapiens

<400> SEQUENCE: 842
tagcttctga gatcagggcg tgttc                                    25

<210> SEQ ID NO 843
<211> LENGTH: 25
<212> TYPE: DNA
<213> ORGANISM: Homo sapiens

<400> SEQUENCE: 843
caaacagttt cagtttcggt gttcg                                    25

<210> SEQ ID NO 844
<211> LENGTH: 25
<212> TYPE: DNA
<213> ORGANISM: Homo sapiens

<400> SEQUENCE: 844
aggtttgctc gtttctcagg aagag                                    25

<210> SEQ ID NO 845
<211> LENGTH: 25
<212> TYPE: DNA
<213> ORGANISM: Homo sapiens

<400> SEQUENCE: 845
ccctctgaag ctgagagagt agctt                                    25

<210> SEQ ID NO 846
<211> LENGTH: 25
<212> TYPE: DNA
<213> ORGANISM: Homo sapiens

<400> SEQUENCE: 846
tccctctgaa gctgagagag tagct                                    25

<210> SEQ ID NO 847
<211> LENGTH: 25
<212> TYPE: DNA
<213> ORGANISM: Homo sapiens

<400> SEQUENCE: 847
ttccctctga agctgagaga gtagc                                    25

<210> SEQ ID NO 848
<211> LENGTH: 25
<212> TYPE: DNA
<213> ORGANISM: Homo sapiens

<400> SEQUENCE: 848
tgaaatgtct gctcccaagt ccaga                                    25

<210> SEQ ID NO 849
```

```
<211> LENGTH: 25
<212> TYPE: DNA
<213> ORGANISM: Homo sapiens

<400> SEQUENCE: 849
ttgaaatgtc tgctcccaag tccag                                          25

<210> SEQ ID NO 850
<211> LENGTH: 25
<212> TYPE: DNA
<213> ORGANISM: Homo sapiens

<400> SEQUENCE: 850
aacttcagcg tccatgtggc ccggg                                          25

<210> SEQ ID NO 851
<211> LENGTH: 25
<212> TYPE: DNA
<213> ORGANISM: Homo sapiens

<400> SEQUENCE: 851
cagtctagct gaaggttgcc atcca                                          25

<210> SEQ ID NO 852
<211> LENGTH: 25
<212> TYPE: DNA
<213> ORGANISM: Homo sapiens

<400> SEQUENCE: 852
gtattgcttc caccttgag ccagg                                           25

<210> SEQ ID NO 853
<211> LENGTH: 25
<212> TYPE: DNA
<213> ORGANISM: Homo sapiens

<400> SEQUENCE: 853
ggtattgctt ccaccttga gccag                                           25

<210> SEQ ID NO 854
<211> LENGTH: 25
<212> TYPE: DNA
<213> ORGANISM: Homo sapiens

<400> SEQUENCE: 854
cagccaaatg ctctctgttg gtatt                                          25

<210> SEQ ID NO 855
<211> LENGTH: 25
<212> TYPE: DNA
<213> ORGANISM: Homo sapiens

<400> SEQUENCE: 855
cagaatctgc acttgggcgg aagcc                                          25

<210> SEQ ID NO 856
<211> LENGTH: 25
<212> TYPE: DNA
<213> ORGANISM: Homo sapiens

<400> SEQUENCE: 856
tcaggcatct catattggga ccagg                                          25
```

```
<210> SEQ ID NO 857
<211> LENGTH: 25
<212> TYPE: DNA
<213> ORGANISM: Homo sapiens

<400> SEQUENCE: 857
ggttgctcag aatcctcatg gtgct                                   25

<210> SEQ ID NO 858
<211> LENGTH: 25
<212> TYPE: DNA
<213> ORGANISM: Homo sapiens

<400> SEQUENCE: 858
tgtgtcatgg gatccttcca gggac                                   25

<210> SEQ ID NO 859
<211> LENGTH: 25
<212> TYPE: DNA
<213> ORGANISM: Homo sapiens

<400> SEQUENCE: 859
tcttggcttg gtttgcgagg tacac                                   25

<210> SEQ ID NO 860
<211> LENGTH: 25
<212> TYPE: DNA
<213> ORGANISM: Homo sapiens

<400> SEQUENCE: 860
gatctgggtc tcgactgggc cctaa                                   25

<210> SEQ ID NO 861
<211> LENGTH: 25
<212> TYPE: DNA
<213> ORGANISM: Homo sapiens

<400> SEQUENCE: 861
cagttatatt aaagtggcag ccagt                                   25

<210> SEQ ID NO 862
<211> LENGTH: 25
<212> TYPE: DNA
<213> ORGANISM: Homo sapiens

<400> SEQUENCE: 862
ttcagaggat ggctaggaaa ccagt                                   25

<210> SEQ ID NO 863
<211> LENGTH: 25
<212> TYPE: DNA
<213> ORGANISM: Homo sapiens

<400> SEQUENCE: 863
agtcatgcat atgttgggag acacc                                   25

<210> SEQ ID NO 864
<211> LENGTH: 25
<212> TYPE: DNA
<213> ORGANISM: Homo sapiens

<400> SEQUENCE: 864
ggttcttatc cacccggaca atatg                                   25
```

<210> SEQ ID NO 865
<211> LENGTH: 25
<212> TYPE: DNA
<213> ORGANISM: Homo sapiens

<400> SEQUENCE: 865
gagcttgttg cctccctgtt acaaa                                           25

<210> SEQ ID NO 866
<211> LENGTH: 25
<212> TYPE: DNA
<213> ORGANISM: Homo sapiens

<400> SEQUENCE: 866
tatacaacca gagctacagg cctta                                           25

<210> SEQ ID NO 867
<211> LENGTH: 25
<212> TYPE: DNA
<213> ORGANISM: Homo sapiens

<400> SEQUENCE: 867
tacaggtatg agtttagata gtctc                                           25

<210> SEQ ID NO 868
<211> LENGTH: 25
<212> TYPE: DNA
<213> ORGANISM: Homo sapiens

<400> SEQUENCE: 868
accacactcc tgatttttgt tcctg                                           25

<210> SEQ ID NO 869
<211> LENGTH: 25
<212> TYPE: DNA
<213> ORGANISM: Homo sapiens

<400> SEQUENCE: 869
cctggctgcc agtgctttca aaaaa                                           25

<210> SEQ ID NO 870
<211> LENGTH: 25
<212> TYPE: DNA
<213> ORGANISM: Homo sapiens

<400> SEQUENCE: 870
gaactgaggt atggactagt ccttg                                           25

<210> SEQ ID NO 871
<211> LENGTH: 25
<212> TYPE: DNA
<213> ORGANISM: Homo sapiens

<400> SEQUENCE: 871
tcagaatgaa cctagagaaa gcatc                                           25

<210> SEQ ID NO 872
<211> LENGTH: 25
<212> TYPE: DNA
<213> ORGANISM: Homo sapiens

<400> SEQUENCE: 872
tcaagattaa taagaacaga cttac                                           25

<210> SEQ ID NO 873
<211> LENGTH: 25
<212> TYPE: DNA
<213> ORGANISM: Homo sapiens

<400> SEQUENCE: 873
aattatgcac catatgtaac cctca                                   25

<210> SEQ ID NO 874
<211> LENGTH: 25
<212> TYPE: DNA
<213> ORGANISM: Homo sapiens

<400> SEQUENCE: 874
tcattagata actggaggct cctgt                                   25

<210> SEQ ID NO 875
<211> LENGTH: 25
<212> TYPE: DNA
<213> ORGANISM: Homo sapiens

<400> SEQUENCE: 875
caatgacagg gcagaaattc ttgct                                   25

<210> SEQ ID NO 876
<211> LENGTH: 25
<212> TYPE: DNA
<213> ORGANISM: Homo sapiens

<400> SEQUENCE: 876
caaagtgccc tggtaattga tcaca                                   25

<210> SEQ ID NO 877
<211> LENGTH: 25
<212> TYPE: DNA
<213> ORGANISM: Homo sapiens

<400> SEQUENCE: 877
ggaggtcaat gtgcctttat ctgca                                   25

<210> SEQ ID NO 878
<211> LENGTH: 25
<212> TYPE: DNA
<213> ORGANISM: Homo sapiens

<400> SEQUENCE: 878
ggtcaatgtg cctttatctg cataa                                   25

<210> SEQ ID NO 879
<211> LENGTH: 25
<212> TYPE: DNA
<213> ORGANISM: Homo sapiens

<400> SEQUENCE: 879
tattgagact aaagagcact tcgct                                   25

<210> SEQ ID NO 880
<211> LENGTH: 25
<212> TYPE: DNA
<213> ORGANISM: Homo sapiens

<400> SEQUENCE: 880
tatcaggcat acaacaaagg cagga 25

<210> SEQ ID NO 881
<211> LENGTH: 25
<212> TYPE: DNA
<213> ORGANISM: Homo sapiens

<400> SEQUENCE: 881
tatacactgg ctgatttggg acagg 25

<210> SEQ ID NO 882
<211> LENGTH: 25
<212> TYPE: DNA
<213> ORGANISM: Homo sapiens

<400> SEQUENCE: 882
gggtagccac tatatcctgg aggtc 25

<210> SEQ ID NO 883
<211> LENGTH: 25
<212> TYPE: DNA
<213> ORGANISM: Homo sapiens

<400> SEQUENCE: 883
gaggaggata cccaactggc aagtt 25

<210> SEQ ID NO 884
<211> LENGTH: 25
<212> TYPE: DNA
<213> ORGANISM: Homo sapiens

<400> SEQUENCE: 884
gcaagtttgt ttccgggtga gaagc 25

<210> SEQ ID NO 885
<211> LENGTH: 25
<212> TYPE: DNA
<213> ORGANISM: Homo sapiens

<400> SEQUENCE: 885
taacacactg tctacaaggc cacaa 25

<210> SEQ ID NO 886
<211> LENGTH: 25
<212> TYPE: DNA
<213> ORGANISM: Homo sapiens

<400> SEQUENCE: 886
tgaatcggga tactctaaaa ctaca 25

<210> SEQ ID NO 887
<211> LENGTH: 25
<212> TYPE: DNA
<213> ORGANISM: Homo sapiens

<400> SEQUENCE: 887
gatacgggat gaaactgagg tgact 25

<210> SEQ ID NO 888
<211> LENGTH: 25
<212> TYPE: DNA
<213> ORGANISM: Homo sapiens

<400> SEQUENCE: 888
cttgtaacaa ggagccattc cataa                                          25

<210> SEQ ID NO 889
<211> LENGTH: 25
<212> TYPE: DNA
<213> ORGANISM: Homo sapiens

<400> SEQUENCE: 889
gccattccat aaaaatcctc ttgtg                                          25

<210> SEQ ID NO 890
<211> LENGTH: 25
<212> TYPE: DNA
<213> ORGANISM: Homo sapiens

<400> SEQUENCE: 890
tgggagtaac ctttgcgcca acacc                                          25

<210> SEQ ID NO 891
<211> LENGTH: 25
<212> TYPE: DNA
<213> ORGANISM: Homo sapiens

<400> SEQUENCE: 891
ggactcaagg gtgcgcccgc attcg                                          25

<210> SEQ ID NO 892
<211> LENGTH: 25
<212> TYPE: DNA
<213> ORGANISM: Homo sapiens

<400> SEQUENCE: 892
ctggaccgct gggatcaaac cgcgg                                          25

<210> SEQ ID NO 893
<211> LENGTH: 25
<212> TYPE: DNA
<213> ORGANISM: Homo sapiens

<400> SEQUENCE: 893
acggccagac gtcggacgac tactc                                          25

<210> SEQ ID NO 894
<211> LENGTH: 25
<212> TYPE: DNA
<213> ORGANISM: Homo sapiens

<400> SEQUENCE: 894
tcatgtctgc ggtggagaga ctccg                                          25

<210> SEQ ID NO 895
<211> LENGTH: 25
<212> TYPE: DNA
<213> ORGANISM: Homo sapiens

<400> SEQUENCE: 895
aattctctcc tgcacttgtg aactg                                          25

<210> SEQ ID NO 896
<211> LENGTH: 25
<212> TYPE: DNA
<213> ORGANISM: Homo sapiens

```
<400> SEQUENCE: 896
cataaaaggt tcgagtcttc cctgc                                          25

<210> SEQ ID NO 897
<211> LENGTH: 25
<212> TYPE: DNA
<213> ORGANISM: Homo sapiens

<400> SEQUENCE: 897
tgatgcagac cataaaaggt tcgag                                          25

<210> SEQ ID NO 898
<211> LENGTH: 25
<212> TYPE: DNA
<213> ORGANISM: Homo sapiens

<400> SEQUENCE: 898
gagggtttac caaatgatca cgttc                                          25

<210> SEQ ID NO 899
<211> LENGTH: 25
<212> TYPE: DNA
<213> ORGANISM: Homo sapiens

<400> SEQUENCE: 899
tatgactaga cagccccaat acttg                                          25

<210> SEQ ID NO 900
<211> LENGTH: 25
<212> TYPE: DNA
<213> ORGANISM: Homo sapiens

<400> SEQUENCE: 900
cagctgcctt tttgccgagg ccaac                                          25

<210> SEQ ID NO 901
<211> LENGTH: 25
<212> TYPE: DNA
<213> ORGANISM: Homo sapiens

<400> SEQUENCE: 901
tcatcaaaaa gagtggatcc tcagg                                          25

<210> SEQ ID NO 902
<211> LENGTH: 25
<212> TYPE: DNA
<213> ORGANISM: Homo sapiens

<400> SEQUENCE: 902
caaccatatt cagcaagagg aactg                                          25

<210> SEQ ID NO 903
<211> LENGTH: 25
<212> TYPE: DNA
<213> ORGANISM: Homo sapiens

<400> SEQUENCE: 903
tatgacaaga gcgaacaaat ggtag                                          25

<210> SEQ ID NO 904
<211> LENGTH: 25
<212> TYPE: DNA
<213> ORGANISM: Homo sapiens
```

```
<400> SEQUENCE: 904
tgggaaaaca cagctctaat atgac                                          25

<210> SEQ ID NO 905
<211> LENGTH: 25
<212> TYPE: DNA
<213> ORGANISM: Homo sapiens

<400> SEQUENCE: 905
tggagtcagt ccaagacaac tcaaa                                          25

<210> SEQ ID NO 906
<211> LENGTH: 25
<212> TYPE: DNA
<213> ORGANISM: Homo sapiens

<400> SEQUENCE: 906
gaatcagaaa actggagtca gtcca                                          25

<210> SEQ ID NO 907
<211> LENGTH: 25
<212> TYPE: DNA
<213> ORGANISM: Homo sapiens

<400> SEQUENCE: 907
aggtcttgaa tctgcctgca ccccg                                          25

<210> SEQ ID NO 908
<211> LENGTH: 25
<212> TYPE: DNA
<213> ORGANISM: Homo sapiens

<400> SEQUENCE: 908
gtattcatag agaccaagca ccgct                                          25

<210> SEQ ID NO 909
<211> LENGTH: 25
<212> TYPE: DNA
<213> ORGANISM: Homo sapiens

<400> SEQUENCE: 909
gctttgccga cacagccatc ttctt                                          25

<210> SEQ ID NO 910
<211> LENGTH: 25
<212> TYPE: DNA
<213> ORGANISM: Homo sapiens

<400> SEQUENCE: 910
tccatagagc tttgccgaca cagcc                                          25

<210> SEQ ID NO 911
<211> LENGTH: 25
<212> TYPE: DNA
<213> ORGANISM: Homo sapiens

<400> SEQUENCE: 911
gattcatttt ttgtgatctg accca                                          25

<210> SEQ ID NO 912
<211> LENGTH: 25
<212> TYPE: DNA
```

```
<213> ORGANISM: Homo sapiens

<400> SEQUENCE: 912
aattggcgtg ccaagttctg cccag                                            25

<210> SEQ ID NO 913
<211> LENGTH: 25
<212> TYPE: DNA
<213> ORGANISM: Homo sapiens

<400> SEQUENCE: 913
ggctgtaaca tctcgagtct gtgac                                            25

<210> SEQ ID NO 914
<211> LENGTH: 25
<212> TYPE: DNA
<213> ORGANISM: Homo sapiens

<400> SEQUENCE: 914
gatagaaaga acctcaaact cagct                                            25

<210> SEQ ID NO 915
<211> LENGTH: 25
<212> TYPE: DNA
<213> ORGANISM: Homo sapiens

<400> SEQUENCE: 915
gacacctggg agcaccaatg ctgga                                            25

<210> SEQ ID NO 916
<211> LENGTH: 25
<212> TYPE: DNA
<213> ORGANISM: Homo sapiens

<400> SEQUENCE: 916
tggagatccc aagagagcga cggaa                                            25

<210> SEQ ID NO 917
<211> LENGTH: 25
<212> TYPE: DNA
<213> ORGANISM: Homo sapiens

<400> SEQUENCE: 917
cctgttcctc aatccaagac ttggg                                            25

<210> SEQ ID NO 918
<211> LENGTH: 25
<212> TYPE: DNA
<213> ORGANISM: Homo sapiens

<400> SEQUENCE: 918
gagcatatag ttgcagctcc tccca                                            25

<210> SEQ ID NO 919
<211> LENGTH: 25
<212> TYPE: DNA
<213> ORGANISM: Homo sapiens

<400> SEQUENCE: 919
gctttgcagc agacacgatg gctga                                            25

<210> SEQ ID NO 920
<211> LENGTH: 25
```

<212> TYPE: DNA
<213> ORGANISM: Homo sapiens

<400> SEQUENCE: 920
gccgctgggc atattttcac aaaga                                  25

<210> SEQ ID NO 921
<211> LENGTH: 25
<212> TYPE: DNA
<213> ORGANISM: Homo sapiens

<400> SEQUENCE: 921
gatggtcttc ccgtttttgg ctcta                                  25

<210> SEQ ID NO 922
<211> LENGTH: 25
<212> TYPE: DNA
<213> ORGANISM: Homo sapiens

<400> SEQUENCE: 922
tgtgcgtaac agagcgcatc agcca                                  25

<210> SEQ ID NO 923
<211> LENGTH: 25
<212> TYPE: DNA
<213> ORGANISM: Homo sapiens

<400> SEQUENCE: 923
cggcattgag gatgaccttc gggtt                                  25

<210> SEQ ID NO 924
<211> LENGTH: 25
<212> TYPE: DNA
<213> ORGANISM: Homo sapiens

<400> SEQUENCE: 924
gagtttgttc cagagccagg atgaa                                  25

<210> SEQ ID NO 925
<211> LENGTH: 25
<212> TYPE: DNA
<213> ORGANISM: Homo sapiens

<400> SEQUENCE: 925
taatgttcga agagaggcat cctcc                                  25

<210> SEQ ID NO 926
<211> LENGTH: 25
<212> TYPE: DNA
<213> ORGANISM: Homo sapiens

<400> SEQUENCE: 926
tgttgttaac atcagcaagc tggca                                  25

<210> SEQ ID NO 927
<211> LENGTH: 25
<212> TYPE: DNA
<213> ORGANISM: Homo sapiens

<400> SEQUENCE: 927
cgcctgctat gtctaaatgt gccca                                  25

<210> SEQ ID NO 928

<211> LENGTH: 25
<212> TYPE: DNA
<213> ORGANISM: Homo sapiens

<400> SEQUENCE: 928
cagagtgaag acattttga gtatc                                       25

<210> SEQ ID NO 929
<211> LENGTH: 25
<212> TYPE: DNA
<213> ORGANISM: Homo sapiens

<400> SEQUENCE: 929
gttcctagca tcacaaatct gagtt                                      25

<210> SEQ ID NO 930
<211> LENGTH: 25
<212> TYPE: DNA
<213> ORGANISM: Homo sapiens

<400> SEQUENCE: 930
gactgggtgc gcgatgattt cctga                                      25

<210> SEQ ID NO 931
<211> LENGTH: 25
<212> TYPE: DNA
<213> ORGANISM: Homo sapiens

<400> SEQUENCE: 931
agtcggcgcc ccaacagaag tacat                                      25

<210> SEQ ID NO 932
<211> LENGTH: 25
<212> TYPE: DNA
<213> ORGANISM: Homo sapiens

<400> SEQUENCE: 932 gaagacccctt cctttgtggc acaca                                     25

<210> SEQ ID NO 933
<211> LENGTH: 25
<212> TYPE: DNA
<213> ORGANISM: Homo sapiens

<400> SEQUENCE: 933
taatgccagg gagtggtagt gtcca                                      25

<210> SEQ ID NO 934
<211> LENGTH: 25
<212> TYPE: DNA
<213> ORGANISM: Homo sapiens

<400> SEQUENCE: 934
agccaaacga agtcccacag agaga                                      25

<210> SEQ ID NO 935
<211> LENGTH: 25
<212> TYPE: DNA
<213> ORGANISM: Homo sapiens

<400> SEQUENCE: 935
caagttgtgg acctctcttc tcagg                                      25

```
<210> SEQ ID NO 936
<211> LENGTH: 25
<212> TYPE: DNA
<213> ORGANISM: Homo sapiens

<400> SEQUENCE: 936
gaccagtggt gtgcacatat gccag                                        25

<210> SEQ ID NO 937
<211> LENGTH: 25
<212> TYPE: DNA
<213> ORGANISM: Homo sapiens

<400> SEQUENCE: 937
aaagtcataa atccatgctt agagt                                        25

<210> SEQ ID NO 938
<211> LENGTH: 25
<212> TYPE: DNA
<213> ORGANISM: Homo sapiens

<400> SEQUENCE: 938
caaagttggc atatgttcca gcaaa                                        25

<210> SEQ ID NO 939
<211> LENGTH: 25
<212> TYPE: DNA
<213> ORGANISM: Homo sapiens

<400> SEQUENCE: 939
tacatattta tggtccggcc ctgcc                                        25

<210> SEQ ID NO 940
<211> LENGTH: 25
<212> TYPE: DNA
<213> ORGANISM: Homo sapiens

<400> SEQUENCE: 940
tcccgggagc acgtgtggaa ctagt                                        25

<210> SEQ ID NO 941
<211> LENGTH: 25
<212> TYPE: DNA
<213> ORGANISM: Homo sapiens

<400> SEQUENCE: 941
cttataattt atcagacaga gccac                                        25

<210> SEQ ID NO 942
<211> LENGTH: 25
<212> TYPE: DNA
<213> ORGANISM: Homo sapiens

<400> SEQUENCE: 942
gaaggtatct cttgccattt ctaag                                        25

<210> SEQ ID NO 943
<211> LENGTH: 25
<212> TYPE: DNA
<213> ORGANISM: Homo sapiens

<400> SEQUENCE: 943
gcagatcatc ctcgagacac gtagt                                        25
```

```
<210> SEQ ID NO 944
<211> LENGTH: 25
<212> TYPE: DNA
<213> ORGANISM: Homo sapiens

<400> SEQUENCE: 944
taagcatctg gatcagcgga ttcag                                  25

<210> SEQ ID NO 945
<211> LENGTH: 25
<212> TYPE: DNA
<213> ORGANISM: Homo sapiens

<400> SEQUENCE: 945
ggtggttatc ccgaaagagc tgtct                                  25

<210> SEQ ID NO 946
<211> LENGTH: 25
<212> TYPE: DNA
<213> ORGANISM: Homo sapiens

<400> SEQUENCE: 946
tgtgaatcag cttgcaataa tttaa                                  25

<210> SEQ ID NO 947
<211> LENGTH: 25
<212> TYPE: DNA
<213> ORGANISM: Homo sapiens

<400> SEQUENCE: 947
gagcatcttt aaccaggcga cttcg                                  25

<210> SEQ ID NO 948
<211> LENGTH: 25
<212> TYPE: DNA
<213> ORGANISM: Homo sapiens

<400> SEQUENCE: 948
catgcaggaa cccatttcag gatac                                  25

<210> SEQ ID NO 949
<211> LENGTH: 25
<212> TYPE: DNA
<213> ORGANISM: Homo sapiens

<400> SEQUENCE: 949
gagtccacac agcattccaa agagg                                  25

<210> SEQ ID NO 950
<211> LENGTH: 25
<212> TYPE: DNA
<213> ORGANISM: Homo sapiens

<400> SEQUENCE: 950
aaagcgtatg cagagcgcat ctcca                                  25

<210> SEQ ID NO 951
<211> LENGTH: 25
<212> TYPE: DNA
<213> ORGANISM: Homo sapiens

<400> SEQUENCE: 951
tttggtccac aggtatggag atccc                                  25
```

<210> SEQ ID NO 952
<211> LENGTH: 25
<212> TYPE: DNA
<213> ORGANISM: Homo sapiens

<400> SEQUENCE: 952
gctgtcatta gttcttcagg gtaga                                              25

<210> SEQ ID NO 953
<211> LENGTH: 25
<212> TYPE: DNA
<213> ORGANISM: Homo sapiens

<400> SEQUENCE: 953
catccaaggt tagtttgtgg aaagc                                              25

<210> SEQ ID NO 954
<211> LENGTH: 25
<212> TYPE: DNA
<213> ORGANISM: Homo sapiens

<400> SEQUENCE: 954
ccagagattc gtgccctatg cggat                                              25

<210> SEQ ID NO 955
<211> LENGTH: 25
<212> TYPE: DNA
<213> ORGANISM: Homo sapiens

<400> SEQUENCE: 955
tgagcatggg tgagacaaat cctct                                              25

<210> SEQ ID NO 956
<211> LENGTH: 25
<212> TYPE: DNA
<213> ORGANISM: Homo sapiens

<400> SEQUENCE: 956
ttgcgctgca gagcgggaac cagct                                              25

<210> SEQ ID NO 957
<211> LENGTH: 25
<212> TYPE: DNA
<213> ORGANISM: Homo sapiens

<400> SEQUENCE: 957
gagcagcaga gttggcgcgt cacct                                              25

<210> SEQ ID NO 958
<211> LENGTH: 25
<212> TYPE: DNA
<213> ORGANISM: Homo sapiens

<400> SEQUENCE: 958
gaaggccaag gtaaaatccc atcac                                              25

<210> SEQ ID NO 959
<211> LENGTH: 25
<212> TYPE: DNA
<213> ORGANISM: Homo sapiens

<400> SEQUENCE: 959

```
gagaatcagc atgtgctctg ctcct                                          25

<210> SEQ ID NO 960
<211> LENGTH: 25
<212> TYPE: DNA
<213> ORGANISM: Homo sapiens

<400> SEQUENCE: 960
gcaagagaat ggtaatctcc acatg                                          25

<210> SEQ ID NO 961
<211> LENGTH: 25
<212> TYPE: DNA
<213> ORGANISM: Homo sapiens

<400> SEQUENCE: 961
tccagcaccg aaagtaaaca gcagc                                          25

<210> SEQ ID NO 962
<211> LENGTH: 25
<212> TYPE: DNA
<213> ORGANISM: Homo sapiens

<400> SEQUENCE: 962
gatgatactt tcactggaag cggca                                          25

<210> SEQ ID NO 963
<211> LENGTH: 25
<212> TYPE: DNA
<213> ORGANISM: Homo sapiens

<400> SEQUENCE: 963
tgttacttga ggtcaccact aagct                                          25

<210> SEQ ID NO 964
<211> LENGTH: 25
<212> TYPE: DNA
<213> ORGANISM: Homo sapiens

<400> SEQUENCE: 964
ttaactcctt ttctgaggta tggct                                          25

<210> SEQ ID NO 965
<211> LENGTH: 25
<212> TYPE: DNA
<213> ORGANISM: Homo sapiens

<400> SEQUENCE: 965
ccttcattca gagtaggaat tgtcc                                          25

<210> SEQ ID NO 966
<211> LENGTH: 25
<212> TYPE: DNA
<213> ORGANISM: Homo sapiens

<400> SEQUENCE: 966
catgttagta atccagtcct tttgg                                          25

<210> SEQ ID NO 967
<211> LENGTH: 25
<212> TYPE: DNA
<213> ORGANISM: Homo sapiens

<400> SEQUENCE: 967
```
tggagcacct gcaaaaagaa aacct 25

<210> SEQ ID NO 968
<211> LENGTH: 25
<212> TYPE: DNA
<213> ORGANISM: Homo sapiens

<400> SEQUENCE: 968
cagcactaag tgttgtaggg tccca 25

<210> SEQ ID NO 969
<211> LENGTH: 25
<212> TYPE: DNA
<213> ORGANISM: Homo sapiens

<400> SEQUENCE: 969
gcagattatc tttgaggcag gtggt 25

<210> SEQ ID NO 970
<211> LENGTH: 25
<212> TYPE: DNA
<213> ORGANISM: Homo sapiens

<400> SEQUENCE: 970
aatccaactg gcatatgacg gctgt 25

<210> SEQ ID NO 971
<211> LENGTH: 25
<212> TYPE: DNA
<213> ORGANISM: Homo sapiens

<400> SEQUENCE: 971
gaaagtgact gaatatgacg cagca 25

<210> SEQ ID NO 972
<211> LENGTH: 25
<212> TYPE: DNA
<213> ORGANISM: Homo sapiens

<400> SEQUENCE: 972
tagatcaaac gtgggcctca aagcg 25

<210> SEQ ID NO 973
<211> LENGTH: 25
<212> TYPE: DNA
<213> ORGANISM: Homo sapiens

<400> SEQUENCE: 973
tgaacatccc atattccggc tggat 25

<210> SEQ ID NO 974
<211> LENGTH: 25
<212> TYPE: DNA
<213> ORGANISM: Homo sapiens

<400> SEQUENCE: 974
tcaaagttat caccttcatc atcca 25

<210> SEQ ID NO 975
<211> LENGTH: 25
<212> TYPE: DNA
<213> ORGANISM: Homo sapiens -continued

```
<400> SEQUENCE: 975
taagtttgtg tcgtttctgt cccag                                          25

<210> SEQ ID NO 976
<211> LENGTH: 25
<212> TYPE: DNA
<213> ORGANISM: Homo sapiens

<400> SEQUENCE: 976
taggaaggaa aactgaattt aatca                                          25

<210> SEQ ID NO 977
<211> LENGTH: 25
<212> TYPE: DNA
<213> ORGANISM: Homo sapiens

<400> SEQUENCE: 977
cagtcacggg ttctaaccgg ccagt                                          25

<210> SEQ ID NO 978
<211> LENGTH: 25
<212> TYPE: DNA
<213> ORGANISM: Homo sapiens

<400> SEQUENCE: 978
tagctgctat ttactgaaca ctgga                                          25

<210> SEQ ID NO 979
<211> LENGTH: 25
<212> TYPE: DNA
<213> ORGANISM: Homo sapiens

<400> SEQUENCE: 979
tcatagaagg ctcagatcaa caaag                                          25

<210> SEQ ID NO 980
<211> LENGTH: 25
<212> TYPE: DNA
<213> ORGANISM: Homo sapiens

<400> SEQUENCE: 980
tgtgtatgct tgtcactctt gggcc                                          25

<210> SEQ ID NO 981
<211> LENGTH: 25
<212> TYPE: DNA
<213> ORGANISM: Homo sapiens

<400> SEQUENCE: 981
tcagcacctg ttccctatca tattg                                          25

<210> SEQ ID NO 982
<211> LENGTH: 25
<212> TYPE: DNA
<213> ORGANISM: Homo sapiens

<400> SEQUENCE: 982
gaatttgggc cgttgcatct gatta                                          25

<210> SEQ ID NO 983
<211> LENGTH: 25
<212> TYPE: DNA
<213> ORGANISM: Homo sapiens
```

```
<400> SEQUENCE: 983
tgagaacgtt ggattgaaag cggca                                     25

<210> SEQ ID NO 984
<211> LENGTH: 25
<212> TYPE: DNA
<213> ORGANISM: Homo sapiens

<400> SEQUENCE: 984
aaaagagatg gttgtctgtc aggga                                     25

<210> SEQ ID NO 985
<211> LENGTH: 25
<212> TYPE: DNA
<213> ORGANISM: Homo sapiens

<400> SEQUENCE: 985
tgagtttcac tgtggccttg ggcct                                     25

<210> SEQ ID NO 986
<211> LENGTH: 25
<212> TYPE: DNA
<213> ORGANISM: Homo sapiens

<400> SEQUENCE: 986
gaggctggaa gtcacctgct gcata                                     25

<210> SEQ ID NO 987
<211> LENGTH: 25
<212> TYPE: DNA
<213> ORGANISM: Homo sapiens

<400> SEQUENCE: 987
tcctgcaggg cttgattcca gtaag                                     25

<210> SEQ ID NO 988
<211> LENGTH: 25
<212> TYPE: DNA
<213> ORGANISM: Homo sapiens

<400> SEQUENCE: 988
tcagcagcga aagcctggca catgc                                     25

<210> SEQ ID NO 989
<211> LENGTH: 25
<212> TYPE: DNA
<213> ORGANISM: Homo sapiens

<400> SEQUENCE: 989
tgtgttgcgg cagtcgacac gaagc                                     25

<210> SEQ ID NO 990
<211> LENGTH: 25
<212> TYPE: DNA
<213> ORGANISM: Homo sapiens

<400> SEQUENCE: 990
gacgcatagt gcaggaatct ctccc                                     25

<210> SEQ ID NO 991
<211> LENGTH: 25
<212> TYPE: DNA
```

```
<213> ORGANISM: Homo sapiens

<400> SEQUENCE: 991
gaacacaagt gggacgagtc accct                                     25

<210> SEQ ID NO 992
<211> LENGTH: 25
<212> TYPE: DNA
<213> ORGANISM: Homo sapiens

<400> SEQUENCE: 992
aacacaagtg ggacgagtca ccctt                                     25

<210> SEQ ID NO 993
<211> LENGTH: 25
<212> TYPE: DNA
<213> ORGANISM: Homo sapiens

<400> SEQUENCE: 993
cacaagtggg acgagtcacc cttta                                     25

<210> SEQ ID NO 994
<211> LENGTH: 25
<212> TYPE: DNA
<213> ORGANISM: Homo sapiens

<400> SEQUENCE: 994
ttaaagggtg ctgcacaaaa gactc                                     25

<210> SEQ ID NO 995
<211> LENGTH: 25
<212> TYPE: DNA
<213> ORGANISM: Homo sapiens

<400> SEQUENCE: 995
taaagggtgc tgcacaaaag actct                                     25

<210> SEQ ID NO 996
<211> LENGTH: 25
<212> TYPE: DNA
<213> ORGANISM: Homo sapiens

<400> SEQUENCE: 996
agggtgctgc acaaaagact ctttc                                     25

<210> SEQ ID NO 997
<211> LENGTH: 25
<212> TYPE: DNA
<213> ORGANISM: Homo sapiens

<400> SEQUENCE: 997
gggtgctgca caaaagactc tttct                                     25

<210> SEQ ID NO 998
<211> LENGTH: 25
<212> TYPE: DNA
<213> ORGANISM: Homo sapiens

<400> SEQUENCE: 998
ggtgctgcac aaaagactct ttctc                                     25

<210> SEQ ID NO 999
<211> LENGTH: 25
```

```
<212> TYPE: DNA
<213> ORGANISM: Homo sapiens

<400> SEQUENCE: 999
cgtgacctga aaaactacta tggaa                                         25

<210> SEQ ID NO 1000
<211> LENGTH: 25
<212> TYPE: DNA
<213> ORGANISM: Homo sapiens

<400> SEQUENCE: 1000
tgtacctggc ttatagtaac agctc                                         25

<210> SEQ ID NO 1001
<211> LENGTH: 25
<212> TYPE: DNA
<213> ORGANISM: Homo sapiens

<400> SEQUENCE: 1001
tggagcctga gagcgattga caccg                                         25

<210> SEQ ID NO 1002
<211> LENGTH: 25
<212> TYPE: DNA
<213> ORGANISM: Homo sapiens

<400> SEQUENCE: 1002
catcatcaaa gttcccagac agaca                                         25

<210> SEQ ID NO 1003
<211> LENGTH: 25
<212> TYPE: DNA
<213> ORGANISM: Homo sapiens

<400> SEQUENCE: 1003
gtgatacaag tccagcaaac cccat                                         25

<210> SEQ ID NO 1004
<211> LENGTH: 25
<212> TYPE: DNA
<213> ORGANISM: Homo sapiens

<400> SEQUENCE: 1004
agtcaccaca taataagtaa cttat                                         25

<210> SEQ ID NO 1005
<211> LENGTH: 25
<212> TYPE: DNA
<213> ORGANISM: Homo sapiens

<400> SEQUENCE: 1005
catgactctg ggttgcttga aggac                                         25

<210> SEQ ID NO 1006
<211> LENGTH: 25
<212> TYPE: DNA
<213> ORGANISM: Homo sapiens

<400> SEQUENCE: 1006
ggcatgttga cacctaaagc aagtg                                         25

<210> SEQ ID NO 1007
```

<211> LENGTH: 25
<212> TYPE: DNA
<213> ORGANISM: Homo sapiens

<400> SEQUENCE: 1007
ctttgaaact catagcactg tgatg                                          25

<210> SEQ ID NO 1008
<211> LENGTH: 25
<212> TYPE: DNA
<213> ORGANISM: Homo sapiens

<400> SEQUENCE: 1008
gatcagcata tgtgcagtcc tgtgg                                          25

<210> SEQ ID NO 1009
<211> LENGTH: 25
<212> TYPE: DNA
<213> ORGANISM: Homo sapiens

<400> SEQUENCE: 1009
cgaagtttgt tagccatgac atggg                                          25

<210> SEQ ID NO 1010
<211> LENGTH: 25
<212> TYPE: DNA
<213> ORGANISM: Homo sapiens

<400> SEQUENCE: 1010
ggactcaaat ctgcttcagg actaa                                          25

<210> SEQ ID NO 1011
<211> LENGTH: 25
<212> TYPE: DNA
<213> ORGANISM: Homo sapiens

<400> SEQUENCE: 1011
tatctggagg caaatcctct gggag                                          25

<210> SEQ ID NO 1012
<211> LENGTH: 25
<212> TYPE: DNA
<213> ORGANISM: Homo sapiens

<400> SEQUENCE: 1012
tgcattcctg ccacaaaagt ctaga                                          25

<210> SEQ ID NO 1013
<211> LENGTH: 25
<212> TYPE: DNA
<213> ORGANISM: Homo sapiens

<400> SEQUENCE: 1013
tagtctttgg gaaagccggc ctgac                                          25

<210> SEQ ID NO 1014
<211> LENGTH: 25
<212> TYPE: DNA
<213> ORGANISM: Homo sapiens

<400> SEQUENCE: 1014
tcggtgagat gttcaggatt actta                                          25

```
<210> SEQ ID NO 1015
<211> LENGTH: 25
<212> TYPE: DNA
<213> ORGANISM: Homo sapiens

<400> SEQUENCE: 1015
agaatttcaa agcaggcagg cactg                                          25

<210> SEQ ID NO 1016
<211> LENGTH: 25
<212> TYPE: DNA
<213> ORGANISM: Homo sapiens

<400> SEQUENCE: 1016
gcatcatgac gatactccct ggtga                                          25

<210> SEQ ID NO 1017
<211> LENGTH: 25
<212> TYPE: DNA
<213> ORGANISM: Homo sapiens

<400> SEQUENCE: 1017
tatccacaac atcaaggagc tctcg                                          25

<210> SEQ ID NO 1018
<211> LENGTH: 25
<212> TYPE: DNA
<213> ORGANISM: Homo sapiens

<400> SEQUENCE: 1018
ctgggctgga tgtaaagaac ttgcc                                          25

<210> SEQ ID NO 1019
<211> LENGTH: 25
<212> TYPE: DNA
<213> ORGANISM: Homo sapiens

<400> SEQUENCE: 1019
tgcacagatc taagaacacg agggt                                          25

<210> SEQ ID NO 1020
<211> LENGTH: 25
<212> TYPE: DNA
<213> ORGANISM: Homo sapiens

<400> SEQUENCE: 1020
ttgggcacca tttcattgga gctgt                                          25

<210> SEQ ID NO 1021
<211> LENGTH: 25
<212> TYPE: DNA
<213> ORGANISM: Homo sapiens

<400> SEQUENCE: 1021
gaccaacttt gatacggtat tccag                                          25

<210> SEQ ID NO 1022
<211> LENGTH: 25
<212> TYPE: DNA
<213> ORGANISM: Homo sapiens

<400> SEQUENCE: 1022
gctcatcatt taagtcagaa aggtg                                          25
```

<210> SEQ ID NO 1023
<211> LENGTH: 25
<212> TYPE: DNA
<213> ORGANISM: Homo sapiens

<400> SEQUENCE: 1023
tttcctgacc agaggagggc tctct                                25

<210> SEQ ID NO 1024
<211> LENGTH: 25
<212> TYPE: DNA
<213> ORGANISM: Homo sapiens

<400> SEQUENCE: 1024
tctgcccagg cttaaatgat atctc                                25

<210> SEQ ID NO 1025
<211> LENGTH: 25
<212> TYPE: DNA
<213> ORGANISM: Homo sapiens

<400> SEQUENCE: 1025
ttcctgtgaa aatgttgtaa gaaca                                25

<210> SEQ ID NO 1026
<211> LENGTH: 25
<212> TYPE: DNA
<213> ORGANISM: Homo sapiens

<400> SEQUENCE: 1026
tgcctgtgcc tccaacctga actgg                                25

<210> SEQ ID NO 1027
<211> LENGTH: 25
<212> TYPE: DNA
<213> ORGANISM: Homo sapiens

<400> SEQUENCE: 1027
gagtgaaaca gagacctagc gcaga                                25

<210> SEQ ID NO 1028
<211> LENGTH: 25
<212> TYPE: DNA
<213> ORGANISM: Homo sapiens

<400> SEQUENCE: 1028 cagtcttta tgcatccggc gggag                                 25

<210> SEQ ID NO 1029
<211> LENGTH: 25
<212> TYPE: DNA
<213> ORGANISM: Homo sapiens

<400> SEQUENCE: 1029
aaatgtgttg atcctgtgat gaagg                                25

<210> SEQ ID NO 1030
<211> LENGTH: 25
<212> TYPE: DNA
<213> ORGANISM: Homo sapiens

<400> SEQUENCE: 1030
gaagcccaga tgaaatgtgt tgatc                                25

<210> SEQ ID NO 1031
<211> LENGTH: 25
<212> TYPE: DNA
<213> ORGANISM: Homo sapiens

<400> SEQUENCE: 1031
gatttagatt taagaagccc agatg                                              25

<210> SEQ ID NO 1032
<211> LENGTH: 25
<212> TYPE: DNA
<213> ORGANISM: Homo sapiens

<400> SEQUENCE: 1032
catataagcc ccaactatta ggaaa                                              25

<210> SEQ ID NO 1033
<211> LENGTH: 25
<212> TYPE: DNA
<213> ORGANISM: Homo sapiens

<400> SEQUENCE: 1033
cacatgagtc atataagccc caact                                              25

<210> SEQ ID NO 1034
<211> LENGTH: 25
<212> TYPE: DNA
<213> ORGANISM: Homo sapiens

<400> SEQUENCE: 1034
acacatgagt catataagcc ccaac                                              25

<210> SEQ ID NO 1035
<211> LENGTH: 25
<212> TYPE: DNA
<213> ORGANISM: Homo sapiens

<400> SEQUENCE: 1035
taaatggcct ggaatgaggt gacac                                              25

<210> SEQ ID NO 1036
<211> LENGTH: 25
<212> TYPE: DNA
<213> ORGANISM: Homo sapiens

<400> SEQUENCE: 1036
caaacgtgat gtccgccata ctgga                                              25

<210> SEQ ID NO 1037
<211> LENGTH: 25
<212> TYPE: DNA
<213> ORGANISM: Homo sapiens

<400> SEQUENCE: 1037
gcacccactg tggatcaatc agaac                                              25

<210> SEQ ID NO 1038
<211> LENGTH: 25
<212> TYPE: DNA
<213> ORGANISM: Homo sapiens

<400> SEQUENCE: 1038

```
aaagcagcag aatgatttcc aaatc                                              25

<210> SEQ ID NO 1039
<211> LENGTH: 25
<212> TYPE: DNA
<213> ORGANISM: Homo sapiens

<400> SEQUENCE: 1039
catttggttc cagatctaag agagg                                              25

<210> SEQ ID NO 1040
<211> LENGTH: 25
<212> TYPE: DNA
<213> ORGANISM: Homo sapiens

<400> SEQUENCE: 1040
taacagtgac ttctcgcagg gtgtc                                              25

<210> SEQ ID NO 1041
<211> LENGTH: 25
<212> TYPE: DNA
<213> ORGANISM: Homo sapiens

<400> SEQUENCE: 1041
tacaggaatc cttctggcct ttggc                                              25

<210> SEQ ID NO 1042
<211> LENGTH: 25
<212> TYPE: DNA
<213> ORGANISM: Homo sapiens

<400> SEQUENCE: 1042
gagactatag cgtggaagac acctt                                              25

<210> SEQ ID NO 1043
<211> LENGTH: 25
<212> TYPE: DNA
<213> ORGANISM: Homo sapiens

<400> SEQUENCE: 1043
gattccaggc tttgtggcaa cacca                                              25

<210> SEQ ID NO 1044
<211> LENGTH: 25
<212> TYPE: DNA
<213> ORGANISM: Homo sapiens

<400> SEQUENCE: 1044
taacctgcga gcatattagg aaaaa                                              25

<210> SEQ ID NO 1045
<211> LENGTH: 25
<212> TYPE: DNA
<213> ORGANISM: Homo sapiens

<400> SEQUENCE: 1045
ggaccccata tgtgctctgc tttac                                              25

<210> SEQ ID NO 1046
<211> LENGTH: 25
<212> TYPE: DNA
<213> ORGANISM: Homo sapiens

<400> SEQUENCE: 1046
```

```
gacttacaag tgcaaaaatg gaccc                                              25

<210> SEQ ID NO 1047
<211> LENGTH: 25
<212> TYPE: DNA
<213> ORGANISM: Homo sapiens

<400> SEQUENCE: 1047
cagtgacctt attgcccttt ggcga                                              25

<210> SEQ ID NO 1048
<211> LENGTH: 25
<212> TYPE: DNA
<213> ORGANISM: Homo sapiens

<400> SEQUENCE: 1048
tgatccagca gaagttacac ctagt                                              25

<210> SEQ ID NO 1049
<211> LENGTH: 25
<212> TYPE: DNA
<213> ORGANISM: Homo sapiens

<400> SEQUENCE: 1049
taaacatttg ttgcaagggc ctatc                                              25

<210> SEQ ID NO 1050
<211> LENGTH: 25
<212> TYPE: DNA
<213> ORGANISM: Homo sapiens

<400> SEQUENCE: 1050
aatttgctgt ttaactgctt gcaat                                              25

<210> SEQ ID NO 1051
<211> LENGTH: 25
<212> TYPE: DNA
<213> ORGANISM: Homo sapiens

<400> SEQUENCE: 1051
tttgctgttt aactgcttgc aatga                                              25

<210> SEQ ID NO 1052
<211> LENGTH: 25
<212> TYPE: DNA
<213> ORGANISM: Homo sapiens

<400> SEQUENCE: 1052
ttgctgttta actgcttgca atgat                                              25

<210> SEQ ID NO 1053
<211> LENGTH: 25
<212> TYPE: DNA
<213> ORGANISM: Homo sapiens

<400> SEQUENCE: 1053
tcatcacagg actcgccacc agttg                                              25

<210> SEQ ID NO 1054
<211> LENGTH: 25
<212> TYPE: DNA
<213> ORGANISM: Homo sapiens
```

```
<400> SEQUENCE: 1054
cacaggactc gccaccagtt gtgta                                          25

<210> SEQ ID NO 1055
<211> LENGTH: 25
<212> TYPE: DNA
<213> ORGANISM: Homo sapiens

<400> SEQUENCE: 1055
acaggactcg ccaccagttg tgtag                                          25

<210> SEQ ID NO 1056
<211> LENGTH: 25
<212> TYPE: DNA
<213> ORGANISM: Homo sapiens

<400> SEQUENCE: 1056
caggactcgc caccagttgt gtagt                                          25

<210> SEQ ID NO 1057
<211> LENGTH: 25
<212> TYPE: DNA
<213> ORGANISM: Homo sapiens

<400> SEQUENCE: 1057
gactcgccac cagttgtgta gtctg                                          25

<210> SEQ ID NO 1058
<211> LENGTH: 25
<212> TYPE: DNA
<213> ORGANISM: Homo sapiens

<400> SEQUENCE: 1058
caccagttgt gtagtctgtc tcata                                          25

<210> SEQ ID NO 1059
<211> LENGTH: 25
<212> TYPE: DNA
<213> ORGANISM: Homo sapiens

<400> SEQUENCE: 1059
ccagtgtgga catcctgtgg tctgc                                          25

<210> SEQ ID NO 1060
<211> LENGTH: 25
<212> TYPE: DNA
<213> ORGANISM: Homo sapiens

<400> SEQUENCE: 1060
cagtgtggac atcctgtggt ctgcg                                          25

<210> SEQ ID NO 1061
<211> LENGTH: 25
<212> TYPE: DNA
<213> ORGANISM: Homo sapiens

<400> SEQUENCE: 1061
agtgtggaca tcctgtggtc tgcgc                                          25

<210> SEQ ID NO 1062
<211> LENGTH: 25
<212> TYPE: DNA
<213> ORGANISM: Homo sapiens
```

```
<400> SEQUENCE: 1062
tgtggacatc ctgtggtctg cgcgt                                    25

<210> SEQ ID NO 1063
<211> LENGTH: 25
<212> TYPE: DNA
<213> ORGANISM: Homo sapiens

<400> SEQUENCE: 1063
gtggacatcc tgtggtctgc gcgta                                    25

<210> SEQ ID NO 1064
<211> LENGTH: 25
<212> TYPE: DNA
<213> ORGANISM: Homo sapiens

<400> SEQUENCE: 1064
tggacatcct gtggtctgcg cgtac                                    25

<210> SEQ ID NO 1065
<211> LENGTH: 25
<212> TYPE: DNA
<213> ORGANISM: Homo sapiens

<400> SEQUENCE: 1065
ggacatcctg tggtctgcgc gtaca                                    25

<210> SEQ ID NO 1066
<211> LENGTH: 25
<212> TYPE: DNA
<213> ORGANISM: Homo sapiens

<400> SEQUENCE: 1066
gacatcctgt ggtctgcgcg tacac                                    25

<210> SEQ ID NO 1067
<211> LENGTH: 25
<212> TYPE: DNA
<213> ORGANISM: Homo sapiens

<400> SEQUENCE: 1067
acatcctgtg gtctgcgcgt acaca                                    25

<210> SEQ ID NO 1068
<211> LENGTH: 25
<212> TYPE: DNA
<213> ORGANISM: Homo sapiens

<400> SEQUENCE: 1068
catcctgtgg tctgcgcgta cacat                                    25

<210> SEQ ID NO 1069
<211> LENGTH: 25
<212> TYPE: DNA
<213> ORGANISM: Homo sapiens

<400> SEQUENCE: 1069
tggtctgcgc gtacacatgt gacag                                    25

<210> SEQ ID NO 1070
<211> LENGTH: 25
<212> TYPE: DNA
```

<213> ORGANISM: Homo sapiens

<400> SEQUENCE: 1070
ggtctgcgcg tacacatgtg acagg         25

<210> SEQ ID NO 1071
<211> LENGTH: 25
<212> TYPE: DNA
<213> ORGANISM: Homo sapiens

<400> SEQUENCE: 1071
gtctgcgcgt acacatgtga caggt         25

<210> SEQ ID NO 1072
<211> LENGTH: 25
<212> TYPE: DNA
<213> ORGANISM: Homo sapiens

<400> SEQUENCE: 1072
tctgcgcgta cacatgtgac aggta         25

<210> SEQ ID NO 1073
<211> LENGTH: 25
<212> TYPE: DNA
<213> ORGANISM: Homo sapiens

<400> SEQUENCE: 1073
tacacatgtg acaggtacgt gcacg         25

<210> SEQ ID NO 1074
<211> LENGTH: 25
<212> TYPE: DNA
<213> ORGANISM: Homo sapiens

<400> SEQUENCE: 1074
acacatgtga caggtacgtg cacgc         25

<210> SEQ ID NO 1075
<211> LENGTH: 25
<212> TYPE: DNA
<213> ORGANISM: Homo sapiens

<400> SEQUENCE: 1075
cacatgtgac aggtacgtgc acgcc         25

<210> SEQ ID NO 1076
<211> LENGTH: 25
<212> TYPE: DNA
<213> ORGANISM: Homo sapiens

<400> SEQUENCE: 1076
acatgtgaca ggtacgtgca cgccc         25

<210> SEQ ID NO 1077
<211> LENGTH: 25
<212> TYPE: DNA
<213> ORGANISM: Homo sapiens

<400> SEQUENCE: 1077
atgtgacagg tacgtgcacg cccac         25

<210> SEQ ID NO 1078
<211> LENGTH: 25

<212> TYPE: DNA
<213> ORGANISM: Homo sapiens

<400> SEQUENCE: 1078
catttgcatc ctttgaataa ttgta                                25

<210> SEQ ID NO 1079
<211> LENGTH: 25
<212> TYPE: DNA
<213> ORGANISM: Homo sapiens

<400> SEQUENCE: 1079
gcatcctttg aataattgta tttgg                                25

<210> SEQ ID NO 1080
<211> LENGTH: 25
<212> TYPE: DNA
<213> ORGANISM: Homo sapiens

<400> SEQUENCE: 1080
catcctttga ataattgtat ttggg                                25

<210> SEQ ID NO 1081
<211> LENGTH: 25
<212> TYPE: DNA
<213> ORGANISM: Homo sapiens

<400> SEQUENCE: 1081
cctttgaata attgtatttg ggatc                                25

<210> SEQ ID NO 1082
<211> LENGTH: 25
<212> TYPE: DNA
<213> ORGANISM: Homo sapiens

<400> SEQUENCE: 1082
ctttgaataa ttgtatttgg gatcc                                25

<210> SEQ ID NO 1083
<211> LENGTH: 25
<212> TYPE: DNA
<213> ORGANISM: Homo sapiens

<400> SEQUENCE: 1083
ttgaataatt gtatttggga tccac                                25

<210> SEQ ID NO 1084
<211> LENGTH: 25
<212> TYPE: DNA
<213> ORGANISM: Homo sapiens

<400> SEQUENCE: 1084
tgaataattg tatttgggat ccact                                25

<210> SEQ ID NO 1085
<211> LENGTH: 25
<212> TYPE: DNA
<213> ORGANISM: Homo sapiens

<400> SEQUENCE: 1085
gaataattgt atttgggatc cactg                                25

<210> SEQ ID NO 1086

```
<211> LENGTH: 25
<212> TYPE: DNA
<213> ORGANISM: Homo sapiens

<400> SEQUENCE: 1086
ctgtgacaac aagtgttgtt ccact                                  25

<210> SEQ ID NO 1087
<211> LENGTH: 25
<212> TYPE: DNA
<213> ORGANISM: Homo sapiens

<400> SEQUENCE: 1087
tgtgacaaca agtgttgttc cactg                                  25

<210> SEQ ID NO 1088
<211> LENGTH: 25
<212> TYPE: DNA
<213> ORGANISM: Homo sapiens

<400> SEQUENCE: 1088
gtgacaacaa gtgttgttcc actgc                                  25

<210> SEQ ID NO 1089
<211> LENGTH: 25
<212> TYPE: DNA
<213> ORGANISM: Homo sapiens

<400> SEQUENCE: 1089
tgacaacaag tgttgttcca ctgcc                                  25

<210> SEQ ID NO 1090
<211> LENGTH: 25
<212> TYPE: DNA
<213> ORGANISM: Homo sapiens

<400> SEQUENCE: 1090
gacaacaagt gttgttccac tgcca                                  25

<210> SEQ ID NO 1091
<211> LENGTH: 25
<212> TYPE: DNA
<213> ORGANISM: Homo sapiens

<400> SEQUENCE: 1091
acaacaagtg ttgttccact gccaa                                  25

<210> SEQ ID NO 1092
<211> LENGTH: 25
<212> TYPE: DNA
<213> ORGANISM: Homo sapiens

<400> SEQUENCE: 1092
caacaagtgt tgttccactg ccaaa                                  25

<210> SEQ ID NO 1093
<211> LENGTH: 25
<212> TYPE: DNA
<213> ORGANISM: Homo sapiens

<400> SEQUENCE: 1093
aacaagtgtt gttccactgc caaag                                  25
```

```
<210> SEQ ID NO 1094
<211> LENGTH: 25
<212> TYPE: DNA
<213> ORGANISM: Homo sapiens

<400> SEQUENCE: 1094
acaagtgttg ttccactgcc aaaga                                  25

<210> SEQ ID NO 1095
<211> LENGTH: 25
<212> TYPE: DNA
<213> ORGANISM: Homo sapiens

<400> SEQUENCE: 1095
caagtgttgt tccactgcca aagag                                  25

<210> SEQ ID NO 1096
<211> LENGTH: 25
<212> TYPE: DNA
<213> ORGANISM: Homo sapiens

<400> SEQUENCE: 1096
aagtgttgtt ccactgccaa agagt                                  25

<210> SEQ ID NO 1097
<211> LENGTH: 25
<212> TYPE: DNA
<213> ORGANISM: Homo sapiens

<400> SEQUENCE: 1097
agtgttgttc cactgccaaa gagtt                                  25

<210> SEQ ID NO 1098
<211> LENGTH: 25
<212> TYPE: DNA
<213> ORGANISM: Homo sapiens

<400> SEQUENCE: 1098
gtgttgttcc actgccaaag agttt                                  25

<210> SEQ ID NO 1099
<211> LENGTH: 25
<212> TYPE: DNA
<213> ORGANISM: Homo sapiens

<400> SEQUENCE: 1099
tgttgttcca ctgccaaaga gtttc                                  25

<210> SEQ ID NO 1100
<211> LENGTH: 25
<212> TYPE: DNA
<213> ORGANISM: Homo sapiens

<400> SEQUENCE: 1100
tagatttcgc agtatcaatc tcaag                                  25

<210> SEQ ID NO 1101
<211> LENGTH: 25
<212> TYPE: DNA
<213> ORGANISM: Homo sapiens

<400> SEQUENCE: 1101
aagttgttcc ttgtgcttgc gtaag                                  25
```

```
<210> SEQ ID NO 1102
<211> LENGTH: 25
<212> TYPE: DNA
<213> ORGANISM: Homo sapiens

<400> SEQUENCE: 1102
taatacttcc ctggactgac tcctg                                        25

<210> SEQ ID NO 1103
<211> LENGTH: 25
<212> TYPE: DNA
<213> ORGANISM: Homo sapiens

<400> SEQUENCE: 1103
tgattccaac acaaccttgg agttg                                        25

<210> SEQ ID NO 1104
<211> LENGTH: 25
<212> TYPE: DNA
<213> ORGANISM: Homo sapiens

<400> SEQUENCE: 1104
gagtcatagt actgaagacg ctgtg                                        25

<210> SEQ ID NO 1105
<211> LENGTH: 25
<212> TYPE: DNA
<213> ORGANISM: Homo sapiens

<400> SEQUENCE: 1105
gatgtagccg ttacttcctt cagca                                        25

<210> SEQ ID NO 1106
<211> LENGTH: 25
<212> TYPE: DNA
<213> ORGANISM: Homo sapiens

<400> SEQUENCE: 1106
tcaggttcca ctcaacaagg aagtg                                        25

<210> SEQ ID NO 1107
<211> LENGTH: 25
<212> TYPE: DNA
<213> ORGANISM: Homo sapiens

<400> SEQUENCE: 1107
gaggaggtgg tcttcctgag acaca                                        25

<210> SEQ ID NO 1108
<211> LENGTH: 25
<212> TYPE: DNA
<213> ORGANISM: Homo sapiens

<400> SEQUENCE: 1108
gtcttcctga gacacaagca gaggg                                        25

<210> SEQ ID NO 1109
<211> LENGTH: 25
<212> TYPE: DNA
<213> ORGANISM: Homo sapiens

<400> SEQUENCE: 1109
tcctgagaca caagcagagg gaagt                                        25
```

<210> SEQ ID NO 1110
<211> LENGTH: 25
<212> TYPE: DNA
<213> ORGANISM: Homo sapiens

<400> SEQUENCE: 1110
gaatgctgct tgagactgtt ctggc                                   25

<210> SEQ ID NO 1111
<211> LENGTH: 25
<212> TYPE: DNA
<213> ORGANISM: Homo sapiens

<400> SEQUENCE: 1111
ggatggcatt ccttgacact gaaaa                                   25

<210> SEQ ID NO 1112
<211> LENGTH: 25
<212> TYPE: DNA
<213> ORGANISM: Homo sapiens

<400> SEQUENCE: 1112
tgaggaagcc ctctaatcag gcagg                                   25

<210> SEQ ID NO 1113
<211> LENGTH: 25
<212> TYPE: DNA
<213> ORGANISM: Homo sapiens

<400> SEQUENCE: 1113
cagcctgacc agttagacga cgcag                                   25

<210> SEQ ID NO 1114
<211> LENGTH: 25
<212> TYPE: DNA
<213> ORGANISM: Homo sapiens

<400> SEQUENCE: 1114
aaaagtgtgc ttgcctgctt ggacc                                   25

<210> SEQ ID NO 1115
<211> LENGTH: 25
<212> TYPE: DNA
<213> ORGANISM: Homo sapiens

<400> SEQUENCE: 1115
gaggatttcc agtgcagtca agaca                                   25

<210> SEQ ID NO 1116
<211> LENGTH: 25
<212> TYPE: DNA
<213> ORGANISM: Homo sapiens

<400> SEQUENCE: 1116
ataactgaag aagatccacg ggcgg                                   25

<210> SEQ ID NO 1117
<211> LENGTH: 25
<212> TYPE: DNA
<213> ORGANISM: Homo sapiens

<400> SEQUENCE: 1117
aattgtcccg gatcatgatt gtcac                                           25

<210> SEQ ID NO 1118
<211> LENGTH: 25
<212> TYPE: DNA
<213> ORGANISM: Homo sapiens

<400> SEQUENCE: 1118
ttatcaaaag tgctggaccc catgg                                           25

<210> SEQ ID NO 1119
<211> LENGTH: 25
<212> TYPE: DNA
<213> ORGANISM: Homo sapiens

<400> SEQUENCE: 1119
tcttcactga gcagaatttg cccgt                                           25

<210> SEQ ID NO 1120
<211> LENGTH: 25
<212> TYPE: DNA
<213> ORGANISM: Homo sapiens

<400> SEQUENCE: 1120
ctttccgtgc ctccgggaaa ggatg                                           25

<210> SEQ ID NO 1121
<211> LENGTH: 25
<212> TYPE: DNA
<213> ORGANISM: Homo sapiens

<400> SEQUENCE: 1121
ggatgctcag aatcccagct gcagc                                           25

<210> SEQ ID NO 1122
<211> LENGTH: 25
<212> TYPE: DNA
<213> ORGANISM: Homo sapiens

<400> SEQUENCE: 1122
ggctgtttga tctggatccc ttaga                                           25

<210> SEQ ID NO 1123
<211> LENGTH: 25
<212> TYPE: DNA
<213> ORGANISM: Homo sapiens

<400> SEQUENCE: 1123
tagttcccct ttcttgataa tttgc                                           25

<210> SEQ ID NO 1124
<211> LENGTH: 25
<212> TYPE: DNA
<213> ORGANISM: Homo sapiens

<400> SEQUENCE: 1124
gccggaggat atacttgttg agaac                                           25

<210> SEQ ID NO 1125
<211> LENGTH: 25
<212> TYPE: DNA
<213> ORGANISM: Homo sapiens

<400> SEQUENCE: 1125

```
ttcaatgtgg agcaaatcct atggg                                              25

<210> SEQ ID NO 1126
<211> LENGTH: 25
<212> TYPE: DNA
<213> ORGANISM: Homo sapiens

<400> SEQUENCE: 1126
tggtccaagc cttcctcatc tcttt                                              25

<210> SEQ ID NO 1127
<211> LENGTH: 25
<212> TYPE: DNA
<213> ORGANISM: Homo sapiens

<400> SEQUENCE: 1127
gaatagcttc cttgccaggt tccct                                              25

<210> SEQ ID NO 1128
<211> LENGTH: 25
<212> TYPE: DNA
<213> ORGANISM: Homo sapiens

<400> SEQUENCE: 1128
gaatgaggcc atttctcaca cagcg                                              25

<210> SEQ ID NO 1129
<211> LENGTH: 25
<212> TYPE: DNA
<213> ORGANISM: Homo sapiens

<400> SEQUENCE: 1129
cctggaggag gtcccttttg actct                                              25

<210> SEQ ID NO 1130
<211> LENGTH: 25
<212> TYPE: DNA
<213> ORGANISM: Homo sapiens

<400> SEQUENCE: 1130
acagacacag tctgctcggg tgaga                                              25

<210> SEQ ID NO 1131
<211> LENGTH: 25
<212> TYPE: DNA
<213> ORGANISM: Homo sapiens

<400> SEQUENCE: 1131
tcagaaattt aaccagccag tctct                                              25

<210> SEQ ID NO 1132
<211> LENGTH: 25
<212> TYPE: DNA
<213> ORGANISM: Homo sapiens

<400> SEQUENCE: 1132
agaaatttaa ccagccagtc tctct                                              25

<210> SEQ ID NO 1133
<211> LENGTH: 25
<212> TYPE: DNA
<213> ORGANISM: Homo sapiens
```

```
<400> SEQUENCE: 1133
tcagaaactt gaaacaggcc atttg                                            25

<210> SEQ ID NO 1134
<211> LENGTH: 25
<212> TYPE: DNA
<213> ORGANISM: Homo sapiens

<400> SEQUENCE: 1134
tcttctgatg gctaggagac atgaa                                            25

<210> SEQ ID NO 1135
<211> LENGTH: 25
<212> TYPE: DNA
<213> ORGANISM: Homo sapiens

<400> SEQUENCE: 1135
tgtgaagtct tctgttctcc cagta                                            25

<210> SEQ ID NO 1136
<211> LENGTH: 25
<212> TYPE: DNA
<213> ORGANISM: Homo sapiens

<400> SEQUENCE: 1136
caggcctgac tgcaaagaac cgatc                                            25

<210> SEQ ID NO 1137
<211> LENGTH: 25
<212> TYPE: DNA
<213> ORGANISM: Homo sapiens

<400> SEQUENCE: 1137
ggcctgactg caaagaaccg atcgt                                            25

<210> SEQ ID NO 1138
<211> LENGTH: 25
<212> TYPE: DNA
<213> ORGANISM: Homo sapiens

<400> SEQUENCE: 1138
gcctgactgc aaagaaccga tcgtt                                            25

<210> SEQ ID NO 1139
<211> LENGTH: 25
<212> TYPE: DNA
<213> ORGANISM: Homo sapiens

<400> SEQUENCE: 1139
cctgactgca aagaaccgat cgttg                                            25

<210> SEQ ID NO 1140
<211> LENGTH: 25
<212> TYPE: DNA
<213> ORGANISM: Homo sapiens

<400> SEQUENCE: 1140
tgactgcaaa gaaccgatcg ttggg                                            25

<210> SEQ ID NO 1141
<211> LENGTH: 25
<212> TYPE: DNA
<213> ORGANISM: Homo sapiens
```

```
<400> SEQUENCE: 1141
gactgcaaag aaccgatcgt tgggc                                        25

<210> SEQ ID NO 1142
<211> LENGTH: 25
<212> TYPE: DNA
<213> ORGANISM: Homo sapiens

<400> SEQUENCE: 1142
cgttgggcag ccctgagtca tctgc                                        25

<210> SEQ ID NO 1143
<211> LENGTH: 25
<212> TYPE: DNA
<213> ORGANISM: Homo sapiens

<400> SEQUENCE: 1143
tgccgcaccc gtgccttgga agtaa                                        25

<210> SEQ ID NO 1144
<211> LENGTH: 25
<212> TYPE: DNA
<213> ORGANISM: Homo sapiens

<400> SEQUENCE: 1144
tggatcacac ctgagctcta catat                                        25

<210> SEQ ID NO 1145
<211> LENGTH: 25
<212> TYPE: DNA
<213> ORGANISM: Homo sapiens

<400> SEQUENCE: 1145
ccttctctgt gaccttgtta ctggg                                        25

<210> SEQ ID NO 1146
<211> LENGTH: 25
<212> TYPE: DNA
<213> ORGANISM: Homo sapiens

<400> SEQUENCE: 1146
gggagcttta ccagatcagg gtcac                                        25

<210> SEQ ID NO 1147
<211> LENGTH: 25
<212> TYPE: DNA
<213> ORGANISM: Homo sapiens

<400> SEQUENCE: 1147
tgcagactgt ttttagggac caagg                                        25

<210> SEQ ID NO 1148
<211> LENGTH: 25
<212> TYPE: DNA
<213> ORGANISM: Homo sapiens

<400> SEQUENCE: 1148
tagcctaagt aaatcagcac atggg                                        25

<210> SEQ ID NO 1149
<211> LENGTH: 25
<212> TYPE: DNA
```

```
<213> ORGANISM: Homo sapiens

<400> SEQUENCE: 1149
tatgagagct cttgaagtac tactg                                    25

<210> SEQ ID NO 1150
<211> LENGTH: 25
<212> TYPE: DNA
<213> ORGANISM: Homo sapiens

<400> SEQUENCE: 1150
cagatatctt cttgcttgtt cagtc                                    25

<210> SEQ ID NO 1151
<211> LENGTH: 25
<212> TYPE: DNA
<213> ORGANISM: Homo sapiens

<400> SEQUENCE: 1151
tacatggctc ttagaaagca gtggc                                    25

<210> SEQ ID NO 1152
<211> LENGTH: 25
<212> TYPE: DNA
<213> ORGANISM: Homo sapiens

<400> SEQUENCE: 1152
tgccaaagac gttttcaagg tatgc                                    25

<210> SEQ ID NO 1153
<211> LENGTH: 25
<212> TYPE: DNA
<213> ORGANISM: Homo sapiens

<400> SEQUENCE: 1153
gaatcaagtt gcacctattg tcatg                                    25

<210> SEQ ID NO 1154
<211> LENGTH: 25
<212> TYPE: DNA
<213> ORGANISM: Homo sapiens

<400> SEQUENCE: 1154
cagtcaacag ttgagtgcct gattc                                    25

<210> SEQ ID NO 1155
<211> LENGTH: 25
<212> TYPE: DNA
<213> ORGANISM: Homo sapiens

<400> SEQUENCE: 1155
tatctaagac tagtgatttt ctgac                                    25

<210> SEQ ID NO 1156
<211> LENGTH: 25
<212> TYPE: DNA
<213> ORGANISM: Homo sapiens

<400> SEQUENCE: 1156
tcttccaaga aagcaagtgg ctggg                                    25

<210> SEQ ID NO 1157
<211> LENGTH: 25
```

```
<212> TYPE: DNA
<213> ORGANISM: Homo sapiens

<400> SEQUENCE: 1157
tctcctgagc agcaagcgca ttctt                                            25

<210> SEQ ID NO 1158
<211> LENGTH: 25
<212> TYPE: DNA
<213> ORGANISM: Homo sapiens

<400> SEQUENCE: 1158
ggtgtggtac ccagtataga tcttc                                            25

<210> SEQ ID NO 1159
<211> LENGTH: 25
<212> TYPE: DNA
<213> ORGANISM: Homo sapiens

<400> SEQUENCE: 1159
tgagagcttt ctgcccacaa atagg                                            25

<210> SEQ ID NO 1160
<211> LENGTH: 25
<212> TYPE: DNA
<213> ORGANISM: Homo sapiens

<400> SEQUENCE: 1160
tgttcattac caggacatgt gttga                                            25

<210> SEQ ID NO 1161
<211> LENGTH: 25
<212> TYPE: DNA
<213> ORGANISM: Homo sapiens

<400> SEQUENCE: 1161
ttttagcgcc atattaccac catcg                                            25

<210> SEQ ID NO 1162
<211> LENGTH: 25
<212> TYPE: DNA
<213> ORGANISM: Homo sapiens

<400> SEQUENCE: 1162
gctggtggag tgctaaactt ggcta                                            25

<210> SEQ ID NO 1163
<211> LENGTH: 25
<212> TYPE: DNA
<213> ORGANISM: Homo sapiens

<400> SEQUENCE: 1163
ggtaacgtca ctccatgcta cagga                                            25

<210> SEQ ID NO 1164
<211> LENGTH: 25
<212> TYPE: DNA
<213> ORGANISM: Homo sapiens

<400> SEQUENCE: 1164
gataacacag cgtttgcctc cacgg                                            25

<210> SEQ ID NO 1165
```

```
<211> LENGTH: 25
<212> TYPE: DNA
<213> ORGANISM: Homo sapiens

<400> SEQUENCE: 1165
tctcagctga cataagaagc atctc                                         25

<210> SEQ ID NO 1166
<211> LENGTH: 25
<212> TYPE: DNA
<213> ORGANISM: Homo sapiens

<400> SEQUENCE: 1166
tgttctatac aattgccttc aggtg                                         25

<210> SEQ ID NO 1167
<211> LENGTH: 25
<212> TYPE: DNA
<213> ORGANISM: Homo sapiens

<400> SEQUENCE: 1167
gatccatagc tgcacaaggt ttgtg                                         25

<210> SEQ ID NO 1168
<211> LENGTH: 25
<212> TYPE: DNA
<213> ORGANISM: Homo sapiens

<400> SEQUENCE: 1168
catcttgtaa atagccctcc tgttc                                         25

<210> SEQ ID NO 1169
<211> LENGTH: 25
<212> TYPE: DNA
<213> ORGANISM: Homo sapiens

<400> SEQUENCE: 1169
aacgatttcc caaccgctta tgtgc                                         25

<210> SEQ ID NO 1170
<211> LENGTH: 25
<212> TYPE: DNA
<213> ORGANISM: Homo sapiens

<400> SEQUENCE: 1170
tacctcagga ttcagatgat tatgc                                         25

<210> SEQ ID NO 1171
<211> LENGTH: 25
<212> TYPE: DNA
<213> ORGANISM: Homo sapiens

<400> SEQUENCE: 1171
caaggaccct ttatcaattc aggat                                         25

<210> SEQ ID NO 1172
<211> LENGTH: 25
<212> TYPE: DNA
<213> ORGANISM: Homo sapiens

<400> SEQUENCE: 1172
gatgctggca ctgaaaatca gagcg                                         25
```

<210> SEQ ID NO 1173
<211> LENGTH: 25
<212> TYPE: DNA
<213> ORGANISM: Homo sapiens

<400> SEQUENCE: 1173
tgaagatgac tagcaattag agtcc                                    25

<210> SEQ ID NO 1174
<211> LENGTH: 25
<212> TYPE: DNA
<213> ORGANISM: Homo sapiens

<400> SEQUENCE: 1174
cagtcctttt tgttgtggta cttca                                    25

<210> SEQ ID NO 1175
<211> LENGTH: 25
<212> TYPE: DNA
<213> ORGANISM: Homo sapiens

<400> SEQUENCE: 1175
catgatcggc atactgaagg tcatc                                    25

<210> SEQ ID NO 1176
<211> LENGTH: 25
<212> TYPE: DNA
<213> ORGANISM: Homo sapiens

<400> SEQUENCE: 1176
cgtcattcag aaaagagtcg cccga                                    25

<210> SEQ ID NO 1177
<211> LENGTH: 25
<212> TYPE: DNA
<213> ORGANISM: Homo sapiens

<400> SEQUENCE: 1177
cagtcagttt tctctgcgta gcgga                                    25

<210> SEQ ID NO 1178
<211> LENGTH: 25
<212> TYPE: DNA
<213> ORGANISM: Homo sapiens

<400> SEQUENCE: 1178
caagaaacct gcctcgaaga agtgg                                    25

<210> SEQ ID NO 1179
<211> LENGTH: 25
<212> TYPE: DNA
<213> ORGANISM: Homo sapiens

<400> SEQUENCE: 1179
tcagaaatct ggacgcgcat tacgg                                    25

<210> SEQ ID NO 1180
<211> LENGTH: 25
<212> TYPE: DNA
<213> ORGANISM: Homo sapiens

<400> SEQUENCE: 1180
cactagttag gatgcgcggt cttca                                    25

<210> SEQ ID NO 1181
<211> LENGTH: 25
<212> TYPE: DNA
<213> ORGANISM: Homo sapiens

<400> SEQUENCE: 1181
ccctgtcctg gagaataacg cgtga                                          25

<210> SEQ ID NO 1182
<211> LENGTH: 25
<212> TYPE: DNA
<213> ORGANISM: Homo sapiens

<400> SEQUENCE: 1182
aaatctatca taacctggta gcagg                                          25

<210> SEQ ID NO 1183
<211> LENGTH: 25
<212> TYPE: DNA
<213> ORGANISM: Homo sapiens

<400> SEQUENCE: 1183
ggtagcagga tccaaaaatt caatc                                          25

<210> SEQ ID NO 1184
<211> LENGTH: 25
<212> TYPE: DNA
<213> ORGANISM: Homo sapiens

<400> SEQUENCE: 1184
gcaggtgcca ttactgtgag gccag                                          25

<210> SEQ ID NO 1185
<211> LENGTH: 25
<212> TYPE: DNA
<213> ORGANISM: Homo sapiens

<400> SEQUENCE: 1185
caatgttttc agctactaac ccagc                                          25

<210> SEQ ID NO 1186
<211> LENGTH: 25
<212> TYPE: DNA
<213> ORGANISM: Homo sapiens

<400> SEQUENCE: 1186
tactaaccca gccatgtgtg accac                                          25

<210> SEQ ID NO 1187
<211> LENGTH: 25
<212> TYPE: DNA
<213> ORGANISM: Homo sapiens

<400> SEQUENCE: 1187
ccagtggccc atgatgatct agtga                                          25

<210> SEQ ID NO 1188
<211> LENGTH: 25
<212> TYPE: DNA
<213> ORGANISM: Homo sapiens

<400> SEQUENCE: 1188
gagaggacgc ttcggtctct gtacg                                          25

```
<210> SEQ ID NO 1189
<211> LENGTH: 25
<212> TYPE: DNA
<213> ORGANISM: Homo sapiens

<400> SEQUENCE: 1189
ggtaccagct gcagccgaca ggtaa                                              25

<210> SEQ ID NO 1190
<211> LENGTH: 25
<212> TYPE: DNA
<213> ORGANISM: Homo sapiens

<400> SEQUENCE: 1190
gacaggtaac tgtttctttc actct                                              25

<210> SEQ ID NO 1191
<211> LENGTH: 25
<212> TYPE: DNA
<213> ORGANISM: Homo sapiens

<400> SEQUENCE: 1191
taaattgggc aatgtcctct cctca                                              25

<210> SEQ ID NO 1192
<211> LENGTH: 25
<212> TYPE: DNA
<213> ORGANISM: Homo sapiens

<400> SEQUENCE: 1192
tggctcccgg aggttaggaa tcaac                                              25

<210> SEQ ID NO 1193
<211> LENGTH: 25
<212> TYPE: DNA
<213> ORGANISM: Homo sapiens

<400> SEQUENCE: 1193
tacactctga taggtggtgc cagcc                                              25

<210> SEQ ID NO 1194
<211> LENGTH: 25
<212> TYPE: DNA
<213> ORGANISM: Homo sapiens

<400> SEQUENCE: 1194
aaacacacag gtacactggc gggca                                              25

<210> SEQ ID NO 1195
<211> LENGTH: 25
<212> TYPE: DNA
<213> ORGANISM: Homo sapiens

<400> SEQUENCE: 1195
ggaccagtaa cgagtcccag tgcgc                                              25

<210> SEQ ID NO 1196
<211> LENGTH: 25
<212> TYPE: DNA
<213> ORGANISM: Homo sapiens

<400> SEQUENCE: 1196
```
agtaacgagt cccagtgcgc agtgg                                              25

<210> SEQ ID NO 1197
<211> LENGTH: 25
<212> TYPE: DNA
<213> ORGANISM: Homo sapiens

<400> SEQUENCE: 1197
agtccactct gggtgtcccg cagtc                                              25

<210> SEQ ID NO 1198
<211> LENGTH: 25
<212> TYPE: DNA
<213> ORGANISM: Homo sapiens

<400> SEQUENCE: 1198
ggtgtcccgc agtccactcc tggtg                                              25

<210> SEQ ID NO 1199
<211> LENGTH: 25
<212> TYPE: DNA
<213> ORGANISM: Homo sapiens

<400> SEQUENCE: 1199
aagccgggtc cagctgtcac ggaat                                              25

<210> SEQ ID NO 1200
<211> LENGTH: 25
<212> TYPE: DNA
<213> ORGANISM: Homo sapiens

<400> SEQUENCE: 1200
cgggtccagc tgtcacggaa tccaa                                              25

<210> SEQ ID NO 1201
<211> LENGTH: 25
<212> TYPE: DNA
<213> ORGANISM: Homo sapiens

<400> SEQUENCE: 1201
gggtccagct gtcacggaat ccaaa                                              25

<210> SEQ ID NO 1202
<211> LENGTH: 25
<212> TYPE: DNA
<213> ORGANISM: Homo sapiens

<400> SEQUENCE: 1202
tgtcacggaa tccaaaacca agcgg                                              25

<210> SEQ ID NO 1203
<211> LENGTH: 25
<212> TYPE: DNA
<213> ORGANISM: Homo sapiens

<400> SEQUENCE: 1203
gagcaagcgt tcctctaaca gtggg                                              25

<210> SEQ ID NO 1204
<211> LENGTH: 25
<212> TYPE: DNA
<213> ORGANISM: Homo sapiens

<400> SEQUENCE: 1204
tcgggccagt cggtaagaag ttcca        25

<210> SEQ ID NO 1205
<211> LENGTH: 25
<212> TYPE: DNA
<213> ORGANISM: Homo sapiens

<400> SEQUENCE: 1205
gacgctatct gcaggtaccg gaatg        25

<210> SEQ ID NO 1206
<211> LENGTH: 25
<212> TYPE: DNA
<213> ORGANISM: Homo sapiens

<400> SEQUENCE: 1206
cagaactgat ggcttgctcg gtggc        25

<210> SEQ ID NO 1207
<211> LENGTH: 25
<212> TYPE: DNA
<213> ORGANISM: Homo sapiens

<400> SEQUENCE: 1207
ccgaacacaa cgaggactgt ccagg        25

<210> SEQ ID NO 1208
<211> LENGTH: 25
<212> TYPE: DNA
<213> ORGANISM: Homo sapiens

<400> SEQUENCE: 1208
cgaacacaac gaggactgtc caggt        25

<210> SEQ ID NO 1209
<211> LENGTH: 25
<212> TYPE: DNA
<213> ORGANISM: Homo sapiens

<400> SEQUENCE: 1209
actgtccagg tgtcagtgac ggtca        25

<210> SEQ ID NO 1210
<211> LENGTH: 25
<212> TYPE: DNA
<213> ORGANISM: Homo sapiens

<400> SEQUENCE: 1210
tcagtgacgg tcaccccgac ctggt        25

<210> SEQ ID NO 1211
<211> LENGTH: 25
<212> TYPE: DNA
<213> ORGANISM: Homo sapiens

<400> SEQUENCE: 1211
tcaacagggc caaatgcgca gaggt        25

<210> SEQ ID NO 1212
<211> LENGTH: 25
<212> TYPE: DNA
<213> ORGANISM: Homo sapiens

<400> SEQUENCE: 1212
tacgtcagct gtgtaacatg ccaag    25

<210> SEQ ID NO 1213
<211> LENGTH: 25
<212> TYPE: DNA
<213> ORGANISM: Homo sapiens

<400> SEQUENCE: 1213
aatactgctt cgtcccatgt ctgaa    25

<210> SEQ ID NO 1214
<211> LENGTH: 25
<212> TYPE: DNA
<213> ORGANISM: Homo sapiens

<400> SEQUENCE: 1214
gaaggaagca cttgctacct cttgc    25

<210> SEQ ID NO 1215
<211> LENGTH: 25
<212> TYPE: DNA
<213> ORGANISM: Homo sapiens

<400> SEQUENCE: 1215
ccaatataca cttctgtgcc gggag    25

<210> SEQ ID NO 1216
<211> LENGTH: 25
<212> TYPE: DNA
<213> ORGANISM: Homo sapiens

<400> SEQUENCE: 1216
tgccacgtcc agtcaatatg ccagg    25

<210> SEQ ID NO 1217
<211> LENGTH: 25
<212> TYPE: DNA
<213> ORGANISM: Homo sapiens

<400> SEQUENCE: 1217
cctgctgctc ggacattgct gaaga    25

<210> SEQ ID NO 1218
<211> LENGTH: 25
<212> TYPE: DNA
<213> ORGANISM: Homo sapiens

<400> SEQUENCE: 1218
aaatttgtcg ctaatccgtg attcc    25

<210> SEQ ID NO 1219
<211> LENGTH: 25
<212> TYPE: DNA
<213> ORGANISM: Homo sapiens

<400> SEQUENCE: 1219
cagtgggcct gaagatcctc caagt    25

<210> SEQ ID NO 1220
<211> LENGTH: 25
<212> TYPE: DNA
<213> ORGANISM: Homo sapiens

```
<400> SEQUENCE: 1220
catacactgg gatctgattc gcaaa                                           25

<210> SEQ ID NO 1221
<211> LENGTH: 25
<212> TYPE: DNA
<213> ORGANISM: Homo sapiens

<400> SEQUENCE: 1221
ttcatagcag gcaaagcaag ctcta                                           25

<210> SEQ ID NO 1222
<211> LENGTH: 25
<212> TYPE: DNA
<213> ORGANISM: Homo sapiens

<400> SEQUENCE: 1222
taaatgggct gtacaagttt gtatc                                           25

<210> SEQ ID NO 1223
<211> LENGTH: 25
<212> TYPE: DNA
<213> ORGANISM: Homo sapiens

<400> SEQUENCE: 1223
gaaggtggac atgaattctc actaa                                           25

<210> SEQ ID NO 1224
<211> LENGTH: 25
<212> TYPE: DNA
<213> ORGANISM: Homo sapiens

<400> SEQUENCE: 1224
tctgatctga gaaggcattc cacca                                           25

<210> SEQ ID NO 1225
<211> LENGTH: 25
<212> TYPE: DNA
<213> ORGANISM: Homo sapiens

<400> SEQUENCE: 1225
gcccaggtgc atgcttctac tttca                                           25

<210> SEQ ID NO 1226
<211> LENGTH: 25
<212> TYPE: DNA
<213> ORGANISM: Homo sapiens

<400> SEQUENCE: 1226
aaatggccac catgcagact gcaac                                           25

<210> SEQ ID NO 1227
<211> LENGTH: 25
<212> TYPE: DNA
<213> ORGANISM: Homo sapiens

<400> SEQUENCE: 1227
ggtctagggc atccaaaaag ccacg                                           25

<210> SEQ ID NO 1228
<211> LENGTH: 25
<212> TYPE: DNA
```

```
<213> ORGANISM: Homo sapiens

<400> SEQUENCE: 1228
tgtgcctcac tagctttaaa gccgg                                              25
```

SAFE AND EFFECTIVE METHOD OF TREATING LUPUS WITH ANTI-IL12/IL23 ANTIBODY

CROSS REFERENCE TO RELATED APPLICATION

This application claims the benefit of priority to U.S. Provisional Application No. 62/673,426, filed May 18, 2018, which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "JBI5162-SEQLIST.txt", creation date of May 17, 2018 and having a size of 192 kb. The sequence listing submitted via EFS-Web is part of the specification and is herein incorporated by reference in its entirety.

FIELD OF THE INVENTION

The present invention relates to methods for treating lupus with an antibody that binds human IL-12 and/or human IL-23 proteins. In particular, the present invention relates to methods for selecting and treating patients with active Systemic Lupus Erythematosus (SLE) that are predicted to have an increased likelihood of having a positive response to a treatment with an anti-IL-12/IL-23p40 antibody, wherein the treatment comprises administering a safe and effective amount of an anti-IL-12 and/or anti-IL-23 antibody, e.g., the anti-IL-12/IL-23p40 antibody ustekinumab.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12101 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). IL-12 has also been shown to play a critical role in the pathogenesis of SLE in two independent mouse models of systemic lupus erythematosus (Kikawada et al, 2003; Dai et al, 2007).

Systemic lupus erythematosus (SLE) is a complex, chronic, heterogeneous autoimmune disease of unknown etiology that can affect almost any organ system, and which follows a waxing and waning disease course. Systemic lupus erythematosus occurs much more often in women than in men, up to 9 times more frequently in some studies, and often appears during the child-bearing years between ages 15 and 45. This disease is more prevalent in Afro-Caribbean, Asian, and Hispanic populations. In SLE, the immune system attacks the body's cells and tissue, resulting in inflammation and tissue damage which can harm the heart, joints, skin, lungs, blood vessels, liver, kidneys and nervous system. About half of the subjects diagnosed with SLE present with organ-threatening disease, but it can take several years to diagnose subjects who do not present with organ involvement. Some of the primary complaints of newly diagnosed lupus patients are arthralgia (62%) and cutaneous symptoms (new photosensitivity; 20%), followed by persistent fever and malaise (Wallace, 2008). The estimated annual incidence of lupus varies from 1.8 to 7.6 cases per 100,000 and the worldwide prevalence ranges from 14 to 172 cases per 100,000 people (Wallace, 2008). Patients with mild disease have mostly skin rashes and joint pain and require less aggressive therapy; regimens include nonsteroidal anti-inflammatory drugs (NSAIDs), anti-malarials (e.g., hydroxychloroquine, chloroquine, or quinacrine) and/or low dose corticosteroids. With more severe disease, patients may experience a variety of serious conditions depending on the organ systems involved, including lupus nephritis with potential renal failure, endocarditis or myocarditis, pneumonitis, pregnancy complications, stroke, neurological complications, vasculitis and cytopenias with associated risks of bleeding or infection. Common treatments for more severe disease include immunomodulatory agents, such as methotrexate (MTX), azathioprine, cyclophosphamide, cyclosporine, high dose corticosteroids, biologic B cell cytotoxic agents or B cell modulators, and other immunomodulators. Patients with serious SLE have a shortening of life expectancy by 10 to 30 years, largely due to the complications of the disease, of standard of care therapy, and/or accelerated atherosclerosis. In addition, SLE has a substantial impact on quality of life, work productivity, and healthcare expenditures. Existing therapies for SLE are generally either cytotoxic or immunomodulatory, and may have notable safety risks. Newer treatments for SLE have provided only modest benefits over standard of care therapy. Thus, there is a large unmet need for new alternative treatments that can provide significant benefit in this disease without incurring a high safety risk.

SUMMARY OF THE INVENTION

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In certain embodiments, the invention provides methods for selecting and treating patients with active Systemic Lupus Erythematosus (SLE) that are predicted to have an increased likelihood of having a positive response to a safe and effective treatment of an anti-IL-12 and/or anti-IL-23 antibody. In a preferred embodiment, such treatment comprises administering intravenously (IV) and/or subcutaneously (SC) to the patient an anti-IL-12 and/or anti-IL-23 antibody, wherein the anti-IL-12 and/or anti-IL-23 antibody is an anti-IL-12/23p40 antibody, such as ustekinumab.

In certain embodiments, the invention provides methods for selecting and treating patients with active Systemic Lupus Erythematosus (SLE) that are predicted to have an increased likelihood of having a positive response to a safe and effective treatment comprising intravenously (IV) and/or subcutaneously (SC) administering to the patient an anti-IL-12 and/or anti-IL-23 antibody. The anti-IL-12 and/or anti-IL-23 antibody may be an anti-IL-12/23p40 antibody comprising: (1) (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6; (2) (i) the heavy chain variable domain amino acid sequence of SEQ ID NO:7; and (ii) the light chain variable domain amino acid sequence of SEQ ID NO:8; and/or (3) the anti-IL-12/23p40 antibody ustekinumab (STELARA®), comprising: (i) the heavy chain amino acid sequence of SEQ ID NO:10; and (ii) the light chain amino acid sequence of SEQ ID NO:11.

In certain embodiments, the present invention provides methods for selecting and treating patients with active Systemic Lupus Erythematosus (SLE) that are predicted to have an increased likelihood of having a positive response to a safe and effective treatment comprising intravenously (IV) administering to the patient a pharmaceutical composition comprising an anti-IL-12/IL-23p40 antibody comprising: (1) (i) the heavy chain CDR amino acid sequences of SEQ ID NO:1, SEQ ID NO:2, and SEQ ID NO:3; and (ii) the light chain CDR amino acid sequences of SEQ ID NO:4, SEQ ID NO:5, and SEQ ID NO:6; (2) (i) the heavy chain variable domain amino acid sequence of SEQ ID NO:7; and (ii) the light chain variable domain amino acid sequence of SEQ ID NO:8; and/or (3) the anti-IL-12/23p40 antibody ustekinumab (STELARA®), comprising: (i) the heavy chain amino acid sequence of SEQ ID NO:10; and (ii) the light chain amino acid sequence of SEQ ID NO:11 in a solution comprising 10 mM L-histidine, 8.5% (w/v) sucrose, 0.04% (w/v) polysorbate 80, 0.4 mg/mLL methionine, and 20 µg/mL EDTA disodium salt, dehydrate, at pH 6.0 or in a solution comprising 6.7 mM L-histidine, 7.6% (w/v) sucrose, 0.004% (w/v) polysorbate 80, at pH 6.0.

In certain embodiments, the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w).

In certain embodiments, the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 6.0 mg/kg±1.5 mg/kg.

In certain embodiments, the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), and wherein the initial IV dose is 260 mg for patients with body weight ≥35 kg and ≤55 kg, 390 mg for patients with body weight >55 kg and ≤85 kg, and 520 mg for patients with body weight >85 kg.

In certain embodiments, the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w), wherein the SC dose is 90 mg.

In certain embodiments, the present invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining levels of one or more cytotoxic cell markers in biological samples from the patients, wherein the one or more cytotoxic cell markers is selected from the group consisting of: expression level of one or more cytotoxic cell-associated transcriptional genes and percentage of natural killer cells; b.) determining levels of one or more Interferon I (IFN-I) markers in biological samples from the patients, wherein the one or more IFN-I markers is selected from the group consisting of: expression level of one or more Interferon I (IFN-I) inducible genes and expression level of Interferon alpha; c.) calculating mean levels of the one or more cytotoxic cell markers and the one or more IFN-I markers in the biological samples from the patients; d.) comparing the calculated mean levels to the levels in individual patients for the one or more cytotoxic cell markers and the one or more IFN-I markers; e.) determining if individual patients have higher levels or lower levels compared to the calculated mean levels of the one or more cytotoxic cell markers and the one or more IFN-I markers; f.) selecting the individual patients from the group consisting of: individual patients with higher levels of the one or more cytotoxic cell markers and higher levels of the one or more IFN-I markers, individual patients with higher levels of the one or more cytotoxic cell markers and lower levels of the one or more IFN-I markers, and individual patients with lower levels of the one or more cytotoxic cell markers and lower levels of the one or more IFN-I markers, wherein the selected patients are predicted to have an increased likelihood of having a positive response to the treatment with an anti-IL-12/IL-23p40 antibody; and, g.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the anti-IL/IL-23p40 antibody comprises (1) a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; (2) (i) the heavy chain variable domain amino acid sequence of SEQ ID NO:7; and (ii) the light chain variable domain amino acid sequence of SEQ ID NO:8; and/or (3) the anti-IL-12/23p40 antibody ustekinumab (STELARA®), comprising: (i) the heavy chain amino acid sequence of SEQ ID NO:10; and (ii) the light chain amino acid sequence of SEQ ID NO:11.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, wherein the positive response is response selected from the group consisting of: a significant improvement in disease activity as determined by a decrease from baseline in the Systemic Lupus Erythematosus Disease Activity Index 2000 (SLEDAI-2K) score of ≥4 (SRI-4 response) at 24 weeks of treatment with the anti-IL-12/IL-23p40 antibody; a statistically significant reduction in the risk of a new British Isles Lupus Assessment Group (BILAG) flare, defined as ≥1 new BILAG A domain score or ≥2 new BILAG B domain score, by week 24 of treatment with the anti-IL-12/IL-23p40 antibody; a statistically significant increase in the proportion of patients with a 50% improvement from baseline in Cutaneous Lupus Erythematosus Disease Area and Severity Index (CLASI) score; and a statistically significant improvement in disease activity as determined by a 50% improvement from baseline joint disease activity by week 24 of treatment with the anti-IL-12/IL-23p40 antibody.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, wherein the positive response is a significant improvement in disease activity as determined by a decrease from baseline in the Systemic Lupus Erythematosus Disease Activity Index 2000 (SLEDAI-2K) score of ≥4 (SRI-4 response) at 24 weeks of treatment with the anti-IL-12/IL-23p40 antibody.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the one or more cytotoxic cell-associated transcriptional genes is selected from the group consisting of: FCRL6, FGFBP2, GNLY, GPR56, GZMH, GZMK, XRRA1, GSTM4, KLRC3, KLRD1, KLRG1, LOC387895, MYBL1, NKG7, PRF1, TARP, TRGC2, CXCR3, GZMA, and TRGV2; and wherein the one or more IFN-I inducible genes is selected from the group consisting of: BST2, CARD17, CMPK2, DDX58, DDX60, DHX58, EIF2AK2, EPSTI1, FBXO39, HERC5, HERC6, IFIT1, IFIT2, IFIT3, IRF7, LAP3, LOC100133669, OAS3, OASL, OTOF, PLSCR1, RSAD2, RTP4, SAMD9L, SIGLEC1, SPATS2L, TIMM10, USP18, ISG15 IFI27, IFI44, IFI44L, and ZBP1.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the one or more cytotoxic cell-associated transcriptional genes is selected from the group consisting of: FCRL6, FGFBP2, GNLY, GZMH, GZMK, NKG7 and PRF1; and wherein the one or more IFN-I inducible genes is selected from the group consisting of: BST2, CMPK2, DDX58, DDX60, DHX58, EIF2AK2, EPSTI1, HERC5, IFIT1, IFIT2, IFIT3, IRF7, ISG15, LAP3, OAS3, OASL, PLSCR1, RSAD2, RTP4, SAMD9L, SIGLEC1, TIMM10, USP18 and ZBP1.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the one or more cytotoxic cell-associated transcriptional genes comprises FCRL6, FGFBP2, GNLY, GZMH, NKG7, and PRF1; and wherein the one or more IFN-I inducible genes comprises IFIT3 and RSAD2.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) calculating the mean expression levels of the one or more cytotoxic cell-associated transcriptional genes in the biological samples from the patients; c.) comparing the calculated mean expression levels to the expression levels in individual patients for the one or more cytotoxic cell-associated transcriptional genes; d.) determining if the individual patients have higher expression levels or lower expression levels compared to the mean expression levels of the one or more cytotoxic cell-associated transcriptional; e.) selecting individual patients with higher expression levels of the one or more cytotoxic cell-associated transcriptional genes, wherein the selected patients are predicted to have an increased likelihood of having a positive response to the treatment comprising administering an anti-IL-12/IL-23p40 antibody; and f) treating the selected patients by administering the anti-IL-12/IL-23p40 antibody.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) calculating the mean expression levels of the one or more cytotoxic cell-associated transcriptional genes in the biological samples from the patients; c.) comparing the calculated mean expression levels to the expression levels in individual patients for the one or more cytotoxic cell-associated transcriptional genes; d.) determining if the individual patients have higher expression levels or lower expression levels compared to the mean expression levels of the one or more cytotoxic cell-associated transcriptional; e.) selecting individual patients with higher expression levels of the one or more cytotoxic cell-associated transcriptional genes, wherein the selected patients are predicted to have an increased likelihood of having a positive response to the treatment comprising administering an anti-IL-12/IL-23p40 antibody; and f) treating the selected patients by administering the anti-IL-12/IL-23p40 antibody, wherein the one or more cytotoxic cell-associated transcriptional genes is selected from the group consisting of: FCRL6, FGFBP2, GNLY, GPR56, GZMH, GZMK, XRRA1, GSTM4, KLRC3, KLRD1, KLRG1, LOC387895, MYBL1, NKG7, PRF1, TARP, TRGC2, CXCR3, GZMA, and TRGV2.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) calculating the mean expression levels of the one or more cytotoxic cell-associated transcriptional genes in the biological samples from the patients; c.) comparing the calculated mean expression levels to the expression levels in individual patients for the one or more cytotoxic cell-associated transcriptional genes; d.) determining if the individual patients have higher expression levels or lower expression levels compared to the mean expression levels of the one or more cytotoxic cell-associated transcriptional; e.) selecting individual patients with higher expression levels of the one or more cytotoxic cell-associated transcriptional genes, wherein the selected patients are predicted to have an increased likelihood of having a positive response to the treatment comprising administering an anti-IL-12/IL-23p40 antibody; and f) treating the selected patients by administering the anti-IL-12/IL-23p40 antibody, wherein the one or more cytotoxic cell-associated transcriptional genes is selected from the group consisting of: FCRL6, FGFBP2, GNLY, GZMH, GZMK, NKG7 and PRF1.

In certain embodiments, the present invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the expression level of one or more cytotoxic cell-associated transcriptional genes in biological samples from the patients; b.) comparing the expression levels in individual patients to the average expression levels in healthy controls for the one or more cytotoxic cell-associated transcriptional genes; c.) determining if the individual patients have lower expression levels compared to the average expression levels in healthy controls for the one or more cytotoxic cell-associated transcriptional genes; d.) selecting the individual patients that do not have lower expression levels compared to the average expression levels in healthy controls for the one or more cytotoxic cell-associated transcriptional genes, wherein the selected patients are predicted to have an increased likelihood of having a positive response to the treatment with an anti-IL-12/IL-23p40 antibody; and e.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the present invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the expression level of one or more cytotoxic cell-associated transcriptional genes in biological samples from the patients; b.) comparing the expression levels in individual patients to the average expression levels in healthy controls for the one or more cytotoxic cell-associated transcriptional genes; c.) determining if the individual patients have lower expression levels compared to the average expression levels in healthy controls for the one or more cytotoxic cell-associated transcriptional genes, wherein the lower expression levels of the one or more cytotoxic cell-associated transcriptional genes compared to the average expression levels in healthy controls is a cytotoxic signature score 0.4 below the median of the healthy controls; d.) selecting the individual patients that do not have lower expression levels compared to the average expression levels in healthy controls for the one or more cytotoxic cell-associated transcriptional genes, wherein the selected patients are predicted to have an increased likelihood of having a positive response to the treatment with an anti-IL-12/IL-23p40 antibody; and e.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the present invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the expression level of one or more cytotoxic cell-associated transcriptional genes in biological samples from the patients; b.) comparing the expression levels in individual patients to the average expression levels in healthy controls for the one or more cytotoxic cell-associated transcriptional genes; c.) determining if the individual patients have lower expression levels compared to the average expression levels in healthy controls for the one or more cytotoxic cell-associated transcriptional genes; d.) selecting the individual patients that do not have lower expression levels compared to the average expression levels in healthy controls for the one or more cytotoxic cell-associated transcriptional genes, wherein the selected patients are predicted to have an increased likelihood of having a positive response to the treatment with an anti-IL-12/IL-23p40 antibody; and e.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein the one or more cytotoxic cell-associated transcriptional genes is selected from the group consisting of: FCRL6, FGFBP2, GNLY, GPR56, GZMH, GZMK, XRR1, GSTM4, KLRC3, KLRD1, KLRG1, LOC387895, MYBL1, NKG7, PRF1, TARP, TRGC2, CXCR3, GZMA, and TRGV2.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the expression level of the one or more cytotoxic cell-associated transcriptional genes and the expression level of the one or more IFN-I inducible genes are determined by quantifying RNA transcripts in the biological samples or quantifying protein expression levels in the biological samples.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the biological sample is selected from the group consisting of: skin biopsies, whole blood, serum, and urine.

In certain embodiments, the invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the percentage of natural killer cells in biological samples from the patients; b.) determining the expression level of one or more Interferon I (IFN-I) inducible genes in biological samples from the patients; c.) calculating the mean percentage of natural killer cells and the mean expression level of and the one or more Interferon I (IFN-I) inducible genes in the biological samples from the patients; d.) comparing the calculated mean percentage of natural killer cells and the mean expression levels of the one or more Interferon I (IFN-I) inducible genes to the percentage of natural killer cells and expression levels of the one or more Interferon I (IFN-I) inducible genes in individual patients; e.) determining if the individual patients have higher or lower percentage of natural killer cells compared to the mean percentage of natural killer cells and higher expression levels or lower expression levels compared to the mean expression levels of the one or more Interferon I (IFN-I) inducible genes; f) selecting the individual patients from the group consisting of: individual patients with higher percentage of natural killer cells and higher expression levels of the one or more Interferon I (IFN-I) inducible genes, individual patients with higher percentage of natural killer cells and lower expression levels of the one or more Interferon I (IFN-I) inducible genes, and individual patients with lower percentage of natural killer cells and lower expression levels of the one or more Interferon I (IFN-I) inducible genes, wherein the selected patients are predicted to have an increased likelihood of having a positive response to the treatment with an anti-IL-12/IL-23p40 antibody; and, g.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the expression level of one or more cytotoxic cell-associated transcriptional genes in biological samples from the patients; b.) determining the expression level of Interferon alpha in biological samples from the patients; c.) calculating the mean expression levels of the one or more cytotoxic cell-associated transcriptional genes and the Interferon alpha in the biological samples from the patients; d.) comparing the calculated mean expression levels to the expression levels in individual patients for the one or more cytotoxic cell-associated transcriptional genes and the Interferon alpha; e.) determining if the individual patients have higher expression levels or lower expression levels compared to the mean expression levels of the one or more cytotoxic cell-associated transcriptional genes and the Interferon alpha; f.) selecting the individual patients from the group consisting of: individual patients with higher expression levels of the one or more cytotoxic cell-associated transcriptional genes and higher expression levels of the Interferon alpha, individual patients with higher expression levels of the one or more cytotoxic cell-associated transcriptional genes and lower expression levels of the Interferon alpha, and individual patients with lower expression levels of the one or more cytotoxic cell-associated transcriptional genes and lower expression levels of the Interferon alpha, wherein the selected patients are predicted to have an increased likelihood of having a positive response to the treatment with an anti-IL-12/IL-23p40 antibody; and, g.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the invention provides methods for selecting and treating patients with active Systemic Lupus Erythematosus (SLE) that are predicted to have an increased likelihood of having a positive response to a treatment with an anti-IL-12/IL-23p40 antibody, the method comprising: a.) determining the percentage of natural killer cells in biological samples from the patients; b.) determining the expression level of Interferon alpha in biological samples from the patients; c.) calculating the mean percentage of natural killer cells and the mean expression level of and the Interferon alpha in the biological samples from the patients; d.) comparing the calculated mean percentage of natural killer cells and the mean expression levels of the Interferon alpha to the percentage of natural killer cells and expression levels of the one or more Interferon I (IFN-I) inducible genes in individual patients; e.) determining if the individual patients have higher or lower percentage of natural killer cells compared to the mean percentage of natural killer cells and higher expression levels or lower expression levels compared to the mean expression levels of the Interferon alpha; f.) selecting the individual patients from the group consisting of: individual patients with higher percentage of natural killer cells and higher expression levels of the Interferon alpha, individual patients with higher percentage of natural killer cells and lower expression levels of the Interferon alpha, and individual patients with lower percentage of natural killer cells and lower expression levels of the Interferon alpha, wherein the selected patients are predicted to have an increased likelihood of having a positive response to the treatment with an anti-IL-12/IL-23p40 antibody; and, g.) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w) and wherein the initial IV dose is 6.0 mg/kg 1.5 mg/kg and the SC dose is 90 mg, and/or wherein the initial IV dose is 260 mg for patients with body weight ≥35 kg and ≤55 kg, 390 mg for patients with body weight >55 kg and ≤85 kg, and 520 mg for patients with body weight >85 kg.

In certain embodiments, the present invention provides methods for selecting and treating patients with active Systemic Lupus Erythematosus (SLE) that are predicted to have an increased likelihood of having a positive response to a treatment comprising administering an anti-IL-12/IL-23p40 antibody, the method comprising: a.) determining the expression level one or more cytotoxic cell-associated transcriptional genes in biological samples from the patients; b.) determining the expression level of one or more Interferon I (IFN-I) inducible genes in biological samples from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients from the group consisting of: individual patients with higher expression levels of the one or more cytotoxic cell-associated transcriptional genes and higher expression levels of the one or more Interferon I (IFN-I) inducible genes, individual patients with higher expression levels of the one or more cytotoxic cell-associated transcriptional genes and lower expression levels of the one or more Interferon I (IFN-I) inducible genes, and individual patients with lower expression levels of the one or more cytotoxic cell-associated transcriptional genes and lower expression levels of the one or more Interferon I (IFN-I) inducible genes, wherein the selected patients are predicted to have an increased likelihood of having a positive response to the treatment comprising administering an anti-IL-12/IL-23p40 antibody; and g.) treating the selected patients by administering the anti-IL-12/IL-23p40 antibody, wherein the predicted increased likelihood of having a positive response to the treatment comprising administering the anti-IL-12/IL-23p40 antibody is determined with a logistic regression model of the formula:

$$\min_{\beta o, \beta} - \left[ \frac{1}{N} \sum_{i=1}^{N} y_i(\beta o + \beta^T x_i) - \log\left(1 + e^{(\beta o + \beta^T x_i)}\right) \right] +$$

$$\lambda \left[ \frac{(1-\alpha)}{2} \|\beta\|_2^2 + \alpha \|\beta\|_1 \right]$$

wherein N is the number of patients used to learn the model, $x_i$ is a vector of the centered gene expression data of patient i, $y_i$ is the response outcome for patient i (responder/non-responder), $\lambda$ controls the total penalty weight, $\alpha$ controls the elastic-net penalty weight: form lasso ($\alpha$=1) to ridge ($\alpha$=0), and $\alpha$, $\lambda$ are optimized using grid search based on best training accuracy; and, wherein after $\beta o$, $\beta$ parameters are determined a response probability is determined by the formula:

$$P(x_{new}) = \frac{1}{1 + e^{-(\beta^T x_{new})}}$$

and response prediction is determined with a threshold of 0.5 using the formula:

$$\text{Response}(x_{new}) = \begin{cases} \text{responder,} & \text{if } P(x) \geq \text{threshlod} \\ \text{non-responder,} & \text{else} \end{cases}.$$

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, wherein the positive response is a response selected from the group consisting of: a significant improvement in disease activity as determined by a decrease from baseline in the Systemic Lupus Erythematosus Disease Activity Index 2000 (SLEDAI-2K) score of ≥4 (SRI-4 response) at 24 weeks of treatment with the anti-IL-12/IL-23p40 antibody; a statistically significant reduction in the risk of a new British Isles Lupus Assessment Group (BILAG) flare, defined as ≥1 new BILAG A domain score or ≥2 new BILAG B domain score, by week 24 of treatment with the anti-IL-12/IL-23p40 antibody; a statistically significant increase in the proportion of patients with a 50% improvement from baseline in Cutaneous Lupus Erythematosus Disease Area and Severity Index (CLASI) score; and a statistically significant improvement in disease activity as determined by a 50% improvement from baseline joint disease activity by week 24 of treatment with the anti-IL-12/IL-23p40 antibody.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, wherein the positive response is a significant improvement in disease activity as determined by a decrease from baseline in the Systemic Lupus Erythematosus Disease Activity Index 2000 (SLEDAI-2K) score of ≥4 (SRI-4 response) at 24 weeks of treatment with the anti-IL-12/IL-23p40 antibody.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the one or more cytotoxic cell-associated transcriptional genes is selected from the group consisting of: FCRL6, FGFBP2, GNLY, GPR56, GZMH, GZMK, XRRA1, GSTM4, KLRC3, KLRD1, KLRG1, LOC387895, MYBL1, NKG7, PRF1, TARP, TRGC2, CXCR3, GZMA, and TRGV2; and wherein the one or more IFN-I inducible genes is selected from the group consisting of: BST2, CARD17, CMPK2, DDX58, DDX60, DHX58, EIF2AK2, EPSTI1, FBXO39, HERC5, HERC6, IFIT1, IFIT2, IFIT3, IRF7, LAP3, LOC100133669, OAS3, OASL, OTOF, PLSCR1, RSAD2, RTP4, SAMD9L, SIGLEC1, SPATS2L, TIMM10, USP18, ISG15 IFI27, IFI44, IFI44L, and ZBP1.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the one or more cytotoxic cell-associated transcriptional genes is selected from the group consisting of: FCRL6, FGFBP2, GNLY, GZMH, GZMK, NKG7 and PRF1; and wherein the one or more IFN-I inducible genes is selected from the group consisting of: BST2, CMPK2, DDX58, DDX60, DHX58, EIF2AK2, EPSTI1, HERC5, IFIT1, IFIT2, IFIT3, IRF7, ISG15, LAP3, OAS3, OASL, PLSCR1, RSAD2, RTP4, SAMD9L, SIGLEC1, TIMM10, USP18 and ZBP1.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the one or more cytotoxic cell-associated transcriptional genes comprises FCRL6, FGFBP2, GNLY, GZMH, NKG7, and PRF1; and wherein the one or more IFN-I inducible genes comprises IFIT3 and RSAD2.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the administering of the anti-IL-12/IL-23p40 antibody and the IFN-I inhibitor is at the same time or at different times.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the predicted increased likelihood of having a positive response to the treatment comprising administering the anti-IL-12/IL-23p40 antibody and the IFN-I inhibitor is determined with a logistic regression model of the formula:

$$\min_{\beta o, \beta} -\left[\frac{1}{N}\sum_{i=1}^{N} y_i(\beta o + \beta^T x_i) - \log\left(1 + e^{(\beta o + \beta^T x_i)}\right)\right] + \lambda\left[\frac{(1-\alpha)}{2}\|\beta\|_2^2 + \alpha\|\beta\|_1\right]$$

wherein N is the number of patients used to learn the model, $x_i$ is a vector of the centered gene expression data of patient i, $y_i$ is the response outcome for patient i (responder/non-responder), $\lambda$ controls the total penalty weight, $\alpha$ controls the elastic-net penalty weight: form lasso ($\alpha$=1) to ridge ($\alpha$=0), and $\alpha$, $\lambda$ are optimized using grid search based on best training accuracy; and, wherein after $\beta o$, $\beta$ parameters are determined a response probability is determined by the formula:

$$P(x_{new}) = \frac{1}{1 + e^{-(\beta o + \beta^T x_{new})}}$$

and response prediction is determined with a threshold of 0.5 using the formula:

$$\text{Response}(x_{new}) = \begin{cases} \text{responder}, & \text{if } P(x) \geq \text{threshlod} \\ \text{non-responder}, & \text{else} \end{cases}.$$

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the expression level of the one or more cytotoxic cell-associated transcriptional genes and the expression level of the one or more IFN-I inducible genes are determined by quantifying RNA transcripts in the biological samples or quantifying protein expression levels in the biological samples.

In certain embodiments, the present invention provides method for selecting patients with active Systemic Lupus Erythematosus (SLE) that are predicted to have an increased likelihood of having a positive response to a treatment comprising administering an anti-IL-12/IL-23p40 antibody and an IFN-I inhibitor, the method comprising: a.) determining the expression level one or more cytotoxic cell-associated transcriptional genes in a biological sample from the patients; b.) determining the expression level of one or more Interferon I (IFN-I) inducible genes in a biological sample from the patients; c.) calculating the mean expression levels of the one or more cytotoxic cell-associated transcriptional genes and the one or more Interferon I (IFN-I) inducible genes in the biological samples from the patients; d.) comparing the calculated mean expression levels to the expression levels in individual patients for the one or more cytotoxic cell-associated transcriptional genes and the one or more Interferon I (IFN-I) inducible genes; e.) determining if the individual patients have higher expression levels or lower expression levels compared to the mean expression levels of the one or more cytotoxic cell-associated transcriptional genes and the one or more Interferon I (IFN-I) inducible genes; f.) selecting the individual patients with lower expression levels of the one or more cytotoxic cell-associated transcriptional genes and higher expression levels of the one or more Interferon I (IFN-I) inducible genes, wherein the selected individual patients are predicted to have an increased likelihood of having a positive response to the treatment comprising administering an anti-IL-12/IL-23p40 antibody and an IFN-I inhibitor; and g.) treating the selected patients by administering the anti-IL-12/IL-23p40 antibody and the IFN-I inhibitor, wherein the biological sample is selected from the group consisting of: skin biopsies, whole blood, serum, and urine and wherein the IFN-I inhibitor is selected from the group consisting of: an anti-IFN alpha antibody, an anti IFN-I receptor antibody, inhibitors of Toll-Like Receptors (TLRs) 7, 8, and 9, agents that deplete or inhibit plasmacytoid dendritic cell function, and agents that inhibit Janus Kinase 1 (JAK1) and/or wherein the IFN-I inhibitor is selected from the group consisting of: the anti-IFN alpha antibody sifalimumab, the anti-IFN alpha antibody JNJ-55920839 (CNTO 6358) and the anti IFN-I receptor antibody anifrolumab.

BRIEF DESCRIPTION OF THE DRAWINGS

FIG. 3A shows serum IFN-alpha protein levels before and after treatment with ustekinumab or placebo using the Quanterix SIMOA platform (Lexington, Mass.). Samples were analysed by the CRO Myriad RBM (Austin, Tex.) using their QHSP-IFN-alpha Simoa assay. Within-subject Log 2(fold/baseline) of IFN-alpha (Mean±95% CI) is indicated on the y-axis. The x-axis indicates time in weeks post-treatment, 0=baseline prior to treatment. Status for SRI-4 response at 24 weeks is indicated by a solid black line for a positive response and a grey dashed line for non-responder. FIG. 3B shows a scatter plot of gene set variation analysis (GSVA) enrichment scores (ES) using a composite 21-gene published IFN-I signature (Yao et al, 2009) in whole blood. Dots indicate subjects and connected dots indicate longitudinal assessment within same subject. A heavy solid black line shows the median for each group. The x-axis indicates time in weeks post-treatment, 0=baseline prior to treatment. Treatment groups are labelled as PBO for placebo and UST for ustekinumab. Status for SRI-4 response at 24 weeks is indicated after treatment group name by "—R" for a positive response and "—NR" for a non-responder. ES from a healthy donor cohort (Healthy) are also shown.

FIG. 4A shows scatter plots of GSVA ES using a plasma blast cell signature composed of the following genes: CD38, CD27, P63, CD43, IRF4, CAV1, BCMA, GAS6, CD126, IL15RA, DCN, PRG1, CCR2, CXCR3, CD162, CD102, ITGA6, XBP1, CD138, PRDM1, IGJ. FIG. 4B shows scatter plots of GSVA ES using a plasma cell gene signature of DC.M4.11 Plasma Cells (Banchereau et al, 2016). For both plots (FIG. 4A and FIG. 4B), dots indicate subjects and connected dots indicate longitudinal assessment within same subject. A heavy solid black line shows the median for each group. The X axis indicates time in weeks post-treatment, 0=baseline prior to treatment. Treatment groups are labelled as PBO for placebo and UST for ustekinumab. Status for SRI-4 response at 24 weeks is indicated after treatment group name by "—R" for a positive response and "—NR" for a non-responder. ES from a healthy donor cohort (Healthy) are also shown.

FIG. 8A consisted of ~90% Caucasian (N=31 SLE donors), FIG. 8B consisted of ~50% African American/~40% Hispanic (N=52 SLE donors), and FIG. 8C consisted of Asian (N=30 SLE donors). For FIG. 8A, FIG. 8B, and FIG. 8C, the upper x-axis shows predicted clinical responders and predicted non-responders in black and light grey, respectively, for predictions based on the 8-gene signature* and the 31-gene signature**. Data was scaled for the purpose of better visualization in the heatmap. Scaled expression is computed by subtracting sample mean of the lupus patients and dividing by the standard deviation. The mean is set to zero and higher expression levels are represented as a gradient from >0 to 2, and low expression are represented as a gradient from <0 to −2. The 8-gene signature includes (in order from top to bottom): RSAD2 and IFIT3 from the IFN-I inducible gene cluster (FIG. 8A, FIG. 8B, and FIG. 8C) and GNLY, NKG7, PRF1, FCRL6, FGFBP2, GZMH from the cytotoxic cell-associated transcriptional gene cluster (FIG. 8A, FIG. 8B, and FIG. 8C).

DETAILED DESCRIPTION OF THE PREFERRED EMBODIMENTS

Figure 1:
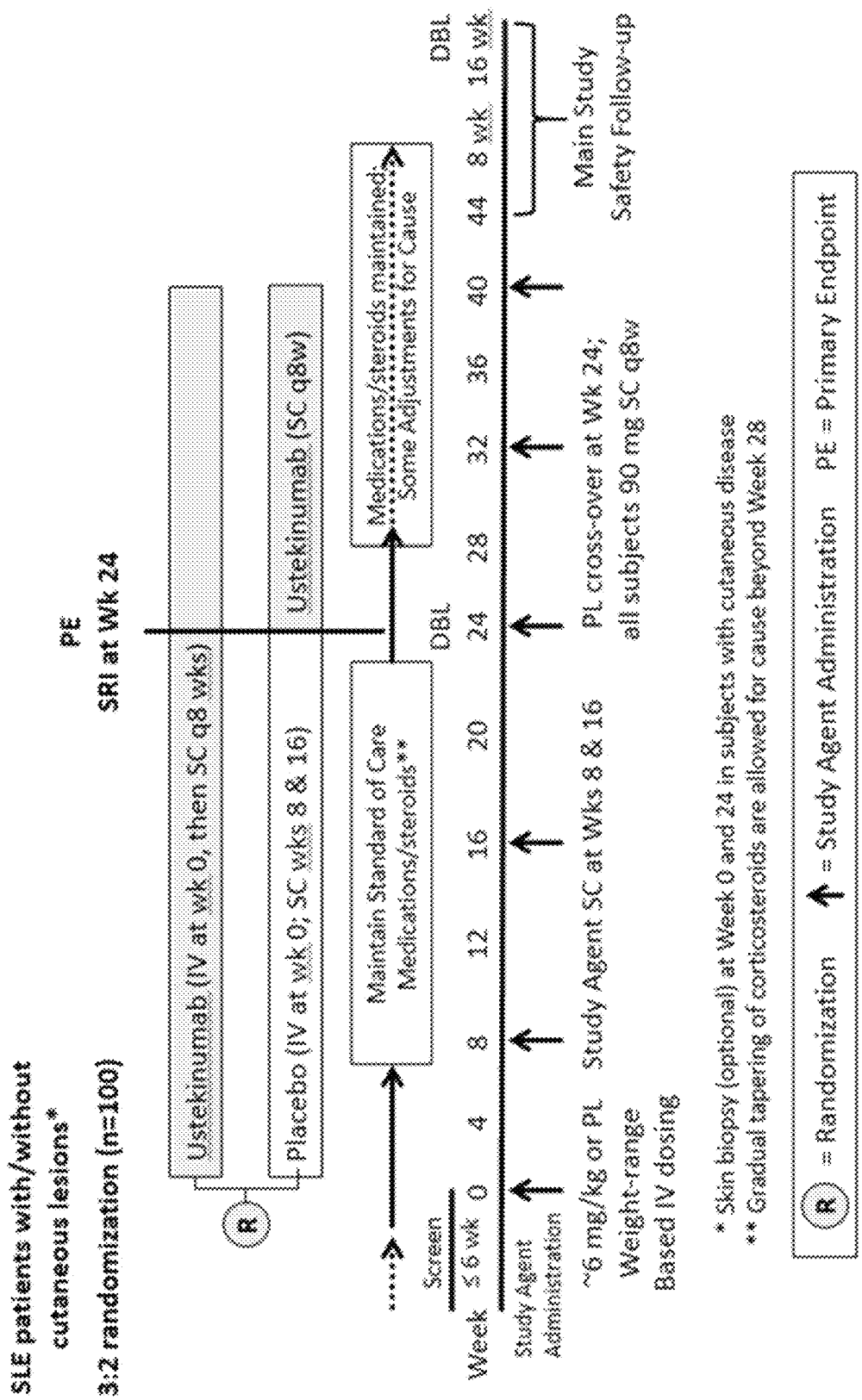
FIG. 1 shows a Schematic Overview of the Main Study (Screening through 16-Week Safety Follow-Up. Abbreviations: DBL=database lock; FU=follow-up; IV=intravenous; PE=primary endpoint; PL=placebo; q8w=every 8 weeks; SC=subcutaneous; SLE=systemic lupus erythematosus; SRI=SLEDAI-2K Responder Index; Wks=weeks.

As used herein the method of treatment of lupus comprises administering isolated, recombinant and/or synthetic anti-IL-12, IL-23 and IL12/23p40 human antibodies and diagnostic and therapeutic compositions, methods and devices.

As used herein, an "anti-IL-12 antibody," "anti-IL-23 antibody," "anti-IL-12/23p40 antibody," "IL-12/23p40 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-12 and/or IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-12/23 activity or binding, or with IL-12/23 receptor activity or binding, in vitro, in situ and/or in vivo. As a non-limiting example, a suitable anti-IL-12/23p40 antibody, specified portion or variant of the present invention can bind at least one IL-12/23 molecule, or specified portions, variants or domains thereof. A suitable anti-IL-12/23p40 antibody, specified portion, or variant can also optionally affect at least one of IL-12/23 activity or function, such as but not limited to, RNA, DNA or protein synthesis, IL-12/23 release, IL-12/23 receptor signaling, membrane IL-12/23 cleavage, IL-12/23 activity, IL-12/23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-12/23. For example, antibody fragments capable of binding to IL-12/23 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Anti-IL-12/23p40 antibodies (also termed IL-12/23p40 antibodies) (or antibodies to IL-23) useful in the methods and compositions of the present invention can optionally be characterized by high affinity binding to IL-12/23p40 (or to IL-23) and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344: 1125-1127 (1994), entirely incorporated herein by reference). "Low immunogenicity" can also be defined as the incidence of titrable levels of antibodies to the anti-IL-12 antibody in patients treated with anti-IL-12 antibody as occurring in less than 25% of patients treated, preferably, in less than 10% of patients treated with the recommended dose for the recommended course of therapy during the treatment period.

The terms "efficacy" and "effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IL12/23p40 or anti-IL23 antibody of the present invention (e.g., the anti-IL12/23p40 antibody ustekinumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, an anti-IL12/23p40 or anti-IL23 antibody of the present invention may be administered to achieve an improvement in a patient's condition related to Systemic Lupus Erythematosus (SLE). Improvement may be indicated by an improvement in an index of disease activity, by amelioration of clinical symptoms or by any other measure of disease activity. One such index of disease is the Systemic Lupus Erythematosus Disease Activity Index 2000 (SLEDAI-2K) score. The SLEDAI-2K is an established, validated disease activity index for Systemic Lupus Erythematosus (SLE) that is based on the presence of 24 features in 9 organ systems and measures disease activity in SLE patients in the previous 30 days. Features are scored if present within the last 30 days with more severe features having higher scores and the scores are added to determine the total SLEDAI-2K score, which ranges from 0 to 105. Other disease activity indexes for systemic lupus erythematosus (SLE) disease activity assessment include, for example, the Cutaneous Lupus Erythematosus Disease Area and Severity Index (CLASI) and the British Isles Lupus Assessment Group (BILAG) index. The CLASI index consists of 2 scores; the first summarizes the activity of the disease while the second is a measure of the damage done by the disease. The scores are calculated by simple addition based on the extent of the symptoms. Higher activity and damage scores indicate worse disease activity. The BILAG index is a measure of disease activity consisting of 97 questions in 9 organ systems, each put into 1 of 5 categories (A, B, C, D, E) depending on presence of items. Higher scores indicate more disease involvement.

The term "safe", as it relates to a dose, dosage regimen, treatment or method with an anti-IL12/23p40 or anti-IL23 antibody of the present invention (e.g., the anti-IL12/23p40 antibody usetkinumab), refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. In particular, safe as it relates to a dose, dosage regimen or treatment with an anti-IL12/23p40 or anti-IL23 antibody of the present invention refers to with an acceptable frequency and/or acceptable severity of adverse events associated with administration of the antibody if attribution is considered to be possible, probable, or very likely due to the use of the anti-IL12/23p40 or anti-IL23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

Utility

The isolated nucleic acids of the present invention can be used for production of at least one anti-IL-12/23p40 (or anti-IL-23) antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-12/23 condition, selected from, but not limited to, at least one of an immune disorder or disease, a cardiovascular disorder or disease, an infectious, malignant, and/or neurologic disorder or disease, or other known or specified IL-12/23 related condition.

Such a method can comprise administering an effective amount of a composition or a pharmaceutical composition comprising at least one anti-IL-12/23p40 (or anti-IL-23) antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

CITATIONS

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention—Production and Generation

At least one anti-IL-12/23p40 (or anti-IL-23) used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y.

(1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-12/23p40 antibody is ustekinumab (STELARA®) having the heavy chain variable region amino acid sequence of SEQ ID NO:7 and the light chain variable region amino acid sequence of SEQ ID NO:8 and having the heavy chain CDR amino acid sequences of SEQ ID NO:1, SEQ ID NO:2, and SEQ ID NO: 3; and the light chain CDR amino acid sequences of SEQ ID NO:4, SEQ ID NO:5, and SEQ ID NO:6. A preferred anti-IL-23 antibody is guselkumab (also referred to as CNTO1959). Other anti-IL-23 antibodies have sequences listed herein and are described in U.S. Pat. No. 7,935,344, the entire contents of which are incorporated herein by reference).

Human antibodies that are specific for human IL-12/23p40 or IL-23 proteins or fragments thereof can be raised against an appropriate immunogenic antigen, such as an isolated IL-12/23p40 protein, IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsried/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(5/12/94); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g.,
www.ncbi.nlm.nih.gov/entrez/query.fcgi;
www.ncbi.nih.gov/igblast;
www.atcc.org/phage/hdb.html;
www.mrc-cpe.cam.ac.uk/ALIGNMENTS.php;
www.kabatdatabase.com/top.html;
ftp.ncbi.nih.gov/repository/kabat;
www.sciquest.com;
www.abcam.com;
www.antibodyresource.com/onlinecomp.html;
www.public.iastate.edu/~pedro/research_tools.html;

www.whfreeman.com/immunology/CH05/kuby05.htm;
www.hhmi.org/grants/lectures/1996/vlab;
www.path.cam.ac.uk/~mrc7/mikeimages.html;
mcb.harvard.edu/BioLinks/Immunology.html;
www.immunologylink.com;
pathbox.wustl.edu/~hcenter/index.html;
www.appliedbiosystems.com;
www.nal.usda.gov/awic/pubs/antibody;
www.m.ehime-u.ac.jp/~yasuhito/Elisa.html;
www.biodesign.com;
www.cancerresearchuk.org;
www.biotech.ufl.edu;
www.isac-net.org;
baserv.uci kun.nl/~jraats/links1.html;
www.recab.uni-hd.de/immuno.bme.nwu.edu;
www.mrc-cpe.cam.ac.uk;
www.ibt.unam.mx/vir/V_mice.html;
www.bioinf.org.uk/abs;
antibody.bath.ac.uk;
www.unizh.ch;
www.cryst.bbk.ac.uk/~ubcg07s;
www.nimr.mrc.ac.uk/CC/ccaewg/ccaewg.html;
www.path.cam.ac.uk/~mrc7/humanisation/TAHHP.html;
www.ibt.unam.mx/vir/structure/stat_aim.html;
www.biosci.missouri.edu/smithgp/index.html;
www.jerini.de;
and Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human anti-IL-12/23p40 (or anti-IL-23) specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human anti-IL-12/23p40 (or anti-IL-23) specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human anti-IL-12/23p40 (or anti-IL-23) specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human anti-IL-12/23p40 (or anti-IL-23) antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human anti-IL-12/23p40 (or anti-IL-23) specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human anti-IL-12/23p40 (or anti-IL-23) specific antibody of the present invention is expressed in cells that express beta (1,4)-N-acetylglucosaminyltransferase III (GnT III), such that GnT III adds GlcNAc to the human anti-IL-12/23p40 (or anti-IL-23) antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The human anti-IL-12/23p40 (or anti-IL-23) antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-12/23p40 (or anti-IL-23) antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL-12/23p40 (or anti-IL-23) antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616; 5,565, 362; 5,304,489, and the like, each of which is entirely incorporated herein by reference.

Antibodies used in the method of the present invention can additionally be prepared using at least one anti-IL-12/ 23p40 (or anti-IL-23) antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbiol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-12/IL-23p40 or IL-23 with a wide range of affinities ($K_D$). In a preferred embodiment, a human mAb can optionally bind human IL-12/IL-23p40 or IL-23 with high affinity. For example, a human mAb can bind human IL-12/IL-23p40 or IL-23 with a $K_D$ equal to or less than about $10^{-7}$M, such as but not limited to, 0.1-9.9 (or any range or value therein)×10', $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N Y (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one IL-12/IL-23p40 or IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-12/IL-23p40 or IL-23 antibody or variable region; and nucleic acid molecules which comprise a nucleotide sequence substantially different from those described above but which, due to the degeneracy of the genetic code, still encode at least one anti-IL-12/IL-23p40 or IL-23 antibody as described herein and/or as known in the art. Of course, the genetic code is well known in the art. Thus, it would be routine for one skilled in the art to generate such degenerate nucleic acid variants that code for specific anti-IL-12/IL-23p40 or IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-12/IL-23p40 or IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-12/IL-23p40 or IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-12/IL-23p40 or IL-23 Antibodies

An anti-IL-12/IL-23p40 or IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-12/IL-23p40 or IL-23 and, thereby, partially or substantially neutralizes at least one biological activity of the protein. An antibody, or specified portion or variant thereof, that partially or preferably substantially neutralizes at least one biological activity of at least one IL-12/IL-23p40 or IL-23 protein or fragment can bind the protein or fragment and thereby inhibit activities mediated through the binding of IL-12/IL-23p40 or IL-23 to the IL-12 and/or IL-23 receptor or through other IL-12/IL-23p40 or IL-23-dependent or mediated mechanisms. As used herein, the term "neutralizing antibody" refers to an antibody that can inhibit an IL-12/IL-23p40 or IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-12/IL-23p40 or IL-23 antibody to inhibit an IL-12/IL-23p40 or IL-23-dependent activity is preferably assessed by at least one suitable IL-12/IL-23p40 or IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-12/IL-23p40 or IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-12/IL-23p40 or IL-23 specific antibody can comprise at least one of a heavy or light chain variable region having a defined amino acid sequence. For example, in a preferred embodiment, the anti-IL-12/IL-23p40 or IL-23 antibody comprises an anti-IL-12/IL-23p40 antibody with a heavy chain variable region comprising the amino acid sequence of SEQ ID NO:7 and a light chain variable region comprising the amino acid sequence of SEQ ID NO:8. The anti-IL-12/IL-23p40 or IL-23 specific antibody can also comprise at least one of a heavy or light chain having a defined amino acid sequence. In another preferred embodiment, the anti-IL-12/IL-23p40 or IL-23 antibody comprises an anti-IL-12/IL-23p40 antibody with a heavy chain comprising the amino acid sequence of SEQ ID NO:10 and a light chain comprising the amino acid sequence of SEQ ID NO:11. Antibodies that bind to human IL-12/IL-23p40 or IL-23 and that comprise a defined heavy or light chain variable region can be prepared using suitable methods, such as phage display (Katsube, Y., et al., *Int J Mol. Med*, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-12/IL-23p40 or IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/IL-23p40 or IL-23 with high affinity (e.g., $K_D$ less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-12/IL-23p40 or IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

Sequences

Example anti-IL-12/IL-23p40 antibody sequences—STELARA® (ustekinumab)

Amino acid sequence of anti-IL-12/IL-23p40 antibody complementarity determining region heavy chain 1 (CDRH1): (SEQ ID NO:1)

TYWLG

Amino acid sequence of anti-IL-12/IL-23p40 antibody complementarity determining region heavy chain 2 (CDRH2): (SEQ ID NO:2)

IMSPVDSDIRYSPSFQG

Amino acid sequence of anti-IL-12/IL-23p40 antibody complementarity determining region heavy chain 3 (CDRH3): (SEQ ID NO:3)

RRPGQGYFDF

Amino acid sequence of anti-IL-12/IL-23p40 antibody complementarity determining region light chain 1 (CDRL1): (SEQ ID NO:4)

```
RASQGISSWLA
```

Amino acid sequence of anti-IL-12/IL-23p40 antibody complementarity determining region light chain 2 (CDRL2): (SEQ ID NO:5)

```
AASSLQS
```

Amino acid sequence of anti-IL-12/IL-23p40 antibody complementarity determining region light chain 3 (CDRL3): (SEQ ID NO:6)

```
QQYNIYPYT
```

Amino acid sequence of anti-IL-12/IL-23p40 antibody variable heavy chain region (CDRs underlined): (SEQ ID NO:7)

```
  1  EVQLVQSGAE VKKPGESLKI SCKGSGYSFT TYWLGWVRQM PGKGLDWIGI MSPVDSDIRY
 61  SPSFQGQVTM SVDKSITTAY LQWNSLKASD TAMYYCARRR PGQGYFDFWG QGTLVTVSS
```

Amino acid sequence of anti-IL-12/IL-23p40 antibody variable light chain region (CDRs underlined): (SEQ ID NO:8)

```
  1  DIQMTQSPSS LSASVGDRVT ITCRASQGIS SWLAWYQQKP EKAPKSLIYA ASSLQSGVPS
 61  RFSGSGSGTD FTLTISSLQP EDFATYYCQQ YNIYPYTFGQ GTKLEIKR
```

Amino acid sequence of anti-IL-12/IL-23p40 antibody heavy chain (CDRs underlined): (SEQ ID NO:10)

```
  1  EVQLVQSGAE VKKPGESLKI SCKGSGYSFT TYWLGWVRQM PGKGLDWIGI MSPVDSDIRY
 61  SPSFQGQVTM SVDKSITTAY LQWNSLKASD TAMYYCARRR PGQGYFDFWG QGTLVTVSSS
121  STKGPSVFPL APSSKSTSGG TAALGCLVKD YFPEPVTVSW NSGALTSGVH TFPAVLQSSG
181  LYSLSSVVTV PSSSLGTQTY ICNVNHKPSN TKVDKRVEPK SCDKTHTCPP CPAPELLGGP
241  SVFLFPPKPK DTLMISRTPE VTCVVVDVSH EDPEVKFNWY VDGVEVHNAK TKPREEQYNS
301  TYRVVSVLTV LHQDWLNGKE YKCKVSNKAL PAPIEKTISK AKGQPREPQV YTLPPSRDEL
361  TKNQVSLTCL VKGFYPSDIA VEWESNGQPE NNYKTTPPVL DSDGSFFLYS KLTVDKSRWQ
421  QGNVFSCSVM HEALHNHYTQ KSLSLSPGK
```

Amino acid sequence of anti-IL-12/IL-23p40 antibody light chain (CDRs underlined): (SEQ ID NO:11)

```
  1  DIQMTQSPSS LSASVGDRVT ITCRASQGIS SWLAWYQQKP EKAPKSLIYA ASSLQSGVPS
 61  RFSGSGSGTD FTLTISSLQP EDFATYYCQQ YNIYPYTFGQ GTKLEIKRTV AAPSVFIFPP
121  SDEQLKSGTA SVVCLLNNFY PREAKVQWKV DNALQSGNSQ ESVTEQDSKD STYSLSSTLT
181  LSKADYEKHK VYACEVTHQG LSSPVTKSFN RGEC
```

Amino Acid Sequence IL-12
Amino acid sequence of human interleukin (IL)-12 with alpha and beta subunits: (SEQ ID NO:9)

```
  1  RNLPVATPDP GMFPCLHHSQ NLLRAVSNML QKARQTLEFY PCTSEEIDHE DITKDKTSTV
 61  EACLPLELTK NESCLNSRET SFITNGSCLA SRKTSFMMAL CLSSIYEDLK MYQVEFKTMN
121  AKLLMDPKRQ IFLDQNMLAV IDELMQALNF NSETVPQKSS LEEPDFYKTK IKLCILLHAF
181  RIRAVTIDRV MSYLNASIWE LKKDVYVVEL DWYPDAPGEM VVLTCDTPEE DGITWTLDQS
```

```
241  SEVLGSGKTL TIQVKEFGDA GQYTCHKGGE VLSHSLLLLH KKEDGIWSTD ILKDQKEPKN

301  KTFLRCEAKN YSGRFTCWWL TTISTDLTFS VKSSRGSSDP QGVTCGAATL SAERVRGDNK

361  EYEYSVECQE DSACPAAEES LPIEVMVDAV HKLKYENYTS SFFIRDIIKP DPPKNLQLKP

421  LKNSRQVEVS WEYPDTWSTP HSYFSLTFCV QVQGKSKREK KDRVFTDKTS ATVICRKNAS

481  ISVRAQDRYY SSSWSEWASV PCS
```

An anti-IL-12/IL-23p40 or IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-12/IL-23p40 or IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-12/IL-23p40 or IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-12/IL-23p40 or IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-12/IL-23p40 or IL-23 antibodies can include, but are not limited to, at least one portion, sequence or combination selected from 5 to all of the contiguous amino acids of at least one of SEQ ID NOs 1, 2, 3, 4, 5, 6, 7, 8, 10, or 11.

IL-12/IL-23p40 or IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-12/IL-23p40 or IL-23 antibody can further optionally comprise a polypeptide of at least one of 70-100% of 5, 17, 10, 11, 7, 9, 119, 108, 449, or 214 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or: $n_n \le x_n - (x_n \cdot y)$,
wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or: $n_a \le x_a - (x_a \cdot y)$, wherein $n_a$ is the number of amino acid alterations, $x_a$ is the total number of amino acids in the SEQ ID NOs above, and y is, for instance 0.70 for 70%, 0.80 for 80%, 0.85 for 85% etc., and wherein any non-integer produce of $x_a$ and y is rounded down to the nearest integer prior to subtracting it from $x_a$.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-12/IL-23p40 or IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and dicarboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NETS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O— $CH$—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

The method of the present invention also uses an anti-IL-12/IL-23p40 or IL-23 antibody composition comprising at least one, at least two, at least three, at least four, at least five, at least six or more anti-IL-12/IL-23p40 or IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-12/IL-23p40 or IL-23 antibody amino acid sequence selected from the group consisting of 70-100% of the contiguous amino acids of the SEQ ID NOs above, or specified fragments, domains or variants thereof. Preferred anti-IL-12/IL-23p40 or IL-23 antibody compositions include at least one or two full length, fragments, domains or variants as at least one CDR or LBP containing portions of the anti-IL-12/IL-23p40 or IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, P A, 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, 6-mercaptopurine, methotrexate, mizoribine, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook*.)

Anti-IL-12/IL-23p40 or IL-23 antibody compositions can further comprise at least one of any suitable and effective amount of a composition or pharmaceutical composition comprising at least one anti-IL-12/IL-23p40 or IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-IL-12/IL-23p40 or IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-12/IL-23p40 or IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-12/IL-23p40 or IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN®20" and "TWEEN®80"), lipids (e.g., phospholipids, fatty acids), steroids (e.g., cholesterol), and chelating agents (e.g., EDTA).

These and additional known pharmaceutical excipients and/or additives suitable for use in the anti-IL-12/IL-23p40 or IL-23 antibody, portion or variant compositions according to the invention are known in the art, e.g., as listed in "Remington: The Science & Practice of Pharmacy," 19$^{th}$ ed., Williams & Williams, (1995), and in the "Physician's Desk Reference," 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-12/IL-23p40 or IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-12/IL-23p40 or IL-23 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-12/IL-23p40 or IL-23 antibody, and a second vial comprising an aqueous diluent of prescribed buffer or preservative, wherein said packaging material comprises a label that instructs a patient to reconstitute the anti-IL-12/IL-23p40 or IL-23 antibody in the aqueous diluent to form a solution that can be held over a period of twenty-four hours or greater.

The anti-IL-12/IL-23p40 or IL-23 antibody used in accordance with the present invention can be produced by recombinant means, including from mammalian cell or transgenic preparations, or can be purified from other biological sources, as described herein or as known in the art.

The range of the anti-IL-12/IL-23p40 or IL-23 antibody includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like TWEEN®20 (polyoxyethylene (20) sorbitan monolaurate), TWEEN®40 (polyoxyethylene (20) sorbitan monopalmitate), TWEEN®80 (polyoxyethylene (20) sorbitan monooleate), PLURONIC® (polyIs)F68 (polyoxyethylene polyoxypropylene block copolymers), and PEG (polyethylene glycol) or non-ionic surfactants, such as polysorbate 20 or 80 or poloxamer 184 or 188, PLURONIC® (polyls), other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-12/IL-23p40 or IL-23 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-12/IL-23p40 or IL-23 specific antibody and preservative in an aqueous diluent is carried out using conventional dissolution and mixing procedures. To prepare a suitable formulation, for example, a measured amount of at least one anti-IL-12/IL-23p40 or IL-23 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-12/IL-23p40 or IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-12/IL-23p40 or IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-12/IL-23p40 or IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-12/IL-23p40 or IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as B-D® (pen injector device), Humaject NOVOPEN® (pen injector device), AUTOPEN® (pen injector device), OPTI-PEN® (pen injector device), GENOTROPIN PEN® (pen injector device), HUMATROPEN® (pen injector device), Reco-Pen, BIOJECTOR® (pen injector device), J-tip Needle-Free Injector, Intraject, Medi-Ject, and SMART-JECT® (autoinjector device) e.g., as made or developed by Becton Dickensen (Franklin Lakes, N.J., www. bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www. mediject.com), and similarly suitable devices. Recognized devices comprising a dual vial system include those pen-injector systems for reconstituting a lyophilized drug in a cartridge for delivery of the reconstituted solution, such as the HUMATROPEN® (pen injector device). Examples of other devices suitable include pre-filled syringes, auto-injectors, needle free injectors, SELF-DOSE™ (injector device) (West Pharmaceuticals, Inc. of Exton, Pa.) and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-12/IL-23p40 or IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-12/IL-23p40 or IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-12/IL-23p40 or IL-23 specific mAbs bind to similar or different epitopes and/or compete with each other. Abs are individually coated on ELISA plates. Competing mAbs are added, followed by the addition of biotinylated hrIL-12 or IL-23. For positive control, the same mAb for coating may be used as the competing mAb ("self-competition"). IL-12/IL-23p40 or IL-23 binding is detected using streptavidin. These results demonstrate whether the mAbs recognize similar or partially overlapping epitopes on IL-12/IL-23p40 or IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(ß-hydroxy butyric acid), polyethylene oxide, polyethylene, poly (alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating lupus, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-12/1L-23p40 or IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanercept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, $21^{st}$ edition, Springhouse Corp., Springhouse, P A, 2001; Health Professional's Drug Guide 2001, ed., Shannon, Wilson, Stang, Prentice-Hall, Inc, Upper Saddle River, N.J., each of which references are entirely incorporated herein by reference.

Therapeutic Treatments

Typically, treatment of lupus is affected by administering an effective amount or dosage of an anti-IL-12/23p40 or anti-IL-23 antibody composition that total, on average, a range from at least about 0.01 to 500 milligrams of an anti-IL-12/23p40 or anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin.

Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-12/IL-23p40 or IL-23 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-12/IL-23p40 or IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-12/IL-23p40 or IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EXAMPLES

Example 1: A Multicenter, Randomized, Double-blind, Placebo-controlled, Proof-of-Concept Study of Ustekinumab in Subjects with Active Systemic Lupus Erythematosus Synopsis STELARA® (ustekinumab) is a fully human G1 kappa monoclonal antibody that binds with high affinity and specificity to the shared p40 subunit of human interleukin (IL)-12 and IL-23 cytokines. The binding of ustekinumab to the IL-12/23p40 subunit blocks the binding of IL-12 or IL-23 to the IL-12Rβ1 receptor on the surface of natural killer and CD4⁺ T cells, inhibiting IL-12- and IL-23-specific intracellular signaling and subsequent activation and cytokine production. Abnormal regulation of IL-12 and IL-23 has been associated with multiple immune-mediated diseases including Systemic Lupus Erythematosus (SLE). Therefore, inhibition of IL-12 and IL-23 has the potential to be effective in the treatment of SLE.

Objective and Hypothesis

Primary Objective

The primary objective is to evaluate the efficacy of ustekinumab as measured by a reduction in disease activity for subjects with active SLE.

Secondary Objectives

The secondary objectives are to evaluate:

The safety and tolerability of ustekinumab in subjects with SLE.

The effect of ustekinumab administration on health-related quality of life in subjects with SLE.

The effects of ustekinumab on cutaneous manifestations of SLE.

Pharmacokinetics and immunogenicity of ustekinumab in subjects with SLE.

Exploratory Objective

The exploratory objectives are to evaluate:

Safety and efficacy during long-term administration of ustekinumab.

Reduction in corticosteroid dosing during long-term administration of ustekinumab.

Additional composite clinical endpoints or methods of calculation of clinical response with potential for greater sensitivity to improvement and/or worsening of SLE.

Biomarkers related to lupus disease (genetic, systemic, and skin-related).

Hypothesis

The hypothesis is that dosing with ustekinumab is significantly superior to placebo as measured by the Systemic Lupus Erythematosus Disease Activity Index 2000 (SLE-DAI-2K) Responder Index (SRI-4) composite measure at Week 24.

Overview of Study Design

CNTO1275SLE2001 is a Phase 2a, proof-of-concept, multicenter, randomized, double-blind, placebo-controlled study of the efficacy and safety of ustekinumab added to standard of care background in subjects with active SLE. Subjects to be enrolled must have SLE according to Systemic Lupus International Collaborating Clinics (SLICC) criteria and Systemic Lupus Erythematosus Disease Activity Index 2000 (SLEDAI-2K) score≥6, despite conventional treatment (e.g., immunomodulators, antimalarial drugs, corticosteroids, nonsteroidal anti-inflammatory drugs, anti-hypertensive drugs, and/or topical medications). In addition, subjects must have at least 1 positive autoantibody test (antinuclear antibodies [ANA], anti-double stranded deoxyribonucleic acid (anti-dsDNA) antibodies, and/or anti-Smith antibodies) observed during screening, as well as a well-documented positive autoantibody test in medical history. Subjects must also demonstrate at least 1 British Isles Lupus Assessment Group (BILAG) A and/or 2 BILAG B domain scores observed during screening. In addition, subjects must have a clinical SLEDAI-2K score ≥4 (excluding laboratory results) at week 0, prior to randomization.

Approximately 100 subjects will be randomly assigned in a 3:2 ratio to receive either ustekinumab or placebo through Week 24. Following randomization at Week 0, subjects will receive an initial body weight-range based IV dose approximating 6 mg/kg of ustekinumab (ustekinumab 260 mg [weight ≥35 kg to ≤55 kg]; ustekinumab 390 mg [weight >55 kg and ≤85 kg]; ustekinumab 520 mg [weight >85 kg]) followed by 90 mg SC administered every 8 weeks (q8w).

At Week 24, subjects receiving placebo will cross-over and all subjects will receive ustekinumab 90 mg SC at Weeks 24, 32, and 40 followed by safety follow-up through Week 56 in a blinded fashion for 16 weeks (i.e., approximately 5 half-lives) after last study agent SC administration.

A placebo comparator (added to standard of care background therapy) will be used through Week 24 for the evaluation of the efficacy and safety of ustekinumab in subjects with SLE. From Week 24 through Week 40, the placebo group will cross-over to receive ustekinumab 90 mg SC q8w. This cross-over design will permit placebo subjects to receive study agent and provide experience with ustekinumab 90 mg SC without the IV loading dose in subjects with SLE. The 40-Week dosing period will be useful to understand the longer-term safety and time course of potential clinical response of ustekinumab in the SLE population.

Every reasonable effort should be made to keep concomitant medications stable as defined in the protocol. All concomitant therapies must be recorded throughout the study beginning at entry into screening and any changes must be recorded throughout the study.

All subjects with cutaneous disease will be evaluated using Cutaneous Lupus Erythematosus Disease Area and Severity Index (CLASI) scoring. Additionally, subjects with cutaneous disease who consent to participate in the cutaneous lupus substudy will have other assessments including collection of skin biopsies (optional consent) and/or photographs of a cutaneous lesion or area of active disease (optional consent). There will not be any restrictions on the number of subjects with cutaneous disease who can enroll into either the main study or the cutaneous lupus substudy.

Interim analyses (IA) will be conducted when approximately ⅓ and ⅔ of subjects reach Week 24. In the first IA, only an assessment of notable efficacy will be performed. In the second IA, evidence for notable efficacy as well as treatment futility will be analyzed. Database locks (DBLs) will occur at Weeks 24 and following the last subject's Week 56 visit, or the final subject's Week 16 safety follow-up visit from the main study. In addition, an independent data monitoring committee (DMC) will review interim safety data periodically including a formal review when approximately ⅓ and ⅔ of subjects reach Week 24, as well as at the Week 24 DBL. The DMC will make a recommendation to the Sponsor committee whether the study should be stopped for futility or for safety concerns or if data meet prespecified criteria demonstrating notable efficacy. The content of the summaries, the DMC role and responsibilities, and the general procedures (including communications) will be defined in the DMC charter.

The amended study design will continue to provide open-label ustekinumab 90 mg q8w SC administration through Week 104. Subjects will be eligible to continue study treatment through Week 104 if they meet the study inclusion criteria (Section 4.1.3) including:

must not have permanently discontinued study treatment on or before their Week 40 visit, and are able to continue q8 week study treatment at approximately 8 weeks (±2 weeks) after their Week 40 visit or are able to resume study treatment with no more than 16 weeks (±2 weeks) since their Week 40 visit.

In addition to the DBL planned after the final subject's Week 56 visit, or after the last subject's Week 16 safety follow-up visit from the main study, there will be an additional DBL at the end of the study extension (following Study Extension 16-week safety follow-up visit).

Subject Population

Screening for eligible subjects must be performed no more than 6 weeks prior to the randomization visit (Week 0). The target study population is subjects with SLE according to SLICC criteria and SLEDAI-2K score ≥6, despite conventional treatment (e.g., immunomodulators, antimalarial drugs, corticosteroids, nonsteroidal anti-inflammatory drugs, anti-hypertensive drugs, and/or topical medications). In addition, subjects must have at least 1 positive autoantibody test (ANA, anti-dsDNA antibodies, and/or anti-Smith antibodies) observed during screening, as well as a well-documented positive autoantibody test in medical history. Subjects must also have at least 1 BILAG A and/or 2 BILAG B domain scores observed during screening prior to first administration of study agent.

In addition, to be eligible for study participation, subjects must have a clinical SLEDAI-2K score ≥4 (excluding laboratory results) for clinical features at Week 0 (prior to randomization) and have received approval for study randomization following review and adjudication of screening lupus assessments by the Sponsor and/or Sponsor-selected independent reviewer(s).

SLE subjects enrolling into the main study with active cutaneous lupus (including subjects with discoid lupus erythematosus, subacute cutaneous lupus erythematosus, alopecia or SLE malar rash or other SLE skin lesions characterized by erythema and or scale) will be evaluated using CLASI scoring. In addition, subjects who provide consent will be enrolled in the cutaneous lupus substudy evaluating the histology of cutaneous biopsies and/or skin photographs. Subjects participating in the cutaneous lupus substudy are not required to undergo biopsies, and may allow only photographs to document changes in an identified lesion or area of active disease.

Dosage and Administration

All subjects will receive a body weight range-based IV administration of study agent (placebo or ustekinumab) at Week 0 and then SC administration of placebo or ustekinumab at Weeks 8 and 16, followed by all subjects receiving ustekinumab dosing at Weeks 24, 32, and 40. Every reasonable effort should be made to keep concomitant medications stable at least through Week 28, with some adjustments allowed beyond Week 28 through the 8-Week Safety Follow-Up or study extension as defined in the protocol. A concomitant medication may be reduced or medication temporarily discontinued because of abnormal laboratory values, side effects, concurrent illness, or the performance of a surgical procedure, but the change and reason for the medication change should be clearly documented in the subject's medical record. If concomitant medications have been adjusted after randomization as allowed per protocol, every effort should be made to return subject back to the baseline (Week 0) dose level by the Week 12 visit; or increased medication use may render a subject to be considered a treatment failure.

Subjects who are enrolled in the study extension will continue to receive ustekinumab 90 mg SC administration every 8 weeks through Week 104. With the exception of corticosteroids, concomitant medications should be maintained at stable doses through the study extension.

Week 0 Up to Week 24 (Blinded Study Agent Administration Phase)

Group 1: Subjects will receive weight-range based IV dosing of approximately 6 mg/kg of ustekinumab at Week 0 followed by ustekinumab 90 mg SC administrations at Weeks 8 and 16.

Group 2: Subjects will receive weight-range based IV dosing of placebo at Week 0 followed by placebo SC administrations at Weeks 8 and 16.

Week 24 to Week 40 (Cross-over Administration Phase)

Group 1: Subjects will receive an ustekinumab 90 mg SC administration at Week 24 followed by q8w administrations through Week 40.

Group 2: Subjects in the placebo dosing group will cross-over to ustekinumab 90 mg SC administrations at Week 24 followed by q8w administrations through Week 40.

After Week 40 to 16-Week Safety Follow-Up (Safety Follow-Up Phase)

Groups 1 and 2: Subjects who do not participate in the study extension are expected to return for safety follow-up visits at Week 44 and for 8- and 16-weeks safety follow up.

Study Extension (Week 48/Week 56 Through Week 120)

Subjects who meet the study extension inclusion criteria (Section 4.1.3) will receive an additional 1 year of open label ustekinumab administration for the purpose of expanding the safety experience and maintenance of efficacy in lupus patients exposed to ustekinumab 90 mg q8w. Subjects who continue dosing in the extended study starting at Week 48 or at Week 56 will receive open-label ustekinumab SC dosing through Week 104. If the development of ustekinumab in SLE is terminated, then the study extension will also be discontinued.

Efficacy Evaluations

The primary efficacy endpoint of this study is to compare the proportion of subjects with a composite SRI-4 response at Week 24 for subjects receiving ustekinumab as compared to placebo treatment.

Efficacy evaluations and patient reported quality of life measures include:
SLEDAI-2K
S2K RI-50
BILAG
CLASI
Physician's Global Assessment of Disease Activity
Patient's Global Assessment of Disease Activity
Short-form 36 questionnaire
Fatigue Severity Scale
Patient's Assessment of Pain Pharmacokinetic and Immunogenicity Evaluations Serum samples will be used to evaluate the pharmacokinetics of ustekinumab, as well as the immunogenicity of ustekinumab (antibodies to ustekinumab).

Biomarker Evaluations and Serologic Markers

The collection, preparation, storage and shipment of skin biopsies, blood, serum and urine are detailed in the Laboratory Manual. Biomarkers may include, but are not limited to, inflammatory markers, ribonucleic acid (RNA), cell surface markers, autoantibodies, T cell and B cell repertoire, target specific markers, and other categories of biomarkers potentially involved in the development and the progression of lupus.

Serum Analyses

Serum will be analyzed for levels of specific proteins including but not limited to soluble CD40 ligand (sCD154), interleukin (IL)-6, IL-12p40, IL-17, IL-21, IL-22, IL-23p19, C—X—C motif chemokine 10 (CXCL10), B cell activating factor (BAFF), interferons, autoantibodies and other inflammation-related molecules.

Skin Biopsy Analyses

Skin biopsies will be utilized for cellular, molecular, and gene expression analyses.

Whole Blood Gene Expression Analyses

Whole blood will be collected from all subjects for RNA, flow cytometry, T cell and B cell repertoire and epigenetics analysis (e.g., deoxyribonucleic acid [DNA] methylation).

Serologic Markers

Autoantibodies (e.g., ANA, anti-dsDNA, etc.), complement C3 and C4 will be collected as described in the Table of Events (Table 1).

Pharmacogenomic (DNA) Evaluations

DNA samples will be used for research related to this study (CNTO1275SLE2001). Specific genomic testing will be undertaken for consenting subjects (subjects participating in this portion of the study must sign a separate informed consent form. The procedure will involve taking a blood sample that may be analyzed for specific target genes that may play a role in lupus. Any genomic assessments will be performed in strict adherence to current subject confidentiality standards for genetic testing. Refusal to participate in genomics testing will not result in ineligibility for participation in the rest of the clinical study.

Cutaneous Lupus Substudy

All subjects with cutaneous disease will be evaluated using CLASI scoring. Additionally, subjects with cutaneous disease who consent to participate in the cutaneous lupus sub study will have other assessments including collection of skin biopsies (optional consent) and/or photographs of an identified cutaneous lesion or area of active disease (optional consent). There will not be any restrictions on the number of subjects with cutaneous disease who can enroll into either the main study or the cutaneous lupus substudy.

Subjects who provide consent will be enrolled in the cutaneous lupus substudy evaluating the histology of cutaneous biopsies and/or skin photographs. Biopsy samples (2 samples, 4 mm size) from consenting subjects will be collected prior to dosing at Week 0 and at Week 24 from a single lesion or area of active cutaneous disease. Photographs and skin biopsies can target a different area of active disease, but the follow-up photographs or biopsies should re-evaluate the same area of active disease as originally assessed at week 0. Subjects participating in the cutaneous lupus substudy are not required to undergo biopsies, and may allow only photographs to document changes in an identified lesion or area of active disease. Subjects with cutaneous lupus deemed unsuitable for biopsy (e.g., malar rash or alopecia) can also be enrolled in the substudy, and may be evaluated by photography.

Independent of cutaneous biopsy collection, subjects who participate in the cutaneous lupus substudy will be requested to provide consent for photographs to be collected from an identified lesion or area of active disease. The photographs are for exploratory purposes only. The photographs will be used to assist in a qualitative evaluation of clinical response. Confidentiality of the subjects involved in this study will be maintained; specifically photographs of subjects in this study will not be published or otherwise made public without blocking adequate portions of the subject's face or body so that the individual cannot be identified.

Safety Evaluations

Safety assessments include vital signs, general physical exam and skin evaluations, adverse events (AE), serious AEs, concomitant medication review, pregnancy testing, infusion reactions, chemistry and hematology laboratory tests, and antibodies to ustekinumab. Chest x-ray and tuberculosis, human immunodeficiency virus, hepatitis B, and hepatitis C testing will be required at time of screening. Any clinically significant abnormalities persisting at the end of the study will be followed by the investigator until resolution or until a clinically stable endpoint is reached. Subject diary cards will be used to capture medication changes that occur in between study visits during the main portion of this study. Safety data collected up to 16 weeks after the final administration of study agent will be evaluated.

Statistical Methods

Sample Size Determination

Approximately 100 subjects will be randomly assigned in a 3:2 ratio to receive either ustekinumab or placebo through Week 24. Approximately sixty subjects treated with ustekinumab and approximately 40 subjects with placebo is projected to give approximately 80% power to detect a significant difference in response rate compared with placebo (assume 35% and 60% response rates in placebo and ustekinumab respectively, which translates to 25% absolute increase over placebo or an odds ratio of 2.79) with an alpha level of 0.1.

Efficacy Analyses

The primary endpoint of this study is the proportion of subjects with a composite measure of SLE disease activity (SLE Responder Index [SRI]-4 response) at Week 24. The primary analysis will be based upon the primary endpoint and will be conducted on the modified intent-to-treat (mITT) population, which includes all randomized subjects who receive at least 1 dose of study agent, have at least 1 measurement prior to the administration, and have at least 1 post-baseline SRI-4 measurement.

Last observation carried forward (LOCF) procedure will be used to impute the missing SRI-4 component if the subjects have data for at least 1 SRI-4 component at Week 24. If the subjects do not have data for any SRI components at Week 24, the subjects will be considered not to have achieved the SRI-4 response.

In addition, subjects who meet any of a variety of treatment failure criteria, such as receiving a dose of immunomodulator that is higher at Week 24 than at baseline, or initiated prohibited treatment (dose or timing) with corticosteroids, or discontinued study agent due to a lack of efficacy will be considered to have not achieved the primary endpoint, SRI-4 response at Week 24.

Logistic regression, adjusting for baseline stratifications and baseline SLEDAI, will be used to analyze the primary endpoint. The baseline SLEDAI value is defined as the closest non-missing measurement taken prior to the Week 0 infusion. If significant non-normality is observed, appropriate nonparametric tests will be used to evaluate the differences between treatments.

The study will be considered positive if the primary analysis achieves statistical significance at a significance level of 0.1 (2-sided) and ustekinumab shows a positive treatment effect relative to placebo treatment.

Safety Analyses

Safety will be assessed by analyses of the incidence and type of AEs, SAES, reasonably related AEs, infections, and infusion reactions. Safety assessments will also include analyses of laboratory parameters and change from baseline in laboratory parameters (hematology and chemistry) and incidence of abnormal laboratory parameters (hematology and chemistry).

TABLE 1

Time and Events Schedule for Main Study (Screening through 8-Week/16-Week Safety Follow-up)

| | Screening[a] | Blinded Study Agent Administration Phase Week | | | | | Cross-over Administration Phase Week | | | | | | Safety Follow-up | |
|---|---|---|---|---|---|---|---|---|---|---|---|---|---|---|
| | | 4 | 8 | 12 | 16 | 20 | 24 | 28 | 32 | 36 | 40 | 44 | 8-Week Safety Follow-up[b] | 16-Week Safety Follow-up/Final visit[b] |
| Study Procedures: | | | | | | | | | | | | | | |
| Screening/Administrative | | | | | | | | | | | | | | |
| Informed consent | X | | | | | | | | | | | | | |
| Inclusion/exclusion criteria | X | X[a] | | | | | | | | | | | | |
| Medical history sod demographics | X | | | | | | | | | | | | | |
| SLE classification by SLICC criteria | X | | | | | | | | | | | | | |
| Study Drug Administration | | | | | | | | | | | | | | |
| Randomization | X | | | | | | | | | | | | | |
| Study agent administration | | X[c] | X | X | X | X | X | X | | | | | | |
| Diary card | | | | | | | | | | | | | | |
| Train on diary card and distribute | X | | | | | | | | | | | | | |
| Collect, review and distribute diary cards | | X | X | X | X | X | X | X | X | X | X | X | X | X |
| Safety Assessments | | | | | | | | | | | | | | |
| Physical examination | X | | | | | | X | | | | | | X | X |
| HIV, HBV, and HCV | X | | | | | | | | | | | | | |
| QuantiFERON ®-TB Gold test | X | | | | | | | | | | | | | |
| Tuberculin skin test[e] | X | | | | | | | | | | | | | |
| TB evaluation[f] | X | X | | X | | X | | X | | X | | X | X | X |
| Serum pregnancy test[g] | X | | | | | | | | | | | | | |
| Urine pregnancy | | X | | X | | X | | X | | X | | X | X | X |
| Vital signs | X | X | X | X | X | X | X | X | X | X | X | X | X | X |
| Height | | X | | | | | | | | | | | | |
| Weight | X | X | | | | | X | | | | | | | |
| Chest x-ray[i] | X | | | | | | | | | | | | | |
| Concomitant therapy | X | X | X | X | X | X | X | X | X | X | X | X | X | X |
| Adverse Events | X | X | X | X | X | X | X | X | X | X | X | X | X | X |
| Study Procedures: | | | | | | | | | | | | | | |
| Urinalysis (dipstick, all study subjects)[q] | X | X | X | X | X | X | X | X | X | X | X | X | X | X |
| Urine sample for biomarkers (all subjects) | | X | X | X | X | | X | X | X | | X | | X | X |
| Protein/Creatinine ratio[s] | X | X | X | X | X | X | X | X | X | X | X | X | X | X |
| Microscopy of urine sediment[t] | X | X | X | X | X | X | X | X | X | X | X | X | X | X |
| Pharmacokinetics/Immunogenicity | | | | | | | | | | | | | | |
| Serum ustekinumab concentrations[s,t] | | 2X[r] | X | X | X | X | | X | X | | X | | X | X |
| Antibodies to study agent[s,t] | | X | X | X | X | X | | X | | | X | | | X |
| Pharmacogenomics (DNA)[u] | | | | | | | | | | | | | | |
| Whole blood DNA | | X | | | | | | | | | | | | |
| Biomarkers | | | | | | | | | | | | | | |
| Serum sample | X | X | X | X | X | | X | X | X | | X | | X | X |
| Whole blood for RNA gene expression | X | X | X | | X | | X | X | | | X | | X | X |

TABLE 1-continued

Time and Events Schedule for Main Study (Screening through 8-Week/16-Week Safety Follow-up)

|  | Screening[a] | Blinded Study Agent Administration Phase | | | | | Cross-over Administration Phase Week | | | | | | Safety Follow-up | |
|---|---|---|---|---|---|---|---|---|---|---|---|---|---|---|
|  |  | 4 | 8 | 12 | 16 | 20 | 24 | 28 | 32 | 36 | 40 | 44 | 8-Week Safety Follow-up[b] | 16-Week Safety Follow-up/ Final visit[b] |
| T cell and B cell repertoire | X |  |  | X |  |  | X |  |  |  |  |  | X |  |
| Epigenetics | X |  |  | X |  |  | X |  |  |  |  |  | X |  |
| Flow cytometry[v] | X |  |  | X |  |  | X |  |  |  |  |  | X |  |
| Study Procedures[c] |  |  |  |  |  |  |  |  |  |  |  |  |  |  |

[a]Screening visit must be performed no more than 6 weeks prior to the randomization visit (Week 0). To be eligible for study participation, subjects must have SLEDAI score ≥4 (excluding laboratory results) for clinical features at Week 0 and have received approval for study randomization following review and adjudication of screening lupus assessments by the Sponsor and/or Sponsor-selected independent reviewer(s).
[b]Subjects, who discontinue study agent administrations on or before the Week 40 visit, must return, approximately 8 and 16 weeks after last study agent administration for safety follow-up visits. The 8-week and/or 16-week safety follow-up visits are not required for subjects who continue treatment in the study extension within 8 (±2 weeks) or 16 (±2 weeks) weeks, respectively, of their Week 40 visit (refer to Table 2).
[c]All assessments (except for injection-site evaluation) are to be completed prior to study agent administration, unless otherwise specified.
[d]Intravenous administration of study agent at Week 0, all other doses will be SC.
[e]Only required if QuantiFERON ®-TB is not registered/approved locally or the tuberculin skin test (TST) is mandated by local health authorities.
[f]If TB is suspected at any time during the study, a chest x-ray (local), and QuantiFERON ®-TB Gold test should be performed. A TST is additionally required if the QuantiFERON ®-TB Gold test is not registered/approved locally or the TST is mandated by local health authorities.
[g]In addition to the screening evaluation, the pregnancy test may be repeated at any time at the discretion of investigator or subject.
[h]May conduct urine pregnancy test more frequently (e.g. monthly basis) if required by local regulations.
[i]Posterior/anterior and lateral views must be taken within 3 months prior to the first administration of study agent for TB detection.
[j]Subjects should be monitored for the occurrence of infusion or injection-site reactions for 30 minutes after the infusion (IV administration) or injection.
[k]Only for subjects who consented to participate in the cutaneous lupus substudy for biopsy and/or photograph collection.
[l]All visit-specific patient reported outcome assessments should be conducted before any tests, procedures, or other consultations for that visit to prevent influencing subjects' perceptions.
[m]Complete SLEDAI-2K (Baseline) will be evaluated during screening and at Week 0, although at Week 0 only the clinical (non-laboratory) features will be considered to confirm eligibility for study enrollment. The photographs and skin biopsies can target a different location of active disease, but the follow-up photographs or biopsies should re-evaluate the same area of active disease as originally assessed at week 0.
[n]CLASI scoring will be obtained for all enrolled subjects with cutaneous lupus regardless of enrollment in the cutaneous lupus substudy.
[o]Also perform B cell analyses at screening for subjects previously exposed to B cell depleting therapies.
[p]If abnormal test result is not obtained at screening or at Week 0, no additional follow-up testing is required. However, additional testing may be performed if needed.
[q]These tests will be performed on-site or at local lab(s).
[r]Anti-dsDNA should be analyzed at every specified visit. If the other autoantibody tests are negative at both the screening and Week 0 visits, then those autoantibody test need only be analyzed again at Weeks 24 and 48. However, if the other autoantibodies tests are positive at either screening or Week 0, then they should be analyzed at all visits.
[s]The same blood draw will be used for the measurement of ustekinumab concentration and detection of antibodies to ustekinumab. For visits with study agent administration, all blood samples for assessing pre-dose ustekinumab concentration and antibodies to ustekinumab MUST be collected BEFORE the administration of the study agent.
[t]At Week 0 visit, 2 separate samples for serum ustekinumab concentrations (indicated by "2X" in the Schedule above) will be collected (1 sample will be collected prior to IV infusion and the other collected 1 hour after the end of the infusion) for all subjects.
[u]Only for subjects who consent to allow genomic analyses.
[v]Flow cytometry samples will be analyzed from subjects at selected sites.
[w]Biopsies are allowed to occur 1-2 days prior to randomization and at the Week 24 visit.
[x]Photographs do not need to be taken at the same area of active disease as the biopsy; however, follow-up photographs or biopsies should re-evaluate the same area of active disease as originally assessed at week 0.

TABLE 2

Time and Events Schedule in Study Extension (Week 48/56 through Extension Safety Follow-up)

|  | Study Extension Week | | | | | | | | Extension Safety Follow-up[a] | |
|---|---|---|---|---|---|---|---|---|---|---|
|  | Wk 48 | Wk 56 | Wk 64 | Wk 72 | Wk 80 | Wk 88 | Wk 96 | Wk 104 | Extension 8-Week Safety Follow-up | Extension 16-Week Safety Follow-up/Final Visit |
| Study Procedures[c] |  |  |  |  |  |  |  |  |  |  |
| Screening/Administrative |  |  |  |  |  |  |  |  |  |  |
| Informed consent[c] | X | X |  |  |  |  |  |  |  |  |
| Study Drug Administration |  |  |  |  |  |  |  |  |  |  |
| Study agent administration | X[c] | X[c] | X | X | X | X | X | X |  |  |
| Safety Assessments |  |  |  |  |  |  |  |  |  |  |
| Physical examination | X |  | X |  | X |  | X | X | X | X |
| TB evaluation[d] | X | X | X | X | X | X | X | X | X | X |
| Urine pregnancy test[e] | X | X | X | X | X | X | X | X | X | X |

TABLE 2-continued

Time and Events Schedule in Study Extension (Week 48/56 through Extension Safety Follow-up)

|  | Study Extension Week | | | | | | | | Extension Safety Follow-up[a] | |
|---|---|---|---|---|---|---|---|---|---|---|
|  | Wk 48 | Wk 56 | Wk 64 | Wk 72 | Wk 80 | Wk 88 | Wk 96 | Wk 104 | Extension 8-Week Safety Follow-up | Extension 16-Week Safety Follow-up/Final Visit |
| Vital signs | X | X | X | X | X | X | X | X | X | X |
| Concomitant therapy | X | X | X | X | X | X | X | X | X | X |
| Adverse Events | X | X | X | X | X | X | X | X | X | X |
| Injection-site reaction | X | X | X | X | X | X | X | X | | |
| Efficacy Assessments[g] | | | | | | | | | | |
| S2K RI-50 | X | | | X | | X | | X | X | |
| CLASI[h] | X | | | X | | X | | X | X | |
| BILAG | X | | | X | | X | | X | X | |
| Physician's Global Assessment of Disease Activity | X | | | X | | X | | X | X | |
| Patient's Global Assessments (Pain and Disease Activity) | X | | | X | | X | | X | X | |
| SF-36 | X | | | X | | | | X | X | |
| Fatigue Severity Scale | X | | | X | | | | X | X | |
| Clinical Laboratory Assessments | | | | | | | | | | |
| Hematology[i] | X | X | X | X | X | X | X | X | X | X |
| C3, C4 | X | X | X | X | X | X | X | X | X | X |
| Coombs direct test[i,k] (as needed) | X | | | | X | | | X | X | X |
| Coagulation Labs (as needed)[i,j] | X | | | | X | | | X | X | X |
| Chemistry[k] | X | X | X | X | X | X | X | X | X | X |
| Anti-dsDNA | X | X | X | X | X | X | X | X | X | X |
| Other autoantibodies[l] | X | | | | X[l] | | | X | | |
| Study Procedures[k] | | | | | | | | | | |
| Anti-phospholipid antibodies[j] | X | | | | X | | | X | | |
| Ig isotype profile | X | | | | | | | X | | |
| Urine Analyses (spot urine)[i] | | | | | | | | | | |
| Urinalysis (dipstick, all study | X | X | X | X | X | X | X | X | X | X |
| Urine sample for biomarkers (all subjects) | X | | | | X | | | X | X | X |
| Protein/Creatinine ratio[j] | X | X | X | X | X | X | X | X | X | X |
| Microscopy of urine sediment[k,m] | X | X | X | X | X | X | X | X | X | X |
| Pharmacokinetics/Immunogenicity | | | | | | | | | | |
| Serum ustekinumab concentrations[n] | X | | | | X | | | X | X | X |
| Antibodies to study agent[n] | X | | | | X | | | X | X | X |
| Biomarkers | | | | | | | | | | |
| Serum sample | X | | | | X | | | X | X | X |
| Whole blood for RNA gene expression | X | | | | X | | | X | X | X |
| Study Procedures[k] | | | | | | | | | | |

[a]Subjects, who complete all scheduled doses or discontinue study agent administration before the end of the study extension, must return at approximately 8 and 16 weeks after last study agent administration for safety follow-up visits.
[b]All assessments (except for injection-site evaluation) are to be completed prior to study agent administration.
[c]Prior to dosing in the study extension, subjects must sign a revised ICF indicating agreement to participate in the extended study.
[d]TB evaluation includes an assessment of recent exposure or risk of TB including new or chronic cough, fever, night sweats, unintentional weight loss or recent contact with someone with active TB. If TB is suspected at any time during the study, a chest x-ray (local), and QuantiFERON®-TB Gold test should be performed. A TST is additionally required if the QuantiFERON®-TB Gold test is not registered/approved locally or the TST is mandated by local health authorities.
[e]In addition to scheduled urine dipstick testing, a serum or urine pregnancy test may be conducted at any time at the discretion of investigator or subject, or if required by local regulations.
[f]Subjects should be monitored for the occurrence of injection-site reactions for 30 minutes after the injection.
[g]All visit-specific patient reported outcome assessments should be conducted before any tests, procedures, or other consultations for that visit to prevent influencing subjects' perceptions.
[h]CLASI scoring will be obtained for all enrolled subjects who have cutaneous lupus.
[i]If clinical concerns or abnormal results from prior visit observed in these assessments, then strong consideration should be given to more frequent testing (at least q4 week assesments) until normalized
[j]If history of abnormal test result was observed in main study, then follow scheduled assessments. Additional testing may be performed if needed.
[k]These tests will be performed on-site or at local lab(s).
[l]If the "other autoantibody" tests were routinely negative prior to Week 48, then those, autoantibody tests need only be analyzed annually. However, if the other autoantibodies tests were positive at either screening or Week 0, then they should be analyzed every 6 months as shown.
[m]Urine sediment analyses to be performed at study site or local lab if possible. If necessary with agreement from study sponsor, urine sediment analyses can be conducted at the Cental Lab for specific sites that cannot arrange local analyses.
[n]The same blood draw will be used for the measurement of ustekinumab concentration and detection of antibodies to ustekinumab. All blood samples collected for assessing pre-dose ustekinumab concentration and antibodies to ustekinumab MUST be collected BEFORE the administration of the study agent.

ABBREVIATIONS

ACE angiotensin-converting enzyme
AE adverse event
ANA antinuclear antibodies
ANCOVA analysis of covariance
anti-dsDNA anti-double stranded deoxyribonucleic acid
anti-HBc total HBV core antibody total
anti HBs HBV surface antibody
ARB angiotensin II receptor blocker
AZA/6 MP azathioprine/6 mercaptopurine
BAFF B cell activating factor, also known as B lymphocyte stimulator (BLyS)
BCG Bacille Calmette-Guérin
β-hCG β human chorionic gonadotropin
BICLA BILAG-based Combined Lupus Assessment
BILAG British Isles Lupus Assessment Group
BLyS B lymphocyte stimulator, also known as B cell activating factor (BAFF)
CLASI Cutaneous Lupus Erythematosus Disease Area and Severity Index
CLE cutaneous lupus erythematosus
CNS central nervous system
COX-2 cyclooxygenase-2
CD Crohn's disease
CTCAE Common Terminology Criteria for Adverse Events
CXCL10 C—X—C motif chemokine 10
DMC data monitoring committee
DNA deoxyribonucleic acid
eDC Electronic Data Capture
EDTA ethylenediaminetetraacetic acid
ELISA enzyme-linked immunosorbent assay
FSS Fatigue Severity Scale
FVP Final Vialed Product
GCP Good Clinical Practice
HBsAg HBV surface antigen
HBV hepatitis B virus
HCV hepatitis C virus
HIV human immunodeficiency virus
IA interim analyses
ICF informed consent form
ICH International Conference on Harmonisation
IEC Independent Ethics Committee
Ig Immunoglobulin
IL Interleukin
IM Intramuscular
IP Investigative Product
IRB Institutional Review Board
IV Intravenous
IWRS interactive web response system
JAK j anus kinase
mITT modified intent to-treat
MMF mycophenolate mofetil
MPA mycophenolic acid
MTX Methotrexate
NAbs neutralizing antibodies
NSAIDs nonsteroidal anti inflammatory drugs
PFS prefilled syringe
PGA Physician's Global Assessment of Disease Activity
PK Pharmacokinetic
PQC product quality complaint
PROs patient reported outcomes
PsA psoriatic arthritis
PtGA Patient's Global Assessment of Disease Activity
q8w every 8 weeks
RA rheumatoid arthritis
RNA ribonucleic acid
RNP Ribonucleoprotein
S2K RI-50 SLEDAI-2K Responder Index
SAE serious AE
SAP statistical analysis plan
SC Subcutaneous
SF Short-form
SLE Systemic Lupus Erythematosus
SLEDAI Systemic Lupus Erythematosus Disease Activity Index
SLEDAI-2K Systemic Lupus Erythematosus Disease Activity Index 2000
SLICC Systemic Lupus International Collaborating Clinics
SRI-4 SLE Responder Index
SSA anti-Sjögren's-syndrome-related antigen A
SSB anti-Sjögren's-syndrome-related antigen B
TB Tuberculosis
Th T helper
TNFα tumor necrosis factor alpha
ULN upper limit of normal
VAS visual analogue scale
WBC white blood cells

1. Introduction

STELARA® (ustekinumab) is a fully human G1 kappa monoclonal antibody that binds with high affinity and specificity to the shared p40 subunit of human interleukin (IL)-12 and IL-23 cytokines. The binding of ustekinumab to the IL-12/23p40 subunit blocks the binding of IL-12 or IL-23 to the IL-12Rβ1 receptor on the surface of natural killer and CD4$^+$ T cells, inhibiting IL-12- and IL-23-specific intracellular signaling and subsequent activation and cytokine production. Abnormal regulation of IL-12 and IL-23 has been associated with multiple immune-mediated diseases including systemic lupus erythematosus (SLE). Therefore, inhibition of IL-12 and IL-23 has the potential to be effective in the treatment of SLE.

Systemic lupus erythematosus is a complex, chronic heterogeneous autoimmune disease of unknown etiology that can affect almost any organ system, and which follows a waxing and waning disease course. Systemic lupus erythematosus occurs much more often in women than in men, up to 9 times more frequently in some studies, and often appears during the child-bearing years between ages 15 and 45. This disease is more prevalent in Afro-Caribbean, Asian, and Hispanic populations. In SLE, the immune system attacks the body's cells and tissue, resulting in inflammation and tissue damage which can harm the heart, joints, skin, lungs, blood vessels, liver, kidneys and nervous system. About half of the subjects diagnosed with SLE present with organ-threatening disease, but it can take several years to diagnose subjects who do not present with organ involvement. Some of the primary complaints of newly diagnosed lupus patients are arthralgia (62%) and cutaneous symptoms (new photosensitivity; 20%), followed by persistent fever and malaise (Wallace, 2008). The estimated annual incidence of lupus varies from 1.8 to 7.6 cases per 100,000 and the worldwide prevalence ranges from 14 to 172 cases per 100,000 people (Wallace, 2008). Patients with mild disease have mostly skin rashes and joint pain and require less aggressive therapy; regimens include nonsteroidal anti-inflammatory drugs (NSAIDs), anti-malarials (e.g., hydroxychloroquine, chloroquine, or quinacrine) and/or low dose corticosteroids. With more severe disease patients may experience a variety of serious conditions depending on the organ systems involved, including lupus nephritis with potential renal failure, endocarditis or myocarditis, pneumonitis, pregnancy complications, stroke, neurological complications, vasculitis and cytopenias with associated risks of bleeding or infection. Common treatments for more severe disease include immunomodulatory agents, such as methotrexate (MTX), azathioprine, cyclophosphamide, cyclosporine, high dose corticosteroids, biologic B cell cytotoxic agents or B cell modulators, and other immunomodulators. Patients with serious SLE have a shortening of life expectancy by 10 to 30 years, largely due to the complications of the disease, of standard of care therapy, and/or accelerated atherosclerosis. In addition, SLE has a substantial impact on quality of life, work productivity, and healthcare expenditures. Existing therapies for SLE are generally either cytotoxic or immunomodulatory, and may have notable safety risks. Newer treatments for SLE have provided only modest benefits over standard of care therapy. Thus, there is a large unmet need for new alternative treatments that can provide significant benefit in this disease without incurring a high safety risk.

The long-term outcome for patients with lupus depends on a variety of factors including whether they have organ involvement, the presence of certain laboratory measures (such as anti-phospholipid antibodies), race, gender, age of consent, access to health care, adherence to treatment, education and other comorbidities. Only about 5% of patients who are diagnosed with SLE will demonstrate a spontaneous remission without treatment. A variety of new therapeutic agents are being evaluated for the treatment of subjects with refractory lupus, however to date very few have demonstrated notable clinical efficacy beyond those medications currently considered standard of care for patients with this disease.

In this study, the target population is subjects with SLE according to Systemic Lupus International Collaborating Clinics (SLICC) criteria and Systemic Lupus Erythematosus Disease Activity Index (SLEDAI) score ≥6 (Gladman et al, 2002), despite conventional treatment (e.g., immunomodulators, antimalarial drugs, corticosteroids, NSAIDs, antihypertensive drugs, and/or topical medications). In addition, subjects must have at least 1 positive autoantibody test (antinuclear antibodies [ANA], anti-double stranded deoxyribonucleic acid [anti-dsDNA] antibodies, and/or anti-Smith antibodies) observed during screening, as well as a well-documented positive autoantibody test in medical history. Subjects must also demonstrate at least 1 British Isles Lupus Assessment Group (BILAG) (Wallace et al, 2011) A and/or 2 BILAG B domain scores during screening. In addition, subjects must have a SLEDAI score ≥4 at Week 0 (prior to randomization) for clinical features (excluding laboratory results). This level of disease activity is consistent with prior studies that have investigated an experimental therapy for systemic lupus (Van Vollenhoven et al, 2012).

1.1. Background

To date, ustekinumab has received marketing approval globally, including countries in North America, Europe, South America, and the Asia-Pacific region, for the treatment of adult patients including those with chronic moderate to severe plaque psoriasis and/or active psoriatic arthritis. Ustekinumab is also being evaluated in a Phase 3 studies for Crohn's disease (CD).

1.2. Overall Rationale for the Study 1.2.1. Scientific Rationale for Use of Anti-IL-12/23p40 Therapy in Systemic Lupus Erythematosus Systemic lupus erythematosus is a complex, immune-mediated inflammatory disorder exhibiting dysregulated B lymphocytes that produce destructive autoantibodies. B cell targeted therapies (e.g., belimumab) for SLE, however, have shown only modest clinical results beyond a limited standard of care control (Navarra et al, 2011), suggesting that additional immune pathways play an important role in SLE pathogenesis. Chronic immune activation in SLE leads to the increased production of inflammatory cytokines that contribute actively to local inflammation and to processes that mediate tissue damage. Many SLE patients, for example, have a characteristic type I interferon signature observed in their blood cells (Bennett e al, 2003). Interferon signatures have also been observed to occur more frequently in lupus families and may be a risk factor for development of SLE (Niewold et al, 2007). Several studies have also reported an elevation of IL-12, IL-6, and IL-23 in both serum and tissues of patients (Crispin et al, 2008; Linker-Israeli et al, 1991; Oh et al, 2011; Qiu et al, 2013; Shah et al, 2010; Wong et al, 2008) suggesting that the inflammatory environment in SLE is prone to induce T helper (Th)1 and Th17 cells. Increased levels of IL-17 in the serum have been observed in SLE patients (Chen et al, 2010; Tanasescu et al, 2010; Van Vollenhoven et al, 2012; Wong et al, 2008; Yang et al, 2013; Zhao et al, 2010), but the correlation of IL-17 levels to disease activity is not strong (Vincent et al, 2013; Zhao et al, 2010). No direct genetic links have been established in SLE to the IL-12/IL-23/Th17 pathway (Kim et al, 2009; Sánchez et al, 2007; Sestak et al, 2011), although genome-wide association studies in SLE have identified STAT4, which mediates IL-12 signaling, as a susceptibility gene in both the Caucasian and Asian populations (Han et al, 2009; Harley et al, 2008). In patients with active SLE, messenger RNA levels of p19, p40, and p35 were significantly higher compared with those in the inactive SLE patients (Huang et al, 2007). Targeting IL-12/23p40 with ustekinumab has been shown in 3 separate case reports to be associated with a marked improvement of cutaneous lupus (Dahl et al, 2013; De Souza et al, 2011; Winchester et al, 2012). Taken together, there is accumulating evidence to demonstrate the importance of the IL-12 and IL-23 cytokine pathways in SLE pathogenesis, warranting further clinical investigation of ustekinumab as an interventional therapy in this disease.

In addition, 2 disease-related groups, the Alliance for Lupus Research and Lupus Research Institute, independently commissioned a scientific review of a large set of commercially available lupus drug candidates, from which ustekinumab was recommended to be evaluated in SLE based on its molecular mechanism, which further supports the scientific rationale for a placebo-controlled clinical study to evaluate the efficacy and safety of ustekinumab in subjects with active SLE.

1.1.2.1. Subgroup of Subjects with Active Cutaneous Manifestations of Systemic Lupus Erythematosus The above-mentioned case reports of patients with refractory cutaneous lupus responding to ustekinumab treatment prompts an evaluation of the effects of ustekinumab on cutaneous lesions. Given the relatively common occurrence of cutaneous manifestations in SLE, the feasibility of repeated punch biopsy and/or photographs of an identified lesion or area of active disease, and the availability of cutaneous lupus erythematosus (CLE)-specific disease assessment tools, this patient population may provide useful data regarding the effects of ustekinumab on SLE and the symptoms of cutaneous disease. All subjects with cutaneous disease will be evaluated using CLASI scoring. Additionally, subjects with cutaneous disease who consent to participate in the cutaneous lupus substudy will be requested to provide potential collection of skin biopsies (optional consent) and/or photographs of an identified lesion or area of active disease (optional consent). There are no pre-specified numbers of subjects to be enrolled with cutaneous disease for either the main study or the cutaneous lupus substudy.

1.3. Justification for Dosing Regimen

The dosing regimen for this study was selected based on experience with the use of ustekinumab in the treatment of subjects with moderately to severely active CD (C0743T26, CNTO1275CRD3001, and CNTO1275CRD3002). Both CD and SLE are immune-mediated inflammatory diseases, which are commonly treated with immunomodulators, such as methotrexate (MTX), azathioprine and corticosteroids, and thus this indication serves as a useful model for risk assessment of ustekinumab in lupus. Although the dosing rationale has not changed, additional safety and efficacy information has become available from the ustekinumab Phase 3 CD (UNITI) studies which supports amending the protocol to further extend treatment with ustekinumab 90 mg SC q8w for an additional year. These results from the UNITI CD studies are summarized later in this section.

Although the dosing rationale has not changed, some additional safety and efficacy information has become available from the ustekinumab Phase 3 CD (UNITI) studies which supports the treatment extension planned for this study. These results from the UNITI CD studies are summarized later in this section (Section 1.3).

In the Phase 2b dose ranging study C0743T26, a single IV ustekinumab dose of 6 mg/kg was the highest loading dose tested in subjects with CD. In this study, the 6 mg/kg IV dose was shown to be effective in inducing clinical response through Week 8 and was well tolerated with a safety profile generally comparable to the other treatment groups. Results from ustekinumab CD studies also suggest that an IV loading dose may provide a rapid onset of clinical response following IL-12 and IL-23 inhibition. In the Phase 3 studies CNTO1275CRD3001 and CNTO1275CRD3002, body weight-range dosing approach (ustekinumab 260 mg [weight ≤55 kg]; ustekinumab 390 mg [weight >55 kg and ≤85 kg]; ustekinumab 520 mg [weight >85 kg]) was used to approximate the IV loading dose of 6 mg/kg. The body weight-range based dosing allows administration of complete vials to patients to simplify dose calculation and reduce the potential for errors in dosing. This weight range dosing is intended to achieve drug exposure similar to that observed with 6 mg/kg weight-adjusted dosing. Thus, in this study, a strategy of IV loading dose based on body weight range at Week 0 will be evaluated to assess the ability of the drug to rapidly reduce the disease activity of SLE without causing significant concern for increased safety risk based on data obtained from previous studies.

The ustekinumab maintenance dosing regimen of 90 mg SC every 8 weeks (q8w) was studied in subjects with CD (C0743T26). The results from C0743T26 study suggest that ustekinumab 90 mg SC q8w was safe and effective in maintaining subjects in clinical remission. The q8w dosing frequency is selected to maintain sufficient ustekinumab exposure to determine if treatment with ustekinumab can provide sustained clinical response. In addition, SC administration is considered more convenient compared with IV administration. A 16-week follow-up period following last ustekinumab study dose was selected to allow more than 5 half-lives for drug elimination and adequate safety follow-up.

In addition, there were also 3 Phase 3 studies in subjects with CD initiated in 2011 that have recently provided additional safety and efficacy data; UNITI-1, UNITI 2, and IM-UNITI. UNITI-1 and UNITI-2 were 8-week induction studies and were identical in design but studied distinct patient populations. UNITI-1 studied subjects who had failed or were intolerant to anti-TNF agents while UNITI-2 studied subjects who had not failed a TNF antagonist but who had failed conventional immunomodulator or steroid therapies. The IM-UNITI study evaluated maintenance treatment for patients enrolled from both UNITI-1 and UNITI-2 studies. The UNITI studies randomized 1,367 subjects to either placebo, 130 mg IV or approximately 6 mg/kg IV. After Week 8 of therapy, subjects in both UNITI-1 and UNITI-2 studies could enter into IM-UNITI, which primarily evaluated two maintenance regimens of 90 mg every 8 or 12 weeks compared to placebo in induction responders. While the IM-UNITI study is still ongoing in long-term extension phase, the primary results of all 3 studies have been published (Feagan et al, 2016), and the results supported the approval of ustekinumab in patients with active moderate to severe CD. The approved dose in induction is a single IV weight-based dose approximating 6 mg/kg and the approved maintenance dose is 90 mg either every 8 or 12 weeks depending on the approval region. The results of these studies are particularly relevant to the CNTO1275SLE2001 SLE study in that a similar dose is being evaluated. In addition, similar to the SLE population, about ⅓ of the CD patients enrolled into the UNITI studies were using concomitant immunomodulators (e.g MTX, AZA, 6-MP) and approximately 46% were on concomitant glucocorticoids. The results of these studies are reviewed in detail. in the primary publication (Feagan et al, 2016), and the highlights are presented below:

In the 2 UNITI induction studies, the primary endpoint and all major secondary endpoints were met for both doses studied including the 6 mg/kg dose.

In the IM-UNITI maintenance study, both the 90 mg every 8 or every 12 week regimens were superior to placebo in maintaining response or achieving remission compared to placebo at Week 44.

Importantly, the safety profiles of both maintenance doses were comparable to placebo over 44 weeks and no new safety signals were identified. The safety profile was similar to that seen in the psoriatic indications.

In summary, these CD studies support the dosing regimen planned for this proof-of concept SLE study including body weight-range based IV loading dose approximating 6 mg/kg followed by 90 mg SC q8w to ensure a high level of systemic exposure of ustekinumab to inhibit the actions of IL-12/23.

Open label 90 mg SC q8w ustekinumab dosing will be provided to subjects starting at Week 24 though Week 40. Per the amended study design, subjects who are able to continue q8w study treatment at approximately 8 weeks (±2 weeks) after their Week 40 visit, or are able to resume study treatment with no more than 16 weeks (±2 weeks) since their Week 40 visit will be eligible for continued 90 mg SC q8w ustekinumab treatment through Week 104, followed by an additional 16-week safety follow-up period.

2. Objectives and Hypothesis 2.1. Objectives

Primary Objective

The primary objective is to evaluate the efficacy of ustekinumab as measured by a reduction in disease activity for subjects with active SLE.

Secondary Objectives

The secondary objectives are to evaluate:
The safety and tolerability of ustekinumab in subjects with SLE.

The effect of ustekinumab administration on health-related quality of life in subjects with SLE.

The effects of ustekinumab on cutaneous manifestations of SLE.

Pharmacokinetics and immunogenicity of ustekinumab in subjects with SLE.

Exploratory Objectives

The exploratory objectives are to evaluate:

Safety and efficacy during long-term administration of ustekinumab.

Reduction in corticosteroid dosing during long-term administration of ustekinumab.

Additional composite clinical endpoints or methods for calculation of response with potential for greater sensitivity to improvement and/or worsening of SLE.

Biomarkers related to lupus disease (genetic, systemic, and skin-related).

2.2. Hypothesis

The hypothesis is that ustekinumab is significantly superior to placebo as measured by the Systemic Lupus Erythematosus Disease Activity Index 2000 (SLEDAI-2K) Responder Index (SRI-4) composite measure at Week 24.

3. Study Design and Rationale

A complete list describing all efficacy evaluations and endpoints, and which evaluations are included in the composite endpoints is provided in Appendix 1. The main study is defined from the original protocol as screening through the Main Study 8-week and 16-week safety follow-up visits. Note that the Main Study 8-week and 16-week safety follow-up visits were previously described in the original protocol as the Week 48 and Week 56 visits. However, with this amendment, the Week 48 and Week 56 visits will only be used to describe treatment visits for those subjects who are participating in the study extension. The study extension (applicable to subjects meeting the inclusion criteria) is defined as the Week 48 or Week 56 visits through the Study Extension 16-week safety follow-up visit.

3.1. Overview of Study Design

CNTO1275SLE2001 is a Phase 2a, proof-of-concept, multicenter, randomized, double-blind, placebo-controlled study of the efficacy and safety of ustekinumab added to standard of care background therapy in subjects with active SLE. Subjects between 18 and 75 years of age must have SLE according to SLICC criteria and SLEDAI-2K score ≥6, despite conventional treatment (e.g., immunomodulators, antimalarial drugs, corticosteroids, NSAIDs, anti-hypertensive drugs, and/or topical medications). In addition, subjects must have at least 1 positive autoantibody test (ANA, anti-dsDNA antibodies, and/or anti-Smith antibodies) observed during screening, as well as a well-documented positive autoantibody test in their medical history. Subjects must also demonstrate at least 1 BILAG A and/or 2 BILAG B domain scores observed during screening. In addition, subjects must have a clinical SLEDAI-2K score ≥4 (excluding laboratory results) at week 0, prior to randomization.

Subject randomization will be stratified according to consent for skin biopsy collection (y/n), and other features (e.g., presence of lupus nephritis [y/n], baseline SLE medications and SLEDAI score), site/region, and race, or concomitant medications as described in Section 8.

Approximately 100 subjects will be randomly assigned by 3:2 ratio to receive either ustekinumab or placebo through Week 24. Following randomization at Week 0, subjects will receive an initial body weight-range based IV dose approximating 6 mg/kg of ustekinumab (ustekinumab 260 mg [weight ≥35 kg to ≤55 kg]; ustekinumab 390 mg [weight >55 kg and ≤85 kg]; ustekinumab 520 mg [weight >85 kg]) followed by 90 mg SC administered q8w (Section 6). At Week 24, subjects receiving placebo will cross-over and all subjects will receive ustekinumab 90 mg SC at Weeks 24, 32, and 40 followed by safety follow-up through Week 56 in a blinded fashion for 16 weeks (i.e., approximately 5 half-lives) after last study agent SC administration.

A placebo comparator (added to standard of care background therapy) will be used through Week 24 for the evaluation of the efficacy and safety of ustekinumab in subjects with SLE. From Week 24 through Week 40, the placebo group will cross-over to ustekinumab 90 mg SC q8w. This cross-over design will permit placebo subjects to receive study agent and provide experience with ustekinumab 90 mg SC without the IV loading dose in subjects with SLE. The 40-Week dosing period will be useful to understand the longer-term safety and time course of potential clinical response of ustekinumab in the SLE population.

Every reasonable effort should be made to keep concomitant medications stable as defined in the protocol. All concomitant therapies must be recorded throughout the study beginning at entry into screening and any changes must be recorded throughout the study.

All subjects with cutaneous disease will be evaluated using CLASI scoring. Additionally, subjects with cutaneous disease who consent to participate in the cutaneous lupus sub study will have other assessments including collection of skin biopsies (optional consent) and/or photographs of an identified cutaneous lesion or area of active disease (optional consent). There will not be any restrictions on the number of subjects with cutaneous disease who can enroll into either the main study or the cutaneous lupus substudy.

Interim analyses (IA) will be conducted when approximately ⅓ and ⅔ of subjects reach Week 24. In the first IA, only evidence for notable efficacy will be assessed. In the second IA, evidence for notable efficacy as well as treatment futility will be analyzed. Variations in placebo effect across regions will be incorporated into the interim analyses. Database locks (DBLs) will occur at Weeks 24 and after the final subject's Week 56 visit or following the last subject's 16-week safety follow-up visit from the main study. In addition, an independent data monitoring committee (DMC) will review interim safety data periodically including a formal review when approximately ⅓ and ⅔ of subjects reach Week 24, as well as at the Week 24 DBL. The DMC will make a recommendation to the Sponsor committee whether the study should be stopped for futility or for safety concerns or if data meet prespecified criteria demonstrating notable efficacy. The content of the summaries, the DMC role and responsibilities, and the general procedures (including communications) will be defined in the DMC charter.

The amended study design will continue to provide open-label ustekinumab 90 mg q8w SC administration through Week 104 (study extension). Subjects will be eligible to continue study treatment through Week 104 if they meet the study inclusion criteria (Section 4.13):

must not have permanently discontinued study treatment on or before their Week 40 visit, and are able to continue q8 week study treatment at approximately 8 weeks (±2 weeks) after their Week 40 visit or are able to resume study treatment with no more than 16 weeks (±2 weeks) since their Week 40 visit In addition to the DBL planned following the last subject's Week 56 visit or the final 16-week safety follow-up visit from the main study, there will be an additional DBL following the Extension 16-Week Safety Follow-up period.

Figure 2:
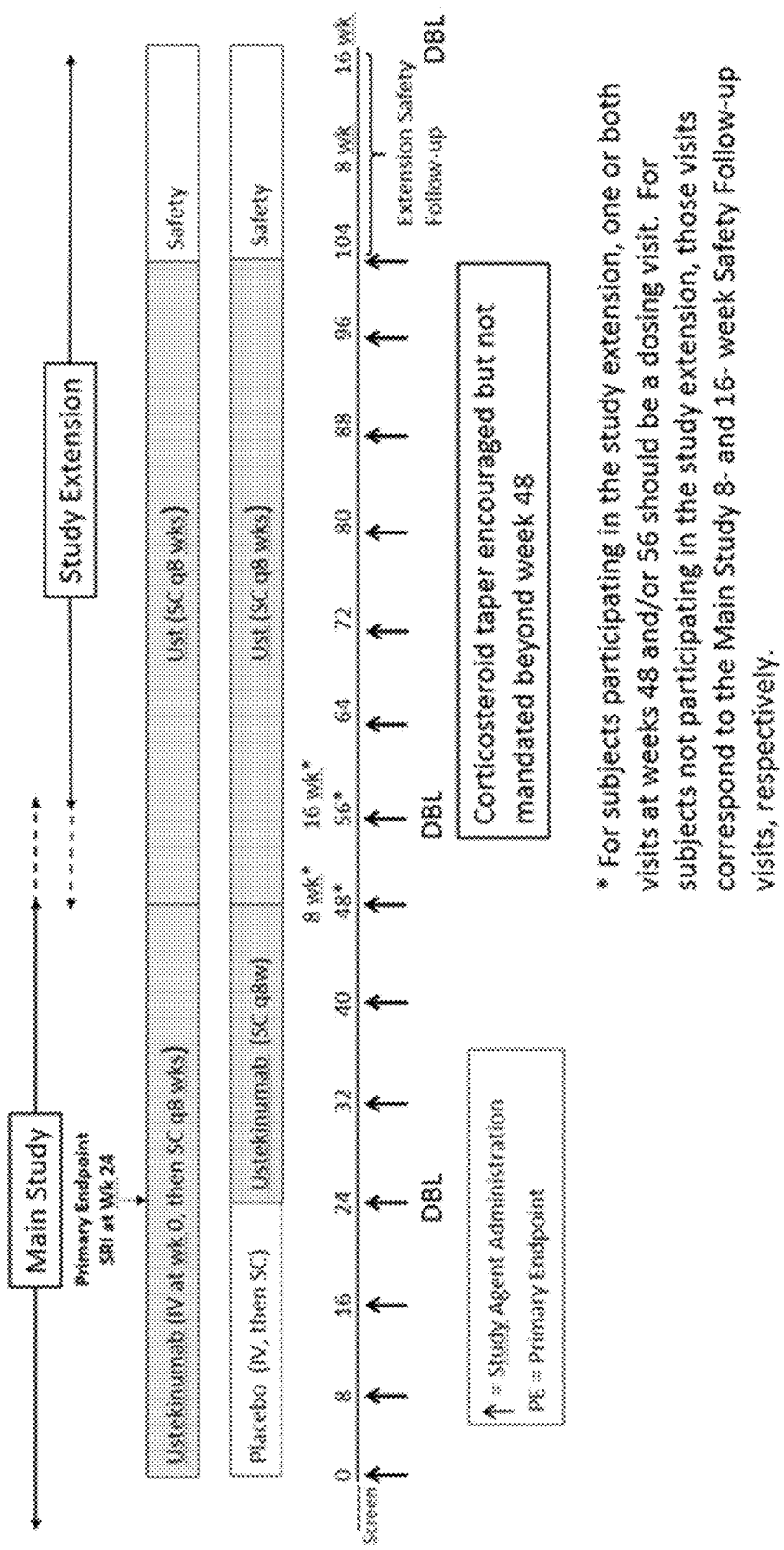
FIG. 2 shows a Schematic Overview of the Study Including the Study Extension. Abbreviations: DBL=database lock; FU=follow-up; IV=intravenous; PE=primary endpoint; PL=placebo; q8w=every 8 weeks; SC=subcutaneous; SLE=systemic lupus erythematosus; SRI=SLEDAI-2K Responder Index; Wks=weeks.

A diagram of the main study design is provided in FIG. 1, and a diagram of the extended study is provided in FIG. 2.

3.2. Study Design Rationale

Blinding, Control, Study Phase/Periods, Treatment Groups

A placebo control will be used to establish the frequency and magnitude of changes in clinical endpoints that may occur in the absence of active treatment. Randomization will be used to minimize bias in the assignment of subjects to treatment groups, to increase the likelihood that known and unknown subject attributes (e.g., demographic and baseline characteristics) are evenly balanced across treatment groups, and to enhance the validity of statistical comparisons across treatment groups. Blinded treatment will be used to reduce potential bias during data collection and evaluation of clinical endpoints.

DNA and Biomarker Collection

It is recognized that genetic variation can be an important contributory factor to interindividual differences in drug distribution and response and can also serve as a marker for disease susceptibility and prognosis. Pharmacogenomic research may help to explain interindividual variability in clinical outcomes and may help to identify population subgroups that respond differently to a drug. The goal of the pharmacogenomic component is to collect deoxyribonucleic acid (DNA) to allow the identification of genetic factors that may influence the pharmacokinetics, pharmacodynamics, efficacy, safety, or tolerability of ustekinumab and to identify genetic factors associated with SLE.

Biomarker samples will be collected to evaluate the mechanism of action of ustekinumab or help to explain inter-individual variability in clinical outcomes or may help to identify population subgroups that respond differently to a drug. The goal of the biomarker analyses is to evaluate the pharmacodynamics of ustekinumab and aid in evaluating the drug-clinical response relationship.

DNA and Biomarker samples may be used to help address emerging issues and to enable the development of safer, more effective, and ultimately individualized therapies.

4. Subject Population

The target study population is subjects with SLE according to SLICC criteria and SLEDAI-2K score ≥6, despite conventional treatment (e.g., immunomodulators, antimalarial drugs, corticosteroids, NSAIDs, anti-hypertensive drugs, and/or topical medications). Subjects must have at least 1 BILAG A and/or 2 BILAG B domain scores observed during screening. In addition, subjects must have at least 1 positive autoantibody test (ANA, anti-dsDNA antibodies, and/or anti-Smith antibodies) observed during screening, as well as a well-documented positive autoantibody test in their medical history, and they must also have a clinical SLEDAI-2K score ≥4 (excluding laboratory results) prior to randomization at week 0.

The inclusion and exclusion criteria for enrolling subjects in this study are described in the following 2 subsections. If there is a question about the inclusion or exclusion criteria, the investigator should consult with the appropriate Sponsor representative before enrolling a subject in the study.

Subjects with SLE enrolling into the main study with active cutaneous lupus (including subjects with discoid lupus erythematosus, subacute cutaneous lupus erythematosus, or SLE malar rash or other SLE skin lesions characterized by erythema and/or scale) will be evaluated using CLASI scoring. In addition, subjects who provide consent will be enrolled in the cutaneous lupus substudy evaluating the histology of cutaneous biopsies and/or skin photographs. Biopsy samples (2 samples, 4 mm size) from consenting subjects will be collected prior to dosing at Week 0 and at Week 24 from a lesion demonstrating active cutaneous disease. Subjects participating in the cutaneous lupus substudy are not required to undergo biopsies, and may allow only photographs to document changes in an identified cutaneous lesion or area of active disease. Subjects with cutaneous lupus deemed unsuitable for biopsy (e.g., malar rash or alopecia) can also be enrolled in the substudy, and may be evaluated by photography.

If a subject has failed screening and investigator wishes to rescreen the subject, this should be discussed with the study Sponsor and/or their designee. Only 1 rescreening is allowed per subject (also see Section 9.1.2).

The study extension population will be comprised of those subjects who have not permanently discontinued study treatment before or at the Week 40 dose and for whom the investigators judge that there is a potential benefit that outweighs the potential risks to continued ustekinumab treatment.

For a discussion of the statistical considerations of subject selection, refer to Section 11.2, Sample Size Determination.

4.1. Inclusion Criteria

4.1.1. Inclusion Criteria Applicable to all Subjects

Each potential subject must satisfy all of the following criteria to be enrolled in the study.

1. Subject must be between 18 (or older as per local requirements) and 75 years of age, inclusive, and weigh at least 35 kg.

2. Subjects must have documented medical history to meet SLICC classification criteria for SLE for a minimum of 3 months prior to first dose (Table 3).

Subjects eligible for enrollment in this study must qualify as having SLE by meeting the SLICC classification criteria for SLE25 based upon 1 or both of the following:

Meeting 4 criteria with at least 1 clinical criterion and at least 1 immunologic criterion, or A diagnosis of lupus nephritis with presence of at least 1 of the immunological variables

TABLE 3

Clinical and Immunological Criteria Used in the SLICC Classification Criteria* (Petri et al, 2012)

| | Clinical Criteria | Specific Criteria |
|---|---|---|
| 1. | Acute Cutaneous Lupus including lupus malar rash (do not count if malar discoid) | Bullous lupus<br>Toxic epidermal necrolysis variant of SLE<br>Maculopapular lupus rash<br>Photosensitive lupus rash (in absence of dermatomyositis)<br>Subacute cutaneous lupus (nonindurated psoriaform and/or annular polycyclic lesions that resolve without scarring, although occasionally with postinflammatory dyspigmentation or telangiectasias) |
| 2. | Chronic cutaneous lupus including classical discoid rash | Localized (above the neck)<br>Generalized (above and below the neck)<br>Hypertrophic (verrucous) lupus<br>Lupus panniculitis (profundus)<br>Mucosal lupus<br>Lupus erythematosus tumidus<br>Chilblains lupus<br>Discoid lupus/lichen planus overlap |
| 3. | Oral ulcers: palate | Buccal<br>Tongue<br>Nasal<br>In the absence of other causes such as vasculitis, Behcets, infection (herpes), inflammatory bowel disease, reactive arthritis, and acidic foods |
| 4. | Non-scarring alopecia (diffuse thinning or hair fragility with visible broken hairs) | In the absence of other causes such as alopecia areata, drugs, iron deficiency and androgenic alopecia |
| 5. | Synovitis involving two or more joints | Characterized by swelling or effusion OR tenderness in 2 or more joints and thirty minutes or more of morning stiffness |
| 6. | Serositis | Typical pleurisy for more than 1 day<br>Or pleural effusions<br>Or pleural rub<br>Typical pericardial pain (pain with recumbency improved by sitting forward) for more than 1 day<br>Or pericardial effusion<br>Or pericardial rub<br>Or pericarditis by EKG<br>In the absence of other causes such as infection, uremia and Dressier's pericarditis |
| 7. | Renal | Urine protein/creatinine (or 24-hour urine protein) representing 500 mg of protein/24 hour, or<br>Red blood cell casts |
| 8. | Neurologic | Seizures<br>Psychosis<br>Mononeuritis multiplex (in the absence of other known causes such as primary vasculitis)<br>Myelitis<br>Peripheral or cranial neuropathy (in the absence of other known causes such as primary vasculitis, infection and diabetes mellitus)<br>Acute confusional state (in the absence of other causes including toxic-metabolic, uremia, drugs) |
| 9. | Hemolytic anemia | Presence |
| | 10a. Leukopenia (<4000/mm$^3$ at least once), or | In the absence of other known causes such as Felty's, drugs, and portal hypertension |
| | 10b. Lymphopenia (<1000/mm3 at least once) | In the absence of other known causes such as corticosteroids, drugs, and infection |
| | 11. Thrombocytopenia (<100,000/mm$^3$ at least once) | In the absence of other known causes such as drugs, portal hypertension, and TTP |

| | Immunological Criteria | Specific Criteria |
|---|---|---|
| 1. | ANA | above laboratory reference range |
| 2. | Anti-dsDNA | above laboratory reference range, except ELISA; twice above laboratory reference range |

TABLE 3-continued

Clinical and Immunological Criteria Used in the SLICC
Classification Criteria* (Petri et al, 2012)

| | | |
|---|---|---|
| 3. | Anti-Smith | Presence |
| 4. | Anti-phospholipid antibody (any shown to right) | Lupus anticoagulant<br>False-positive RPR<br>Medium or high titer anticardiolipin (IgA, IgG or IgM)<br>Anit-$\beta_2$ glycoprotein 1 (IgA, IgG or IgM) |
| 5. | Low Complement | Low C3<br>Low C4<br>Low CH50 |
| 6. | Direct Coombs test | In the absence of hemolytic anemia |

*Criteria are cumulative and do not need to be present concurrently

3. To be eligible for study enrollment, subjects must have:
    At least 1 well-documented (subject file, referring physician letter, or laboratory result) unequivocally positive, documented test for autoantibodies in medical history including either of the following: ANA, and/or anti dsDNA antibodies, and/or anti Smith antibodies (Section 9.1.2).
    At least 1 unequivocally positive autoantibody test including ANA and/or anti dsDNA antibodies and/or anti Smith antibodies (Section 9.1.2) detected during screening.
    At least 1 BILAG A and/or 2 BILAG B domain scores observed during screening prior to first administration of study agent.
4. Demonstrate active disease based on SLEDAI-2K score ≥6 observed during screening and assessed approximately 2 to 6 weeks prior to randomization. Must also have SLEDAI-2K≥4 for clinical features (i.e., SLEDAI excluding laboratory results) at Week 0 prior to the first administration of study agent.
5. Data from the SLICC, SLEDAI and BILAG evaluations will be reviewed and adjudicated by the Sponsor and/or the Sponsor-selected independent reviewer(s). For subjects to receive their first administration of study agent, approval must be received by the Sponsor and/or Sponsor-selected independent reviewers.
6. If using oral corticosteroids, subjects must be receiving this medication for at least 6 weeks and on a stable dose equivalent to an average dose of ≥20 mg/day of prednisone for at least 4 weeks prior to the first administration of study agent. If currently not using corticosteroids, must have not received oral corticosteroids for at least 6 weeks prior to the first administration of study agent.
7. If using antimalarials (e.g., chloroquine, hydroxychloroquine, or quinacrine), subjects must have used the medication for ≥8 weeks and be on a stable dose for at least 6 weeks prior to the first administration of study agent.
8. If using immunomodulatory drugs (mycophenolate mofetil [MMF]/mycophenolic acid [MPA]≤2 g/day, azathioprine/6 mercaptopurine (AZA/6 MP)≤2 mg/kg/day and/or MTX≤25 mg/wk with concomitant folic acid [recommend ≥5 mg/wk]), subjects must be receiving a stable dose for at least 6 weeks prior to the first administration of study agent.
9. If receiving regular treatment with NSAIDs or other analgesics, subjects must be receiving stable dosing for at least 2 weeks prior to first administration of study agent.
10. Before randomization, a woman must be either:
    Not of childbearing potential: premenarchal; postmenopausal (>45 years of age with amenorrhea for at least 12 months); permanently sterilized (e.g., tubal occlusion, hysterectomy, bilateral salpingectomy); or otherwise be incapable of pregnancy.
    Of childbearing potential and practicing a highly effective method of birth control consistent with local regulations regarding the use of birth control methods for subjects participating in clinical studies: e.g., established use of oral, injected or implanted hormonal methods of contraception associated with inhibition of ovulation; placement of an intrauterine device or intrauterine system; male partner sterilization (the vasectomized partner should be the sole partner for that subject); true abstinence (when this is in line with the preferred and usual lifestyle of the subject).
    Note: If the childbearing potential changes after start of the study (e.g., woman who is not heterosexually active becomes active, premenarchal woman experiences menarche) a woman must begin a highly effective method of birth control, as described above.
11. A woman of childbearing potential must have a negative serum pregnancy test β-human chorionic gonadotropin [β-hCG]) at screening, and a negative urine pregnancy test at Week 0 before the first administration of study agent.
12. Women of childbearing potential must be willing to remain on a highly effective method of birth control during the study and for 4 months after receiving the last study agent. Also, women of childbearing potential must agree to not donate eggs (ova, oocytes) for the purposes of assisted reproduction during the study and for 4 months after receiving the last dose of study agent.
13. A man who is sexually active with a woman of childbearing potential and has not had a vasectomy must agree to use a barrier method of birth control e.g., either condom with spermicidal foam/gel/film/cream/suppository or partner with occlusive cap (diaphragm or cervical/vault caps) with spermicidal foam/gel/film/cream/suppository, and all men must also not donate sperm during the study and for 4 months after receiving the last dose of study agent.
14. Are considered eligible according to the following tuberculosis (TB) screening criteria:
    a. Have no history of latent or active TB prior to screening. An exception is made for subjects who have a history of latent TB and are currently receiving treatment for latent TB, will initiate treatment for latent TB prior to first administration of study agent, or have documentation of having completed appropriate treatment for latent TB within 3 years prior to the first administration of study agent. It is the responsibility of the investigator to verify the adequacy of previous anti-tuberculous treatment and provide appropriate documentation.
    b. Have no signs or symptoms suggestive of active TB upon medical history and/or physical examination.

c. Have had no recent close contact with a person with active TB or, if there has been such contact, will be referred to a physician specializing in TB to undergo additional evaluation and, if warranted, receive appropriate treatment for latent TB prior to the first administration of study agent.

d. Within 6 weeks prior to the first administration of study agent, have a negative QUANTIFERON®-TB Gold (blood test for tuberculosis) test result, or have a newly identified positive QUANTIFERON®-TB Gold (blood test for tuberculosis) test result in which active TB has been ruled out and for which appropriate treatment for latent TB has been initiated prior to the first administration of study agent. Within 6 weeks prior to the first administration of study agent, a negative tuberculin skin test, or a newly identified positive tuberculin skin test in which active TB has been ruled out and for which appropriate treatment for latent TB has been initiated prior to the first administration of study agent, is additionally required if the QUANTIFERON®-TB Gold (blood test for tuberculosis) test is not approved/registered in that country or the tuberculin skin test is mandated by local health authorities.

i. Subjects with persistently indeterminate QUANTIFERON®-TB Gold (blood test for tuberculosis) test results may be enrolled without treatment for latent TB, if active TB is ruled out, their chest radiograph shows no abnormality suggestive of TB (active or old, inactive TB), and the subject has no additional risk factors for TB as determined by the investigator. This determination must be promptly reported to the Sponsor's medical monitor and recorded in the subject's source documents and initialed by the investigator.

ii. The QUANTIFERON®-TB Gold (blood test for tuberculosis) test and the tuberculin skin test are not required at screening for subjects with a history of latent TB and ongoing treatment for latent TB or documentation of having completed adequate treatment as described above; Subjects with documentation of having completed adequate treatment as described above are not required to initiate additional treatment for latent TB.

e. Subjects who test positive for TB by a TB test other than QUANTIFERON®-TB Gold (blood test for tuberculosis) and TB skin test and who have no evidence of TB on chest radiograph will in the context of this protocol be considered latent TB positive and be required to undergo evaluation by a TB specialist and receive treatment for TB to be eligible for this study.

f. Have a chest radiograph (both posterior-anterior and lateral views) taken within 3 months prior to the first administration of study agent and read by a qualified radiologist or pulmonologist, with no evidence of current, active TB or old, inactive TB.

15. Have laboratory test results within the following parameters at screening:

| | | |
|---|---|---|
| Hemoglobin | ≥8.5 g/dL | (SI: ≥85 g/L) |
| Lymphocytes | ≥0.5 × 10³/μL | (SI: ≥0.5 GI/L) |
| Neutrophils | ≥1.0 × 10³/μL | (SI: ≥1.0 GI/L) |
| Platelets | ≥75 × 10³/μL | (SI: ≥75 GI/L) |
| Serum creatinine | ≤1.8 mg/dL | (SI: ≤159 μmol/L) |
| White blood cells | ≥2.0 × 10³/μL | (SI: ≥2.0 GI/L) |

The aspartate aminotransferase, alanine aminotransferase, and alkaline phosphatase levels must be within 2×upper limit of normal (ULN) range for the laboratory conducting the test. For subjects within the range of 1.5 to 2×ULN for transaminases, the subject may be included only if the investigator judges the abnormalities or deviations from normal to not be clinically significant or to be appropriate and reasonable for the population under study. This determination must be promptly reported to the Sponsor's medical monitor and recorded in the subject's source documents and initialed by the investigator.

Subjects with other marked disease-associated laboratory abnormalities may be included only if the investigator judges the abnormalities or deviations from normal to be not clinically significant or to be appropriate and reasonable for the population under study. This determination must be promptly reported to the Sponsor's medical monitor and recorded in the subject's source documents and initialed by the investigator.

16. Subject must be willing and able to adhere to the prohibitions and restrictions specified in this protocol.

17. Each subject must sign an informed consent form (ICF) indicating that he or she understands the purpose of and procedures required for the study and are willing to participate in the study.

18. Each subject must sign a separate informed consent form if he or she agrees to provide an optional DNA sample for research (where local regulations permit). Refusal to give consent for the optional DNA research sample does not exclude a subject from participation in the study.

4.1.2. Additional Inclusion Criteria for the Cutaneous Lupus Substudy

To be enrolled in the cutaneous lupus substudy, an SLE subject must satisfy all previously listed inclusion criteria (Section 4.1.1) in addition to the criteria listed below:

1. Have diagnosis of active CLE at screening as well as documented cutaneous disease prior to study enrollment, including subjects with discoid lupus erythematosus, subacute cutaneous lupus erythematosus, or SLE malar rash or other SLE skin lesions including those characterized by erythema and/or scale.

2. Subjects taking systemic, topical, or intra-lesional medications for CLE must be on a stable dose or treatment regimen for 4 weeks prior to first study agent administration.

3. Subjects who consent to participate in the cutaneous lupus substudy will be asked to provide biopsies of an active CLE target lesion prior to dosing at Weeks 0 and 24. An active CLE lesion is characterized by scale and/or erythema, excluding previously scarred tissue. In addition, separate consent will be obtained to collect photographs of a cutaneous lesion or area of active disease according to the schedule defined in Table 1.

4. Subjects with cutaneous lupus deemed unsuitable for biopsy (e.g., malar rash or alopecia) can also be enrolled in the substudy, and may be evaluated by photography.

4.1.3. Inclusion Criteria Applicable to all Subjects Entering into the Study Extension (Week 48 or Week 56 Visits)

Any subjects who do not meet the inclusion criteria for the study extension must follow the Time and Events schedule for the main study design (Table 1), and have safety follow-up visits conducted at 8 and 16 weeks following their Week 40 or final study dose.

1. Subjects must not have permanently discontinued study treatment on or before their Week 40 visit, and are able to either continue q8w SC dosing at approximately 8 weeks (±2 weeks) after their Week 40 visit, or are able to resume dosing at Week 56 with no more than 16 weeks (±2 weeks) since their Week 40 visit.
2. In the judgment of the study investigator, the potential benefit of continuing ustekinumab long-term treatment outweighs the potential risks for the subject.
3. Each subject must sign a revised informed consent indicating agreement to participate in the extended study.

4.2. Exclusion Criteria

Any potential subject who meets any of the following criteria will be excluded from participating in the study.

1. Have other inflammatory diseases that might confound the evaluations of efficacy, including but not limited to rheumatoid arthritis (RA), psoriatic arthritis (PsA), RA/lupus overlap, psoriasis, or active Lyme disease.
2. Are pregnant, nursing, or planning a pregnancy or fathering a child while enrolled in the study or within 4 months after receiving the last administration of study agent.
3. Have received systemic or topical cream/ointment preparations of cyclosporine A or other systemic immunomodulatory agents other than those described in inclusion criteria within the past 3 months prior to first administration of study agent (Section 4.1). Corticosteroids are not included in this criterion; see Sections 4.3 and 8.3 regarding corticosteroids.
4. Have received a single B cell targeting agent within 3 months prior to first study agent administration; or received more than 1 previous B cell targeting therapy including belimumab or epratuzamab within 6 months prior to first administration of the study agent; or received B cell depleting therapy (e.g., rituximab) within 12 months prior to first administration of the study agent or have evidence of continued B cell depletion following such therapy.
5. Have ever received ustekinumab.
6. Have received prior immunomodulatory biologic therapy for lupus not described in Exclusion Criterion #4 including, but not limited to, tocilizumab, alefacept, efalizumab, natalizumab, abatacept, anakinra, brodalumab, secukinumab, ixekizumab, or inhibitors of TNF, IL-1, IL-6, IL-17, or interferon pathways, less than 5 half-lives or 3 months, whichever is longer, prior to first administration of the study agent.
7. Have a known hypersensitivity to human immunoglobulin (Ig) proteins (e.g., intravenous Ig).
8. Have used oral cyclophosphamide within 90 days or IV cyclophosphamide within 180 days of starting screening.
9. Have a history of active granulomatous infection, including histoplasmosis, or coccidioidomycosis, prior to screening. Refer to inclusion criteria for information regarding eligibility with a history of latent TB.
10. Have had a Bacille Calmette-Guérin (BCG) vaccination within 12 months of screening.
11. Have a chest radiograph within 3 months prior to the first administration of study agent that shows an abnormality suggestive of a malignancy or current active infection, including TB.
12. Have had a nontuberculous mycobacterial infection or opportunistic infection (e.g., cytomegalovirus, pneumocystosis, aspergillosis) within 6 months prior to screening.
13. Have received, or are expected to receive, any live virus or bacterial vaccination within 3 months before the first administration of study agent, during the study, or within 3 months after the last administration of study agent. For BCG vaccination criterion, see Exclusion Criterion 10 and Prohibition/Restriction Criterion 8.
14. Have had a serious infection (including but not limited to, hepatitis, pneumonia, sepsis, or pyelonephritis), or have been hospitalized for an infection, or have been treated with intravenous antibiotics for an infection within 2 months prior to first administration of study agent. Less serious infections (e.g., acute upper respiratory tract infection, simple urinary tract infection) need not be considered exclusionary at the discretion of the investigator.
15. Have a history of, or ongoing, chronic or recurrent infectious disease, including but not limited to, chronic renal infection, chronic chest infection (e.g., bronchiectasis), sinusitis, recurrent urinary tract infection (e.g., recurrent pyelonephritis), an open, draining, or infected skin wound, or an ulcer.
16. Subject has a history of human immunodeficiency virus (HIV) antibody positive, or tests positive for HIV at screening.
17. Has a hepatitis B infection. Subjects must undergo screening for hepatitis B virus (HBV). At a minimum, this includes testing for HBsAg (HBV surface antigen), anti HBs (HBV surface antibody), and anti-HBc total (HBV core antibody total).
18. Subjects who are seropositive for antibodies to hepatitis C virus (HCV), unless they have 2 negative HCV RNA test results 6 months apart prior to screening and have a third negative HCV RNA test result at screening.
19. Subjects having experienced a recent single dermatomal herpes zoster eruption within the past 4 months are excluded. Those with multi-dermatomal herpes zoster or central nervous system (CNS) zoster within the past 5 years are excluded.
20. Subjects with a history or suspected occurrence of drug-induced lupus.
21. Have urinary protein >4 g/day or protein/creatinine ratio >4.
22. Have inherited complement deficiency or combined variable immunodeficiency.
23. Have end-stage renal disease, or severe or rapidly progressive glomerulonephritis, including severe, active lupus nephritis reported in recent biopsy and/or other assessments such as active urinary sediment, rapidly increasing creatinine, or other factors that suggest severe or rapidly progressing nephritis (see also limits on serum creatinine in Inclusion Criterion #15).
24. Have severe CNS lupus including but not limited to seizures, psychosis, transverse myelitis, CNS vasculitis and optic neuritis.
25. Have severe, progressive, or uncontrolled hepatic, hematological, gastrointestinal, endocrine, pulmonary, cardiac, neurologic/cerebral, or psychiatric disease, or current signs and symptoms thereof.
26. Have a known history of lymphoproliferative disease, including lymphoma, or signs and symptoms suggestive of possible lymphoproliferative disease, such as lymphadenopathy of unusual size or location, clinically significant splenomegaly, or history of monoclonal gammopathy of undetermined significance.
27. Subject has a history of malignancy within 5 years before screening (exceptions are squamous and basal cell carcinomas of the skin that has been treated with no evidence of recurrence for at least 3 months before the first study agent administration and carcinoma in situ of the cervix that has been surgically cured).
28. Has known allergies, hypersensitivity, or intolerance to ustekinumab, its excipients or latex (contained in the syringe needle cover, see Section 14.1).
29. Are currently receiving venom immunotherapy (honeybee, wasp, yellow jacket, hornet, or fire ant).

30. Has received an investigational drug that is not previously defined in other exclusion criteria (including investigational vaccines or other medications specified in section 4.3, Prohibition/Restriction No. 3) within 5 half lives or 3 months, whichever is longer, or used an invasive investigational medical device within 3 months before the planned first dose of study drug, or is currently enrolled in an interventional study.

31. Has any condition for which, in the opinion of the investigator and/or Sponsor, participation would not be in the best interest of the subject (e.g., compromise the well being) or that could prevent, limit, or confound the protocol-specified assessments including a previous pattern of non-compliance with medical follow-up or being deemed unlikely to be compliant with a study visit schedule.

32. Has had major surgery, (e.g., requiring general anesthesia) within 1 month before screening, or will not have fully recovered from surgery, or has major surgery (e.g., requiring general anesthesia) planned during the time the subject is expected to participate in the study or within 1 month after the last dose of study drug administration.

Note: Subjects with planned minor surgical procedures to be conducted under local anesthesia may participate.

33. Have a transplanted organ (with the exception of a corneal transplant performed ≥3 months prior to first administration of study agent).

34. Have or have had a substance abuse (drug or alcohol) problem within the previous 3 years.

35. Are unwilling or unable to undergo multiple venipunctures because of poor tolerability or lack of easy venous access.

36. Subject is an employee of the investigator or study site (i.e. personnel to whom the investigator has delegated a role or responsibility for conducting the study), with direct involvement in the proposed study or other studies under the direction of that investigator or study site, as well as family members of the employees or the investigator.

37. Lives in an institution on court or authority order, unless permitted by local regulations.

NOTE: Investigators should ensure that all study enrollment criteria have been met at screening. If a subject's status changes (including laboratory results or receipt of additional medical records) after screening but before the first dose of study drug is given such that he or she no longer meets all eligibility criteria, then the subject should be excluded from participation in the study. Sponsor reserves the right to discontinue the subject for any operational or safety reasons.

4.3. Prohibitions and Restrictions

Potential subjects must be willing and able to adhere to the following prohibitions and restrictions during the course of the study (including the study extension) to be eligible for continued dosing in the study:

1. If a woman is capable of pregnancy, she must remain on a highly effective method of birth control during the study and for 4 months after receiving the last study agent. The exception to this restriction is if the subject or her male partner is sterilized; this situation does not require birth control. A woman must not donate eggs (ova, oocytes) for the purposes of assisted reproduction during the study and for 4 months after receiving the last dose of study agent.

2. If a man, he is to use an effective method of birth control and not donate sperm during the study and for 4 months after receiving the last dose of study agent. The exception to this is if the subject or his female partner is sterilized; this situation does not require birth control.

3. Use of additional immunosuppressants or immunomodulators, other than those explicitly allowed in the inclusion/exclusion criteria, are prohibited including but not limited to the following:

Biologic agents targeted at reducing TNF☐ (including but not limited to infliximab, golimumab, certolizumab pegol, etanercept, yisaipu, CT-P13 [Remsima®] and adalimumab)
B cell depleting agents (anti-CD20 [e.g., rituximab], anti-B cell activating factor [BAFF], also known as B lymphocyte stimulator [BLyS], [e.g., belimumab], or anti CD22 [e.g., epratuzumab])
Interleukin-1 inhibitors (e.g., canakinumab)
Interferon inhibitors
IL-1ra (e.g., anakinra)
Tocilizumab or any other biologic targeting IL-6 or IL-6 receptor
Tofacitinib or any other j anus kinase (JAK) inhibitor
Abatacept
Anti-IL-17 agents (e.g., brodalumab, secukinumab, and ixekizumab)
Leflunomide
Cyclosporine A (oral or topical ointment/cream preparations)
Tacrolimus or picrolimus, oral or topical preparations
Toll-like receptor inhibitors
Thalidomide or lenalidomide
Dapsone
Adrenocorticotropic hormone (ACTH) by injection 4. Use of cytotoxic drugs is prohibited including, but not limited to, cyclophosphamide, chlorambucil, nitrogen mustard, or other alkylating agents.

5. Multiple administrations of high doses of corticosteroids, and initiation of medium or high potency topical corticosteroids, are prohibited during the study as defined in Section 8.3.

6. The initiation of a new permitted immunomodulatory agent (MTX, azathioprine, 6-mercaptopurine, mycophenolate mofetil/mycophenolic acid) in addition to an ongoing immunomodulatory therapy is prohibited.

7. Initiation of new angiotensin II receptor blocker (ARB) or angiotensin-converting enzyme (ACE) inhibitor therapy after first dose of study agent is not permitted for the treatment of lupus-related disease through Week 28.

8. Must agree not to receive a live virus or live bacterial vaccination during the study. Subjects must also agree not to receive BCG vaccination for 12 months after last dose of study agent, or any other live vaccine for 3 months after receiving the last administration of study agent.

9. Must agree not to receive an investigational medical device or an investigational drug other than study agent for the duration of this study.

10. The use of complementary therapies that may trigger activation of lupus or mitigate the symptoms of SLE, including but not limited to, traditional medicine (e.g., herbal/alternative preparations [e.g., *Echinacea*], Chinese, acupuncture, ayurvedic) is prohibited through Week 40.

11. Study subjects should avoid excessive sun exposure and may not participate in commercial ultraviolet tanning or ultraviolet phototherapy during the study.

12. Skin concealers or topical tan preparations should be avoided due to their potential to obscure skin disease activity.

13. Sulfa-based antibiotics, where reasonable, should generally be avoided.

5. Treatment Allocation and Blinding

5.1. Procedures for Randomization

Dynamic central randomization will be implemented in conducting this study. Subjects will be assigned to 1 of 2 treatment groups based on a minimization randomization algorithm implemented in the interactive web response system (IWRS) before the study. Dynamic central randomization targets to balance the distribution of subjects to achieve the randomization ratio (3:2) at the study level and within the levels of each individual stratification factor: skin biopsy (y/n, when n<16 for y), presence of lupus nephritis (y/n), baseline SLE medications and SLEDAI-2K score (combined factor)*, site, region (approximately 4 categories), and race (3 categories). Based on the algorithm, each subject will be assigned to the treatment group which will produce minimum total imbalance score with a high probability, where the total imbalance score is a weighted average of the imbalance scores for each stratification factor and for the whole study. The IWRS will the assign a unique treatment code, which will dictate the treatment assignment for the subject.

*The baseline SLE medications and SLEDAI-2K score will be calculated as a combined factor, including:

SLEDAI-2K score (<10 or ≥10) combined with
Baseline medications:
  High medications defined as ≥15 mg/wk MTX, or ≥1.5 mg/kg/day AZA/6-MP, or ≥1.5 g/day MMF/MPA, and/or ≥15 mg/day prednisone.
  Low medications defined as <15 mg/wk MTX, or <1.5 mg/kg/day AZA/6-MP, or <1.5 g/day MMF/MPA, and/or <15 mg/day prednisone.

5.2. Blinding

The investigator will not be provided with randomization codes. The codes will be maintained within the IWRS, which has the functionality to allow the investigator to break the blind for an individual subject.

Under normal circumstances, the blind should not be broken until all subjects have completed the study at Week 56 or terminated study participation, and the database is finalized. Otherwise, the blind should be broken only if specific emergency treatment/course of action would be dictated by knowing the treatment status of the subject. In such cases, the investigator may in an emergency determine the identity of the treatment by contacting IWRS. It is recommended that the investigator contact the Sponsor or its designee if possible to discuss the particular situation, before breaking the blind. Telephone contact with the Sponsor or its designee will be available 24 hours per day, 7 days per week. In the event the blind is broken, the Sponsor must be informed as soon as possible. The date and reason for the unblinding must be documented by the IWRS. The documentation received from the IWRS indicating the code break must be retained with the subject's source documents in a secure manner.

Subjects who have had their treatment assignment unblinded may be discontinued from further administration of study agent and should return for safety follow-up.

In general, randomization codes will be disclosed fully only if the study is completed and the clinical database is closed. The Sponsor will be blinded through the Week 24 evaluation and until the database is cleaned and finalized for planned analyses. The clinical site, subjects, investigators, and site personnel will remain blinded through the end of the study until Week 56 data are finalized. Data that may potentially unblind the treatment assignment will be handled with special care.

6. Dosage and Administration

6.1. IV Administration

For IV administration, the study agent will be administered to each subject over a period of not less than 1 hour.

Ustekinumab 5 mg/mL Final Vialed Product (FVP) (IV) is supplied as a single-use, sterile solution in 30 mL vials with 1 dose strength (i.e., 130 mg in 26 mL nominal volume). In addition to ustekinumab, the solution contains 10 mM L-histidine, 8.5% (w/v) sucrose, 0.04% (w/v) polysorbate 80, 0.4 mg/mL L-methionine, and 20 μg/mL ethylenediaminetetraacetic acid (EDTA) disodium salt dihydrate at pH 6.0. No preservatives are present.

Placebo for FVP (IV) is supplied as single-use, sterile solution in 30 mL vials with a 26 mL nominal volume. The composition of the placebo is 10 mM L-histidine, 8.5% (w/v) sucrose, 0.04% (w/v) polysorbate 80, 0.4 mg/mL L-methionine, and 20 μg/mL EDTA disodium salt dihydrate at pH 6.0. No preservatives are present.

Body weight-range based dosing will allow administration of complete vials to patients to simplify dose calculation and reduce the potential for errors in dosing. This body weight-range based IV dosing is intended to achieve drug exposure similar to that observed with weight adjusted 6 mg/kg dosing. Comparable numbers of vials will be administered to subjects receiving placebo based on their body weight-range. The body weight-range doses are based on the following:

Body weight ≥35 kg and ≤55 kg: 260 mg ustekinumab (2 vials)
Body weight >55 kg and ≤85 kg: 390 mg ustekinumab (3 vials)
Body weight >85 kg: 520 mg ustekinumab (4 vials)

6.2. SC Administration

Ustekinumab will also be supplied as a single-use latex-free prefilled syringe (PFS) in a strength of 90 mg in 1 mL nominal volume for SC administration. Each 1 mL of ustekinumab solution in the PFS contains 90 mg ustekinumab with nominal excipient concentrations of 6.7 mM L-histidine, 7.6% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Placebo administrations will have the same appearance as the respective ustekinumab administrations. Liquid placebo will also be supplied in a 1 mL PFS, and have a composition 10 mM L-histidine, 8.5% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Week 0 Up to Week 24 (Blinded Study Agent Administration Phase)

Group 1: Subjects will receive weight-range based IV dosing of approximately 6 mg/kg of ustekinumab at Week 0 followed by ustekinumab 90 mg SC administrations at Weeks 8 and 16.

Group 2: Subjects will receive weight-range based IV dosing of placebo at Week 0 followed by placebo SC administrations at Weeks 8 and 16.

Week 24 to Week 40 (Cross-Over Administration Phase)

Group 1: Subjects will receive an ustekinumab 90 mg SC administration at Week 24 followed by q8w administrations through Week 40.

Group 2: Subjects will cross-over to ustekinumab 90 mg SC administrations at Week 24 followed by q8w administrations through Week 40.

After Week 40 to 16-Week Safety Follow-Up (Safety Follow-Up Phase)

Groups 1 and 2: Subjects who do not participate in the study extension are expected to return for safety follow-up visits at Weeks 44 and for 8- and 16-weeks safety follow-up.

Study Extension (Week 48/Week 56 Through Week 120)

Subjects who meet the study extension inclusion criteria will receive open-label ustekinumab administration for the purpose of expanding the safety experience and maintenance of efficacy in lupus patients continuously exposed to ustekinumab 90 mg q8w. Subjects who continue dosing in the extended study starting at Week 48 or at Week 56 will receive open-label ustekinumab SC dosing through Week 104. If the development of ustekinumab in SLE is terminated, then the study extension will also be discontinued.

7. Treatment Compliance

Study personnel will maintain a log of all study agent administrations. Study agent supplies for each subject will be inventoried and accounted for. All ongoing therapies administered at the time of screening must be recorded.

Compliance with the treatment schedule is strongly encouraged. It is understood that treatment may be interrupted for health-related or safety reasons. The Weeks 0, 24, and 48 visits are essential for assessing efficacy and safety of ustekinumab as therapy for active SLE.

Therefore, if for any reason a subject cannot receive a dose of study agent at the scheduled visits, the subjects must make every effort to come for scheduled assessments. Through the Week 32 visit, the visit and study agent administration should occur within ±7 days of the scheduled visit day (relative to Week 0). Following the Week 32 visit, the study agent administrations are allowed to occur within ±2 weeks of the scheduled visit day (relative to Week 0). The study agent administrations are scheduled to occur approximately 8 weeks apart, and cannot occur <14 days apart. If there is a delay in treatment, the subject should resume the normal study schedule relative to the baseline visit (Week 0).

All subjects will be monitored by a site monitor designated by the Sponsor. During these monitoring visits, all procedures will be evaluated for compliance with the protocol. Subject charts will be reviewed and compared with earlier data entries on the to ensure accuracy. The Sponsor must be contacted for any deviation to the timeframes above.

8. Concomitant Therapy

All prestudy therapies administered up to 90 days before entry into screening must be recorded at screening. Modification of an effective preexisting therapy should not be made for the explicit purpose of entering a subject into the study. All concomitant therapies must be recorded throughout the study beginning at entry into screening and any changes must be recorded throughout the study.

Every reasonable effort should be made to keep concomitant medications stable at least through Week 28, and if possible also through the main study 8-week safety follow-up or through the study extension (if applicable). With the exception of corticosteroids (see Section 8.3 regarding corticosteroid tapering), all other concomitant medications should be maintained at stable doses throughout the study. A concomitant medication may be reduced or medication temporarily discontinued because of abnormal laboratory values, side effects, concurrent illness, or the performance of a surgical procedure, but the change and reason for the medication change should be clearly documented in the subject's medical record. If concomitant medications have been adjusted after randomization as allowed per protocol, every effort should be made to return subject back to the baseline (Week 0) dose level by the Week 12 visit; or increased medication use (relative to baseline) may render a subject to be considered a treatment failure. Corticosteroid adjustments for cause are permitted as defined in Section 8.3.

The Sponsor must be notified in advance (or as soon as possible thereafter) of any instances in which prohibited therapies are administered.

All pharmacologic therapies (prescription or over-the-counter medications, including vaccines, vitamins, herbal supplements) different from the study agent must be recorded. Subject diary cards will be used to capture changes in subject-administered medications that occur in between study visits during the main portion of this study, and these changes must also be recorded.

8.1. Immunomodulators

If receiving immunomodulators, subjects should be receiving stable dosing from screening through Week 28. Subjects can be receiving MMF/MPA (≤2 g/day), azathioprine/6-mercaptopurine (≤2 mg/kg/day) and/or MTX (≤25 mg/wk) with concomitant folic acid (recommend ≥5 mg/wk), during screening and through Week 28. A reduction in immunomodulators from Week 12 through Week 28 is allowed only if the subject develops unacceptable side effects, with the implication that this may affect interpretation of the subjects' clinical data. A higher dose of an immunomodulator (relative to the baseline dose) or the addition of a new immunomodulator to the existing treatment regimen between the Week 12 and 24 visit will cause subjects to be considered a treatment failure for the purposes of the primary endpoint analysis. Permanent discontinuation of the study treatment must be considered for subjects receiving an increase (relative to baseline) in their immunomodulator dose. Beyond Week 28, immunomodulators should remain as stable as possible through the 8-week safety follow-up or through the study extension (if applicable); however, dose adjustment is allowed for unacceptable side effects.

8.2. Antimalarial Medications

Stable treatment with hydroxychloroquine, chloroquine, or quinacrine is permitted through the 8-week safety follow-up. Beyond Week 28, it is permitted to introduce or adjust dosing of antimalarials. Antimalarials produced by a licensed compounding pharmacy (e.g., quinacrine) in the country of administration and using pharmacaceutical grade components are allowed.

8.3. Corticosteroid Therapy

Unnecessary dose changes are discouraged, and any dose adjustments should be made in increments. Changes in corticosteroids through the 8-week safety follow-up or through the study extension (if applicable) are allowed for medical necessity, but the degree and timing of the adjustment should be carefully considered as this may have an impact on the study results, especially during the period between 12 and 28 weeks.

Oral Corticosteroids*

If using oral corticosteroids, must be receiving this medication for at least 6 weeks and on a stable dose equivalent to an average dose of ≤20 mg of prednisone/day for at least 4 weeks prior to the first administration of study agent. Corticosteroid dose adjustment (increase or decrease) of no more than 5 mg prednisone (equivalent/day) to a maximum dose of 25 mg/day is permitted through Week 6. From Week 6 through Week 12, no corticosteroid dose increases are permitted, and within this window only a gradual decrease of up to 5.0 mg prednisone (equivalent/day) adjustment towards the baseline dose are allowed up to the Week 12 visit. No further adjustments in doses of corticosteroid for the treatment of SLE disease are permitted between Weeks 12 and 28. Following Week 28, changes in corticosteroid dosing through the 8-week safety follow up is allowed for medical necessity, but the degree and timing of the adjustment should be carefully considered as this may have an impact on the study. Dose increases of oral corticosteroids of 40 mg/day or more should be discussed with the medical monitor and may result in discontinuation of study agent administration.

Subjects may receive short courses (2 weeks or less) of oral corticosteroids for reasons such as prophylactic therapy before surgery (stress-dose corticosteroids) or therapy for limited infections, exacerbation of asthma, or chronic obstructive pulmonary disease.

Subjects likely to require multiple courses of steroids for reasons other than SLE should be excluded from study participation.

Gradual tapering of oral corticosteroid dosing in the study extension (recommended reductions of no more than 10 to 20% of the original dose per week) is encouraged starting after the Week 48 dose at the discretion of the study investigator. Tapering to the lowest possible maintenance dose of corticosteroids is recommended, including complete weaning off of corticosteroids if possible. It is recommended that subjects should be educated and monitored by study staff for symptoms of steroid deficiency (e.g., Addisonian symptoms) during periods of steroid tapering, as appropriate.

If subjects experience a worsening in their disease activity while tapering corticosteroids, further dose decreases may be suspended, and/or their oral corticosteroid dose may be temporarily increased if deemed necessary by the investigator. For subjects whose corticosteroid taper is interrupted, investigators are encouraged to resume tapering within 4 weeks.

In the event of increased corticosteroid dosing, it is recommended that the average dose should not be increased above the baseline dose unless medically necessary. Discretion should be used as any corticosteroid increases may render a subject to be considered a treatment or steroid tapering failure. Sustained oral corticosteroid doses of 40 mg/day or higher may result in discontinuation of study agent.

*Rectal administration of corticosteroids, if necessary, should be short-term and using topical preparations.

Epidural, Intravenous, Intramuscular, Intra-Articular, and Intra-Lesional Corticosteroids Epidural, IV, IM, IA, or intra-lesional administration of corticosteroids is strongly discouraged within 4 weeks prior to the first administration of study agent and is not allowed for the treatment of SLE through Week 28. Drugs that induce release of endogenous steroids such as ACTH administered by injection are not allowed within 3 months prior to the first administration of study agent and throughout the study. Short-term (≤2 weeks) epidural, IV, IM, IA, or intra-lesional corticosteroid use for the treatment of indications other than SLE should be limited to situations where, in the opinion of the treating physician, there are no adequate alternatives. If clinically necessary, a total of 1 or 2 IA injections may be permitted up to the Week 16 dosing, however this would render those joints unevaluable for subsequent assessments. For conditions other than SLE, corticosteroid therapy should be limited to situations in which, in the opinion of the treating physician, there are no adequate alternatives. Intravenous corticosteroids of >625 mg prednisone equivalent/day for 2 or more days total in the 24-week period will be evaluated for treatment failure as per the statistical analysis plan (SAP).

Inhalation Corticosteroids

Corticosteroids administered by bronchial or nasal inhalation for treatment of conditions other than SLE may be given as needed.

Corticosteroid Use in Cutaneous Lupus Substudy

For subjects in the cutaneous lupus substudy, the initiation of, or an increase from baseline in, the use of potent topical corticosteroids, or intra-lesional corticosteroid injections, is not allowed and should be avoided through the 8-week safety follow-up or in the study extension.

8.4. Nonsteroidal Anti-Inflammatory Drugs

Subjects treated with NSAIDs, including aspirin and selective cyclooxygenase-2 (COX-2) inhibitors, and other analgesics should receive the usual marketed doses approved in the country in which the study is being conducted. Prescriptions of NSAIDs and other regularly administered analgesics should not be adjusted for at least 2 weeks prior to the first administration of the study drug and through Week 28, and may be changed only if the subject develops unacceptable side effects. After Week 16 and through Week 28 the addition of new NSAIDs to the treatment regimen is not permitted. Minor adjustments in NSAID therapy are allowed after Week 28 although it is recommended that the use of any NSAIDS remain as stable as possible, and any notable changes should be recorded.

8.5. Anti-Hypertensive Medications

Subjects are permitted to receive stable doses of ARB or ACE inhibitors for the treatment of hypertension and lupus. Initiation of new ARB or ACE inhibitor therapy after first dose of study agent is not permitted for the treatment of lupus-related disease through Week 28. Subjects should not initiate any new ARB or ACE inhibitor therapy between randomization and Week 28. New or adjusted ARB or ACE inhibitor therapy is allowed beyond Week 28.

8.6. Topical Medications

Topical medications are permitted; however, topical compounds cannot include a prohibited medication. Topical ointments or creams of cyclosporine A are prohibited through Week 28; however ophthalmic use is permitted. Low potency topical steroids are allowed except on day of study visit. Medium to high potency topical corticosteroids are disallowed for all subjects through the 8-week safety follow-up, and high potency topical corticosteroids are not allowed during the study extension. For subjects in the cutaneous lupus substudy, topical treatment of target lesions should remain stable during the cutaneous lupus substudy period. For 72 hours prior to study visit, topical medications should not be applied to lesions under evaluation.

9. Study Evaluations 9.1. Study Procedures 9.1.1. Overview

The Time and Events Schedule summarizes the frequency and timing of efficacy, pharmacokinetics, antibodies to ustekinumab, pharmacodynamics, pharmacogenomics, health-related quality of life, safety, and other measurements applicable to this study.

Additional serum or urine pregnancy tests may be performed, as determined necessary by the investigator or required by local regulation, to establish the absence of pregnancy at any time during the subject's participation in the study.

The total blood volume to be collected from each subject over the course of the main portion of the study will be approximately 640 mL. The total blood volume to be collected in the study extension between Weeks 48 and 120 will be approximately 250 mL.

Repeat or unscheduled samples may be taken for safety reasons or for technical issues with the collection or analysis of specific samples.

A blood sample will be collected from subjects who have consented to participate in the pharmacogenomics component of the study. In the event of DNA extraction failure, a replacement pharmacogenomics blood sample may be requested from the subject. A separate informed consent would not be required to obtain a replacement sample.

Subjects who have consented to participate in the cutaneous lupus substudy will be requested to allow collection of skin biopsy samples at Week 0 and at Week 24. In addition, photographs will be taken of a target cutaneous lesion or area of active disease as noted in the Time and Events Schedule (Table 1). For additional detail regarding the cutaneous lupus substudy, refer to Section 9.7.

9.1.2. Screening Phase
9.1.2.1. Screening Procedures

Written informed consent must be obtained and reviewed by investigator before any screening data is collected.

Screening procedures will be performed as indicated in the Time and Events Schedule (Table 1). The screening visit must be performed no more than 6 weeks prior to the randomization visit (Week 0). In addition, to be eligible for study participation, subjects must have SLEDAI score 4 for clinical features at Week 0 and have received approval for study randomization following review and adjudication of screening lupus assessments by the Sponsor and/or Sponsor-selected independent reviewer(s).

Subjects will be trained on how to complete the Diary cards. Diary cards will be distributed to subjects for completion during the screening period.

Women of childbearing potential must have a negative serum β-hCG pregnancy test at screening and a negative urine β-hCG pregnancy test before randomization. Women of childbearing potential and men must consent to use highly effective methods of contraception (see inclusion criteria, Section 4.1) and continue to use contraception for the duration of the study and for 4 months after the last study agent administration. The method(s) of contraception used by each subject must be documented.

All screening evaluations establishing subject eligibility will be performed and reviewed by investigator before subject can be randomized. Although the SLICC criteria may not have been formally assessed, to be eligible for enrollment subjects must have demonstrated symptoms (documented in subject file) of SLE sufficient to meet SLICC criteria for a minimum of 3 months prior to first dose of study agent. Subjects eligible for enrollment in this study must qualify as having SLE by meeting the SLICC classification criteria for SLE based upon 1 or both of the following (as described in Inclusion Criterion #2):

Meeting 4 criteria with at least 1 clinical criterion and at least 1 immunologic criterion, or
A diagnosis of lupus nephritis with presence of at least 1 of the immunological variables, Subjects must also have 1 well-documented (subject file, referring physician letter, or laboratory result) medical historical value for unequivocally positive ANA, anti-dsDNA antibodies, and/or anti-Smith antibodies. Medical historical documentation of a positive test of ANA (e.g., ANA by HEp-2 titer, ANA by enzyme-linked immunosorbent assay) or anti-dsDNA (e.g., anti-dsDNA by Farr assay or ELISA) must include the date and type of the test, the testing laboratory name, numerical reference range, and a key that explains that the values provided are positive versus negative/equivocal or borderline. Only unequivocally positive values as defined in the laboratory's reference range are acceptable; borderline values will not be accepted.

In addition, in order to assess the stability of SLE disease activity, subjects must demonstrate SLEDAI-2K score ≥6, despite conventional treatment (e.g., immunomodulators, antimalarial drugs, corticosteroids, NSAIDs, anti-hypertensive drugs, and/or topical medications). In addition, subjects must have at least 1 positive autoantibody test (ANA, anti-dsDNA antibodies, and/or anti-Smith antibodies) observed during screening. Subjects must also demonstrate at least 1 BILAG A and/or 2 BILAG B domain scores observed prior to first administration of study agent.

9.1.2.2. Retesting

If a subject has signed the ICF and failed to meet at least 1 entry requirement, a one-time retest of screening laboratory test(s) will be allowed in the event of suspected error in sample collection or analysis performance, or a study entry procedure may be repeated once during the screening period if needed. A request to use a local test to replace the central lab test should be discussed with the medical monitor prior to retesting. This is inclusive of only 1 additional blood draw to be completed for retesting, regardless of whether an additional laboratory value is found to be out of range. The goal of the retest procedure is to assess if the subject is eligible for randomization within the screening window or should be screen failed. Subjects that have laboratory values that do not meet entry criteria following the retest or do not meet disease activity criteria following the repeat procedure are to be deemed a screen failure. Exceptions to this are positive QUANTIFERON®-TB Gold (blood test for tuberculosis), hepatitis C or B, or HIV tests; unless there is a suspected error in sample collection or analysis performance, these tests may not be repeated to meet eligibility criteria.

9.1.2.3. Rescreening

If a subject has failed screening and investigator wishes to rescreen the subject, this should be discussed with the study Sponsor and/or their designee. Only 1 rescreening is allowed per subject. Subjects who are rescreened will be assigned a new subject number, undergo the informed consent process, and then restart a new screening phase.

9.1.3. Double-Blind Treatment Phase
9.1.3.1. Week 0/Day of Randomization

At Week 0, eligible subjects will be randomly assigned by the IWRS in a 3:2 ratio to receive either ustekinumab or placebo in a blinded manner. Assessments will be performed as indicated in the Time and Events Schedule (Table 1). Subjects participating in the cutaneous lupus substudy will have baseline, pre-treatment photographs and/or skin biopsies collected. Subject's diary card which was distributed during screening will be reviewed at Week 0, and a new card will be provided at each study visit to record medication changes during the subsequent 4 weeks through the main portion of the study.

9.1.3.2. Placebo-Controlled Treatment Period (Through Week 24)

After randomization and the first administration of study agent by IV infusion, subjects will have blinded study agent administrations SC q8w through the Week 24 visit. Assessments will be performed as indicated in the Time and Events Schedule (Table 1).

9.1.4. Cross-Over Treatment (Through Week 40)

At Week 24, subjects in the placebo group will cross-over to receive ustekinumab dosing, and all subjects will continue to receive SC administrations q8w through Week 40. All subjects will continue to remain blinded to study treatment received during the placebo-controlled treatment period as described in Section 9.1.3.2.

9.1.5. Study Extension (Week 48/Week 56 Through Week 104)

Subjects who qualify for participation in the study extension through Week 104 will continue ustekinumab 90 mg q8w SC dosing at approximately 8 weeks (±2 weeks) after their Week 40 visit, or resume ustekinumab dosing at Week 56 with no more than 16 weeks (±2 weeks) since their Week 40 visit.

9.1.6. Subjects Withdrawing from Study Participation

Subjects who withdraw from study participation will not be required to return for any follow-up assessments.

9.1.7. Post-Treatment Safety Follow-Up

Subjects who permanently discontinue study agent at or before Week 40, or permanently discontinue at or before Week 104 if they are participating in the study extension, but do not withdraw from study participation, should be followed for approximately 16 weeks (5 half-lives) after the last study agent administration according to the visit schedule and assessments indicated in the appropriate Time and Events Schedules (Table 1 and Table 2). Follow-up visits should occur approximately 8 weeks and 16 weeks after the last study agent administration. Subjects who permanently discontinue study agent before or at Week 40 will not be eligible to participate in the study extension.

Telephone contact will be made to determine reasons for study discontinuation for up to 16 weeks after the last dose of study drug, unless the subject is lost to follow-up, or has withdrawn consent. If the information on reason for discontinuation is obtained via telephone contact, written documentation of the communication must be available for review in the source documents. If the subject has died, the date and cause of death will be collected and documented.

9.2. Efficacy

All efficacy evaluations should be consistently performed by the study investigator or sub-investigator to achieve comparable measures over time. Independent adjudication by Sponsor or Sponsor-designated independent reviewer(s) will be performed for key lupus assessments (e.g., SLEDAI, BILAG, and CLASI). These data will be reviewed at every visit that these data are collected and may require reconciliation of inconsistencies across assessments.

9.2.1. Evaluations

A complete list describing all efficacy evaluations and endpoints, and which evaluations are included in the composite endpoints is provided in Appendix 1.

9.2.1.1. SLEDAI-2K and S2K RI-50

The SLE disease activity index 2000 (SLEDAI-2K/S2K RI-50 [Baseline]) is an established, validated SLE activity index. It is based on the presence of 24 features in 9 organ systems and measures disease activity in SLE patients in the previous 30 days. It is weighted according to the feature. At screening, features are scored by the assessing physician if present within the last 30 days with more severe features having higher scores, and then simply added to determine the total SLEDAI-2K score, which ranges from 0 to 105 (Touma et al, 2010a). At baseline, the features assessed in the SLEDAI-2K are used for comparison to the S2K RI-50 index described below.

The SLEDAI-2K has been adapted and developed into the SLEDAI-2K Responder Index (S2K RI-50 [Follow-up]) (Touma et al, 2010b), a measure that can document partial improvement in the 24 disease features between SLEDAI-2K assessments (Touma et al, 2010c). A threshold of 50% improvement was judged to reflect clinically significant improvement and is scored as half the weight for the feature. "When a descriptor is recorded as present at the initial visit, 1 of 3 situations can follow: (1) the descriptor achieves complete remission at follow-up, in which case the score would be "0"; (2) the descriptor does not achieve a minimum of 50% improvement at follow-up, in which case the score would be identical to its corresponding SLEDAI-2K value; or (3) the descriptor improves by ≥50% (according to the S2K RI-50 definition) but has not achieved complete remission, in which case the score is evaluated as one-half the score that would be assigned for SLEDAI-2K (Touma et al, 2011). The S2K RI-50 score is the sum of the 24 scored items, which ranges from 0 to 105.

9.2.1.2. BILAG

The BILAG (Hay et al, 1993; Isenberg et al, 2005) index scores subjects based on the need for alterations or intensification of therapy. The assessing physician will evaluate 97 items divided into the following 9 organ/systems domains.

Constitutional
Mucocutaneous
Neuropsychiatric
Musculoskeletal
Cardiorespiratory
Gastrointestinal
Ophthalmic
Renal
Hematological The assessing physician ought to consider each item as to its presence in the past 4 weeks, and answer 0=not present, 1=improving, 2=same, 3=worse, or 4=new as compared with a specified reference visit. Each organ/system domain is classified as BILAG A, B, C, D, or E based upon organ/system specific items and criteria specific to the domain.

9.2.1.3. CLASI

Cutaneous lupus erythematosus disease activity will be measured by the CLASI. The CLASI is an instrument the assessing physician will use to assess the disease activity and damage caused to the skin for CLE patients with or without systemic involvement. The CLASI consists of 2 scores; the first summarizes the activity of the disease while the second is a measure of the damage done by the disease. Activity is scored on the basis of erythema, scale/hyperkeratosis, mucous membrane involvement, acute hair loss and non-scarring alopecia. Damage is scored in terms of dyspigmentation and scarring, including scarring alopecia. The scores are calculated by simple addition based on the extent of the symptoms (Albrecht et al. 2005). Higher activity and damage scores indicate worse disease activity.

9.2.1.4. Physician Global Assessment of Disease Activity

The physician must complete the Physician Global Assessment of Disease Activity (Felson et al, 1995) independent of subjects' assessment. The assessments will be recorded on a visual analogue scale (VAS; 0 to 10 cm). The scale for the assessment ranges from "no Lupus activity" (0) to 'extremely active Lupus" (10).

The physician assessor should preferably be the same person at every study visit for a given subject.

9.2.1.5. Patient Global Assessments

The subject must complete the Patient Global Assessment of Disease Activity and Patient's Assessment of Pain independent of the Physician's Global Assessment of Disease Activity.

9.2.1.5.1 Patient Global Assessment of Disease Activity

The Global Assessment of Disease Activity will be recorded on a visual analogue scale (VAS; 0 to 10 cm). The scale for the assessment ranges from "very well" (0) to "very poor" (10).

9.2.1.5.2. Patient Assessment of Pain

The Patient's Assessment of Pain is used to assess the patient reported pain intensity. The patient's will be asked to assess their average pain during the past week on a visual analogue scale (VAS; 0 to 10 cm). The anchors of the instrument include 0 to represent 'no pain' and 10 to represent 'the worst possible pain'.

9.2.1.6. Short-Form-36

The RAND short-form (SF)-36 questionnaire is a self-administered multi-domain scale with 36 items. Eight health domains cover a range of functioning:

Limitations in physical function
Limitations in usual role activities
Bodily pain
General mental health (psychological distress and well-being)
Vitality (energy and fatigue)
Limitations in social functioning due to physical or mental health problems
Limitations in usual role activities due to personal or emotional problems
General health perception The subscales are scored from 0 to 100. The scoring yields a Physical Component Summary score and a Mental Component Summary score, a total score, and subscale scores. Higher scores represent better outcomes. It is appropriate for persons over the age of 14 and may be completed in 5 to 10 minutes. Translations are available in most languages; the instrument has undergone extensive linguistic and cultural validation. Version 2 acute will be used in the study.

The concepts measured by the SF-36 are not specific to any age, disease, or treatment group, allowing comparison of relative burden of different diseases and the benefit of different treatments (Ware & Sherbourne, 1992). A change of 3 points in any of the subscales or 5 points for the component score is associated with clinically meaningful change (Samsa et al, 1999; Ware, 2000; Ware et al, 1994). The SF-36 has been used extensively in clinical trials providing evidence of psychometric properties. Reliability estimates for physical and mental component summary scores exceeded 0.90 in early studies (McHorney et al, 1994) and have been further confirmed in later studies. Construct validation was established through comparison to several other generic health surveys.

9.2.1.7. Fatigue Severity Scale

The Fatigue Severity Scale (FSS) is a 9-item questionnaire designed to assess the severity of fatigue and its impact on daily living using 7 response options (1=Completely Disagree, 7=Completely Agree) during a recall period of the past week. It can be completed within 5 minutes by the subject. Scores above 36 of the total possible score of 63 reflect increasing severity of fatigue. The scale was developed for use in SLE (Krupp et al, 1989). The scores on the scale correlate with patient reported pain, sleep, depression, and with each subscale of the SF-36. The FSS has shown a high internal consistency, and differentiates patients from controls in studies with SLE subjects. The instrument was translated from the original English version and is available in several languages.

9.2.2. Definitions

A complete list describing all efficacy evaluations and endpoints, and which evaluations are included in the composite endpoints is provided in Appendix 1.

9.2.2.1. SRI-4

Systemic Lupus Erythematosus Disease Activity Index 2000 SRI-4 response is defined as a composite endpoint requiring at least a 4 point reduction in SLEDAI 2K score (Section 9.2.1.1), no worsening (<10 mm increase) from baseline in the Physician's Global Assessment of Disease Activity score (PGA) (Section 9.2.1.4), and no new BILAG Domain A and no more than 1 new BILAG Domain B scores (Section 9.2.1.2) (Fine et al, 2009). SRI-5 and SRI-6 are similarly defined with response requiring a ≥5 point reduction or ≥6 point reduction in SLEDAI 2K, respectively. SRI-5 and SRI-6 are similarly defined with response requiring a ≥5 point reduction or ≥6 point reduction in SLEDAI-2K, respectively.

9.2.2.2. BILAG-Based Combined Lupus Assessment

The BILAG-based Combined Lupus Assessment (BICLA) requires patients to meet response criteria across 3 assessment tools: (1) the BILAG-2004 index (2) the SLEDAI index and (3) a PGA. Patients are identified as responders or non-responders based upon the following requirements (Wallace, 2008):

| Requirements for BICLA Response | |
|---|---|
| BILAG | BILAG improvement classified as: All BILAG A scores at baseline improved to either BILAG B, C or D All BILAG B scores at baseline improved to either BILAG C or D No worsening in disease activity defined as no new BILAG A scores and ≤1 new BILAG B score |
| SLEDAI-2K | No worsening of total SLEDAI-2K from baseline (change ≤0) |
| PGA | No significant deterioration (<10 mm increase) in 100 mm visual analogue PGA |
| Treatment Failure | No treatment failure (see SAP for definition of treatment failure) |

9.2.2.3. Flares

Flares for this study will be defined as:

SLEDAI Flare: At least a 4+ point increase in SLEDAI-2K score (includes severe flares)

Severe SLEDAI flare: At least a 7+ point increase in SLEDAI-2K score

BILAG flare: At least 1 new BILAG A or 2 new BILAG B scores (from scores <B)

9.2.2.4. S2K RI-50 Response

S2K RI-50 response is defined as a decrease of at least 6 points from baseline in the SLEDAI-2K score.

9.2.2.5. No Worsening in PGA

No worsening in PGA is defined as less than a 10 mm increase on 100 mm VAS.

9.2.3. Endpoints

Primary Endpoint

The primary endpoint of this study is the proportion of subjects with a composite SRI-4 response at Week 24.

Major Secondary Endpoints

The major secondary endpoints are listed in order of importance as specified below:
1. The change from baseline in SLEDAI-2K at Week 24.
2. The change from baseline in PGA at Week 24.
3. The proportion of subjects with BICLA response at Week 24.

Other Endpoints

Flares:
4. Time to first flare (SLEDAI flare, Severe SLEDAI flare, BILAG flare) from Week 12 through Week 24 and from Week 24 through Main Study 8-week Safety Follow-up Visit/Week 48 as well as from Week 48 through Week 104.
5. Number of flare (SLEDAI flare, Severe SLEDAI flare, BILAG flare) free visits from Week 12 through Week 24 and from Week 24 through Main Study 8-week Safety Follow-up Visit/Week 48 as well as from Week 48 through Week 104.

SLE Disease Activity:
6. The proportion of subjects with responses in SRI-4, SRI-5, SRI-6, S2K RI-50 response and BICLA over time.
7. The proportion of subjects with no worsening in SLEDAI, BILAG, PGA, and Patient's Global Assessment of Disease Activity (PtGA) over time.
8. The proportion of subjects with improvement in SLEDAI (4, 5, and 6, points), BILAG, and PGA over time.
9. The absolute change from baseline in SLEDAI-2K, S2K RI-50, PGA over time.
10. The percent change in serological activity (e.g., ANA, anti-dsDNA, other autoantibodies, C3, C4) or SLEDAI feature measurements over time.
11. Shift table of BILAG by organ domain over time.
12. The percent change in CLASI scores (activity and damage) in subjects with cutaneous disease over time.

Pro Outcomes:
13. The change in patient reported outcomes (PROs) (Pain VAS scale, FSS, SF-36 physical and mental component summary scores and individual domains) over time.
14. The proportion of subjects with clinically (the minimally clinical important difference) in PROs (i.e., FSS, improvement in SF-36) over time.
15. The change from baseline in PtGA at Week 24.

Medications:
16. The proportion of subjects with meaningful changes in selected SLE medications from Week 12 through Main Study 8-week Safety Follow-up Visit/Week 48.
17. Change in corticosteroid dose from Week 48 through Week 104 for subjects who participate in the study extension.

Development and analyses of the new endpoint(s) will be included in a separated technical report.

9.3. Pharmacokinetics and Immunogenicity

Serum samples will be used to evaluate the pharmacokinetics (PK) of ustekinumab, as well as the immunogenicity of ustekinumab (antibodies to ustekinumab). Serum collected for PK and immunogenicity analyses may additionally be used to evaluate safety or efficacy aspects that address concerns arising during or after the study period. Genetic analyses will not be performed on these serum samples. Subject confidentiality will be maintained.

9.3.1. Serum Collection and Handling

Venous blood samples will be collected at the time points shown in the Time and Events Schedule for the determination of serum ustekinumab concentrations and antibodies to ustekinumab. Serum samples will also be collected at the final visit from subjects who terminate study participation early. At visits where PK and immunogenicity will be evaluated, 1 blood draw of sufficient volume can be used. Each sample will be split into 3 aliquots (1 aliquot for serum ustekinumab concentration, 1 aliquot for antibodies to ustekinumab, and 1 aliquot as a back-up). Samples must be collected before study drug administration at visits when study drug administration is scheduled. The exact dates and times of blood sample collection must be recorded in the laboratory requisition form.

9.3.2. Analytical Procedures

Serum samples will be analyzed to determine ustekinumab concentrations using a validated, specific, and sensitive immunoassay method by Sponsor's bioanalytical facility or under the supervision of the Sponsor. The Sponsor, or its designee, under conditions in which the subjects' identity remains blinded, will assay these samples.

9.3.3. Immunogenicity Assessments

Antibodies to ustekinumab will be detected using a validated immunoassay method in serum samples collected from all subjects. Serum samples that test positive for antibodies to ustekinumab will be further characterized to determine if antibodies to ustekinumab could neutralize the biological effects of ustekinumab in vitro (i.e., neutralizing antibodies [NAbs] to ustekinumab). All samples will be tested by the Sponsor or Sponsor's designee.

9.4. Biomarkers

The collection, preparation, storage and shipment of skin biopsies, blood, serum and urine are detailed in the Time and Events schedule (Table 1) and the Laboratory Manual. Biomarkers may include, but are not limited to, inflammatory markers, RNA, cell surface markers, auto-antibodies, T cell and B cell repertoire, target specific markers, and other categories of biomarkers potentially involved in the development and the progression of lupus.

Serum Analyses

Serum will be analyzed for levels of specific proteins including but not limited to soluble CD40 ligand (sCD154), interleukin (IL)-6, IL-12p40, IL-17, IL-21, IL-22, IL-23p19, C—X—C motif chemokine 10 (CXCL10), BAFF, interferons, auto-antibodies and other inflammation-related molecules.

Urine Samples

Urine samples will be evaluated for excreted proteins or other markers believed to have relevance in SLE.

Skin Biopsy Analyses

Skin biopsies will be utilized for cellular, molecular, and gene expression analyses.

Whole Blood Gene Expression Analyses

Whole blood will be collected from all subjects for RNA, flow cytometry (samples from selected sites will be analyzed at central laboratory or other analytical laboratory), T cell and B cell repertoire (nucleic acid analyses [RNA and DNA] for specific T and B cell receptors only) and epigenetics analysis (e.g., DNA methylation).

9.5. Pharmacogenomic Evaluations

The DNA samples will be used for research related to this study (CNTO1275SLE2001). Specific genomic testing will be undertaken for consenting subjects (subjects participating in this portion of the study must sign a separate ICF). The procedure will involve taking a blood sample that may be analyzed for specific target genes that may play a role in lupus. Any genomic assessments will be performed in strict adherence to current subject confidentiality standards for genetic testing. Refusal to participate in genomics testing will not result in ineligibility for participation in the rest of the clinical study.

9.6. Serologic Markers

Sample for autoantibodies (including ANA, anti-dsDNA, anti-Smith), complement C3, C4, and other analytes will be collected as described in the Table of Events (Table 1) and Section 9.8 Safety Evaluations (Clinical Laboratory Tests).

9.7. Cutaneous Lupus Substudy

Subjects with cutaneous disease will be evaluated using CLASI scoring. Additionally, subjects with cutaneous disease who consent to participate in the cutaneous lupus sub study will have additional assessments including collection of skin biopsies (optional consent) prior to study agent administration at Week 0 and at Week 24 and/or photographs of a cutaneous lesion or an area of active disease (optional consent) to be performed as shown in the Table of Events (Table 1). There will not be any restrictions on the number of subjects with cutaneous disease who can enroll into either the main study or the cutaneous lupus substudy.

Subjects who consent to the optional biopsy collection will have 2 skin biopsies (4 mm) excised from an active target lesion at Week 0, followed by 2 additional biopsies of the same lesion (regardless of cutaneous disease activity) at Week 24 (Cutaneous Lupus Substudy Manual). Skin biopsies will be utilized for cellular, molecular, and gene expression analyses.

Independent of cutaneous biopsy collection, subjects who participate in the cutaneous lupus substudy will be requested to provide consent for photographs to be collected from an identified cutaneous lesion or an area of active disease. Consenting subjects with cutaneous lupus unsuitable for biopsy (e.g., malar rash or alopecia) may be evaluated by photography. The photographs are for exploratory purposes only. The photographs will be used to assist in a qualitative evaluation of clinical response. The photographs and skin biopsies can target a different area of active disease, but the follow-up photographs or biopsies should re-evaluate the same area of active disease as originally assessed at week 0. Confidentiality of the subjects involved in this study will be maintained; specifically photographs of subjects in this study will not be published or otherwise made public without blocking adequate portions of the subject's face or body so that the individual cannot be identified.

9.8. Safety Evaluations

Safety assessments include vital signs, general physical examinations and skin evaluations (assessed during S2K RI-50 and CLASI evaluations), adverse events, concomitant medication review, pregnancy testing (refer to Section 12.3.3), administration reactions, chemistry and hematology laboratory tests, and antibodies to ustekinumab. Chest x-ray and TB, HIV, hepatitis B, and hepatitis C testing will be required at time of screening (Table 1). Refer to Section 4.1 for tuberculosis screening criteria. Subject diary cards will be used to capture medication changes that occur in between study visits through the main portion of the study.

Any clinically significant abnormalities persisting at the end of the study will be followed by the investigator until resolution or until a clinically stable endpoint is reached.

The study will include the following evaluations of safety and tolerability according to the time points provided in Table 1 and Table 2 for the extended study.

Adverse Events

Adverse events (AE) will be reported by the subject (or, when appropriate, by a caregiver) for the duration of the study, and will be followed by the investigator.

Infections

Subjects will be provided an alert card of signs and symptoms for infections, and will be instructed to contact the site between scheduled visits should any signs and symptoms occur. At each site visit, investigators or other site personnel are required to evaluate subjects for any signs or symptoms of infection, and ask about symptoms of infection or other AEs that may have occurred in between site visits.

Study agent should not be administered to a subject with a clinically important, active infection. Treatment with study agent should be withheld until serious and/or severe infections are completely resolved. If a subject develops a serious or severe infection, including but not limited to sepsis or pneumonia, discontinuation of study treatment must be considered. Treatment must be permanently discontinued for subjects who develop an opportunistic infection. For active varicella-zoster infection or a significant exposure to varicella zoster infection in a subject without history of chickenpox, the subject should be evaluated for symptoms of infection and if the subject has received appropriate treatment and/or recovered or no symptoms of infection, may continue study administration after discussion with the study Sponsor.

Clinical Laboratory Tests

Blood samples for serum chemistry and hematology will be collected according to the Time and Events Schedule (Table 1 and Table 2 for the extended study). The investigator must review the laboratory report immediately upon availability, document this review, and record any clinically relevant changes occurring during the study. Coomb's direct test, urine dipstick, urine sediment microscopy and urine pregnancy test will be performed by site staff or the local laboratory. With the approval of the study Sponsor, the use of local laboratories may also be allowed in cases where initiation of treatment or safety follow-up is time-critical and the central laboratory results are not expected to be available before the need to provide study agent treatment or if actions need to be taken for safety reasons.

A one-time retest of screening laboratory test(s) analyzed by the central laboratory will be allowed in the event of suspected error in sample collection or analysis performance.

Hematology Panel
  hemoglobin
  hematocrit
  white blood cell (WBC) count with differential (basophils, eosinophils, lymphocytes, monocytes, neutrophils)
  platelet count
  CD 19 B-cell analyses during screening only if needed for subjects previously exposed to B-cell depleting therapies (Section 4.1.3)
  Coomb's direct test (local laboratories, if available)

Serology Laboratory
  Ig isotype profile (IgG, IgM, IgA levels)
  C3 and C4 Complement
  ANA
  anti-dsDNA
  anti-phospholipid antibodies including lupus anticoagulant, anti-cardiolipin, and anti-$\beta_2$-glycoprotein-I antibodies
  other autoantibodies including anti-Smith, anti-Sjögren's-syndrome-related antigen A (SSA [anti-Ro], and B (SSB [anti-La]), anti-ribonucleoprotein (anti-RNP)

Coagulation Labs
  Prothrombin Time
  Partial Thromboplastin Time
  International Normalized Ratio

| Serum Chemistry Panel | |
| --- | --- |
| sodium | alkaline phosphatase |
| potassium | calcium |
| chloride | phosphorous |
| bicarbonate | albumin |
| blood urea nitrogen | total protein |
| creatinine | creatinine kinase |
| glucose | aspartate aminotransferase |
| aldolase (if creatine kinase is elevated at screening then aldolase test at Week 0 and follow-up as needed) | alanine aminotransferase total bilirubin, and if total bilirubin is abnormally elevated, then direct bilirubin, and indirect bilirubin |

Urine Analyses—Fresh spot urine
    Urinalysis using urine dipstick. Urine sample will be further analyzed at Central laboratory.
    Urinary protein/creatinine ratio (Fine et al, 2009) will be analyzed at the central laboratory using an aliquot of spot urine collected from subjects.
    Urine Sediment Microscopy (Local Laboratory Assessment using spot urine samples)
        Red blood cells
        WBC, with note if urinary tract infection is present/absent
        epithelial cells
        crystals
        Red blood cells, WBC, or heme-granular casts
        bacteria
    Serum and urine pregnancy testing for women of child-bearing potential only
    Viral serology (HIV antibody, HBsAg, anti-HBs, anti-HBc total, and hepatitis C virus antibody)

Vital Signs
    Weight and temperature will be assessed. Blood pressure and heart rate measurements will be assessed.

Physical Examination
    A full body physical examination will be performed pre-treatment and during the study as shown in Table 1 and Table 2 for the extended study.

9.9. Sample Collection and Handling
    The actual dates and times of sample collection must be recorded on the laboratory requisition form.
    Refer to the Time and Events Schedule (Table 1 and Table 2 for the extended study) for the timing and frequency of all sample collections.
    Instructions for the collection, handling, and shipment of samples are found in the laboratory manual that will be provided for sample collection and handling.

10. Subject Completion/Withdrawal 10.1. Completion

A subject who does not enter into the study extension will be considered to have completed the main study if he or she has completed assessments through 16-week safety follow-up of the main study. A subject who has enrolled into the study extension will be considered to have completed the main portion of this study if he or she has completed assessments through the 8-week safety follow-up visit of the main study. Subjects who prematurely discontinue study treatment for any reason before the Week 8 or Week 16 safety follow-up visits (from the main study), will not be considered to have completed the main portion of the study. A subject who has enrolled into the study extension will be considered to have completed the study extension if he or she has completed assessments through Week 120.

Discontinuation of Study Treatment

If a subject's study treatment must be discontinued before or at Week 40 (for subjects who do not participate in the study extension) or before Week 104 (for subjects who do participate in the study extension), this will not result in automatic withdrawal of the subject from the study and follow-up assessments should be obtained approximately 8 and 16 weeks following the last dose of study agent.

A subject's study treatment must be permanently discontinued if any of the following occur:

1. An AE temporally associated with study agent infusion or injection, resulting in bronchospasm with wheezing and/or dyspnea requiring ventilatory support, or symptomatic hypotension with a greater than 40 mm Hg decrease in systolic blood pressure.
2. The subject withdraws consent for administration of study agent.
3. Pregnancy or planning to become pregnant within the study period or within 16 weeks after the last study agent injection.
4. The initiation of prohibited medications or treatments (as per Section 4.3).
5. Malignancy, with the exception of no more than 2 localized basal cell skin cancers that are treated with no evidence of recurrence or residual disease.
6. An opportunistic infection.
7. The investigator or Sponsor's medical monitor deems it is in the subject's best interest.
8. The subject is deemed ineligible according to the following TB criteria:
   A diagnosis of active TB is made.
   A subject has symptoms suggestive of active TB based on follow-up assessment questions and/or physical examination, or has had recent close contact with a person with active TB, and cannot or will not continue to undergo additional evaluation.
   A subject undergoing continued screening has a chest radiograph with evidence of current active TB and/or a positive QUANTIFERON®-TB Gold (blood test for tuberculosis) test and/or a positive tuberculin skin test result in countries in which the QUANTIFERON®-TB Gold (blood test for tuberculosis) is not approved/registered result and/or an indeterminate QUANTIFERON®-TB Gold (blood test for tuberculosis) test result on repeat testing, unless active TB can be ruled out and appropriate treatment for latent TB can be initiated either prior to or simultaneously with the next administration of study agent and continued to completion.
   A subject receiving treatment for latent TB discontinues this treatment prematurely or is noncompliant with the therapy.
9. Significant worsening of SLE disease activity from baseline or having high disease activity for 2 or more consecutive visits starting at Week 16 based on overall clinical assessments; or if a subject requires the addition of a new immunomodulator to the existing treatment regimen after Week 16.

In addition, permanent discontinuation of study agent treatment must be considered for subjects who:

Receive an increase (relative to baseline) in their immunomodulator dose.

Develop any of the following adverse events that are reported as serious or severe: study agent infusion reaction, injection-site reaction, or infection.

10.3. Withdrawal from the Study

A subject will be withdrawn from the study for any of the following reasons:
  Lost to follow-up
  Withdrawal of consent
  Death If a subject is lost to follow-up, every reasonable effort must be made by the study site personnel to contact the subject and determine the reason for discontinuation/withdrawal. The measures taken to follow-up must be documented.

When a subject withdraws before completing the study, the reason for withdrawal is to be documented. Study drug assigned to the withdrawn subject may not be assigned to another subject. Subjects who withdraw from this study will not be replaced.

A subject who withdraws from the study will have the following options regarding the optional research samples:
  The collected samples will be retained and used in accordance with the subject's original informed consent for optional research samples.
  The subject may withdraw consent for optional research samples, in which case the samples will be destroyed and no further testing will take place. To initiate the sample destruction process, the investigator must notify the Sponsor study site contact (or appropriate designee) of withdrawal of consent for the optional research samples and to request sample destruction. The Sponsor study site contact will, in turn, contact the biomarker representative to execute sample destruction. If requested, the investigator will receive written confirmation from the Sponsor that the samples have been destroyed.

Withdrawal from the Optional Research Samples while Remaining in the Main Study

The subject may withdraw consent for optional research samples while remaining in the study. In such a case, the optional research samples will be destroyed. The sample destruction process will proceed as described above.

Withdrawal from the Use of Samples in Future Research

The subject may withdraw consent for use of samples for research (refer to Section 16.2.5, Long-Term Retention of Samples for Additional Future Research). In such a case, samples will be destroyed after they are no longer needed for the clinical study. Details of the sample retention for research are presented in the main ICF and in the separate ICF for optional research samples.

11. Statistical Methods

Statistical analysis will be done by the Sponsor or under the authority of the Sponsor. A general description of the statistical methods to be used to analyze the efficacy and safety data is outlined below. Specific details will be provided in the Statistical Analysis Plan.

11.1. Subject Information

For all subjects who receive at least 1 dose of study drug descriptive statistics will be provided for demographic data and baseline characteristics, including prior and background SLE therapies. All subjects who are randomized and received at least 1 dose of study agent will be included in the efficacy analyses according to their assigned treatment group. The safety analysis population will include those subjects who received at least 1 dose of study agent, and will be analyzed according to the actual study agent received.

11.2. Sample Size Determination

The sample size calculation is based upon the primary endpoint, proportion of SRI-4 responders at Week 24. Approximately 60 subjects treated with ustekinumab and approximately 40 subjects with placebo is projected to give approximately 80% power to detect a significant difference in response rate compared with placebo (assume 35% and 60% response rates in placebo and ustekinumab respectively, which translates to 25% absolute increase over placebo or an odds ratio of 2.79) with an alpha level of 0.1. The assumption of a 35% responder rate for placebo is based upon a previous study in which a similar SLE population was treated (Van Vollenhoven et al, 2012). Recent studies have shown very high placebo rates in certain regions, thus the power for the study could be reduced (Huang et al, 2007).

The power to detect a significant treatment difference at $\alpha=0.1$ (2-sided) is calculated under various assumptions (see Table 4).

TABLE 4

Power to Detect a Significant Treatment Difference in the Proportion of Subjects with SRI-4 Response at Week 24

| Proportion of Placebo Group with Response (%) | Absolute Increase in Response (%) | Proportion of Ustekinumab Group with Response (%) | Odds Ratio | Power |
| --- | --- | --- | --- | --- |
| 20 | 20 | 40 | 2.67 | 70% |
|    | 25 | 45 | 3.27 | 85% |
|    | 30 | 50 | 4.00 | 94% |
| 25 | 20 | 45 | 2.45 | 67% |
|    | 25 | 50 | 3.00 | 82% |
|    | 30 | 55 | 3.67 | 92% |
| 30 | 20 | 50 | 2.33 | 64% |
|    | 25 | 55 | 2.85 | 80% |
|    | 30 | 60 | 3.50 | 91% |
| 35 | 20 | 55 | 2.27 | 62% |
|    | 25 | 60 | 2.79 | 79% |
|    | 30 | 65 | 3.45 | 91% |

TABLE 4-continued

Power to Detect a Significant Treatment Difference in the
Proportion of Subjects with SRI-4 Response at Week 24

| Proportion of Placebo Group with Response (%) | Absolute Increase in Response (%) | Proportion of Ustekinumab Group with Response (%) | Odds Ratio | Power |
|---|---|---|---|---|
| 40 | 20 | 60 | 2.25 | 62% |
|  | 25 | 65 | 2.79 | 79% |
|  | 30 | 70 | 3.50 | 91% |

*Note:
SRI-4 response is defined as a ≥4-point reduction in SLEDAI-2K score, no new domain scores in either BILAG A or BILAG B and no worsening (<10 mm increase) from baseline in the PGA (Furie et al, 2009).

11.3. Efficacy Analyses

All efficacy analyses will be performed on the modified intent-to-treat (mITT) analysis set. The mITT analysis set will include all subjects who are randomized and received at least 1 dose of study agent. The efficacy analyses will be calculated according to their assigned treatment group.

11.3.1. Primary Endpoint Analysis

The primary endpoint of this study is the proportion of subjects with a composite measure of SLE disease activity (SRI-4 response) at Week 24 (Section 9.2.2.1). The primary analysis will be based upon the primary endpoint and will be conducted on the mITT population, which includes all randomized subjects who receive at least 1 dose of study agent, have at least 1 measurement prior to the administration, and have at least 1 post-baseline SRI-4 measurement.

Last observation carried forward procedure will be used to impute the missing SRI-4 component if the subjects have data for at least 1 SRI-4 component at Week 24. If the subjects do not have data for any SRI components at Week 24, the subjects will be considered not to have achieved the SRI-4 response. In addition, subjects who meet any 1 of the following criteria will be considered to have not achieved the primary endpoint, SRI-4 response at Week 24 (full details will be provided in the SAP):

Between the Week 12 visit and the Week 24 visit, either the dose of an immunomodulator is higher than at baseline, or a new immunomodulator has been added to the existing treatment regimen.

The addition of a new immunomodulator to the existing treatment regimen before Week 12 and subject still was receiving that immunomodulator after Week 12.

Initiate treatment with disallowed dose or disallowed use of oral, IV or IM or other type of corticosteroid administration for SLE, or increase the dose of oral corticosteroids for SLE above baseline between the Week 12 and 24 visits.

Subjects who were not receiving ARB or ACE inhibitor therapy who then initiated a new ARB or ACE inhibitor therapy between Week 12 and Week 24. Subjects who substitute an ARB or ACE inhibitor for a comparable medication would not be considered treatment failures.

Discontinue study agent due to lack of efficacy for an AE of worsening of SLE prior to Week 24.

For subjects who use systemic corticosteroids for another indication, the efficacy measurement will be carried forward from the last observation prior to the initiation of the treatment, for the period of 2 weeks after initiation of the treatment. After the 2 week period, the subject's calculated value will be as measured.

Other situations may confound the primary endpoint, such as a subject initiating NSAIDs after Week 16, or using epidural, IV, IM, IA, or intra-lesional, inhaled corticosteroids, and topical medication. Data handling rules will be specified in the Statistical Analysis Plan.

Logistic regression, adjusting for baseline stratifications and baseline SLEDAI, will be used to analyze the primary endpoint. The baseline SLEDAI value is defined as the closest non-missing measurement taken prior to the Week 0 infusion. If significant non-normality is observed, appropriate nonparametric tests will be used to evaluate the differences between treatments.

The study will be considered positive if the primary analysis achieves statistical significance at a significance level of 0.1 (2-sided) and ustekinumab shows a positive treatment effect relative to placebo treatment.

In addition to the primary analysis, sensitivity analyses will be performed to explore the effects with different data handling rules. If it is deemed necessary, the primary endpoint will be analyzed on the per protocol population. Details of the inclusion/exclusion rules for per protocol population will be provided in the SAP.

Subgroup analysis based on region will be performed. This is due to potential regional differences in evaluating efficacy, and high placebo response rates in certain regions. Subgroup analysis of the primary endpoint by other selected baseline characteristics will be presented. Details will be outlined in the SAP.

11.3.2. Major Secondary Analyses

The change from baseline in SLEDAI-2K at Week 24.
The change from baseline in PGA at Week 24.
The proportion of subjects with BICLA response at Week 24.

Continuous responses will be analyzed using an analysis of covariance model with treatment group as a fixed factor and baseline stratifications (e.g., regions) as a covariate. Nonparametric methods will be adopted when the normality assumption is violated.

11.3.3. Other Planned Efficacy Analyses

For the other efficacy endpoints listed in Section 9.2.3, the following statistical methods will be applied:

Binary data will be analyzed using the same statistical method as in the primary efficacy analysis. Continuous responses will be analyzed using an analysis of covariance model with treatment group as a fixed factor and baseline stratifications (e.g., regions) as a covariate. Nonparametric methods will be adopted when the normality assumption is violated. Log-rank tests will be used to compare endpoints defined by time to an event.

11.3.4. Efficacy Analyses in the Study Extension

Long-term evaluations of efficacy including SRI-4, SLEDAI-2K, PGA, reduction in corticosteroid dosing, and evaluations of flare over time will also be performed for those subjects who participate in the study extension.

11.4. Interim Analyses

Interim analyses (IA) will be conducted when approximately ⅓ and ⅔ of subjects reach Week 24. In the first IA, only evidence for notable efficacy will be assessed. In the second IA, evidence for notable efficacy as well as treatment futility will be analyzed. Variations in placebo effect across regions will be incorporated into the interim analyses. Details concerning the IAs are described in the IA Statistical Analysis Plan.

11.5. Pharmacokinetic Analyses

Serum ustekinumab concentrations will be summarized for each treatment group over time. Descriptive statistics, including arithmetic mean, standard deviation, median, interquartile range, minimum, and maximum will be calculated at each sampling time point.

If feasible, a population PK analysis using nonlinear mixed effects modeling may be used to characterize the disposition characteristics of ustekinumab in the current study. The influence of important variables such as body weight and antibodies to ustekinumab status on the population PK parameter estimates may be evaluated. Details will be given in a population PK analysis plan, and results of the population PK analysis will be presented in a separate technical report.

11.6. Immunogenicity Analyses

The incidence and titers of antibodies to ustekinumab will be summarized for subjects who received at least 1 administration of ustekinumab and have appropriate samples for detection of antibodies to ustekinumab (i.e., subjects with at least 1 sample obtained after their first dose of ustekinumab).

The incidence of NAbs to ustekinumab will be summarized for subjects who are positive for antibodies to ustekinumab and have samples evaluable for NAbs.

11.7. Biomarker Analyses

The following results from treated and untreated SLE subjects will be summarized:
- The concentration of individual serum and urine markers.
- Results from selected biomarkers in skin biopsy tissue by RNA-sequencing and immunohistochemistry.
- Results from whole blood gene expression profiling, flow cytometry, T cell and B cell repertoire, and epigenetics.
- Additional exploratory analyses may be performed following evaluation of the data.

The samples collected from other ongoing clinical studies may also be included in the biomarker data analyses. Results of biomarker analyses may be presented in a separate report.

11.8. Pharmacogenetics Analyses

The DNA research may consist of the analysis of 1 or more candidate genes or of the analysis of genetic markers throughout the genome (as appropriate) in relation to this study.

Results of genomic analyses will be presented in a separate report once the overall number of samples including those collected from other sources is appropriate.

11.9. Pharmacokinetic and Pharmacodynamic Analysis

If data permit, the relationships between serum ustekinumab concentration and efficacy or pharmacodynamic measures may be analyzed graphically.

11.10. Safety Analyses

Safety analyses will be based on the population of subjects who received at least 1 dose of either study agent; subjects will be summarized by the treatment they actually received.

Adverse Events (AEs)

The verbatim terms used to identify AEs will be coded using the Medical Dictionary for Regulatory Activities. All reported AEs with onset during the treatment phase (i.e., treatment-emergent AEs, and AEs that have worsened since baseline) will be included in the analysis. For each AE, the percentage of subjects who experience at least 1 occurrence of the given event will be summarized by treatment group. Routine safety evaluations will be performed. Adverse events, serious AEs (SAEs), reasonably related AEs, and AEs by severity will be summarized by treatment group.

The incidence and types of infections, infusion reaction, and inject site reactions will be analyzed for this study. An infusion reaction is defined as an AE that occurs during or within 1 hour following the infusion of study agent, with the exception of laboratory abnormalities.

Special attention will be given to those subjects who died, or who discontinued treatment due to an adverse event, or who experienced a severe or a serious adverse event (e.g., summaries, listings, and narrative preparation may be provided, as appropriate).

Clinical Laboratory Tests

Laboratory data will be summarized by the type of laboratory test. Reference ranges and Common Terminology Criteria for Adverse Events (CTCAE) will be used in the summary of laboratory data. Descriptive statistics will be calculated for each laboratory analyte at baseline and at each scheduled time point. Changes from baseline results will be presented in pre-versus post-treatment cross-tabulations (with classes for below, within, and above normal ranges based on laboratory reference ranges). The baseline is defined as the last measurement prior to the first dose of the randomized treatment. The number and percentage of subjects by Maximum CTCAE Grade will be summarized for each treatment group for each laboratory analyte. The laboratory parameters and change from baseline in selected laboratory parameters (hematology and chemistry), and the number of subjects with abnormal laboratory parameters (hematology and chemistry) based on CTCAE toxicity grading will be summarized treatment group. Listings of SAEs will also be provided. All safety analyses will be based on the population of subjects who received at least 1 dose of either study agent; subjects will be summarized by the treatment they actually received.

Urine protein and creatinine measurements will be used to calculate the urine protein to creatinine ratio. Descriptive statistics will be calculated for these ratios at baseline and at each scheduled time point.

Vital Signs

Vital sign measures at each scheduled time point and their changes from baseline will be summarized using descriptive statistics. The baseline is defined as the last measurement prior to the first dose of the randomized treatment.

11.11. Data Monitoring Committee

An independent DMC will be established to monitor data on an ongoing basis to ensure the continuing safety of the subjects enrolled in this study and to conduct interim efficacy analysis. The committee will meet at least twice to review interim data, including when ⅓ and ⅔ of subjects reach Week 24. After each review, the DMC will make a recommendation to the Sponsor committee whether the study should be stopped for safety concerns. In the first IA, Sponsor will also be notified for notable efficacy in order to advance to next trial. In the second IA, Sponsor will be notified for notable efficacy as well as futility. The details will be provided in a separate DMC charter and in the IA Statistical Plan.

The DMC will have 3 to 6 members who are independent of the Sponsor. The DMC will consist of at least 1 medical expert in the relevant therapeutic area and at least 1 statistician. The DMC responsibilities, authorities, and procedures will be documented in its charter.

The DMC will no longer be active after the assessment of the primary endpoint in this study.

12. Adverse Event Reporting

Timely, accurate, and complete reporting and analysis of safety information from clinical studies are crucial for the protection of subjects, investigators, and the Sponsor, and are mandated by regulatory agencies worldwide. The Sponsor has established Standard Operating Procedures in conformity with regulatory requirements worldwide to ensure appropriate reporting of safety information; all clinical studies conducted by the Sponsor or its affiliates will be conducted in accordance with those procedures.

12.1. Definitions 12.1.1. Adverse Event Definitions and Classifications

Adverse Event

An adverse event is any untoward medical occurrence in a clinical study subject administered a medicinal (investigational or non-investigational) product. An adverse event does not necessarily have a causal relationship with the treatment. An adverse event can therefore be any unfavorable and unintended sign (including an abnormal finding), symptom, or disease temporally associated with the use of a medicinal (investigational or non-investigational) product, whether or not related to that medicinal (investigational or non-investigational) product. (Definition per International Conference on Harmonisation [ICH])

This includes any occurrence that is new in onset or aggravated in severity or frequency from the baseline condition, or abnormal results of diagnostic procedures, including laboratory test abnormalities.

Note: The Sponsor collects adverse events starting with the signing of the ICF (refer to Section 12.3.1, All Adverse Events, for time of last adverse event recording).

Serious Adverse Event

A serious adverse event based on ICH and EU Guidelines on Pharmacovigilance for Medicinal Products for Human Use is any untoward medical occurrence that at any dose:
  Results in death
  Is life-threatening
  (The subject was at risk of death at the time of the event. It does not refer to an event that hypothetically might have caused death if it were more severe.)
  Requires inpatient hospitalization or prolongation of existing hospitalization
  Results in persistent or significant disability/incapacity
  Is a congenital anomaly/birth defect
  Is a suspected transmission of any infectious agent via a medicinal product
  Is Medically Important*

*Medical and scientific judgment should be exercised in deciding whether expedited reporting is also appropriate in other situations, such as important medical events that may not be immediately life threatening or result in death or hospitalization but may jeopardize the subject or may require intervention to prevent 1 of the other outcomes listed in the definition above. These should usually be considered serious.

If a serious and unexpected adverse event occurs for which there is evidence suggesting a causal relationship between the study drug and the event (e.g., death from anaphylaxis), the event must be reported as a serious and unexpected suspected adverse reaction.

Unlisted (Unexpected) Adverse Event/Reference Safety Information

An adverse event is considered unlisted if the nature or severity is not consistent with the applicable product reference safety information.

Adverse Event Associated With the Use of the Drug

An adverse event is considered associated with the use of the drug if the attribution is possible, probable, or very likely by the definitions.

12.1.2. Attribution Definitions

Not Related

An adverse event that is not related to the use of the drug.

Doubtful

An adverse event for which an alternative explanation is more likely, e.g., concomitant drug(s), concomitant disease(s), or the relationship in time suggests that a causal relationship is unlikely.

Possible

An adverse event that might be due to the use of the drug. An alternative explanation, e.g., concomitant drug(s), concomitant disease(s), is inconclusive. The relationship in time is reasonable; therefore, the causal relationship cannot be excluded.

Probable

An adverse event that might be due to the use of the drug. The relationship in time is suggestive (e.g., confirmed by dechallenge). An alternative explanation is less likely, e.g., concomitant drug(s), concomitant disease(s).

Very Likely

An adverse event that is listed as a possible adverse reaction and cannot be reasonably explained by an alternative explanation, e.g., concomitant drug(s), concomitant disease(s). The relationship in time is very suggestive (e.g., it is confirmed by dechallenge and rechallenge).

12.1.3. Severity Criteria

An assessment of severity grade will be made using the following general categorical descriptors:

Mild:
  Awareness of symptoms that are easily tolerated, causing minimal discomfort and not interfering with everyday activities.

Moderate:
  Sufficient discomfort is present to cause interference with normal activity.

Severe:
  Extreme distress, causing significant impairment of functioning or incapacitation. Prevents normal everyday activities.

The investigator should use clinical judgment in assessing the severity of events not directly experienced by the subject (e.g., laboratory abnormalities).

12.2. Special Reporting Situations

Safety events of interest on a Sponsor study drug that may require expedited reporting and/or safety evaluation include, but are not limited to:
  Overdose of a Sponsor study drug
  Suspected abuse/misuse of a Sponsor study drug
  Inadvertent or accidental exposure to a Sponsor study drug
  Medication error involving a Sponsor product (with or without subject/patient exposure to the Sponsor study drug, e.g., name confusion)
  Adverse events of special interest: any newly identified malignancy, opportunistic infection (i.e., infection by an organism that normally is not pathogenic or does not cause invasive infection in immunocompetent hosts), or case of active TB occurring after the first administration of study agent in subjects participating in this clinical trial must be reported by the investigator following procedures. Investigators are also advised that active TB is considered a reportable disease in most countries. These events are to be considered serious only if they meet the definition of an SAE.

Special reporting situations should also be recorded. Any special reporting situation that meets the criteria of a serious adverse event should be recorded.

12.3. Procedures 12.3.1. All Adverse Events

All adverse events and special reporting situations, whether serious or non-serious, will be reported from the time a signed and dated ICF is obtained until completion of the subject's last study-related procedure (which may include contact for follow-up of safety). Serious adverse events, including those spontaneously reported to the investigator within 16 weeks after the last dose of study drug, must be reported using the Serious Adverse Event Form. The Sponsor will evaluate any safety information that is spontaneously reported by an investigator beyond the time frame specified in the protocol.

All events that meet the definition of a serious adverse event will be reported as serious adverse events, regardless of whether they are protocol-specific assessments.

All adverse events, regardless of seriousness, severity, or presumed relationship to study drug, must be recorded using medical terminology in the source document. Whenever possible, diagnoses should be given when signs and symptoms are due to a common etiology (e.g., cough, runny nose, sneezing, sore throat, and head congestion should be reported as "upper respiratory infection"). Investigators must record their opinion concerning the relationship of the adverse event to study therapy. All measures required for adverse event management must be recorded in the source document and reported according to Sponsor instructions.

The Sponsor assumes responsibility for appropriate reporting of adverse events to the regulatory authorities. The Sponsor will also report to the investigator (and the head of the investigational institute where required) all serious adverse events that are unlisted (unexpected) and associated with the use of the study drug. The investigator (or Sponsor where required) must report these events to the appropriate Independent Ethics Committee/Institutional Review Board (IEC/IRB) that approved the protocol unless otherwise required and documented by the IEC/IRB.

The subject must be provided with a "wallet (study) card" and instructed to carry this card with them for the duration of the study indicating the following:

Study number
Statement, in the local language(s), that the subject is participating in a clinical study
Investigator's name and 24-hour contact telephone number
Local Sponsor's name and 24-hour contact telephone number (for medical staff only)
Site number
Subject number
Any other information that is required to do an emergency breaking of the blind 12.3.2. Serious Adverse Events All serious adverse events occurring during the study must be reported to the appropriate Sponsor contact person by study-site personnel within 24 hours of their knowledge of the event.

Information regarding serious adverse events will be transmitted to the Sponsor using the Serious Adverse Event Form, which must be completed and signed by a physician from the study site, and transmitted to the Sponsor within 24 hours. The initial and follow-up reports of a serious adverse event should be made by facsimile (fax).

All serious adverse events that have not resolved by the end of the study, or that have not resolved upon discontinuation of the subject's participation in the study, must be followed until any of the following occurs:

The event resolves
The event stabilizes
The event returns to baseline, if a baseline value/status is available
The event can be attributed to agents other than the study drug or to factors unrelated to study conduct
It becomes unlikely that any additional information can be obtained (subject or health care practitioner refusal to provide additional information, lost to follow-up after demonstration of due diligence with follow-up efforts)

Suspected transmission of an infectious agent by a medicinal product will be reported as a serious adverse event. Any event requiring hospitalization (or prolongation of hospitalization) that occurs during the course of a subject's participation in a study must be reported as a serious adverse event, except hospitalizations for the following:

Hospitalizations not intended to treat an acute illness or adverse event (e.g., social reasons such as pending placement in long-term care facility)
Surgery or procedure planned before entry into the study (must be documented).

The cause of death of a subject in a study within 16 weeks of the last dose of study drug, whether or not the event is expected or associated with the study drug, is considered a serious adverse event.

12.3.3. Pregnancy

All initial reports of pregnancy must be reported to the Sponsor by the study-site personnel within 24 hours of their knowledge of the event using the appropriate pregnancy notification form. This includes subject report of a positive home over-the-counter pregnancy test. Abnormal pregnancy outcomes (e.g., spontaneous abortion, stillbirth, and congenital anomaly) are considered serious adverse events and must be reported using the Serious Adverse Event Form. Any subject who becomes pregnant during the study must discontinue further study treatment, and followed for 4 months after last study dose.

Because the effect of the study drug on sperm is unknown, pregnancies in partners of male subjects included in the study will be reported by the study-site personnel within 24 hours of their knowledge of the event using the appropriate pregnancy notification form.

Follow-up information regarding the outcome of the pregnancy and any postnatal sequelae in the infant will be required.

13. Product Quality Complaint Handling

A product quality complaint (PQC) is defined as any suspicion of a product defect related to manufacturing, labeling, or packaging, i.e., any dissatisfaction relative to the identity, quality, durability, or reliability of a product, including its labeling or package integrity. A PQC may have an impact on the safety and efficacy of the product. Timely, accurate, and complete reporting and analysis of PQC information from studies are crucial for the protection of subjects, investigators, and the Sponsor, and are mandated by regulatory agencies worldwide. The Sponsor has established procedures in conformity with regulatory requirements worldwide to ensure appropriate reporting of PQC information; all studies conducted by the Sponsor or its affiliates will be conducted in accordance with those procedures.

13.1. Procedures

All initial PQCs must be reported to the Sponsor by the study-site personnel within 24 hours after being made aware of the event.

If the defect is combined with a serious adverse event, the study-site personnel must report the PQC to the Sponsor according to the serious adverse event reporting timelines (refer to Section 12.3.2, Serious Adverse Events). A sample of the suspected product should be maintained for further investigation if requested by the Sponsor.

14. Study Drug Information 14.1. Physical Description of Study Drug
14.1.1. IV Administration Ustekinumab 5 mg/mL FVP (IV) is supplied as a single-use, sterile solution in 30 mL vials with 1 dose strength (i.e., 130 mg in 26 mL nominal volume). In addition to ustekinumab, the solution contains 10 mM L-histidine, 8.5% (w/v) sucrose, 0.04% (w/v) polysorbate 80, 0.4 mg/mL L-methionine, and 20 μg/mL EDTA disodium salt, dihydrate at pH 6.0. No preservatives are present.

Placebo for FVP (IV) is supplied as single-use, sterile solution in 30 mL vials with a 26 mL nominal volume. The composition of the placebo is 10 mM L-histidine, 8.5% (w/v) sucrose, 0.04% (w/v) polysorbate 80, 0.4 mg/mL L-methionine, and 20 μg/mL EDTA disodium salt, dihydrate at pH 6.0. No preservatives are present.

14.1.2. SC Administration

Ustekinumab will also be supplied as a single-use latex-free PFS in a strength of 90 mg in 1 mL nominal volume for SC administration. Each 1 mL of ustekinumab solution in the PFS contains 90 mg ustekinumab with nominal excipient concentrations of 6.7 mM L-histidine, 7.6% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Placebo administrations will have the same appearance as the respective ustekinumab administrations. Liquid placebo will also be supplied in a 1 mL PFS, and have a composition 10 mM L-histidine, 8.5% (w/v) sucrose, 0.004% (w/v) polysorbate 80, at pH 6.0. No preservatives are present. The needle cover on the PFS contains dry natural rubber (a derivative of latex), which may cause allergic reactions in individuals sensitive to latex.

Conclusion

Safety and Efficacy of Ustekinumab in Patients with Systemic Lupus Erythematosus: Results of a Phase 2, Randomized, Placebo-Controlled, Study Background/Purpose:

The IL-12/23 pathway has been implicated in the pathogenesis of Systemic Lupus Erythematosus (SLE). The anti-IL-12/IL-23p40 antibody ustekinumab is used in the treatment of psoriasis, psoriatic arthritis, and Crohn's disease. Here, the safety and efficacy of usetkinumab was evaluated in patients with active SLE.

Methods:

A phase 2, placebo-controlled study, was conducted in 102 adults with seropositive (ANA, anti-dsDNA, and/or anti-Smith antibodies) SLE by SLICC criteria and active disease (SLEDAI-2K≥6 and ≥1 BILAG A and/or ≥2 BILAG B scores) despite conventional therapy. Patients (n=102) were randomized (3:2) to receive ustekinumab intravenous (IV) at ~6 mg/kg or placebo at week 0, then subcutaneous (SC) injections of ustekinumab 90 mg q8w or placebo, both added to standard care; stratification factors were consent for skin biopsy (yes/no), disease features, (e.g., presence of LN, baseline concomitant SLE medications, SLEDAI score), site/region, and race. At week 24, placebo patients crossed over to ustekinumab (90 mg SC q8w). Primary endpoint was SLE response index (SRI-4) response at week 24. Major secondary endpoints at week 24 included change from baseline in SLEDAI-2K, change from baseline in Physician's Global Assessment (PGA), and proportion of patients with BICLA response. Endpoint analyses included all patients who received ≥1 dose of study agent, had ≥1 measurement prior to administration, and had ≥1 post-baseline measurement. Modified intention-to-treat (mITT) analyses across SLE disease activity measures were performed to evaluate for maintenance of response with ustekinumab between week 24 and week 48. Subjects crossing over from placebo to SC ustekinumab were also assessed for de novo clinical responses across disease activity measures. Safety was assessed through week 56. Patients with missing data and treatment failures were imputed as nonresponders.

Results:

Patient demographic and disease characteristics were well-balanced between treatment groups (female=91%; mean age=41 (18-66) years; mean SLEDAI-2K=10.9). At week 24, 61.7% of patients in the ustekinumab group had an SRI-4 response vs 33.3% in the placebo group (p=0.0057), with a treatment effect favoring ustekinumab beginning at week 12. Patients in the ustekinumab group had greater median improvements from week 0 to week 24 in SLEDAI-2K and PGA vs placebo (Table 5). Furthermore, rates of SLEDAI-2K (65% at week 24 vs 66.7% at 1 year), PGA (67.9% at week 24 vs 75% at 1 year), and active joint (86.5% at week 24 vs 86.5% at 1 year) responses were also sustained from week 24 to 1 year in the ustekinumab group (Table 6). CLASI response rate plateaued by week 28 (53.1% at week 24 vs 67.7% at week 28) and was maintained through 1 year in the ustekinumab group (68.6%) (Table 6). No difference was observed in the proportion of patients achieving a BICLA composite response at week 24, although a notable difference in the proportion of patients with no BILAG worsening among BICLA nonresponders was observed. The risk of a new BILAG flare (≥1 new BILAG A or ≥2 new BILAG B) was significantly lower in the ustekinumab group vs. placebo (HR 0.12 [95% CI 0.01-0.94]; p=0.0119). Ustekinumab also demonstrated improvement in musculoskeletal and mucocutaneous disease features vs placebo. Improvements in anti-dsDNA and C3 levels were also noted through week 24 with ustekinumab. Through week 24, 78% of ustekinumab patients and 67% of placebo patients had ≥1 adverse event (Table). Among placebo patients who crossed over to SC ustekinumab at week 24 (n=33), 54.5% achieved an SRI-4 response at 1 year. Placebo patients who crossed over to SC ustekinumab at week 24 also demonstrated greater response rates across multiple efficacy measures including proportion of patients with point improvement from baseline SLEDAI-2K (46% at 24 weeks vs 55% at 1 year), proportion of patients with ≥30% improvement from baseline PGA (56% at 24 weeks vs 77% at 1 year), proportion of patients with 50% improvement in the number of active joints at baseline (61% at week 24 vs 82% at 1 year), and proportion of patients with 50% improvement from baseline CLASI Activity Score (35% at Wk 24 vs. 47% at 1 year). Of ustekinumab-exposed patients, 81.7% had ≥1 TEAE, 15.1% had ≥1 SAE, and 7.5% had ≥1 serious infection through 1 year (Table 7). There were no deaths, malignancies, opportunistic infections, or tuberculosis cases observed in the study. The ustekinumab safety profile was consistent with earlier studies in other diseases.

Conclusion

Ustekinumab showed significantly better efficacy in many clinical and laboratory parameters in active SLE compared to placebo and comparable safety at 24 weeks. Ustekinumab also provided sustained clinical benefit in global and organ-specific SLE activity measures through 1 year. De novo increases in response rates across disease activity measures were observed in patients who crossed over from placebo to SC ustekinumab at week 24. The safety profile of ustekinumab was also consistent with other indications. Thus, ustekinumab is a clinically proven safe and clinically proven effective therapy with a novel mechanism of action for the treatment of SLE.

TABLE 5

Efficacy and Safety results at Week 24.

|  | Placebo | Ustekinumab |
|---|---|---|
| Patients randomized, n | 42 | 60 |
| Efficacy | | |
| Proportion with SRI-4 response, n (%) | 14 (33.3%) | 37 (61.7%) |
| P value | | 0.0057 |
| Median change from baseline in SLEDAI-2K | −2.0 | −6.0 |
| P value | | 0.0265[a] |
| Median change from baseline in PGA | −1.6 | −2.5 |
| P value | | 0.2110[a] |
| Proportion with BICLA response | 14 (33.3) | 21 (35.0) |
| P value | | 0.9939 |
| Proportion with no BILAG worsening, n/N (%) | 11/42 (26.2) | 29/60 (48) |
| P value | 0.3 | 0.0281 |
| Proportion with 50% improvement from baseline joint disease activity[b] | 61 | 86 |
| P value | | 0.0100[d] |
| Proportion with 50% improvement from baseline CLASI activity score[c] | 29.9 | 64.1 |
| P value | | 0.0319[d] |
| Mean (SD) change from baseline in anti-dsDNA (kIU/L) | −3.7 (96.8) | −226.6 (686.5) |
| P value | | 0.2482 |
| Complement C3 (mg/dL) | 3.6 (10.7) | 8.3 (15.1) |
| P value | | 0.2749 |

TABLE 5-continued

Efficacy and Safety results at Week 24.

|  | Placebo | Ustekinumab |
|---|---|---|
| Adverse events | | |
| Proportion with ≥1 TEAE, n (%) | 29 (69.0) | 47 (78.3) |
| Most Common TEAEs, n (%) | | |
| Upper respiratory tract infection | 9 (21.4) | 5 (8.3%) |
| Urinary tract infection | 5 (11.9) | 6 (10.0%) |
| Nasopharyngitis | 3 (7.1) | 6 (10.0%) |
| Headache | 5 (11.9) | 4 (6.7%) |
| Proportion with ≥1 SAE, n (%) | 4 (9.5) | 5 (8.3%) |

[a]One-sided test for no difference between two treatment groups based upon a Wilcoxon non-parametric median test for difference of location.
[b]Patient subpopulation (~70% of total population) with at least 4 joints with pain and signs of inflammation at baseline
[c]Patient subpopulation (~60% of total population) with CLASI activity score of at least 4 at baseline
SRI-4, SLE Response Index; SLEDAI 2K, Systemic Lupus Erythematosus Disease Activity Index; PGA, physician's global assessment; BICLA, BILAG-based Combined Lupus Assessment; BILAG, British Isles Lupus Assessment Group; TEAE, treatment emergent adverse event
[d]Proportions of responders and p values based on a modified intention to treat analysis using a multiple imputation model for missing data from weeks 16 to 24

TABLE 6

Efficacy results at 24 weeks and 1 year in patients initially randomized to ustekinumab

|  | Ustekinumab | |
|---|---|---|
|  | Week 24 | Week 48 |
| Randomized patients (mITT) | 60 | 60 |
| SRI-4 response[a], n/randomized (%) | 37/60 (61.7) | 38/60 (63.3) |
| Improvement from baseline in SLEDAI-2K score[b], n/randomized (%) | 39/60 (65.0) | 40/60 (66.7) |
| ≥30% improvement from baseline in PGA, n/evaluable[c] (%) | 38/56 (67.9) | 39/52 (75.0) |
| ≥50% improvement from baseline in the number of joints with pain and signs of inflammation, n/evaluable[c,d] (%) | 32/37 (86.5) | 32/37 (86.5) |
| ≥50% improvement from baseline CLASI activity score, n/evaluable[c,e] (%) | 17/32 (53.1) | 24/35 (68.6) |

[a]SRI-4 response was defined as a ≥4-point reduction in SLEDAI-2K total score, no new BILAG A and no more than 1 new BILAG B domain score, and no worsening (<10% increase) from baseline in the PGA of disease activity score
[b]SLEDAI-2K response defined as ≥4-point improvement from baseline score
[c]Values for patients meeting treatment failure criteria are set to missing from the point of treatment failure forward
[d]Patient subpopulation (67% of total population) with ≥4 joints with pain and signs of inflammation at baseline
[e]Patient subpopulation (60% of total population) with CLASI activity score of ≥4 at baseline
CLASI, Cutaneous Lupus Erythematosus Disease Area and Severity Index; mITT, modified intention-to-treat; PBO, placebo; PGA, Physician Global Assessment; SLEDAI-2K, Systemic Lupus Erythematosus Disease Activity Index 2000; SRI-4, SLE Responder Index-4; UST, ustekinumab

TABLE 7

Safety results at 24 weeks and 1 year

|  | Placebo-controlled through Week 24 | | Exposed to ustekinumab through 1 year | |
|---|---|---|---|---|
|  | PBO | UST | Randomized to UST | All UST (UST + PBO-UST) |
| Treated patients | 42 | 60 | 60 | 93 |
| Patients with ≥1 TEAE | 29 (69.0) | 47 (78.3) | 54 (90.0) | 76 (81.7) |
| Patients with ≥1 SAE | 4 (9.5) | 5 (8.3) | 10 (16.7) | 14 (15.1) |
| Patients with ≥1 infection[a] | 21 (50.0) | 29 (48.3) | 40 (66.7) | 56 (60.2) |

TABLE 7-continued

Safety results at 24 weeks and 1 year

|  | Placebo-controlled through Week 24 | | Exposed to ustekinumab through 1 year | |
|---|---|---|---|---|
|  | PBO | UST | Randomized to UST | All UST (UST + PBO-UST) |
| Patients with ≥1 serious infection[a] | 0 (0) | 2 (3.3) | 6 (10.0) | 7 (7.5) |
| Patients with ≥1 DCAE | 4 (9.5) | 4 (6.7) | 5 (8.3) | 6 (6.5) |

All data are presented as n (%).
[a]Based on infection system organ class
DCAE, adverse event leading to discontinuation; PBO, placebo; PBO-UST, patients who crossed over from PBO to UST at week 24; SAE, serious adverse event; TEAE, treatment-emergent adverse event; UST, ustekinumab

TABLE 8

Comprehensive Summary of Efficacy Results at Week 24.

| | Placebo | Ustekinumab | Difference | P value |
|---|---|---|---|---|
| Patients randomized, n | 42 | 60 | | |
| *Primary Endpoint* | | | | |
| SRI-4 response, n (%) | 14 (33%) | 37 (62%) | 28.4% (9.5 to 47.2) | 0.0057[a] |
| *Major Secondary Endpoints* | | | | |
| Change from baseline in SLEDAI-2K, mean (SD) | −3.8 (5.4) | −4.4 (2.9) | −0.63 (−2.4 to 1.17) | 0.0929[a] |
| Change from baseline in PGA, mean (SD) | −1.9 (2.2) | −2.2 (1.9) | −0.24 (−1.13 to 0.64) | 0.3944[a,b] |
| BICLA response, n (%) | 14 (33%) | 21 (35%) | 1.7% (−17.0 to 20.3) | 0.9939[a,b] |
| *Additional Endpoints* | | | | |
| SRI-5 response, n (%) | 9 (21%) | 26 (43%) | 21.9% (4.3 to 39.5) | 0.0218[a,b] |
| SRI-6 response, n (%) | 8 (19%) | 26 (43%) | 24.3% (7.0 to 41.6) | 0.0122[a,b] |
| *SLEDAI-2K response[c,d]* | | | | |
| Patients, n/N (%) | 15/31 (48%) | 38/53 (72%) | 23.3% (4.4 to 42.2) | |
| Mean response rate, % (95% CI) | 49.1% (48.2 to 50.0) | 76.8% (76.4 to 77.2) | | 0.0071[a,b] |
| *Modified SLEDAI-2K response[c,e]* | | | | |
| Patients, n/N (%) | 18/32 (56%) | 40/56 (71%) | 15.2% (−3.7 to 34.0) | |
| Mean response rate, % (95% CI) | 51.6% (35.4 to 67.4) | 75.0% (61.4 to 85.0) | | 0.0162[b] |
| PGA improvement from baseline ≥30%, n (%) | 18 (43%) | 37 (62%) | 18.8% (−0.6 to 38.2) | 0.0815[b] |
| No worsening in PGA[c] Patients, n/N (%) | 29/32 (91%) | 51/55 (93%) | 2.1% (−8.9 to 13.1) | |
| Mean response rate, % (95% CI) | 88.9% (73.4 to 95.9) | 92.4% (81.4 to 97.1) | | 0.3121[a,b] |
| No worsening in BILAG score, n (%) | 11 (26%) | 29 (48%) | 22.1% (3.8 to 40.5) | 0.0281[a,b] |
| *≥50% improvement from baseline joint disease activity[c,f], % (95% CI)* | | | | |
| Patients, n/N (%) | 14/23 (61%) | 32/37 (86%) | 25.6% (8.5 to 42.7) | |
| Mean response rate, % (95% CI) | 65.5% (44.6 to 81.7) | 90.1% (75.2 to 96.5) | | 0.0100[b] |

TABLE 8-continued

Comprehensive Summary of Efficacy Results at Week 24.

|  | Placebo | Ustekinumab | Difference | P value |
|---|---|---|---|---|
| ≥50% improvement from baseline CLASI activity score[c,g], % (95% CI) | | | | |
| Patients, n/N (%) | 6/17 (35%) | 17/32 (53%) | 17.8% (−1.4 to 37.0) | |
| Mean response rate, % (95% CI) | 29.9% (12.0 to 57.0) | 64.1% (43.0 to 80.9) | | 0.0319[b] |

[a]Prespecified analyses; all other analyses shown here were post-hoc.
[b]Nominal p value; not adjusted for multiplicity.
[c]Proportion of patients with response are reported as observed values at Week 24 and mean response rates using multiple imputation for missing data.
[d]SLEDAI-2K response is the proportion of patients with at least 4-point improvement from baseline SLEDAI score.
[e]Modified SLEDAI-2K response is the proportion of patients with SLEDAI-2K response excluding serologic markers of disease activity (C3, C4, and anti-double-stranded DNA antibodies).
[f]Patient subpopulation (67% of total population) with ≥4 joints with pain and signs of inflammation at baseline.
[g]Patient subpopulation (58% of total population) with CLASI activity score ≥4 at baseline.
BICLA = BILAG-based Combined Lupus Assessment. BILAG = British Isles Lupus Assessment Group. CI = confidence interval. CLASI = Cutaneous Lupus Erythematosus Disease Area and Severity Index. PGA = physician's global assessment. SD = standard deviation. SLEDAI-2K = Systemic Lupus Erythematosus Disease Activity Index 2000. SRI = Systemic Lupus Erythematosus Disease Activity Index 2000 Responder Index.

Example 2: Gene signatures to predict response to STELARA® (Ustekinumab, UST) for patients with lupus.
Background:

Systemic lupus erythematosus (SLE) is a heterogenous disease in presentation and course affecting virtually any organ system. This heterogeneity has posed a significant challenge to successful drug development and one strategy to overcome this problem is to utilize biomarkers to identify patients exhibiting a disease driven by the mechanism of action modulated by a given therapy. Currently, there is some clinical validation for IFN-I and B-cell targeted mechanisms in the treatment of lupus. In both cases, unique baseline biomarkers have been identified to potentially enrich for responders. For example, for sifalimumab (Khamashta et al, 2016) (an anti-IFN alpha human monoclonal antibody) and anifrolumab (Furie et al, 2017) (an anti IFN-I receptor human monoclonal antibody), whole blood monitoring of IFN-I inducible transcript expression indicated that treatment response was enriched in subjects with higher baseline levels of these transcripts and these same transcripts were downmodulated after treatment. In addition, after a failed phase 2 trial with Benlysta® (a.k.a., belimumab, a human monoclonal antibody that inhibits B-cell activating factor), belimumab was approved after successful phase 3 programs that incorporated a novel composite disease instrument based on clinical assessments and biomarker-based changes in inclusion criteria, i.e., ANA titer ≥1:80 and/or a positive anti-dsDNA test at entry (Stohl & Hilbert, 2012). In spite of these successes, the identification of biomarkers and the routine use of biomarkers to enrich for or predict patient subsets more likely to respond to a given treatment remains an unmet medical need for the treatment of SLE.

Herein are disclosed unexpected gene expression signatures associated with a clinical response to UST in patients with active SLE. Within these signatures are transcripts belonging to the interferon pathway (Interferon I inducible genes) and those associated with cytotoxic lymphocytes (cytotoxic cell-associated transcriptional genes). These transcriptional signatures are differentially expressed prior to treatment when comparing clinical responders to non-responders and they can be used to select patients for treatment based on the predicted response to treatment with UST.
Methods and Results:

Methods and results from serum and whole blood transcriptional biomarker data analysis from a phase 2a study (NCT02349061) to examine the efficacy and safety of UST in SLE are described herein.

Unless otherwise indicated, practice of the present invention employs conventional biological methods known by those skilled in the art, e.g., molecular biology methods (including recombinant methods), microbiology methods, cell biology methods, and biochemistry methods. Such biological methods include gene expression profiling by, e.g., determining cellular RNA or protein levels. Non-limiting examples of methods that measure RNA include, e.g., microarray profiling, reverse transcriptase PCR (RT-PCR), e.g., quantitative RT-PCR (RT-qPCR), and serial analysis of gene expression (SAGE). Non-limiting examples of methods of measuring protein expression levels include, e.g., mass spectrometry, two-dimensional gel electrophoresis, antibody microarrays, tissue microarrays, ELISA, immunohistochemistry, proteomics, flow cytometry, and other methods known by those skilled in the art. An advantage of using microarray profiling is that it provides for assaying large numbers of distinct sequences in parallel, including all known coding and non-coding splice variants. Microarray profiling is also compatible with a variety of clinically relevant biological sample types, e.g., skin biopsies, whole blood, and different isolated cell types from blood or tissue. Quantification can be relative or absolute quantification or a combination of both as applied to the normalization process, e.g., as discussed below in more detail. Briefly, relative quantification references expression of a target gene to a control value for expression such as, for example, expression obtained from a control sample or pretreatment sample or expression of a reference gene. Absolute quantification is based upon an internal or external calibration curve (Pfaffl, 2001; Livak & Schmittgen, 2001).

Microarray Analysis

PAXgene RNA tubes were processed for microarray by Biostorage Technologies, Inc. RNA extraction was performed using the QIAsymphony automation platform (QIAGEN GmbH). The RNA quantity and purity was assessed using the Trinean DropSense (Perkin Elmer). The RNA quality was assessed using the Caliper LabChip Gx (Perkin Elmer). RNA samples (100 ng where available) were amplified using the Affymetrix HT WT Plus Reagent kit (Thermo Fisher, cat #902414) according to manufacturer's instructions. cDNA QC was performed using the Caliper LabChipGX and cDNA is used as input in the fragmentation and labeling reaction that is performed using the Affymetrix HT WT Plus module designed specifically for fragmentation and labeling of cDNA for analysis on Affymetrix GeneChip® arrays. Microarray processing was performed using the Hu Gene 2.1 ST array+PM 96-Array Plate (Thermo Fisher, cat #902138) on the Affymetrix Gene Titan MC instrument (Thermo Fisher) that automates array processing from target hybridization to data generation.

The UST transcriptome microarrays (gene chip: Hu Gene 2.1 ST+PM 96-Array Plate) were generated in two batches. The data contained 282 and 95 CEL files respectively. 31 healthy donor samples obtained from the CROs (BioIVT [formally known as Bioreclamation], Westbury, N.Y., and Biological Specialty Corp., Colmar, Pa.) were measured in both batches to enable data bridging. The data was loaded using the "oligo 1.38.0" (Carvalho et al, 2010) and quantile normalized (bringing all samples to identical statistical properties) using the Robust Multichip Average algorithm (RMA) 1.52.0" (Gautier et al, 2004) packages (Affymetrix, Santa Clara, Calif.). The quantile normalized data has been used as the starting dataset to perform all the analysis. The batch effects were reduced employing LOESS as local non-parametric regression model (Cleveland et al, 1993). The batch effect reduction was achieved by establishing for each gene a batch model using the bridging samples to predict the new corrected expression value. Visual inspection using PCA confirmed reduction of the batch effect.

Determination of Dynamic Genes

A random simulation was implemented to determine genes that exhibited consistent expression differences between distinct groups of lupus patients dosed with UST. That approach was chosen due to the small sample size while having tested a large number of probe sets.

For every probe set measured:
1. 75% of the samples were randomly selected
2. The samples were split into high and low expression groups
3. The difference between the two high and low groups was assessed using a t-test
4. The process was repeated 1000 times, to define the frequency of each probe
5. Probes that had a nominal statistical difference (P<0.05) in more than 60% of the repeats and had a nominal difference between UST responders and non-responders (P<0.05; not adjusted) were retained The initial analysis resulted in the identification of 58 genes (Table 9) that were identified with different probe sets (Appendix 2). Those genes are referred to as dynamic genes because they consistently showed differential expression between distinct groups of lupus patients treated with UST. The group of 58 dynamic genes includes genes from the IFN-I inducible gene cluster, the cytotoxic cell-associated transcriptional gene cluster, and some genes from an assortment of other gene clusters. The expression of those 58 dynamic genes in three different lupus cohorts of distinct ethnic backgrounds for which expression data using RNA sequencing was generated, were examined. Of the 58 dynamic genes identified, 31 of the genes were expressed in all the examined datasets. The 31-gene signature only includes genes from the IFN-I inducible gene cluster and the cytotoxic cell-associated transcriptional gene cluster.

As used herein, the terms "differential expression," "differentially expressed," and their synonyms, which are used interchangeably, refer to a gene whose expression level is higher or lower in a patient suffering from a disease, e.g., active systemic lupus erythematosus (SLE). It is also understood that a differentially expressed gene may be expressed at either a higher or lower level at the nucleic acid level (e.g., RNA transcripts) or at the protein level.

TABLE 9

Dynamic Genes

| Probe ID | Gene Symbol | Gene Name | Accession No. | Gene Cluster |
| --- | --- | --- | --- | --- |
| 16870200 | BST2 | bone marrow stromal cell antigen 2 | NM_004335 | IFN-I inducible |
| 16743922 | CARD17 | caspase recruitment domain family member 17 | NM_001007232 | IFN-I inducible |
| 16894127 | CMPK2 | cytidine/uridine monophosphate kinase 2 | NM_207315 | IFN-I inducible |
| 17093090 | DDX58 | DExD/H-box helicase 58 | NM_014314 | IFN-I inducible |
| 16981219 | DDX60 | DExD/H-box helicase 60 | NM_017631 | IFN-I inducible |
| 16844999 | DHX58 | DExH-box helicase 58 | NM_024119 | IFN-I inducible |
| 16896442 | EIF2AK2 | eukaryotic translation initiation factor 2 alpha kinase 2 | NM_002759 | IFN-I inducible |
| 16778559 | EPSTI1 | epithelial stromal interaction 1 | NM_001002264 | IFN-I inducible |
| 16830214 | FBXO39 | F-box protein 39 | NM_153230 | IFN-I inducible |
| 16968765 | HERC5 | HECT and RLD domain containing E3 ubiquitin protein ligase 5 | NM_016323 | IFN-I inducible |

TABLE 9-continued

| Dynamic Genes | | | | |
|---|---|---|---|---|
| Probe ID | Gene Symbol | Gene Name | Accession No. | Gene Cluster |
| 16968735 | HERC6 | HECT and RLD domain containing E3 ubiquitin protein ligase family member 6 | NM_017912 | IFN-I inducible |
| 16707196 | IFIT1 | interferon induced protein with tetratricopeptide repeats 1 | NM_001548 | IFN-I inducible |
| 16707180 | IFIT2 | interferon induced protein with tetratricopeptide repeats 2 | NM_001547 | IFN-I inducible |
| 16707184 | IFIT3 | interferon induced protein with tetratricopeptide repeats 3 | NM_001549 | IFN-I inducible |
| 16733995 | IRF7 | interferon regulatory factor 7 | NM_001572 | IFN-I inducible |
| 16965313 | LAP3 | leucine aminopeptidase 3 | NM_015907 | IFN-I inducible |
| 17082012 | LOC100133669 | LY6E divergent transcript (LY6E-DT), long non-coding RNA | NR_026913 | IFN-I inducible |
| 16757347 | OAS3 | 2'-5'-oligoadenylate synthetase 3 | NM_006187 | IFN-I inducible |
| 16771417 | OASL | 2'-5'-oligoadenylate synthetase like | NM_003733 | IFN-I inducible |
| 16895530 | OTOF | otoferlin | NM_194248 | IFN-I inducible |
| 16960186 | PLSCR1 | phospholipid scramblase 1 | NM_021105 | IFN-I inducible |
| 16876764 | RSAD2 | radical S-adenosyl methionine domain containing 2 | NM_080657 | IFN-I inducible |
| 16949442 | RTP4 | receptor transporter protein 4 | NM_022147 | IFN-I inducible |
| 17059776 | SAMD9L | sterile alpha motif domain containing 9 like | NM_152703 | IFN-I inducible |
| 16916802 | SIGLEC1 | sialic acid binding Ig like lectin 1 | NM_023068 | IFN-I inducible |
| 16889218 | SPATS2L | spermatogenesis associated serine rich 2 like | NM_015535 | IFN-I inducible |
| 16738536 | TIMM10 | translocase of inner mitochondrial membrane 10 | NM_012456 | IFN-I inducible |
| 16926942 | USP18 | ubiquitin specific peptidase 18 | NM_017414 | IFN-I inducible |
| 16920651 | ZBP1 | Z-DNA binding protein 1 | NM_030776 | IFN-I inducible |
| 16672462 | FCRL6 | Fc receptor like 6 | NM_001004310 | Cytotoxic cell |
| 16974529 | FGFBP2 | fibroblast growth factor binding protein 2 | NM_031950 | Cytotoxic cell |
| 16882332 | GNLY | granulysin | NM_001302758 | Cytotoxic cell |
| 16819539 | GPR56 (ADGRG1) | adhesion G protein-coupled receptor G1 | NM_005682 | Cytotoxic cell |
| 16791436 | GZMH | granzyme H | NM_033423 | Cytotoxic cell |
| 16984783 | GZMK | granzyme K | NM_002104 | Cytotoxic cell |
| 16657594 | ISG15 | ISG15 ubiquitin-like modifier | NM_005101 | IFN-I inducible |
| 16761350 | KLRC3 | killer cell lectin like receptor C3 | NM_002261 | Cytotoxic cell |
| 16748327 | KLRD1 | killer cell lectin like receptor D1 | NM_002262 | Cytotoxic cell |
| 16748095 | KLRG1 | killer cell lectin like receptor G1 | NM_001329099 | Cytotoxic cell |

TABLE 9-continued

Dynamic Genes

| Probe ID | Gene Symbol | Gene Name | Accession No. | Gene Cluster |
|---|---|---|---|---|
| 16772285 | LOC387895 | Homo sapiens cDNA clone IMAGE: 6160413 | BC040060 | Cytotoxic cell |
| 17077826 | MYBL1 | MYB proto-oncogene like 1 | NM_001080416 | Cytotoxic cell |
| 16874828 | NKG7 | natural killer cell granule protein 7 | NM_005601 | Cytotoxic cell |
| 16715170 | PRF1 | perforin 1 | NM_005041 | Cytotoxic cell |
| 17056823 | TARP | TCR gamma alternate reading frame protein | NM_001003799 | Cytotoxic cell |
| 17056807 | TRGC2 | T cell receptor gamma constant 2 | BC039116 | Cytotoxic cell |
| 17056853 | TRGV2 | T cell receptor gamma variable 2 | ENST00000426402 | Cytotoxic cell |
| 16799289 | C15orf54 | chromosome 15 open reading frame 54 | NR_144507 | Others |
| 16668333 | GSTM4 | glutathione S-transferase mu 4 | NM_000850 | Cytotoxic cell |
| 16797490 | IGHV3-20 | immunoglobulin heavy variable 3-20 | ENST00000390606 | Others |
| 16900152 | IGKV1-27 | immunoglobulin kappa variable 1-27 | ENST00000498435 | Others |
| 16900144 | IGKV6-21 | immunoglobulin kappa variable 6-21 (non-functional) | ENST00000390256 | Others |
| 16927801 | IGLV3-21 | immunoglobulin lambda variable 3-21 | ENST00000390308 | Others |
| 16997041 | LOC647859 | occludin pseudogene (LOC647859), non-coding RNA | NR_026578 | Others |
| 17025697 | MIR3939 | microRNA 3939 | NR_037504 | Others |
| 16942367 | RN5S134 | RNA, 5S ribosomal pseudogene 134 | ENST00000516492 | Others |
| 16722960 | RN5S338 | RNA, 5S ribosomal pseudogene 338 | ENST00000410495 | Others |
| 17063828 | TRBV7-3 | T cell receptor beta variable 7-3 | ENST00000390361 | Others |
| 16742150 | XRRA1 | X-ray radiation resistance associated 1 | NM_182969 | Cytotoxic cell |

*Note:
The 58 genes are listed in alphabetical order for each gene cluster: the IFN-I inducible gene cluster (IFN-I inducible), the cytotoxic cell-associated transcriptional gene cluster (Cytotoxic cell), and other gene clusters (Others). For genes with multiple reference transcript variants, only the accession number for reference transcript variant 1 is included in the table.

Clustering & Enrichment Analysis

A co-expression network of the 58 genes based on Pearson correlations computed using the "cor" function of R was constructed (available online at, www.r-project.org). The network was clustered into four clusters using the Ward's algorithm implemented in "hclust" function of R (available online at, www.r-project.org). Gene ontology biological process (GOBP) and Reactome pathway enrichment analysis of the identified clusters was computed using "clusterProfiler 3.2.4" (Yu et al, 2012) package from Bioconductor (Huber et al, 2015).

Prediction Model

Due to the high correlation between the dynamic genes, different groupings of the genes were examined to determine if they could be used to predict response to UST: one that used all 58 dynamic genes (58-genes) identified during the initial analysis (Table 9); one that used a subset of the dynamic genes that included all of the genes from the IFN-I inducible gene cluster and all of the genes from the cytotoxic cell-associated transcriptional gene cluster (48-genes); one that used a subset of the dynamic genes that included the 31 genes expressed in all examined different lupus cohorts (31-genes); and one that used a smaller subset of the 31-genes (8-genes) that were identified by random forest feature selection method (random Forest 4.6-12" package in R) (Liaw & Wiener, 2002).

The 48-gene subset of dynamic genes includes the IFN-I inducible gene cluster component comprising: BST2, CARD17, CMPK2, DDX58, DDX60, DHX58, EIF2AK2, EPSTI1, FBXO39, HERC5, HERC6, IFIT1, IFIT2, IFIT3, IRF7, LAP3, LOC100133669, OAS3, OASL, OTOF, PLSCR1, RSAD2, RTP4, SAMD9L, SIGLEC1, SPATS2L, TIMM10, USP18, ZBP1, ISG15, and the cytotoxic cell-associated transcriptional component comprising: FCRL6, FGFBP2, GNLY, GPR56 (ADGRG1), GZMH, GZMK, XRAA1, GSTM4, KLRC3, KLRD1, KLRG1, LOC387895, MYBL1, NKG7, PRF1, TARP, TRGC2, TRGV2.

The 31-gene subset of dynamic genes includes the IFN-I inducible gene cluster component: BST2, CMPK2, DDX58, DDX60, DHX58, EIF2AK2, EPSTI1, HERC5, IFIT1, IFIT2, IFIT3, IRF7, ISG15, LAP3, OAS3, OASL, PLSCR1, RSAD2, RTP4, SAMD9L, SIGLEC1, TIMM10, USP18 and ZBP1; and the cytotoxic cell-associated transcriptional component: FCRL6, FGFBP2, GNLY, GZMH, GZMK, NKG7 and PRF1.

The 8-gene subset of dynamic genes includes the IFN-I inducible gene cluster component: IFIT3, RSAD2 and the cytotoxic cell-associated transcriptional component: FCRL6, FGFBP2, GNLY, GZMH, NKG7, PRF1.

To avoid any overfitting, feature selection was run 1000 times. Only genes which were identified in >50% of the testing cycles were retained. Using this process, 8 genes were identified. To evaluate the predictability of response using those gene sets (58, 46, 31 and 8 genes), we assessed 1000 different generalized linear models using different sample permutations of the training set and testing sets (before any model learning, the samples were split at a 75 to 25% ratio to provide for a training and testing set). Distributions of prediction performance were reported. Finally, one model for each gene set was generated using random split of training set and testing set (75% and 25%). Machine learning, and performance evaluations were conducted using the "caret 6.0-78" package (available online at, topepo.github.io/caret/index.html).

The logistic regression model optimized the following objective function, $$\min_{\beta o,\beta} -\left[\frac{1}{N}\sum_{i=1}^{N} y_i(\beta o + \beta^T x_i) - \log(1 + e^{(\beta o+\beta^T x_i)})\right] + \lambda\left[\frac{(1-\alpha)}{2}\|\beta\|_2^2 + \alpha\|\beta\|_1\right]$$

Where,
1. N is the number of patients used to learn the model.
2. The $x_i$ a vector of the centered gene expression data (subtracted mean of lupus patients) of patient i.
3. The $y_i$ is the response outcome for patient i (responder/non-responder).
4. The $\lambda$ controls the total penalty weight.
5. The $\alpha$ controls the elastic-net penalty weight: form lasso ($\alpha=1$) to ridge ($\alpha=0$).
6. The $\alpha$, $\lambda$ are optimized using grid search based on best training accuracy.

Once $\beta o$, $\beta$ parameters are determined, response probability is computed as, $$P(x_{new}) = \frac{1}{1 + e^{-(\beta o + \beta^T x_{new})}}$$

and response prediction is determined as $$\text{Response}(x_{new}) = \begin{cases} \text{responder,} & \text{if } P(x) \geq \text{threshlod} \\ \text{non-responder,} & \text{else} \end{cases}.$$

threshold is 0.5.

Prediction Analysis

Prediction analysis using the different groups of genes showed that differential expression of the IFN-1 inducible genes and the cytotoxic cell-associated transcriptional genes could be used to predict the response to treatment with UST. The 46-gene, 31-gene and 8-gene signatures were shown to have a positive predictive value of: 0.746 95% IC [0.740, 0.751], 0.726 95% IC [0.720,0.732] and 0.755 95% IC [0.749,0.761], respectively. The negative predictive values for the 46-gene, 31-gene and 8-gene signatures were: 0.67 95% IC [0.661,0.688], 0.659 95% IC [0.645,0.673] and 0.715 95% IC [0.702,0.728], respectively.

2—Gene Prediction Model

In addition, the possibility of using only two genes to predict response was also explored, e.g., one gene from the IFN-I inducible gene cluster and one gene from the cytotoxic-cell associated transcriptional gene cluster. Fifty dynamic gene pairs (one gene from each of the IFN-I inducible gene cluster and the cytotoxic cell-associated transcriptional gene cluster) were randomly selected to generate 100 prediction models for each 2-gene pair. The 2-gene models had a mean positive predictive value (PPV) of 0.735 95% IC [0.733, 0.738] and negative predictive value (NPV) of 0.678 95% IC [0.671, 0.684] and the average mean accuracy of the models was 70.71% (95% CIs [70.41, 71.01]). Thus, it was concluded that combinations of one or more genes from the IFN-I inducible gene cluster and one or more genes from the cytotoxic-cell associated transcriptional gene cluster have predictive power to predict response.

TABLE 10

Prediction testing with 2-gene combinations

|  | Accuracy | Sensitivity | Specificity | PPV | NPV | AUC | Source |
|---|---|---|---|---|---|---|---|
| Mean1 | 0.7071538 | 0.8352750 | 0.5021600 | 0.7359871 | 0.6782053 | 0.7007335 | Testing |
| CI95lo1 | 0.7041555 | 0.8316300 | 0.4962238 | 0.7334166 | 0.6718727 | 0.6983119 | Testing |
| CI95Hi1 | 0.7101522 | 0.8389200 | 0.5080962 | 0.7385575 | 0.6845379 | 0.7031551 | Testing |

PPV: Positive Predictive Value

NPV: Negative Predictive Value

AUC: Area Under Curve

Simplified Prediction Model

Figure 9:
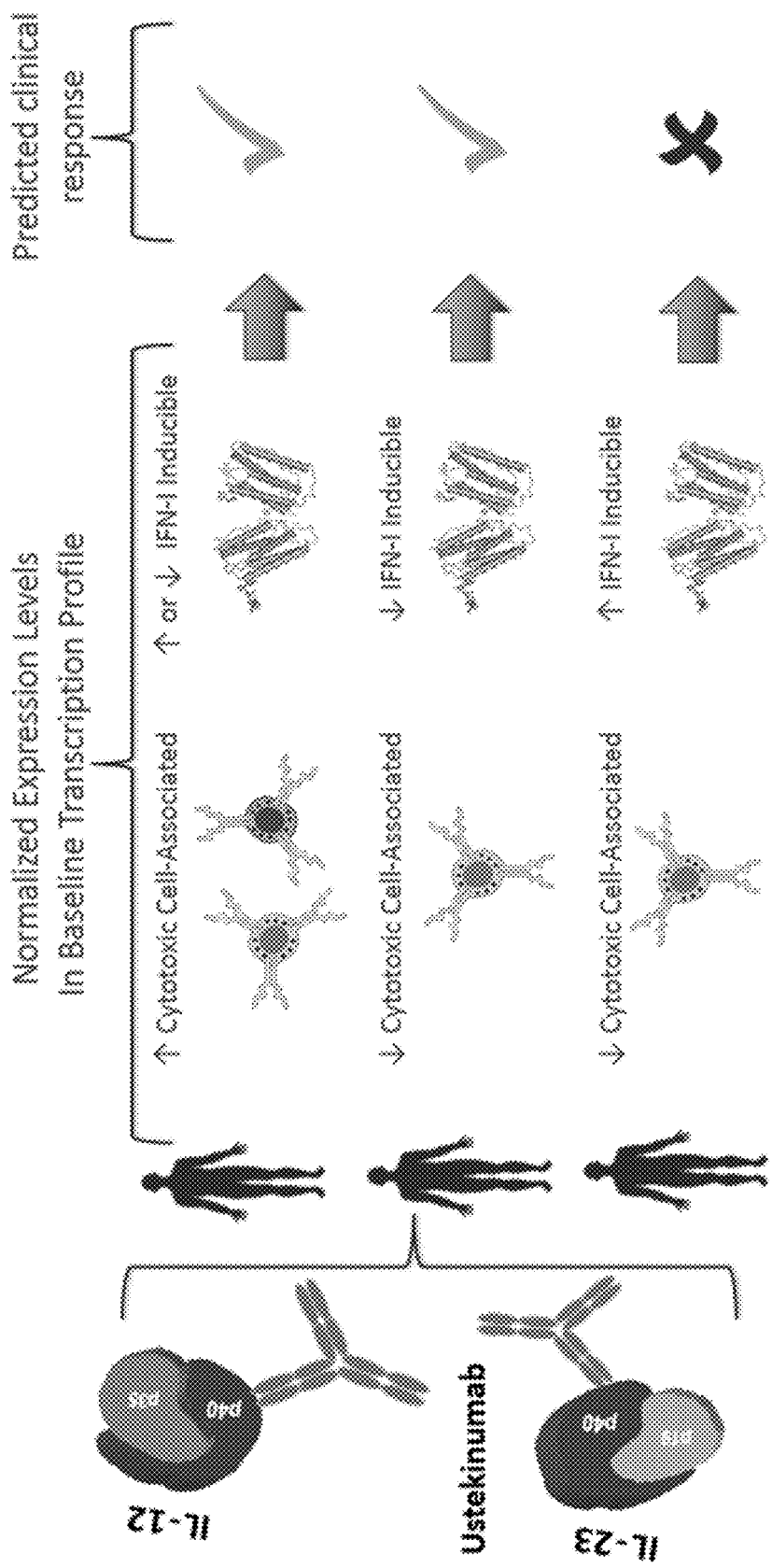
FIG. 9 shows an illustration of the baseline (prior to treatment) whole blood transcription profile and the predicted clinical response for treatment with ustekinumab based on the expression levels of one or more cytotoxic cell-associated transcriptional genes and one or more Interferon I (IFN-I) inducible genes. An up arrow (↑) indicates higher expression levels, a down arrow (↓) indicates lower expression levels, a check mark (✓) indicates a predicted positive clinical response, and X indicates a predicted clinical non-response.

In addition to the prediction model explained above, a simplified model was also generated using scaled expression data. Scaled expression is computed by subtracting the sample mean of the gene expression level in lupus patients and dividing by the standard deviation. After this procedure, the mean expression level of each gene is set to zero and a gene is defined as having "higher expression" in a patient if its value is above 0 and "lower expression" in a patient if its value is below 0. That concept was extended to the entire cluster by calculating the mean of all the genes in the cytotoxic cell-associated transcriptional gene cluster, and the mean of all the genes in the Interferon I (IFN-I) inducible gene cluster. A cluster is defined as having "higher expression" (↑) if the mean is above zero and "lower expression" (↓) if the mean is below zero. This simplified model can be described as shown in Table 11 and FIG. 9.

TABLE 11

Simplified Prediction Model

| Gene Clusters | | |
|---|---|---|
| Cytotoxic cell-associated transcriptional | IFN-I inducible | Predicted Outcome |
| mean genes > 0 (↑) | mean genes < 0 (↓) | Responder |
| mean genes > 0 (↑) | mean genes > 0 (↑) | Responder |
| mean genes < 0 (↓) | mean genes < 0 (↓) | Responder |
| mean genes < 0 (↓) | mean genes > 0 (↑) | Non-Responder |

As used herein, the terms "predict," "prediction," "predicting," or "predicted" refer to the likelihood that a patient will respond either favorably or unfavorably to a drug or set of drugs, e.g., have a positive response (responder) or be a non-responder, e.g., a positive response is a significant improvement in disease activity as determined by a decrease from baseline in the Systemic Lupus Erythematosus Disease Activity Index 2000 (SLEDAI-2K) score of ≥4 (SRI-4 response) at 24 weeks of treatment with the anti-IL-12/IL-23p40 antibody (ustekinumab, UST). The predictive methods of the present invention can be used clinically to make treatment decisions by selecting patients for treatment and/or by choosing the most appropriate treatment modalities for any particular patient, e.g., treatment comprising administering an anti-IL-12/IL-23p40 antibody and/or treatment comprising administering an anti-IL-12/IL-23p40 antibody and an IFN-I inhibitor.

As used herein, a "positive response" to treatment with UST relates to a significant improvement in disease activity as determined by a decrease from baseline in the Systemic Lupus Erythematosus Disease Activity Index 2000 (SLE-DAI-2K) score of ≥4 (SRI-4 response) at 24 weeks of treatment. Other indications of a positive response to treatment with UST include, e.g., a statistically significant reduction in the risk of a new British Isles Lupus Assessment Group (BILAG) flare, defined as ≥1 new BILAG A domain score or ≥2 new BILAG B domain score, by week 24 of treatment with the antibody; a statistically significant increase in the proportion of patients with a 50% improvement from baseline in Cutaneous Lupus Erythematosus Disease Area and Severity Index (CLASI) score; and a statistically significant improvement in disease activity as determined by a 50% improvement from baseline joint disease activity by week 24 of treatment.

Examination of Additional Lupus Cohorts for the Presence of UST Response Signature To determine if the UST response signature is also present in other SLE cohorts, cluster analysis was performed in three different lupus cohorts each enriched for a different racial and ethnic background. Cluster analysis was performed in R using the gene predictive signature from UST data.

Gene Set Variation Analysis

An interferon and cytotoxic signature enrichment scores (ES) were computed for each patient using Gene Set Variation Analysis (GSVA) (Hänzelmann et al, 2013) to be able to track the variation of these signatures over weeks of treatment. Kolmogorov-Smirnov statistics was applied to test if the distribution of gene ranks of the tested gene set (ranking by p-values of association with the phenotype) differed from a uniform distribution (Hänzelmann et al, 2013; Subramanian et al, 2005).

Cross Over Analysis

Expression analysis was extended to placebo patients who crossed over to SC ustekinumab (UST) at week 24. For this population of patients, the positive predictive value (PPV) for the 31-gene signature was 0.645 95% CI [0.645,0.650] and the PPV for the 8-gene signature was 0.649 [0.647, 0.651] for the response to treatment with UST at 48 weeks. The negative predictive values (NPV) were determined to be 0.607 95% CI [0.599,0.615] for the 31-gene signature and 0.626 [0.619, 0.633] for the 8-gene signature.

UST Response Prediction Models Using qPCR, Serum Protein, and Flow Cytometry

An independent analysis of baseline whole blood gene expression was performed using a 103 leukocyte-lineage qPCR array card. From this analysis, 13 genes were identified with significant (P<0.05) baseline expression level differences between responders and non-responders (SRI-4 at 24 weeks) in the UST treatment group (Table 12).

The goal for prediction of response was to identify prediction models for Wk24 SRI-4 response, with: PPV >prevalence of response for UST treatment group; PPV <prevalence of response for placebo treatment group; and at least moderately high sensitivity for UST treatment group. Prediction modeling was performed using logistic regression modeling (GLMnet package) with LOOCV (CARET package) for selection of model coefficients, selecting probability cut-points to fulfil the criteria below (Candia and Tsang, 2019).

TABLE 12

Week 24 SRI4-response associated genes from OpenArray qPCR

| | Group(s) | | | | | |
|---|---|---|---|---|---|---|
| | SLE, Healthy | | SLE: UST, baseline Comparison | | SLE: Placebo, baseline | |
| | Week 0 SLE vs. Healthy | | SRI4 (TF) Wk24: Y vs. N | | SRI4 (TF) Wk24: Y vs. N | |
| Gene* | Fold | P-Value | Fold | P-Value | Fold | P-Value |
| BCL6 | −1.37 | 0.0068 | −1.29 | 0.0122 | −1.53 | 0.1405 |
| CXCR3 | −1.30 | 0.094 | 1.42 | 0.0449 | −1.69 | 0.1035 |
| GZMA | −1.48 | 0.0093 | 1.55 | 0.0253 | −1.14 | 0.63 |
| HLX | −1.13 | 0.2797 | −1.34 | 0.0176 | −1.63 | 0.0681 |
| IFIT3 | 6.79 | <10$^{-4}$ | −1.95 | 0.03 | −2.11 | 0.0262 |
| IFITM3 | 4.04 | <10$^{-4}$ | −1.90 | 0.0106 | −2.00 | 0.0295 |
| KLRD1 | −1.09 | 0.6184 | 1.70 | 0.0151 | −1.56 | 0.148 |
| MX2 | 1.96 | <10$^{-4}$ | −1.39 | 0.0357 | −2.00 | 0.0035 |
| PLSCR1 | 2.87 | <10$^{-4}$ | −1.56 | 0.0221 | −2.06 | 0.015 |

TABLE 12-continued

Week 24 SRI4-response associated genes from OpenArray qPCR

| Gene* | Group(s) | | | | | |
|---|---|---|---|---|---|---|
| | SLE, Healthy | | SLE: UST, baseline Comparison | | SLE: Placebo, baseline | |
| | Week 0 SLE vs. Healthy | | SRI4 (TF) Wk24: Y vs. N | | SRI4 (TF) Wk24: Y vs. N | |
| | Fold | P-Value | Fold | P-Value | Fold | P-Value |
| SPATS2L | 5.84 | <10$^{-4}$ | −2.09 | 0.0252 | −2.37 | 0.0069 |
| TLR5 | 1.41 | 0.0029 | −1.32 | 0.0067 | −1.75 | 0.0525 |
| TNFSF10 | 1.58 | 0.0002 | −1.39 | 0.0288 | −1.73 | 0.0557 |
| USP18 | 10.02 | <10$^{-4}$ | −2.19 | 0.0483 | −2.74 | 0.0112 |

*Genes with p < 0.05 for SRI4 (TF) Wk24: Y vs. N for ustekinumab treatment group.

From these 13 genes, three cytotoxic cell-associated genes (CXCR3, GZMA, KLRD1) were further analyzed due to the greater expression differential between responders versus non-responders in the UST treatment group in comparison to the placebo group indicating that they may exhibit UST response predictive capacity. Correlations between expression levels of CXCR3, GZMA, and KLRD1 ranged from 0.60-0.76 (Pearson's correlation coefficient, R). Since expression of (KLRD1, CXCR3 and GZMA) were well correlated, baseline expression of the cytotoxic cell-associated transcript (KLRD1) was selected for additional modeling strategies to test suitability for prediction of UST response.

Multivariate Prediction Models with qPCR, Serum Protein, and Flow Cytometry

Multivariate models combining KLRD1, a measure of Natural Killer cell (NK cell)/cytotoxic phenotype, and serum IFN-alpha levels were developed, using a training set of 39 patients to build the model (selected as those that had NK cell data available from flow cytometry analyses) and a small test set of 15 subjects to independently evaluate the model performance (those that did not have NK cell data available).

The KLRD1+serum IFN-alpha model exhibited a performance of AUC-ROC=83% and PPV=81% for ustekinumab treatment in the training set. The model applied to the placebo treatment group had no predictive power (AUC-ROC=0.51, PPV=31%, compared to prevalence of 30%) (Table 13). The difference in response rates for UST vs. placebo treatment groups would improve if applying the model for patient selection (81%-31%=50%) compared to no patient selection (59%-30%=29%), with 64% of patients included in the selected population. Application in the small test set of patients had lower performance, with PPV of 67% for ustekinumab group and 40% for placebo treatment group, for a treatment effect difference of 37%.

Alternative measurements representing IFN-alpha activity and NK cell lineage markers were also evaluated to obtain a prediction model. Only subjects with baseline % NK cell data values (flow cytometry) were included in the training set for model development (UST, n=39; placebo, N=27). Compared to the original serum IFN-alpha+KLRD1 (qPCR) model (AUC=0.83 for training set), the model of serum IFN-alpha+% NK cells in whole blood (flow cytometry analysis platform, replacing KLRD1 qPCR) had only slightly numerically lower AUC=0.79 (Table 13).

An additional model was executed based solely on qPCR, using KLRD1 to represent the cytotoxic cell-associated cluster and 4 IFN-inducible transcripts (IFN-4-gene score, defined as median −ddCRT for IFI27+IFI44+IFI44L+RSAD2 genes) replacing serum IFN-alpha as predictor. This KLRD1+IFN-4-gene score model had a performance characteristic of AUC-ROC=0.83 and a favorable balance of PPV (84%) and NPV (80%) (Table 13). The model applied to the placebo group did not have predictive power (AUC-ROC=0.49), with the PPV (40%) (Table 13). The test set (n=15) model statistics, after applying the ustekinumab training model, were consistent with the ustekinumab training set model, with a similar PPV of 80% but a reduced NPV of 67% (Table 13). The placebo test set had no positive predictive power, with the PPV of 25% below the prevalence of response (Table 13). Applying the training model to the full ustekinumab dataset (n=54), the PPV was 81%, compared to a PPV of 33% for the full placebo dataset (n=35) (Table 13). Therefore, the prediction model provides for a treatment effect of 48% compared to 30% without the model, with 61% of patients testing positive for the prediction model.

TABLE 13

Multivariate models from IFN and KLRD1/NK cell predictors

| Endpoint: Wk24 SRI4 | Prob. | AUC | Prev. | Pass | Spec. | Sens. | PPV | NPV |
|---|---|---|---|---|---|---|---|---|
| Ustekinumab | | | | | | | | |
| serum IFNa + KLRD1 (qPCR), TRAIN | 50% | 83.2 | 59% | 64% | 69 | 87 | 81 | 79 |
| serum IFNa + KLRD1 (qPCR), TEST* | 50% | 64.6 | 57% | 43% | 67 | 50 | 67 | 50 |
| serum IFN-alpha + % NK, TRAIN | 50% | 79.3 | 59% | 56% | 50 | 74 | 78 | 65 |
| IFN-4-gene-score + KLDR1, TRAIN | 50% | 83.4 | 59% | 62% | 75 | 87 | 84 | 80 |
| IFN-4-gene-score + KLDR1, TEST* | 50% | 59.3 | 60% | 60% | 67 | 78 | 80 | 67 |
| IFN-4-gene-score + KLDR1, TRAIN + TEST* | 50% | 76.7 | 59% | 61% | 73 | 84 | 81 | 76 |
| Placebo (Ustekinumab model*) | | | | | | | | |
| serum IFNa + KLRD1 (qPCR), TRAIN | 50% | 50.7 | 30% | 59% | 42 | 63 | 31 | 73 |
| serum IFNa + KLRD1 (qPCR), TEST* | 50% | 66.7 | 25% | 38% | 50 | 100 | 40 | 100 |
| serum IFN-alpha + % NK, TRAIN | 50% | 56.6 | 30% | 74% | 21 | 63 | 26 | 60 |
| IFN-4-gene-score + KLDR1, TRAIN | 50% | 49.3 | 30% | 63% | 68 | 50 | 40 | 78 |

TABLE 13-continued

Multivariate models from IFN and KLRD1/NK cell predictors

| Endpoint: Wk24 SRI4 | Prob. | AUC | Prev. | Pass | Spec. | Sens. | PPV | NPV |
|---|---|---|---|---|---|---|---|---|
| IFN-4-gene-score + KLDR1, TEST* | 50% | 41.7 | 25% | 50% | 50 | 50 | 25 | 75 |
| IFN-4-gene-score + KLDR1, TRAIN + TEST* | 50% | 50.8 | 29% | 60% | 64 | 50 | 33 | 75 |

*The ustekinumab training model was applied to the test set and to the placebo group, i.e., models were not built based on test set or placebo treatment group data.

Summary for Prediction Models with qPCR, Serum Protein, and Flow Cytometry

Multiple biomarker data types were assessed for discovery of predictors of response to ustekinumab, including serum proteins, whole blood gene expression, and peripheral blood flow cytometry. Simple models, built by standard logistic regression modeling with cross-validation in a training set (n=39), with confirmation in a test set (n=15) for ustekinumab treatment group were evaluated.

A model of the cytotoxic cell-associated transcript KLRD1+4 IFN-inducible genes ((IFI27, IFI44, IFI44L, RSAD2) all from qPCR evaluation of whole blood gene expression) for the ustekinumab group had: 84% PPV/80% NPV for the training set, 80% PPV/67% NPV for the test set, and 81% PPV/76% NPV for the full dataset (training+test sets).

Serum IFN-alpha levels were highly correlated with IFN-signature gene expression (Rsp=0.83) and % NK cells by flow cytometry were modestly correlated with KLRD1 gene expression levels ($Rs_p$=0.36). Prediction models interchanging serum IFN-alpha with 4 IFN-inducible genes (IF127, IFI44, IFI44L, RSAD2) and % NK cells with KLRD1 expression performed similarly. These observations boost confidence in results from the limited numbers of subjects when alternative methods give similar results.

Cytotoxic Cell-Associated Signature

In addition to the models shown above based on combined cytotoxic cell-associated and IFN-I inducible signatures, tests were also run for models based only on the cytotoxic cell-associated signature (7 genes) or the IFN-I inducible gene signature (24 genes) selected from the 31-gene subset of dynamic genes. The positive predictive value (PPV) was 0.710 95% IC [0.706,0.715] for the cytotoxic cell-associated signature and the PPV was 0.662 95% IC [0.658,0.667] for the IFN-I inducible gene signature. The negative predictive values (NPV) were 0.591 95% IC [0.575,0.607] for the cytotoxic cell-associated signature and 0.488 95% IC [0.470,0.505] for the IFN-I inducible gene signature.

Figure 10:
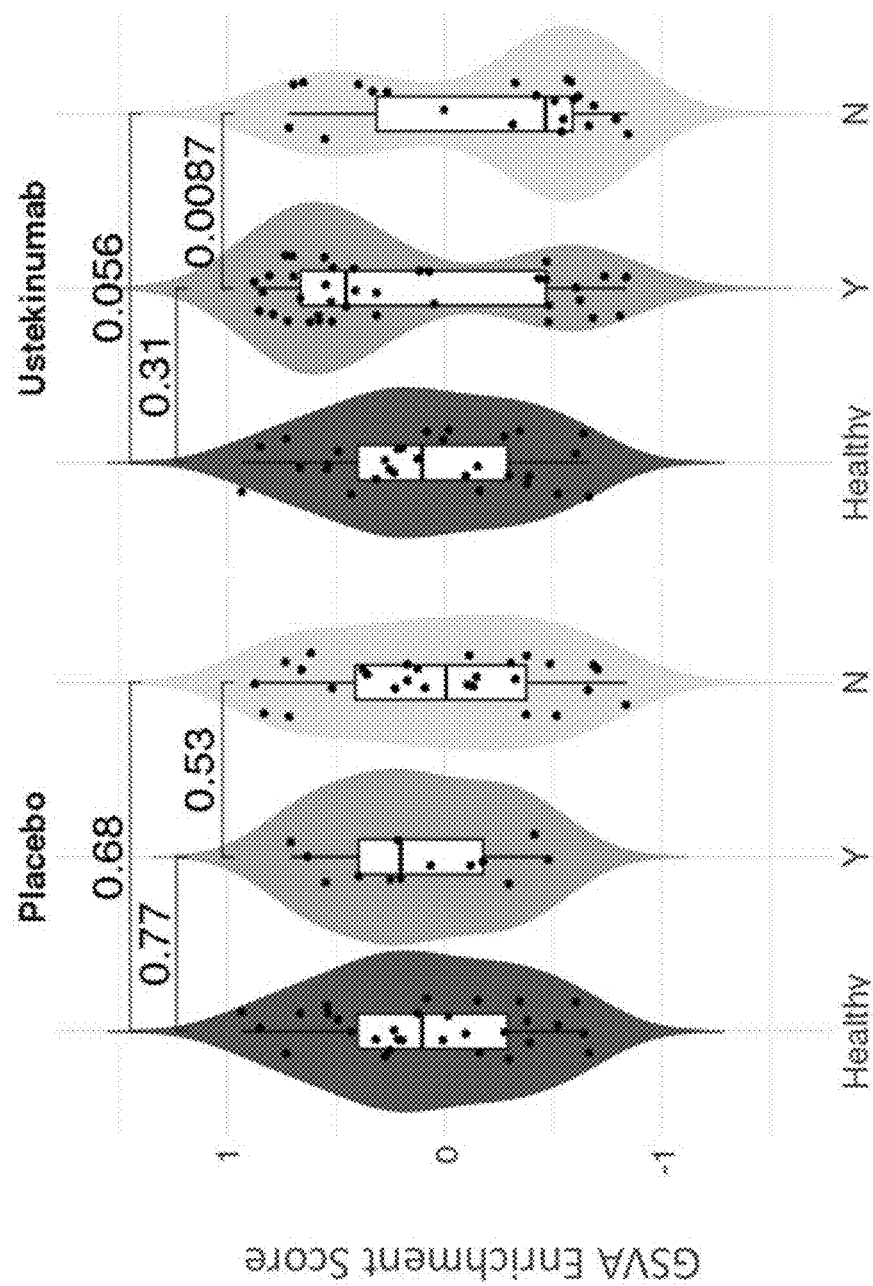
FIG. 10 shows GSVA ES indicating the distribution and median baseline blood expression levels in healthy controls (Healthy), and in responders (Y) and non-responders (N) to treatment with placebo or ustekinumab for a subset of cytotoxic cell-associated genes (PRF1, KLRD1, GZMH, NKG7, GNLY, FGFBP2, TRGC2, TARP, TRGV2). Responders and non-responders were determined after 24 weeks of treatment. P-values from a Student's T-test are indicated for the comparisons illustrated. In this plot the bar indicates median, box represents interquartile range, whiskers show 1.5 IQR, and width indicates density of distribution.
Figure 11:
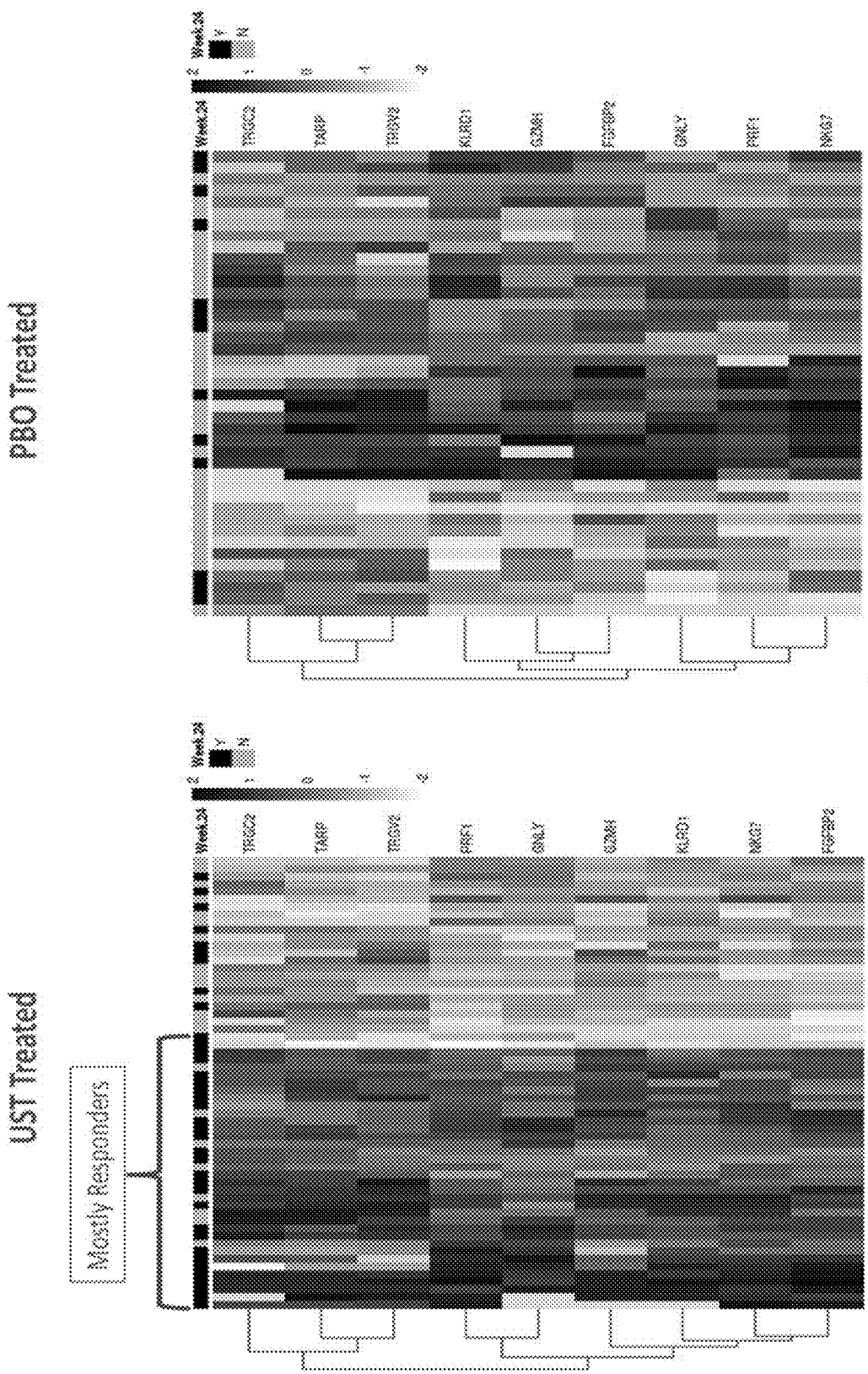
FIG. 11 shows a hierarchical clustering heat map of expression analysis for responders (Y) and non-responders (N) after placebo or ustekinumab treatment at week 24 for a subset of cytotoxic cell-associated genes (PRF1, KLRD1, GZMH, NKG7, GNLY, FGFBP2, TRGC2, TARP, TRGV2) at baseline. The upper x-axis shows clinical responders and non-responders in black and light grey, respectively. As shown in the figure legend, scaled expression levels are represented as a greyscale gradient from black (2) to white (−2). Data was scaled for the purpose of better visualization in the heatmap. Scaled expression is computed by subtracting sample mean of the lupus patients and dividing by the standard deviation. The mean after this procedure is set to zero and higher expression levels are represented as a gradient from >0 to 2, and lower expression levels are represented as a gradient from <0 to −2.
Figure 12:
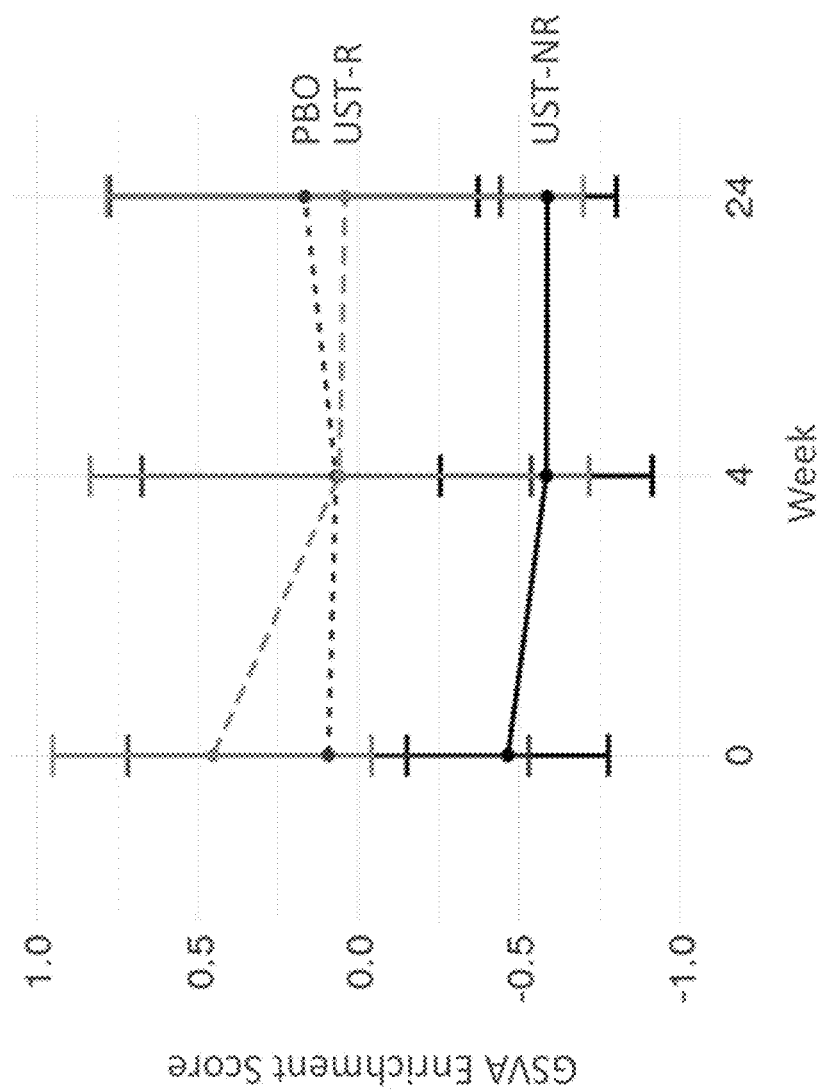
FIG. 12 shows the GSVA ES change over time in the indicated populations from 0-weeks to 24-weeks in UST responders (UST-R), UST non-responders (UST-NR), and patients treated with placebo (PBO) for a subset of cytotoxic cell-associated genes (PRF1, KLRD1, GZMH, NKG7, GNLY, FGFBP2, TRGC2, TARP, TRGV2). Lines indicate median and bars+/−median absolute deviation for populations as indicated.

Furthermore, as shown in FIG. 10, analysis of the baseline gene expression of a subset of genes from the cytotoxic cell-associated signature (PRF1, KLRD1, NKG7, GNLY, FGFBP2, TRGC2, TARP, TRGV2) further indicated that the distribution of healthy control and UST responder populations were largely overlapping (P=0.31), while non-responders exhibited significantly lower levels than UST responders (P=0.0087) and reduced levels compared to healthy controls (P=0.056). Age-matched and sex-matched healthy control donor samples were procured from BioIVT [formally known as Bioreclamation], Westbury, N.Y., and Biological Specialty Corp., Colmar, Pa. Similar cytotoxic cell-associated signature levels were observed at baseline when comparing PBO-responders to non-responders and healthy controls indicating the specificity of these cytotoxic cell-associated transcripts for UST but not PBO response. The higher levels of cytotoxic cell-associated transcripts in the blood of UST responders versus non-responders can be further seen in the hierarchical clustering heat map (FIG. 11). Whereas the majority of UST responders are clustered together and associated with higher baseline expression of these transcripts, the responder distribution within the placebo population appears more randomly distributed in relation to cytotoxic cell-associated signature gene expression. Although the decrease was not statistically significant over the time tested, a trend of decreased cytotoxic cell-associated signature levels was observed only in the UST responders (FIG. 12).

Figure 13:
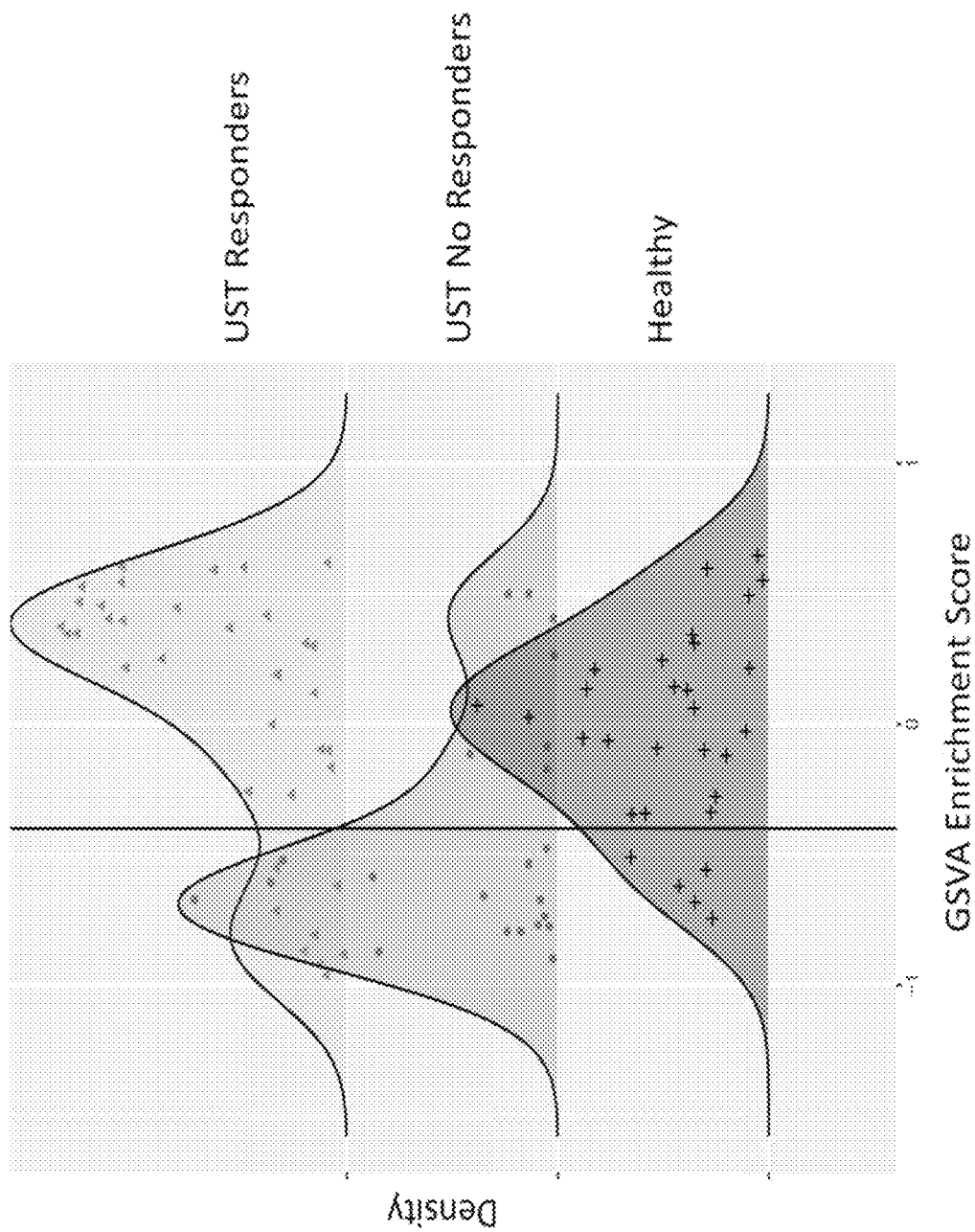
FIG. 13 shows the GSVA ES for healthy donors, UST responders, and UST non-responders at baseline using the following cytotoxic cell-associated transcripts (MYBL1, FCRL6, FGFBP2, KLRD1, TRGV2, KLRG1, LOC387895, NKG7, GPR56, PRF1, GNLY, TARP, GZMH, GSTM4, KLRC3, TRGC2, GZMK, XRRA1). The density of GSVA distribution is indicated for each population. These relative distributions suggest that UST non-responders are enriched for patients with a lower GSVA ES for these cytotoxic cell-associated transcripts versus UST responders and further indicate that a cutoff could be set by using the distribution of a healthy control reference cohort. For example, cytotoxic low is defined as a patient with a cytotoxic signature score 0.4 below the median of the healthy reference cohort as indicated by the vertical line.

Further analysis of cytotoxic cell-associated gene expression in UST responders, UST non-responders, and healthy donors showed that UST non-responders are enriched for patients with a lower GSVA ES for cytotoxic cell-associated transcripts versus UST responders (FIG. 13). The results also indicated that expression levels of cytotoxic cell-associated transcripts could be used to enrich for patient populations with UST responders by using a cutoff based on the distribution of expression of a healthy control reference cohort. For example, cytotoxic low could be defined as a patient with a cytotoxic signature score 0.4 below the median of the healthy reference cohort as indicated by the vertical line shown in FIG. 13.

Cytotoxic Cell-Associated Signature and IL-12

Figure 14:
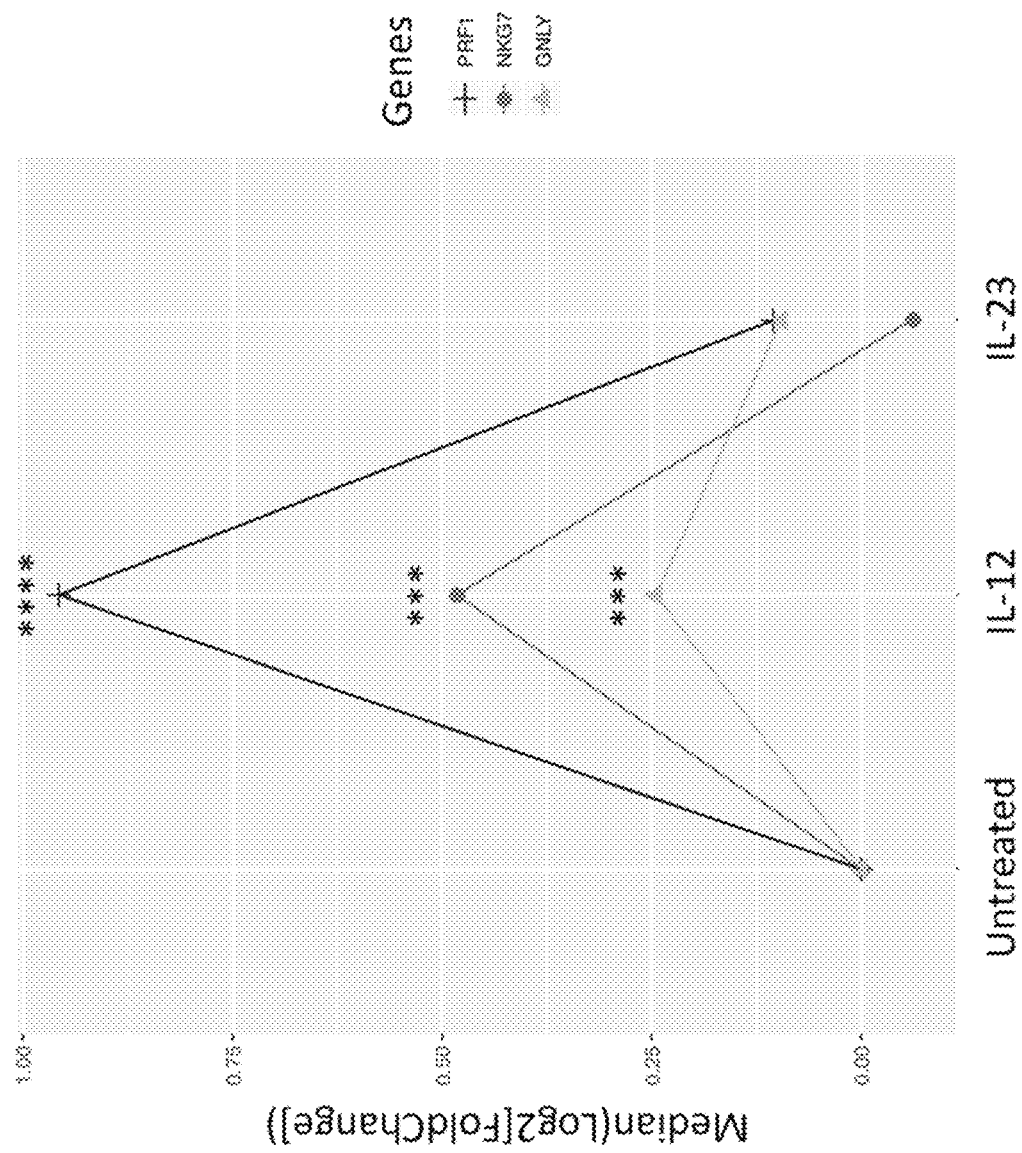
FIG. 14 shows the fold change gene expression results of the indicated cytotoxic cell-associated genes (PRF1, NKG7 and GNLY1) from RNA-sequencing data after 24-hour whole blood in vitro incubation with or without recombinant IL-12 or IL-23. RNA-sequencing data were normalized using edgeR library in R (Robinson et al, 2010). Log 2 fold change was calculated subtracting the median of Untreated to the median of each stimulation (IL-12, IL-23). To determine statistical significance a paired t-test was performed on the expression value. * P<0.01, ** P<0.001

To examine the potential relationship between the cytotoxic cell-associated signature genes and targets of UST (IL-12 and IL-23), in vitro whole blood stimulation studies were performed. Under the conditions tested, the addition of recombinant IL-12 resulted in a significant increase in the expression level of the indicated cytotoxic cell-associated genes across the 6 healthy donor blood samples tested whereas IL-23 stimulation did not induce significant changes in these genes under the conditions tested (FIG. 14). Based on these results of the in vitro whole blood stimulation studies and the analysis of the baseline expression levels of the cytotoxic cell-associated signature in UST responders and non-responders, the role of IL-12 blockade is clearly implicated as a factor in UST efficacy. Furthermore, IL-12 is also known to be an important driver of IFN-γ, which was also shown to be implicated in UST response (FIG. 5), further supporting an important role of IL-12 blockade in the mechanism of action of UST in SLE.

Figure 3A:
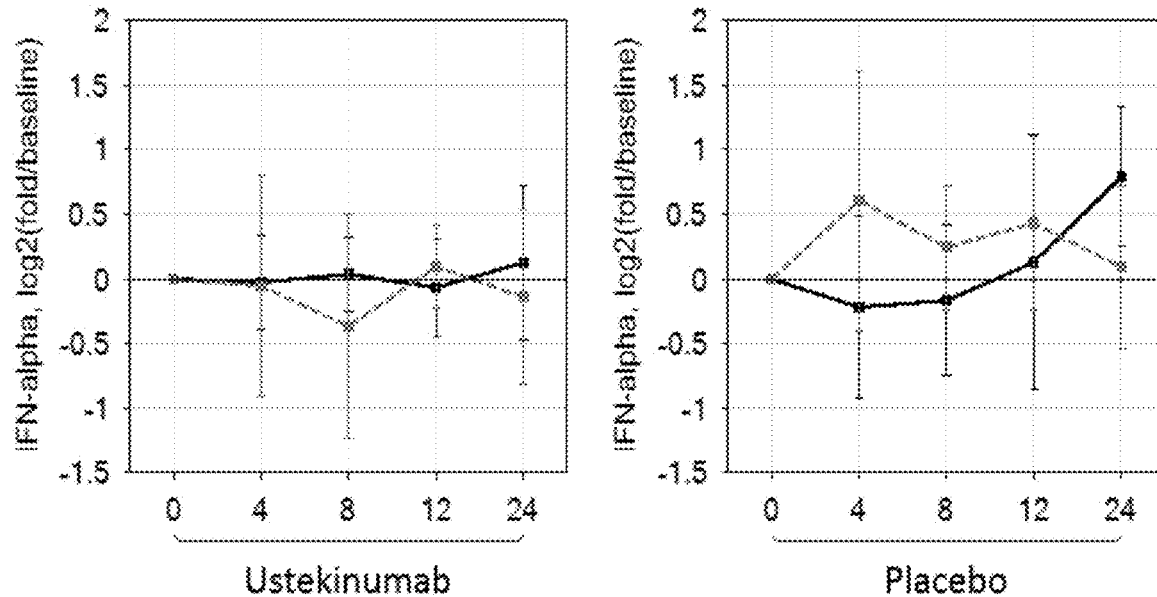
FIGS. 3A and 3B show serum IFN-alpha protein levels and gene set variation analysis (GSVA) enrichment scores (ES) from blood before and after treatment with ustekinumab or placebo.
Figure 3B:
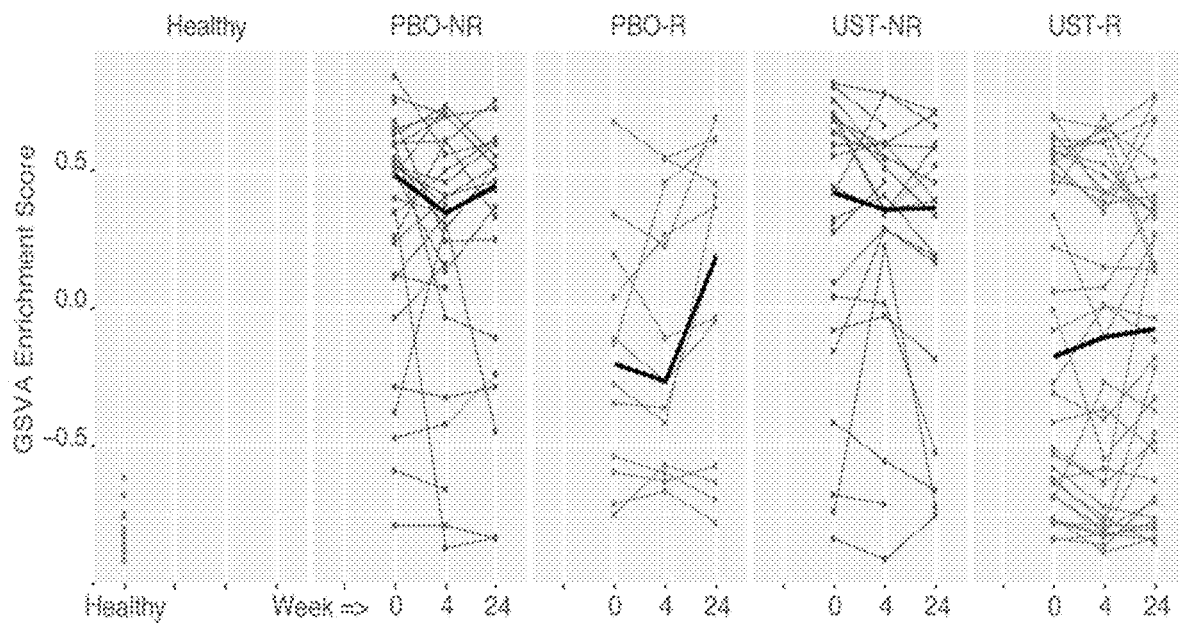
Figure 4A:
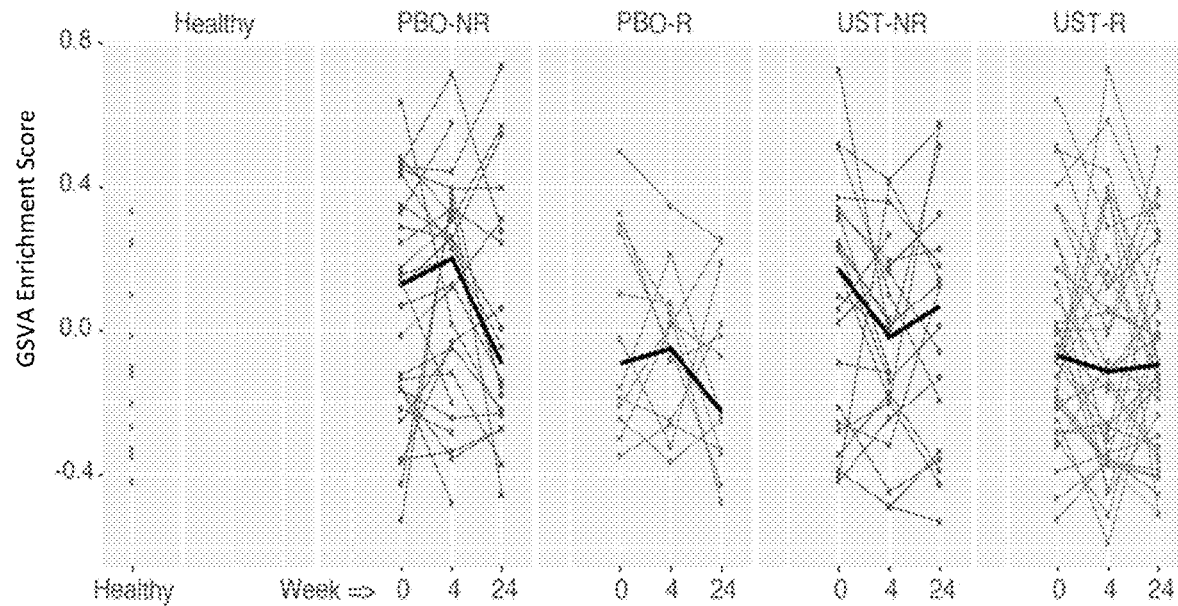
FIGS. 4A and 4B show ES scatter plots from GSVA of a blood plasma blast cell gene signature and a plasma cell gene signature.
Figure 4B:
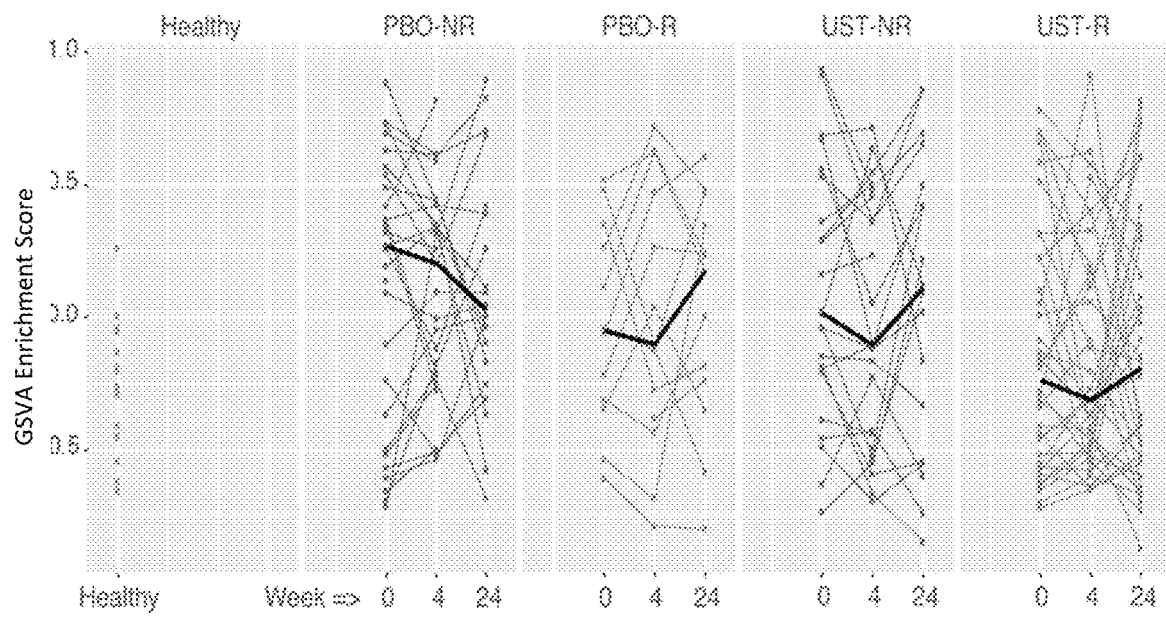
Figure 5:
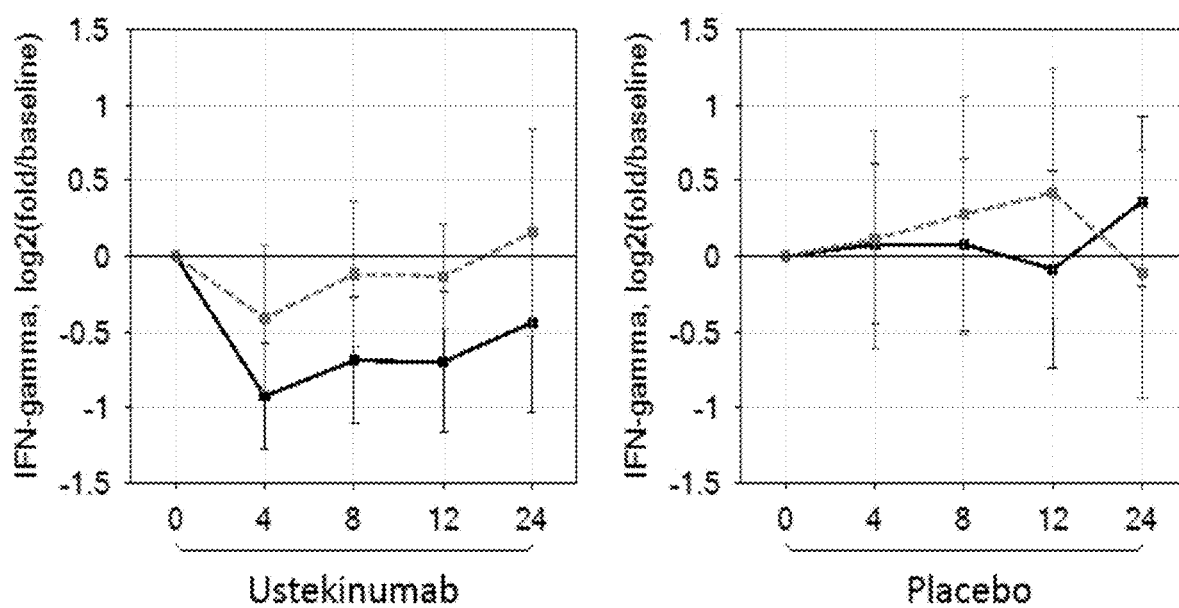
FIG. 5 shows serum IFN-gamma protein levels before and after ustekinumab or placebo treatment using the MSD platform (Rockville, Md.). Data was normalized by indicated population groups and treatment groups as Log 2(fold/baseline) population data. The x-axis indicates the time in weeks post-treatment. 0=baseline prior to treatment. Black symbols with a solid line indicate mean IFN-gamma serum levels from clinical responders at 24 weeks while the grey symbols with a dashed line indicate mean IFN-gamma levels in non-responders at 24 weeks. Error bars represent ±95% confidence interval (CI).

Discussion:

Multiple trials targeting other therapeutic mechanisms distinct from IFN-I and B-cell modulation have failed to meet clinical efficacy and/or safety profiles to merit further development or approval in lupus. In the UST phase 2 lupus trial, no pharmacodynamic treatment effect was observed with IFN-alpha levels (FIG. 3A). Further, no modulation was seen at the level of the type I interferon transcriptional signature (FIG. 3B). Despite a perceptible reduction in anti-dsDNA levels little impact was observed on plasma blast or plasma cell transcriptional gene signatures in the blood indicating that UST efficacy was unlikely due to direct modulation of the B-cell compartment (FIG. 4). Down modulation of type II interferon (IFN-gamma) was observed in UST-treated subjects particularly in the SRI-4 responder group (FIG. 5). Despite the observed reduction of IFN-gamma in the UST lupus trial, direct blockade of IFN-gamma was shown to have minimal clinical efficacy in lupus despite demonstration of target engagement (Boedigheimer et al, 2017; Werth et al, 2017). This data suggests that UST modulates disease through a novel mechanism of action largely differentiated from other therapies either in clinical development or approved for the treatment of lupus.

Figure 6:
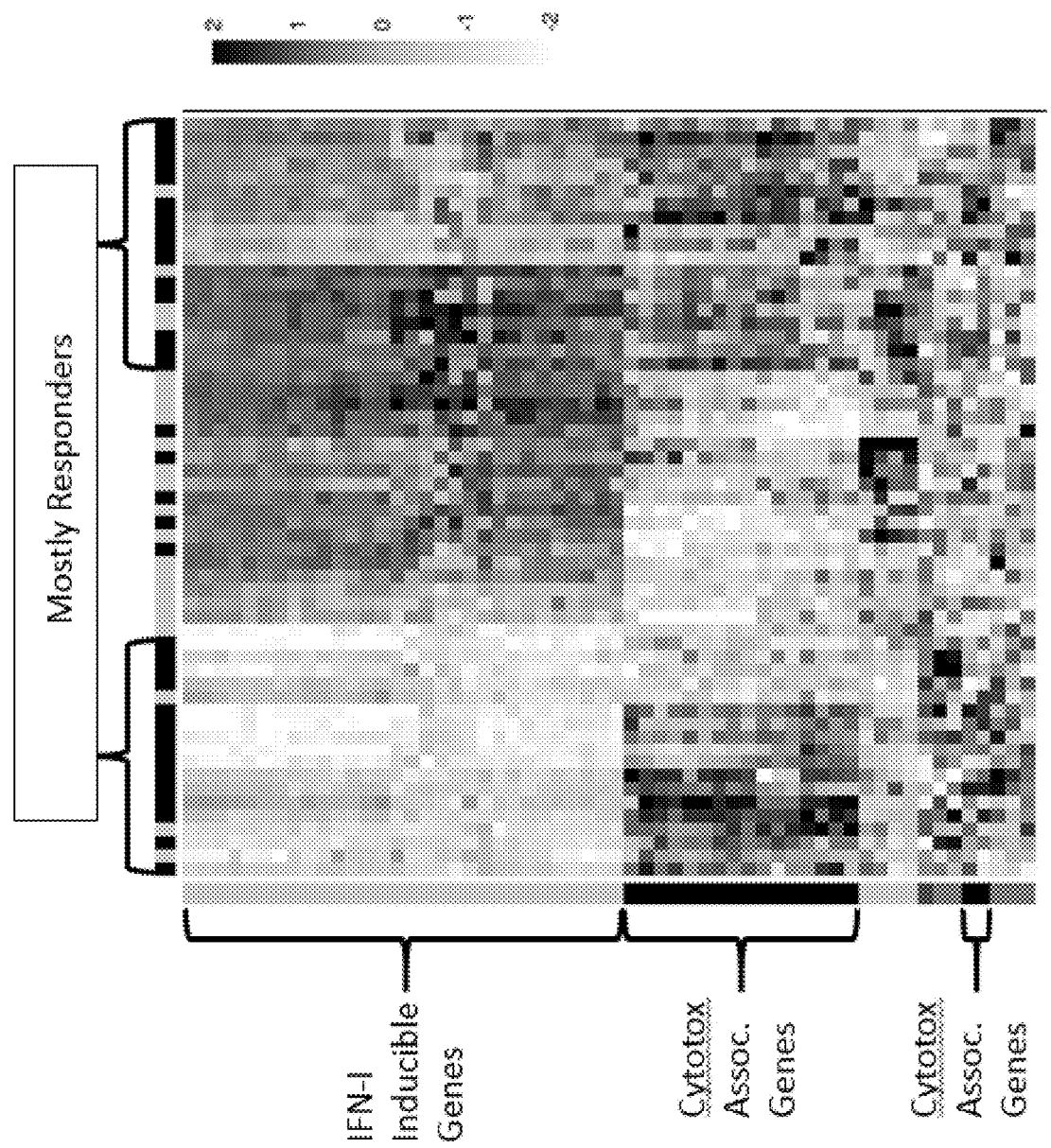
FIG. 6 shows a hierarchical clustering heat map for the expression analysis of 58 genes, including the IFN-I-inducible gene cluster and the cytotoxic cell-associated transcriptional gene cluster that are differentially expressed in baseline whole blood between SRI-4 clinical responders and non-responders at 24 weeks. The y-axis shows 2 predominant clusters comprised of 1) the IFN-I inducible genes and 2) the cytotoxic cell-associated transcriptional genes. The upper x-axis shows clinical responders and non-responders in black and light grey, respectively. As shown in the figure legend, scaled expression levels are represented as a greyscale gradient from black (2) to white (−2). Data was scaled for the purpose of better visualization in the heatmap. Scaled expression is computed by subtracting sample mean of the lupus patients and dividing by the standard deviation. The mean after this procedure is set to zero and higher expression levels are represented as a gradient from 0 to 2, and lower expression levels are represented as a gradient from <0 to −2. The IFN-I inducible gene cluster includes (in order from top to bottom): IFIT1, HERC5, RSAD2, EPSTI1, DDX60, OAS3, CMPK2, SAMD9L, EIF2AK2, DDX58, ZBP1, OASL, IFIT3, IFIT2, CARD17, PLSCR1, FBXO39, OTOF, LOC100133669, TIMM10, LAP3, IRF7, BST2, SPATS2L, RTP4, SIGLEC1, USP18, HERC6, DHX58 and ISG15. The cytotoxic cell-associated transcriptional gene cluster includes (in order from top to bottom): KLRC3, GNLY, GPR56, PRF1, GZMH, KLRD1, FGFBP2, FCRL6, NKG7, TRGC2, TRGV2, TARP, LOC387895, GZMK, MYBL1, and KLRG1. Other genes, except GSTM4 and XRRA1 (also cytotoxic cell-associated transcriptional genes), (in order from top to bottom): IGLV3-21, IGHV3-20, IGKV6-21, IGKV1-27, MIR3939, RN5S338, RN5S134, GSTM4, XRRA1, C15orf54, TRBV7-3, and LOC647859. Brackets show groupings for IFN-I inducible genes (IFN-I Inducible Genes) and cytotoxic cell-associated transcriptional genes (Cytotox Assoc. Genes).
Figure 7:
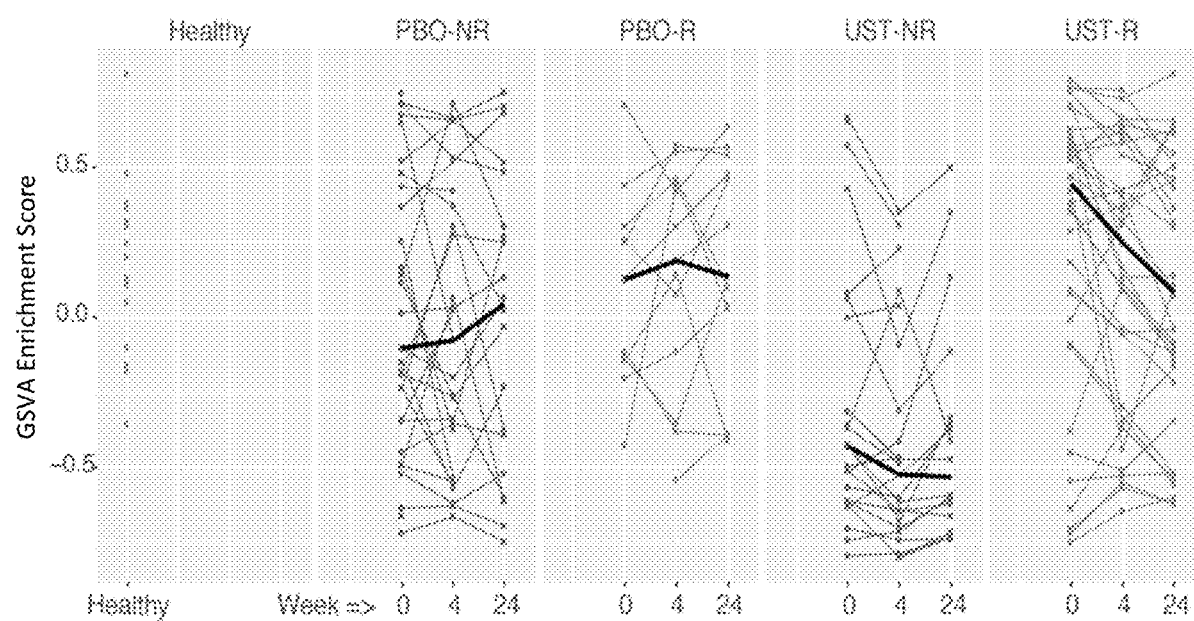
FIG. 7 shows a scatter plot of GSVA ES for genes within the cytotoxic cell-associated transcriptional gene cluster from FIG. 6. Dots indicate subjects and connected dots indicate longitudinal assessment within same subject. A heavy solid black line shows the median for each group. The X axis indicates time in weeks post-treatment, 0=baseline prior to treatment. Treatment groups are labelled as PBO for placebo and UST for ustekinumab. Status for SRI-4 response at 24 weeks is indicated after treatment group name by "—R" for a positive response and "—NR" for a non-responder. T-test was used to calculate a p-value for the following: Healthy vs Week 0>0.05; paired t-test was used to calculate a p-value for the following: Week 0 vs Week 4≤0.05, Week 0 vs Week 24≤0.01, and Week 4 vs Week 24>0.05.

An unbiased analysis of whole blood microarray data from the UST phase 2 trial was performed to identify transcriptional signatures that could potentially discriminate response from non-response as defined by a significant difference in the primary endpoint of SRI-4 at 24 weeks of treatment with UST. This approach led to the identification of gene expression patterns within two gene clusters that can largely distinguish UST responders from non-responders and thus select patients that are predicted to have an increased likelihood of having a positive response to the treatment. The first gene cluster comprised a collection of IFN-I-inducible transcripts and the second gene cluster was composed of transcripts associated with cytotoxic cells (e.g., NK, CD8 T cells) (FIG. 6). Independent analysis of responders versus non-responders utilizing identical methods with the placebo group resulted in no overlap with the individual genes comprising these two clusters. Thus, implying that the gene clusters that discriminated UST response from non-response was specific for this therapeutic agent and not related to general improvement in disease activity using the SRI-4 instrument. The expression levels of the individual genes comprising the IFN-I inducible gene cluster and the cytotoxic cell-associated transcriptional gene cluster are shown in FIG. 6 and collectively map to the IFN-I pathway and pathways associated with cytotoxic cells, respectively. Longitudinal analysis of gene expression for both the identified IFN-I inducible gene cluster and the cytotoxic cell-associated transcriptional gene cluster revealed a novel pharmacodynamic effect in UST responders. Transcripts within the cytotoxic cell-associated transcriptional gene cluster exhibited temporal down-modulation (lower expression levels) only in UST-treated responders (FIG. 7). No transcriptional changes occurred with transcripts comprising the IFN-I inducible gene cluster as also corroborated by analysis using a previously described IFN-I signature (Yao et al, 2009) (FIG. 3). This result is also supported by a lack of modulation of IFN-alpha protein levels (FIG. 3). UST responders in general exhibit a higher baseline level of the expression levels of the cytotoxic cell-associated transcriptional gene signature versus non-responders and exhibit a decrease of this signature over time after drug treatment. Thus, it can be speculated that higher baseline levels of the cytotoxic cell-associated transcriptional gene signature could reflect a disease mechanism largely nurtured by p40 signaling (IL-12 and/or IL-23) which is supported by the observation that blockade of p40 reduces the cytotoxic signature sequestering factors that may drive its perpetuation. Importantly, patients can respond to UST irrespective of IFN-I inducible gene signature status if the cytotoxic cell-associated transcriptional gene signature is sufficiently expressed at baseline (FIG. 6). This observation supports that UST represents a unique mechanism of action that does not modulate IFN-I and which can improve lupus disease outcomes in patients also having evidence of IFN-I dysregulation. Thus, p40 neutralization may be sufficient to improve disease even while IFN-I mediated pathogenic effects are still present. One characteristic of UST non-responders from this data is the presence of elevated IFN-I inducible gene signature (higher expression levels) and lower cytotoxic cell-associated transcriptional gene signature (lower expression levels) in the blood at baseline. In this said population, an IFN-I modulator may offer enhanced clinical benefit. Furthermore, therapy comprising administering UST and an IFN-I inhibitor may even more broadly impact this SLE patient population by targeting patients having a p40-mediated disease and a more IFN-I modulated disease profile. Examples of IFN-I inhibitors include anti-IFN alpha antibodies, anti IFN-I receptor antibodies and other agents that inhibit the IFN-I pathway. Examples of anti-IFN alpha antibodies include, e.g., sifalimumab and JNJ-55920839 (CNTO 6358). Anti IFN-I receptor antibodies include, e.g., anifrolumab. Other agents that inhibit the IFN-I pathway include, e.g., agents that inhibit Toll-Like Receptors (TLRs) 7, 8, and 9, agents that deplete or inhibit plasmacytoid dendritic cell function, and agents that inhibit Janus Kinase 1 (JAK1).

Figure 8A:
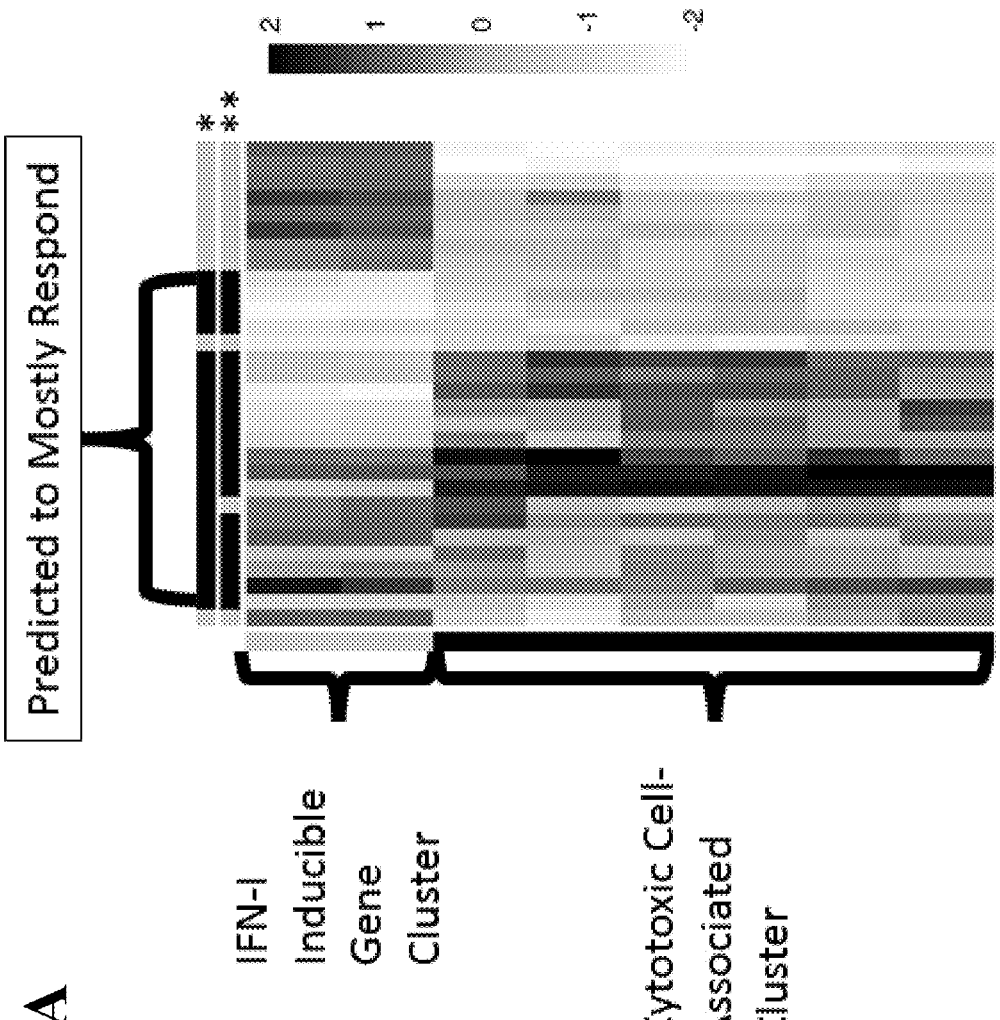
FIGS. 8A, 8B and 8C shows a hierarchical clustering heat map for the 8-gene whole blood transcriptional signature across three racially and ethnically diverse SLE cohorts.
Figure 8B:
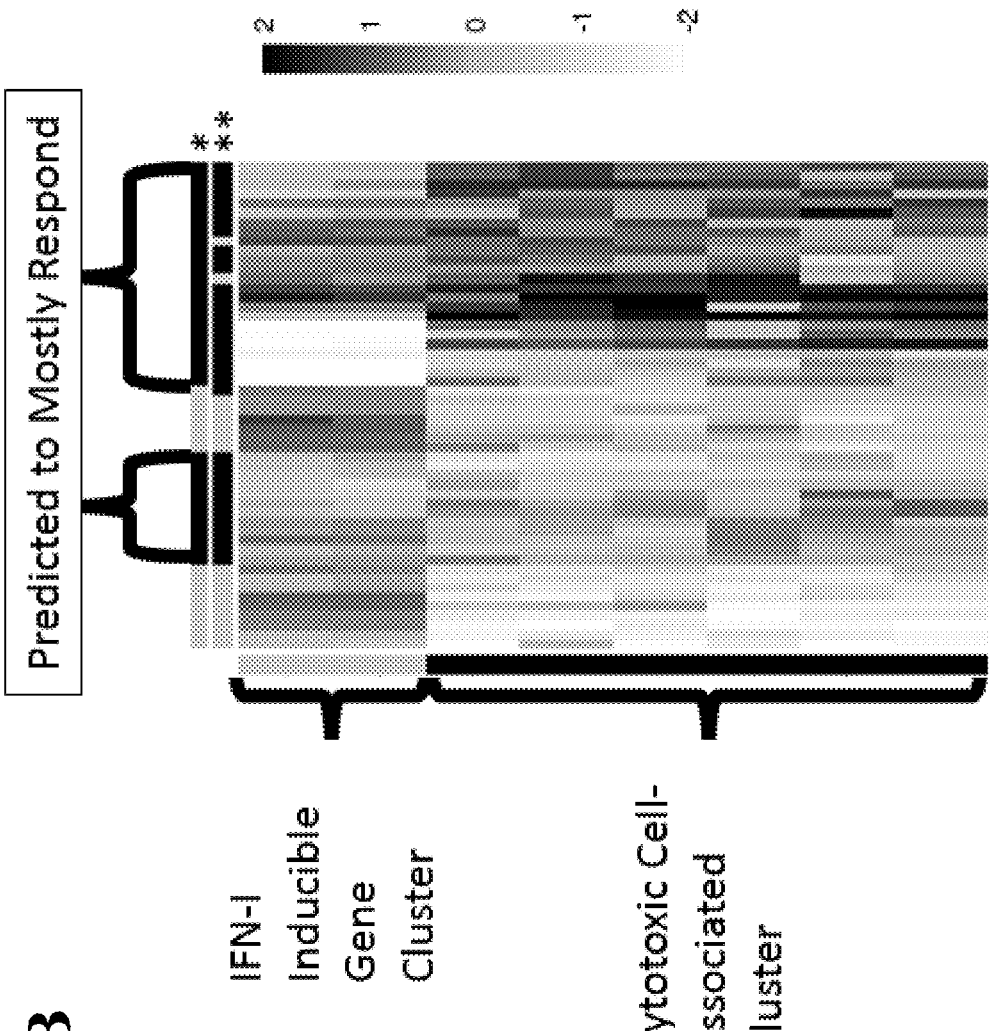
Figure 8C:
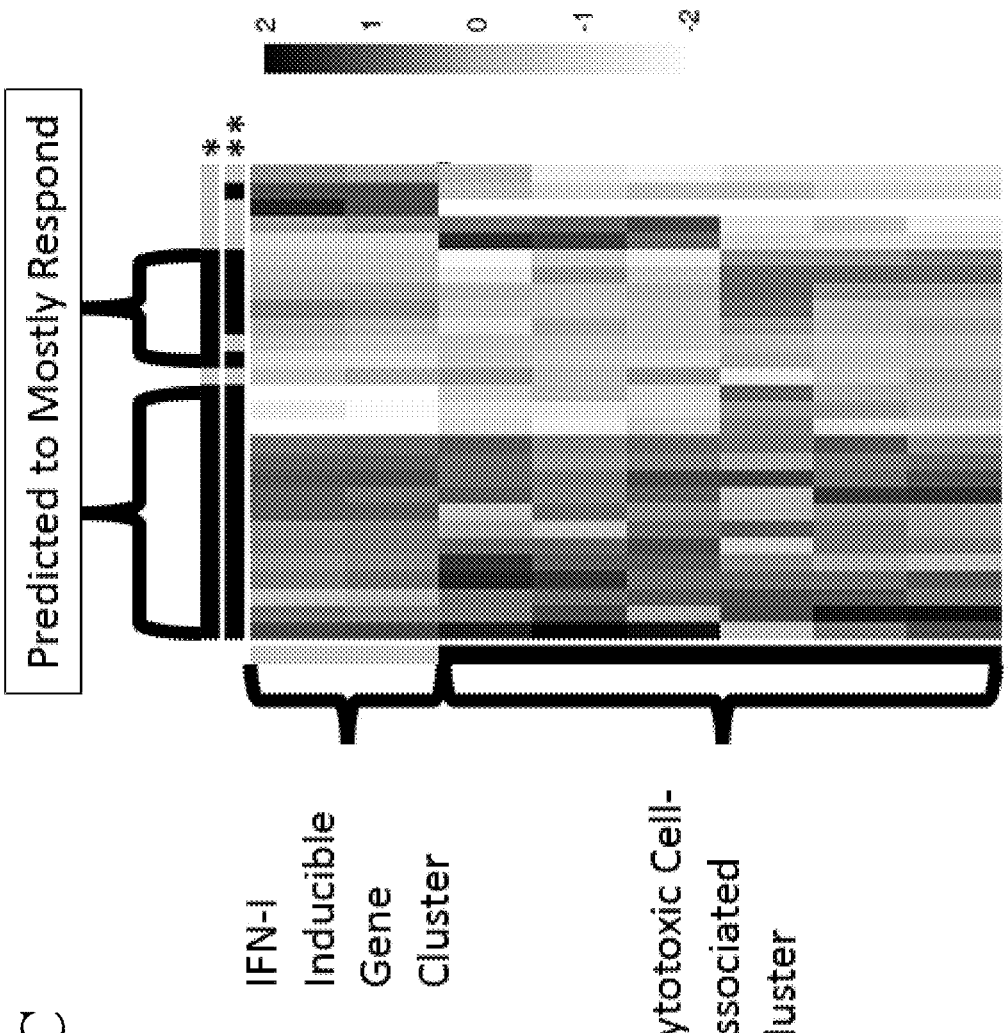

Further refinement of the signature comprising transcripts from the IFN-I inducible gene cluster and the cytotoxic cell-associated transcriptional gene cluster was undertaken using machine learning approaches to define an optimal whole blood signature to predict UST response prior to treatment. To that end, an 8-gene signature was identified which still comprised transcripts from both the IFN-I inducible gene cluster and cytotoxic cell-associated transcriptional gene cluster. This signature exhibited a positive predictive value of 0.78, and a negative predictive value of 0.75. Lupus exhibits a female to male gender bias ratio of 9:1 and can manifest differently based on racial and ethnic background adding to the complexity of developing predictive biomarkers (Manzi & Merrill, 2017). Further examination of this 8-gene signature confirmed its presence in multiple racially and ethnically diverse SLE cohorts indicating that it is universally expressed irrespective of genetic background (FIG. 8).

It was also determined that models based on only the cytotoxic cell-associated signature (7 genes from the 31-gene subset) or only the IFN-I inducible gene signature (24 genes from the 31-gene subset) could be used to predict the likelihood of having a positive response to UST. The positive predictive value (PPV) was 0.710 95% IC [0.706, 0.715] for the cytotoxic cell-associated signature and the PPV was 0.662 95% IC [0.658,0.667] for the IFN-I inducible gene signature. The negative predictive values (NPV) were 0.591 95% IC [0.575,0.607] for the cytotoxic cell-associated signature and 0.488 95% IC [0.470,0.505] for the IFN-I inducible gene signature.

In addition, it was determined that baseline blood expression levels of cytotoxic cell-associated genes where similar between healthy controls and UST responders, but UST non-responders exhibited significantly lower expression levels than UST responders and reduced levels compared to healthy controls. Furthermore, results indicated that expression levels of cytotoxic cell-associated transcripts could be used to enrich for patient populations with UST responders by using a cutoff based on the distribution of expression of a healthy control reference cohort. For example, cytotoxic low could be defined as a patient with a cytotoxic signature score below the median of the healthy controls.

Multiple additional biomarker data types were also assessed with standard logistic regression modeling to determine if they could also be used as predictors of response to ustekinumab. The additional biomarker data types included serum proteins, whole blood gene expression, and peripheral blood flow cytometry. These additional biomarker data types and standard logistic regression models confirmed the relationships identified with sophisticated and extensive analysis of the microarray data.

Conclusion:

As described herein, 58-genes were identified that are differentially expressed in patients with active Systemic Lupus Erythematosus (SLE). The differentially expressed genes are referred to herein as dynamic genes. It was determined that subsets of the dynamic genes including one or more cytotoxic cell-associated transcriptional genes and one or more IFN-I inducible genes can be used to predict the likelihood of having a positive response to treatment with the anti-IL-12/IL-23p40 antibody ustekinumab (UST). A 46-gene signature, a 31-gene signature, and an 8-gene signature were shown to have a positive predictive value of: 0.746 95% IC [0.740,0.751], 0.726 95% IC [0.720,0.732] and 0.755 95% IC [0.749,0.761], respectively. The negative predictive values for the 46-gene, 31-gene and 8-gene signatures were: 0.67 95% IC [0.661,0.688], 0.659 95% IC [0.645,0.673] and 0.715 95% IC [0.702,0.728], respectively. In addition, randomly selected 2-gene prediction models including one cytotoxic cell-associated transcriptional gene and one IFN-I inducible gene were shown to have a mean positive predictive value (PPV) of 0.735 95% IC [0.733, 0.738] and negative predictive value of 0.678 95% IC [0.671, 0. 684]. The average mean accuracy of the 2-gene models was 70.71% (95% CIs [70.41, 71.01]).

Thus, it was concluded that expression levels of one or more genes from the IFN-I inducible gene cluster and one or more genes from the cytotoxic-cell associated transcriptional gene cluster can predict the likelihood of having a positive response to treatment with the anti-IL-12/IL-23p40 antibody ustekinumab (UST). It was also concluded that expression levels of one or more cytotoxic cell-associated transcriptional genes and expression levels of one or more IFN-I inducible genes could be used as a method to pre-screen biological samples (e.g., blood samples) from patients with active SLE to select patients predicted to have an increased likelihood of a positive response to treatment with UST (Table 11 and FIG. 9). Furthermore, it was determined that just a cytotoxic-cell associated signature could also be used to predict the likelihood of having a positive response to treatment with UST. It was also determined that expression levels of the cytotoxic cell-associated transcripts could be used to enrich for patient populations with UST responders by comparison to the expression in healthy controls. The data contained herein further suggests using the expression levels to select patients with active SLE predicted to have an increased likelihood of a positive response to treatment comprising UST and an IFN-I inhibitor.

APPENDIX 1

EFFICACY EVALUATIONS AND ENDPOINTS

| | Efficacy Evaluations | Description | Composed of Other Assessments |
|---|---|---|---|
| BILAG | British Isles Lupus Assessment Group | Measure of alterations to therapy consisting of 97 questions in 9 organ systems, each put into 1 of 5 categories (A, B, C, D, E) depending on presence of items. Higher scores indicate more disease involvement. | |
| BICLA | BILAG-based Combined Lupus Assessment | Composite requiring subjects to meet response criteria across the BILAG, PGA and SLEDAI-2K index. | BILAG PGA SLEDAI-2K |
| CLASI | Cutaneous Lupus Erythematosus Disease Area and Severity Index | Assesses the disease activity and damage caused to the skin for CLE patients. Scored 0-70 for activity and 0-56 for damage with higher scores indicating extremely active Lupus. | |
| Flares | SLEDAI flare Severe SLEDAI flare BILAG flare | SLEDAI flare: At least a 4+ point increase in SLEDAI-2K score (includes severe flares). Severe SLEDAI flare: At least a 7+ point increase in SLEDAI-2K score. BILAG flare: At least 1 new BILAG A or 2 new BILAG B scores (from scores < B) | BILAG SLEDAI-2K |
| FSS | Fatigue Severity Scale | A 9-item questionnaire designed to assess the severity of fatigue and its impact on daily living. Each item scored from 1-7 with higher score indicating more severe impact. Scored 9-63. | |
| Pain VAS | Patients Numeric Rating Scale of Pain | Measures the patient's assessment of pain on a visual analogue scale (VAS; 0 to 10 cm). The anchors of the instrument include 0 to represent 'no pain' and 10 to represent 'the worst pain.' | |
| PGA | Physician's Global Assessment of Disease Activity | Measures the PGA on a VAS scale. Each scored from 0-10 with higher scores indicating worse activity. | |
| PtGA | Patient's Global Assessment of Disease Activity | Measures the PtGA on a VAS scale. Each scored from 0-10 with higher scores indicating worse activity. | |
| SF-36 | RAND Short-Form-36 Health Survey | Measures 36 items within 8 health domains. Scored 0-100 for each health concept with higher scores indicating an improved health state. In addition, health concepts can be combined into either a physical or mental component, also scored 0-100. | |
| SLEDAI-2K (Baseline) | Systemic Lupus Erythematosus Disease Activity Index 2000 | Measures 24 features in 9 organ domains over the previous 30 days. Scored 0-105 with higher scores indicating more disease activity. | |
| S2K RI-50 (Follow-up) | SLEDAI-2K Responder Index 50 | Measures clinically important 50% reduction in SLEDAI-2K score. | SLEDAI-2K |
| SRI-4 | SLE Responder Index-4 | Composite endpoint requiring at least a 4 point reduction in SLEDAI 2K, no worsening (<10 mm increase) from baseline in PGA and no new BILAG Domain A and no more than 1 new BILAG Domain B scores (see Section 9.2.2.1.). | SLEDAI-2K PGA BILAG |

APPENDIX 1-continued

EFFICACY EVALUATIONS AND ENDPOINTS

| Efficacy Evaluations | | Description | Composed of Other Assessments |
|---|---|---|---|
| SRI-5 and SRI-6 | SLEDAI 2-K SLE Responder Index-5 and SLEDAI 2-K SLE Responder Index-6 | Same criteria as SRI-4 however the SRI-5 and SRI-6 require at least a 5 point or 6 point reduction in SLEDAI-2K respectively. | SLEDAI-2K PGA BILAG |

APPENDIX 2

PROBE SEQUENCES

| Probe Set ID | Probe ID | Gene Symbol | Probe Sequence | SEQ ID NO |
|---|---|---|---|---|
| 16657594 | 134419 | ISG15 | TAAGCCTGAGGCACACACGTCAGGG | 12 |
| 16657594 | 250152 | ISG15 | GCAGCACCGGCCCTATTATAAGCCT | 13 |
| 16657594 | 819200 | ISG15 | AGATGAGTTCGCTGCCTCTCAGCCG | 14 |
| 16657594 | 1043700 | ISG15 | TACTGGCAAAGATGAGTTCGCTGCC | 15 |
| 16657594 | 145244 | ISG15 | TCCTGTACTGGCAAAGATGAGTTCG | 16 |
| 16657594 | 295654 | ISG15 | TGTGGGCCACGGCACAAGCTCCTGT | 17 |
| 16657594 | 1272230 | ISG15 | ACACCTGGAATTCGTTGCCCGCCAG | 18 |
| 16657594 | 1394070 | ISG15 | TGACACCGACATGGAGCTGCTCAGG | 19 |
| 16657594 | 306590 | ISG15 | GCGTGCACGCCGATCTTCTGGGTGA | 20 |
| 16657594 | 316346 | ISG15 | TCAGAGGTTCGTCGCATTTGTCCAC | 21 |
| 16657594 | 571659 | ISG15 | TGCGGCCCTTGTTATTCCTCACCAG | 22 |
| 16657594 | 487471 | ISG15 | TGCGTCAGCCGTACCTCGTAGGTGC | 23 |
| 16657594 | 37116 | ISG15 | CCCTCGAAGGTCAGCCAGAACAGGT | 24 |
| 16657594 | 456718 | ISG15 | GCAGGCGCAGATTCATGAACACGGT | 25 |
| 16657594 | 649732 | ISG15 | TCCGGCCCTTGATCCTGCTCGGATG | 26 |
| 16657594 | 162045 | ISG15 | TTCCGGCCCTTGATCCTGCTCGGAT | 27 |
| 16657594 | 250261 | ISG15 | TTTCCGGCCCTTGATCCTGCTCGGA | 28 |
| 16657594 | 250713 | ISG15 | ATTTCCGGCCCTTGATCCTGCTCGG | 29 |
| 16657594 | 116618 | ISG15 | TATTTCCGGCCCTTGATCCTGCTCG | 30 |
| 16657594 | 286930 | ISG15 | TTATTTCCGGCCCTTGATCCTGCTC | 31 |
| 16657594 | 379499 | ISG15 | CAGCCTTTATTTCCGGCCCTTGATC | 32 |
| 16657594 | 1286489 | ISG15 | ACAGCCTTTATTTCCGGCCCTTGAT | 33 |
| 16668333 | 447613 | GSTM4 | TCCGAGTGTTCAGGGAGCAAGGTCC | 34 |
| 16668333 | 1182660 | GSTM4 | AAGGTCGTCACTTCCAACCAACAGG | 35 |
| 16668333 | 1321536 | GSTM4 | TCTGGCCAGCTGATTGGAGACGTCC | 36 |
| 16668333 | 1281870 | GSTM4 | TAGATGGGAATACAAGCCTGGCTTC | 37 |
| 16668333 | 219883 | GSTM4 | GAAAGTTCCTCCTAGTGCAGTGGCA | 38 |
| 16668333 | 450093 | GSTM4 | GAACTGGCTTCAGCTGGACATACCA | 39 |
| 16668333 | 1049169 | GSTM4 | GCTGCATCATTGTAGGAAGTTCCTC | 40 |
| 16668333 | 1251332 | GSTM4 | TGTTGGACCAGCAAAAGAAACGCCA | 41 |

APPENDIX 2-continued

| PROBE SEQUENCES | | | | |
|---|---|---|---|---|
| Probe Set ID | Probe ID | Gene Symbol | Probe Sequence | SEQ ID NO |
| 16668333 | 691418 | GSTM4 | TATGAAGATTCTACCCGGTGCTGGG | 42 |
| 16668333 | 929065 | GSTM4 | CCCTTGTGTACAGAGGTTTTGGGAG | 43 |
| 16668333 | 159093 | GSTM4 | CAGACAGCCACCCTTGTGTACAGAG | 44 |
| 16668333 | 702481 | GSTM4 | GGTGGATGCCTCCTTCATTGCTGAA | 45 |
| 16672462 | 900249 | FCRL6 | TTGTCTTCAACTTCGTTCAGCTGCA | 46 |
| 16672462 | 467434 | FCRL6 | TCCTCTATCGTTCTCTTTCCAACAG | 47 |
| 16672462 | 526066 | FCRL6 | GCAGCACAGCCGTCCAGAGCAGCAT | 48 |
| 16672462 | 1186882 | FCRL6 | GAATATACATCACCTGCCCAGAGCA | 49 |
| 16672462 | 1350826 | FCRL6 | GACCCCGATGGGAGGCAGTTTCATC | 50 |
| 16672462 | 1211745 | FCRL6 | AGGGTCACCAGGCTACCCTCTCGGG | 51 |
| 16672462 | 1199823 | FCRL6 | CCCTGTCCTGCAAGGTGTGGCCGTC | 52 |
| 16672462 | 209810 | FCRL6 | GAGTAGTTCCCAGCATCCTGTTCTG | 53 |
| 16672462 | 51693 | FCRL6 | TTGCTGGCGGGAGTGAACAAGACTT | 54 |
| 16672462 | 882763 | FCRL6 | GGATCTCACATAAACCAGAAGTGCA | 55 |
| 16672462 | 608001 | FCRL6 | TTGGCATATAGTGGGCACTGCTCTC | 56 |
| 16672462 | 1058098 | FCRL6 | CGTTGGCATATAGTGGGCACTGCTC | 57 |
| 16672462 | 910206 | FCRL6 | GAGTAGACAACACCTTCATCTTTCC | 58 |
| 16672462 | 1347482 | FCRL6 | GAGGTTCTATGCACCACAGAGTAGA | 59 |
| 16672462 | 1162501 | FCRL6 | TTCTCCCCACGGTGAACTCAGCAGA | 60 |
| 16672462 | 185716 | FCRL6 | TTTCTCCCCACGGTGAACTCAGCAG | 61 |
| 16672462 | 331310 | FCRL6 | TCTCACCTCCGCACAGATGATAGAA | 62 |
| 16672462 | 700176 | FCRL6 | GGCATCTCACCTCCGCACAGATGAT | 63 |
| 16672462 | 1342090 | FCRL6 | TATTTGTATATGACTAGCGGCGCTG | 64 |
| 16707180 | 644377 | IFIT2 | TGTTTCCCTTCAGCTGACGTTACAA | 65 |
| 16707180 | 1030125 | IFIT2 | TATATATACAAGTGGCCTCTGGTTC | 66 |
| 16707180 | 1296645 | IFIT2 | GACCTATATATACAAGTGGCCTCTG | 67 |
| 16707180 | 669883 | IFIT2 | GAAGAGACCTATATATACAAGTGGC | 68 |
| 16707180 | 808811 | IFIT2 | GCAATTCTCAGCTGTTCGGCAGGGC | 69 |
| 16707180 | 810497 | IFIT2 | TGCAATTCTCAGCTGTTCGGCAGGG | 70 |
| 16707180 | 1200774 | IFIT2 | GGTTGCAGTGCAATTCTCAGCTGTT | 71 |
| 16707180 | 122618 | IFIT2 | CTTTAGATAGGCCAGTAGGTTGCAC | 72 |
| 16707180 | 372297 | IFIT2 | TGGAAGACTTTTGCCCTATAGCAGC | 73 |
| 16707180 | 279980 | IFIT2 | TGAAAGTTGCCATACCGCAGATGGA | 74 |
| 16707180 | 952810 | IFIT2 | TCCTGAAGGAATGCCAAGACATGCA | 75 |
| 16707180 | 597370 | IFIT2 | CCAACTTGGTGGAGGAATTTCAGCT | 76 |
| 16707180 | 191195 | IFIT2 | TCTCAAGACCCAGCAATTCAGGTGT | 77 |
| 16707180 | 1343317 | IFIT2 | TAACCTCTATGGGATGCAAAATGAC | 78 |

APPENDIX 2-continued

PROBE SEQUENCES

| Probe Set ID | Probe ID | Gene Symbol | Probe Sequence | SEQ ID NO |
|---|---|---|---|---|
| 16707180 | 991341 | IFIT2 | CCTATTTAGACTTTGGTCCGCCAGC | 79 |
| 16707180 | 234560 | IFIT2 | AACATTTTCCAACCCAGAGTGTGGC | 80 |
| 16707180 | 495557 | IFIT2 | GATTATGATAGTAGACCAGTCGAGG | 81 |
| 16707180 | 105924 | IFIT2 | GAAGCCCTGGACTCTTAAAGCTGAG | 82 |
| 16707180 | 1047526 | IFIT2 | TGTTCACGTAGGTCAATGGTAGCAG | 83 |
| 16707184 | 363523 | IFIT3 | GCATCAGCTGATGTTTTCTCCGTTT | 84 |
| 16707184 | 714300 | IFIT3 | TCCTGTCTGCCTCAAGTAAATACTG | 85 |
| 16707184 | 303532 | IFIT3 | TCTGCTGTTCCGAAAAGCTGGTGAC | 86 |
| 16707184 | 814868 | IFIT3 | CCCAGGGTGCTGTTAGGTCTGTGCT | 87 |
| 16707184 | 363933 | IFIT3 | TGAAGAGGTTTCCACCCAGGGTGCT | 88 |
| 16707184 | 812070 | IFIT3 | CCAAGCAAATGCTGAAGAGGTTTCC | 89 |
| 16707184 | 1078280 | IFIT3 | GTTTTTAGCTTACTGATTCCAAGCA | 90 |
| 16707184 | 448153 | IFIT3 | AAATGGCATTTCAGCTGTGGAAGGA | 91 |
| 16707184 | 651215 | IFIT3 | TCTAGATCCCTTGAGACACTGTCTT | 92 |
| 16707184 | 502597 | IFIT3 | CCATCTAGGTGTTTATGTAGGCCA | 93 |
| 16707184 | 1030764 | IFIT3 | cCTCACAGTCAAGTTCAGAATACTC | 94 |
| 16707184 | 1173314 | IFIT3 | ATTTCTTCCACACTTCAGTTGTGTC | 95 |
| 16707184 | 616072 | IFIT3 | CCCAATCTGGTGATAGAGGTAGCCA | 96 |
| 16707184 | 799743 | IFIT3 | GAAAATACTGCCTATGCCTGAAGGG | 97 |
| 16707184 | 568911 | IFIT3 | CAGTGATTAGTTGTAAGACCTTCGG | 98 |
| 16707184 | 1255614 | IFIT3 | GAACTAATCAGCATCATGTGGGCCT | 99 |
| 16707184 | 505251 | IFIT3 | CAAATTTGTTGTTAGGCAGTCACC | 100 |
| 16707184 | 1072347 | IFIT3 | TACATGCCTGAAGCTATAAGTGAGA | 101 |
| 16707196 | 502640 | IFIT1 | CCAAGACAGTGTTATATAAGGGAGC | 102 |
| 16707196 | 1291276 | IFIT1 | GAGATCTGGCTATTCTGTCTTGTGG | 103 |
| 16707196 | 410346 | IFIT1 | TGCTGTAAATTAGGCAGCCGTTCTG | 104 |
| 16707196 | 28659 | IFIT1 | CAACATAAGAGGGTTAAGGCTTCAA | 105 |
| 16707196 | 715817 | IFIT1 | GCCTTTCCTCAGTGGCACAGAGAGA | 106 |
| 16707196 | 1058988 | IFIT1 | GAAGTCCTAGATGAAGGTGACAACC | 107 |
| 16707196 | 181106 | IFIT1 | TATCCTTGACCTGATGATCATCACC | 108 |
| 16707196 | 111824 | IFIT1 | TCGTCATCAATGGATAACTCCCATG | 109 |
| 16707196 | 249058 | IFIT1 | TAAAGCCATCCAGGCGATAGGCAGA | 110 |
| 16707196 | 1067392 | IFIT1 | TGGATTTAAGCGGACAGCCTGCCTT | 111 |
| 16707196 | 308116 | IFIT1 | TTTGTAGACGAACCCAAGGAGGCTC | 112 |
| 16707196 | 839469 | IFIT1 | GAAATGTGAAAGTGGCTGATATCTG | 113 |
| 16707196 | 1205612 | IFIT1 | TACTACATAGCACTCATACAAATGA | 114 |
| 16715170 | 1234870 | PRF1 | CAAAGAAGACAGAGCAGCTGGAGCT | 115 |

APPENDIX 2-continued

PROBE SEQUENCES

| Probe Set ID | Probe ID | Gene Symbol | Probe Sequence | SEQ ID NO |
|---|---|---|---|---|
| 16715170 | 1166385 | PRF1 | GCTTTGCCACACCATAGAGGGCTCA | 116 |
| 16715170 | 1080236 | PRF1 | TGTGATCTGTGTAGCTGTGACTGCA | 117 |
| 16715170 | 512217 | PRF1 | GATTAGCGTGTAAACCCAGCCACCT | 118 |
| 16715170 | 308559 | PRF1 | TGGGAATACGAAGACAGCCCTGGCT | 119 |
| 16715170 | 772253 | PRF1 | TCCAAGCATACTGGTCCTTTCCAAG | 120 |
| 16715170 | 1274545 | PRF1 | CATGATAGCGGAATTTTAGGTGGCC | 121 |
| 16715170 | 199396 | PRF1 | TCATGGGAACCAGACTTGGGAGCCT | 122 |
| 16715170 | 212026 | PRF1 | TGTTATTGTCCCACACGGTGCTCGT | 123 |
| 16715170 | 1189366 | PRF1 | GAAGAGCTTCACATAGGCATCCGTG | 124 |
| 16715170 | 605202 | PRF1 | TAATGGAGGTGTGATGGCCGCCAAC | 125 |
| 16715170 | 306915 | PRF1 | CAGTGAGGGCCGATATGCGGCCACC | 126 |
| 16715170 | 306536 | PRF1 | GTGAGGGCCGATATGCGGCCACCCA | 127 |
| 16715170 | 912016 | PRF1 | TGAGGGCCGATATGCGGCCACCCAG | 128 |
| 16715170 | 157011 | PRF1 | CAGCTCCACAGCCCGGATGAAGTGG | 129 |
| 16715170 | 474921 | PRF1 | GTGCCGTAGTTGGAGATAAGCCTGA | 130 |
| 16715170 | 570022 | PRF1 | GAACCTTTGTGTGTCCACTGGGAAG | 131 |
| 16715170 | 310778 | PRF1 | CATGCACCAGGCACGAACTTGTGGC | 132 |
| 16715170 | 290028 | PRF1 | CTGGAATCCCGTATAGAGAAGCGGC | 133 |
| 16715170 | 289880 | PRF1 | TGGAATCCCGTATAGAGAAGCGGCT | 134 |
| 16715170 | 490338 | PRF1 | GAATCCCGTATAGAGAAGCGGCTAC | 135 |
| 16715170 | 933640 | PRF1 | GAAGCGGCTACACAGATGGATATCC | 136 |
| 16715170 | 1084814 | PRF1 | TCTTCACCGAGGCTCCTGGAATGGT | 137 |
| 16722960 | 774657 | RN5S338 | TCAGACGAGACTGGGCATGTTCAGG | 138 |
| 16722960 | 774788 | RN5S338 | ATCAGACGAGACTGGGCATGTTCAG | 139 |
| 16722960 | 994502 | RN5S338 | GATCAGACGAGACTGGGCATGTTCA | 140 |
| 16722960 | 995195 | RN5S338 | AGATCAGACGAGACTGGGCATGTTC | 141 |
| 16722960 | 1102153 | RN5S338 | GAGATCAGACGAGACTGGGCATGTT | 142 |
| 16722960 | 1101964 | RN5S338 | CGAGATCAGACGAGACTGGGCATGT | 143 |
| 16733995 | 409092 | IRF7 | CTTTTTATTAGACTGGGCGGCCGCG | 144 |
| 16733995 | 429973 | IRF7 | TTCTGGAGTTCTCATTAGACTGGGT | 145 |
| 16733995 | 946056 | IRF7 | TCCATAAGGAAGCACTCGATGTCGT | 146 |
| 16733995 | 509264 | IRF7 | TCATAGAGGCTGTTGGCGCTGGACA | 147 |
| 16733995 | 191856 | IRF7 | ccCGAAGCCCAGGTAGATGGTATAG | 148 |
| 16733995 | 43097 | IRF7 | GAAGCCCAGGTAGATGGTATAGCGT | 149 |
| 16733995 | 212818 | IRF7 | TGTCACAGTTCCGAGGCAGCAGGCA | 150 |
| 16733995 | 298384 | IRF7 | TATAGGAACGTGCAGCTCGGGTGTC | 151 |
| 16733995 | 1223216 | IRF7 | GAGGGTGACAGGTACGGCTCTGCCT | 152 |

APPENDIX 2-continued

PROBE SEQUENCES

| Probe Set ID | Probe ID | Gene Symbol | Probe Sequence | SEQ ID NO |
|---|---|---|---|---|
| 16733995 | 296159 | IRF7 | TGACAGGTACGGCTCTGCCTGGTGC | 153 |
| 16733995 | 1017053 | IRF7 | CTGCATCCGGAAGGGAATCCTGTGC | 154 |
| 16733995 | 24829 | IRF7 | CATCCGGAAGGGAATCCTGTGCTGG | 155 |
| 16733995 | 607584 | IRF7 | CTTCTAAAGTGTCCGTCCAGGTGCA | 156 |
| 16733995 | 1265145 | IRF7 | TGACGCTGTCAGCAGATGGTCTGCC | 157 |
| 16733995 | 625497 | IRF7 | AGTCCAGCATGTGTGTGTGCCAGGA | 158 |
| 16733995 | 611948 | IRF7 | AAGTCAGGGTGAACGTAAGCAGCTC | 159 |
| 16733995 | 970667 | IRF7 | AGTCAGGGTGAACGTAAGCAGCTCC | 160 |
| 16733995 | 489112 | IRF7 | CGGCTGAGCGCGTACACCTTGTGCG | 161 |
| 16733995 | 1166142 | IRF7 | TGAGCGCGTACACCTTGTGCGGGTC | 162 |
| 16733995 | 943014 | IRF7 | CAGTGCGCAGCGGAAGTTGGTTTTC | 163 |
| 16733995 | 360488 | IRF7 | AAGTTGGTTTTCCAGCCGGCGCGCT | 164 |
| 16733995 | 299683 | IRF7 | GACAGAACACGTGTGCCGGGCCCGC | 165 |
| 16733995 | 344611 | IRF7 | TCCTTGCGCGCGAAGTGCTTCCAGG | 166 |
| 16733995 | 20562 | IRF7 | TAGGTGGCGGTCAGGTGTTATAACA | 167 |
| 16733995 | 736819 | IRF7 | GACTGAGGGCTTGTAGCCACCGACG | 168 |
| 16733995 | 1220439 | IRF7 | TGTTGAACCAGTGTCCAGGCCTGGC | 169 |
| 16733995 | 832274 | IRF7 | GAAAGCGAAACCTAAACAGTGGCGC | 170 |
| 16733995 | 869962 | IRF7 | GAAACCTAAACAGTGGCGCTTCGCA | 171 |
| 16738536 | 709536 | TIMM10 | AGCGCTACCACTCCGGGATCTTGAA | 172 |
| 16738536 | 1117260 | TIMM10 | TCTCTACAGAGAGCCTAGGCCTGGC | 173 |
| 16738536 | 1130572 | TIMM10 | GATGACACCCAACAGGGAGCACGTT | 174 |
| 16738536 | 18050 | TIMM10 | CACCCCAGGGTGTATACTGACAGGG | 175 |
| 16738536 | 587840 | TIMM10 | AACTTTTTGCCCATCCGCTCATGGA | 176 |
| 16738536 | 1062427 | TIMM10 | GGTACTTAGAGACACATCGGTCCAG | 177 |
| 16738536 | 133813 | TIMM10 | TAGTGAGGAGGCACACACTTCCGGT | 178 |
| 16738536 | 1309190 | TIMM10 | CTGTTGTACATATCGGCCATCATCT | 179 |
| 16738536 | 1307702 | TIMM10 | TGTTGTACATATCGGCCATCATCTC | 180 |
| 16738536 | 250889 | TIMM10 | AGCTGTTGGGCCCTGAGAGGATCCA | 181 |
| 16738536 | 250483 | TIMM10 | GCTGTTGGGCCCTGAGAGGATCCAT | 182 |
| 16738536 | 174896 | TIMM10 | CTCAGCCTAGCACCGTGGAAGGGAT | 183 |
| 16738536 | 598942 | TIMM10 | CCTAGCACCGTGGAAGGGATCTCCT | 184 |
| 16738536 | 100662 | TIMM10 | CTAGCACCGTGGAAGGGATCTCCTT | 185 |
| 16738536 | 225436 | TIMM10 | AAGGGATCTCCTTCTGGCCTCCTAA | 186 |
| 16738536 | 1382104 | TIMM10 | CTGGGAGCAGACATCACCATCAGCA | 187 |
| 16738536 | 1381156 | TIMM10 | TGGGAGCAGACATCACCATCAGCAC | 188 |
| 16738536 | 983930 | TIMM10 | CACTGCCTGGGACGGATCACAATGC | 189 |

APPENDIX 2-continued

PROBE SEQUENCES

| Probe Set ID | Probe ID | Gene Symbol | Probe Sequence | SEQ ID NO |
|---|---|---|---|---|
| 16738536 | 296005 | TIMM10 | CTGCCTGGGACGGATCACAATGCCC | 190 |
| 16738536 | 1141349 | TIMM10 | CAACTTCTGACAAATACTATAACGT | 191 |
| 16738536 | 671461 | TIMM10 | TGACAAATACTATAACGTTACCCGC | 192 |
| 16738536 | 946583 | TIMM10 | GCTCCAGCGGAAGCACGTGGGTTAC | 193 |
| 16738536 | 1074148 | TIMM10 | TCCAGCGGAAGCACGTGGGTTACTT | 194 |
| 16738536 | 1167764 | TIMM10 | CCAGCGGAAGCACGTGGGTTACTTC | 195 |
| 16738536 | 156510 | TIMM10 | GAAAGTCCCGCCTCTTCTTTGATTC | 196 |
| 16742150 | 64395 | XRRA1 | CATGAACTCGAGGAAGTGGCCGAAC | 197 |
| 16742150 | 254835 | XRRA1 | TCTAAGGGCCTTTCCTGCACTGACA | 198 |
| 16742150 | 705895 | XRRA1 | TAGTGGAGCCTCTGTAATGTTCCGG | 199 |
| 16742150 | 611410 | XRRA1 | TTCTGAAGAGTGTCCAGCTTGGGCT | 200 |
| 16742150 | 1373220 | XRRA1 | CAGCAGTTCTTCATAGCCGTGGTAC | 201 |
| 16742150 | 529167 | XRRA1 | GGACAGGGTCTCTTCACTATGCACA | 202 |
| 16742150 | 695327 | XRRA1 | GAGTGAGCAGCTCTACAGCCAGGTT | 203 |
| 16742150 | 437545 | XRRA1 | TAAGTGGATTCCCAGTCGCTCCTGG | 204 |
| 16742150 | 114412 | XRRA1 | TCGTGTATGGGCCACCAGAGGGTTG | 205 |
| 16742150 | 948787 | XRRA1 | TGAAAGACGAACTCGCAGAGAGATG | 206 |
| 16742150 | 743989 | XRRA1 | TAGGCCAGGCTAAGGTATCTCAGCT | 207 |
| 16742150 | 868330 | XRRA1 | TCCAGGGTAAGATGAAAACACAACC | 208 |
| 16742150 | 1063743 | XRRA1 | TGATTGATGCCTAGAGCACCCAGGA | 209 |
| 16742150 | 231585 | XRRA1 | GGTCAACATCCTTTTTCATGGGCAG | 210 |
| 16742150 | 537282 | XRRA1 | GTTGGAGAGTCTGTTGTCATCCAGC | 211 |
| 16742150 | 703987 | XRRA1 | GGATGTACCTCTTGCTTGTCAGCGA | 212 |
| 16742150 | 104352 | XRRA1 | TTAGGGCTGGAAACGTGTGAAATGC | 213 |
| 16742150 | 1325693 | XRRA1 | TCTTTAATGATATGCTCCTATCAAG | 214 |
| 16742150 | 1198852 | XRRA1 | TCTGGAGGTGCAAGAGACAAACCAC | 215 |
| 16742150 | 238872 | XRRA1 | CCAGGATATGTCCAGGAAGGTCCAC | 216 |
| 16742150 | 344281 | XRRA1 | TCCGGCACGCGAAGCAGATTTCTGG | 217 |
| 16742150 | 657775 | XRRA1 | GATCTTTGACTTTGGGAATGGCCCC | 218 |
| 16742150 | 798243 | XRRA1 | TTAGTAACTGCGACGCGACGGCAGA | 219 |
| 16743922 | 1039363 | CARD17 | TACTGGGAAGAGATAGAAACGTCTT | 220 |
| 16743922 | 711361 | CARD17 | CGAAGTAACTCTTTCAGTGCTGGGC | 221 |
| 16743922 | 1026980 | CARD17 | GGAAGGAAGTACTATTTGAGAATCT | 222 |
| 16743922 | 675758 | CARD17 | GGAAGTACTATTTGAGAATCTTGTG | 223 |
| 16743922 | 1289587 | CARD17 | GAAGTACTATTTGAGAATCTTGTGT | 224 |
| 16743922 | 40508 | CARD17 | GTAGTAAGGTGATTTCCAGATGTTG | 225 |
| 16743922 | 373360 | CARD17 | GAGCCCCTTTCCGAATAACAGAGTC | 226 |

APPENDIX 2-continued

PROBE SEQUENCES

| Probe Set ID | Probe ID | Gene Symbol | Probe Sequence | SEQ ID NO |
|---|---|---|---|---|
| 16743922 | 1073423 | CARD17 | AACAGAGTCAAGCAAAGCTCGGGCC | 227 |
| 16743922 | 882591 | CARD17 | TGTCTCCAATAATTCACCCAGTAAG | 228 |
| 16743922 | 176202 | CARD17 | TTATTGTACCTTCGCCCACTGAACG | 229 |
| 16743922 | 972120 | CARD17 | TCGCCCACTGAACGGATAAACTGCT | 230 |
| 16743922 | 888234 | CARD17 | GCCCACTGAACGGATAAACTGCTTT | 231 |
| 16748095 | 322140 | KLRG1 | AGTCGAGACTCGAAGCTTCCACGCG | 232 |
| 16748095 | 1032773 | KLRG1 | TGTCGTTAAGAAAGCCAGGACGCAC | 233 |
| 16748095 | 452740 | KLRG1 | CCAAAGCTTTCATTGTGGGAAAACT | 234 |
| 16748095 | 1127603 | KLRG1 | TCTGGGCCCAAAGCTTTCATTGTGG | 235 |
| 16748095 | 1169308 | KLRG1 | TGTAAGTACACTCTCCCAATTTGGT | 236 |
| 16748095 | 895305 | KLRG1 | AAAGAAAACTTCGTGCTCAGGTGAC | 237 |
| 16748095 | 1326320 | KLRG1 | CTTCAGCTAAGATCTTTCACATGCA | 238 |
| 16748095 | 1190235 | KLRG1 | GCCGTAGGCAACTCTAACATGGAAT | 239 |
| 16748095 | 83998 | KLRG1 | CATAGTCATTCTGGGCTTGGGTTGC | 240 |
| 16748095 | 696857 | KLRG1 | TCTCAGGGCTCTATGTAAAAATGGC | 241 |
| 16748095 | 901717 | KLRG1 | TAGTGGGAACTGAGATCCAGGCCAT | 242 |
| 16748095 | 31823 | KLRG1 | GAAAGTCAGGGAAGGATATCGCATC | 243 |
| 16748095 | 1266182 | KLRG1 | GAAGAACTGCAGTCAGAAGCCCCAA | 244 |
| 16748095 | 775430 | KLRG1 | CACAGGATCCACTGGTATAGCAGCA | 245 |
| 16748095 | 1145312 | KLRG1 | GACAGCTGGCACAAGTGGAGTAGTT | 246 |
| 16748095 | 1049607 | KLRG1 | TCTGGGCAGCTAGGACAGCTGGCAC | 247 |
| 16748095 | 745155 | KLRG1 | TGAGTCTCTGGCTAGGCAGAATTCC | 248 |
| 16748095 | 466685 | KLRG1 | GATTGTCCGTTATCACAAGGAGGTG | 249 |
| 16748095 | 829858 | KLRG1 | TCACTGAGGAAAACTTGGAGCAGGC | 250 |
| 16748095 | 502494 | KLRG1 | CAGCCAGAATTGTTCCTCAGACCAA | 251 |
| 16748095 | 144478 | KLRG1 | TTTGTTGATGGCACCGCATGTCTGC | 252 |
| 16748095 | 898161 | KLRG1 | TAAAGGAACTTCACAGCTTGAGGCT | 253 |
| 16748095 | 248393 | KLRG1 | CAAAGAGAATCCATCAGTTAGGCAT | 254 |
| 16748095 | 59951 | KLRG1 | TACCATCAGGGATCAGTAATGTACA | 255 |
| 16748095 | 584511 | KLRG1 | AATAAAGCTTGATCTGCAAAGGGAC | 256 |
| 16748095 | 740847 | KLRG1 | GAATAAAGCTTGATCTGCAAAGGGA | 257 |
| 16748095 | 648195 | KLRG1 | GAAAATGCCTTATCGAATTGACTGC | 258 |
| 16748095 | 842406 | KLRG1 | TGTATGTCCAAACTCTACTGAGGAG | 259 |
| 16748327 | 857438 | KLRD1 | GAAGTGCCAAATCCAATCCAGCCTG | 260 |
| 16748327 | 969702 | KLRD1 | GAGTCTCTTGAACTTGATGAGCTGA | 261 |
| 16748327 | 974856 | KLRD1 | CACAAGCCTCTGAAGTGTTCCAGGA | 262 |
| 16748327 | 575299 | KLRD1 | GAATCATCTATTGGTGAGACATGTA | 263 |

APPENDIX 2-continued

PROBE SEQUENCES

| Probe Set ID | Probe ID | Gene Symbol | Probe Sequence | SEQ ID NO |
|---|---|---|---|---|
| 16748327 | 513675 | KLRD1 | GGCACGATGTGTACTTTTTCAGAAA | 264 |
| 16748327 | 510571 | KLRD1 | GAAATTATGTTCCAAGAGCGAAGTA | 265 |
| 16748327 | 902011 | KLRD1 | GGTAACAACTTTGAGGCCTGGCTTC | 266 |
| 16748327 | 615724 | KLRD1 | CAGAAACTAGTGACGGAGAATCCAC | 267 |
| 16748327 | 887482 | KLRD1 | CAGAAATTAACCTCCACAGAGTGGT | 268 |
| 16748327 | 659077 | KLRD1 | TTATGGAGACTTGCTTAGAAAAACT | 269 |
| 16748327 | 412402 | KLRD1 | TATTACACATTAGCAAGATGAAGCC | 270 |
| 16748327 | 1089574 | KLRD1 | GGTCCTGGAGTAAATGCTGGCTCAA | 271 |
| 16748327 | 474900 | KLRD1 | CTTTCTGGAGTTCTATGTTGGGTCC | 272 |
| 16748327 | 1224593 | KLRD1 | GAAGTAACAGTTGCACCGGTACCCA | 273 |
| 16748327 | 656895 | KLRD1 | CAGAGATGCCGACTTTCGTTCCAAG | 274 |
| 16748327 | 247282 | KLRD1 | GAGTCCAATCCAGTAAAATTGTTGA | 275 |
| 16748327 | 531680 | KLRD1 | TGTAAGAGAGTCCAATCCAGTAAAA | 276 |
| 16748327 | 1097424 | KLRD1 | TACTGGGAGAGTGCAGAGCCATTCT | 277 |
| 16748327 | 1099245 | KLRD1 | GATACTGGGAGAGTGCAGAGCCATT | 278 |
| 16748327 | 1311956 | KLRD1 | TCCATTTGGATTATACGCTATGCAG | 279 |
| 16748327 | 632568 | KLRD1 | CATAGTGACATGGTGCCTGCAGTCC | 280 |
| 16757347 | 255130 | OAS3 | TCTGGCGCGGCCTTCGGATTTCTGG | 281 |
| 16757347 | 359923 | OAS3 | CTTGACAGTTTTCAGCACCCGCGGG | 282 |
| 16757347 | 60760 | OAS3 | CAAGATCTACGGATGTCAGGCGGAA | 283 |
| 16757347 | 527423 | OAS3 | CCTGGAATGGTCTAGGAACCCCTCA | 284 |
| 16757347 | 141317 | OAS3 | TCCAGGCAGTGGCTGAGGGAAACTC | 285 |
| 16757347 | 832091 | OAS3 | TGTCTGGAGAAACCCTTCCAAGTGG | 286 |
| 16757347 | 1055726 | OAS3 | CCTGGCAGGATAGGGAAAGACTTCT | 287 |
| 16757347 | 962396 | OAS3 | TGACAGTCCAGAAAACACACAGGTG | 288 |
| 16757347 | 123820 | OAS3 | GACTCTTGAGGCCTTGTGAACACAG | 289 |
| 16757347 | 1245424 | OAS3 | AAGAACAGCTCAGATCAGGGACCCT | 290 |
| 16757347 | 1327922 | OAS3 | TCTCATCAAGGATCTCTGCGCGGCG | 291 |
| 16757347 | 1253800 | OAS3 | CAGGTTCTTCAGCTTGACAGGGCGA | 292 |
| 16757347 | 1147136 | OAS3 | TGTTGAAACAATCCTGCCTGCAGCC | 293 |
| 16757347 | 254610 | OAS3 | TATCAACGGCCTTGTTCACCTGGGC | 294 |
| 16757347 | 765105 | OAS3 | TGTTGCCCTGCTCAGTGAACTGGCT | 295 |
| 16757347 | 582051 | OAS3 | TTCAAACTTGACCTCGAACTGCCGC | 296 |
| 16757347 | 290200 | OAS3 | GAAGTCCCGTTGTAGCTCTGTGAAG | 297 |
| 16757347 | 163861 | OAS3 | TGCGGAAGCCCTCAGCCATGTTGAA | 298 |
| 16757347 | 1171829 | OAS3 | GCTCCTATACACTACAGGGCAGGTA | 299 |
| 16757347 | 375500 | OAS3 | CAGTCAAGTCTTTCCATCCGAGGGT | 300 |

APPENDIX 2-continued

PROBE SEQUENCES

| Probe Set ID | Probe ID | Gene Symbol | Probe Sequence | SEQ ID NO |
|---|---|---|---|---|
| 16761350 | 1138120 | KLRC3 | TATTTTCCAATCATAACGGTCTGCA | 301 |
| 16761350 | 1294744 | KLRC3 | TCAAACTATATAGAGAGGGAAAAGT | 302 |
| 16761350 | 472797 | KLRC3 | AACATCATCTAGTTAAAAATAGGGA | 303 |
| 16761350 | 1334607 | KLRC3 | CACAAGCTAAATGGTACATGAGCAC | 304 |
| 16761350 | 485025 | KLRC3 | GCTAAATGGTACATGAGCACTCAGG | 305 |
| 16761350 | 761465 | KLRC3 | TGATGCACTGCAAGCTCAAGCGCTT | 306 |
| 16761350 | 761138 | KLRC3 | GATGCACTGCAAGCTCAAGCGCTTT | 307 |
| 16761350 | 1156635 | KLRC3 | TGCACTGCAAGCTCAAGCGCTTTAA | 308 |
| 16761350 | 1153599 | KLRC3 | GCACTGCAAGCTCAAGCGCTTTAAT | 309 |
| 16761350 | 1320459 | KLRC3 | CACACTGGTCTGATATAAGTCCACG | 310 |
| 16761350 | 880292 | KLRC3 | GGTCTGATATAAGTCCACGTACATG | 311 |
| 16761350 | 1364809 | KLRC3 | TCCACGTACATGTAGCATTGCACAG | 312 |
| 16761350 | 1063513 | KLRC3 | AAAGCAGACTAGAAGAGTTCTTTGA | 313 |
| 16761350 | 960254 | KLRC3 | AAGCAGACTAGAAGAGTTCTTTGAA | 314 |
| 16771417 | 767946 | OASL | CACGTCTGGCCTGGGATAACTCATT | 315 |
| 16771417 | 773191 | OASL | TGTAAAACTGGTGAAGACCTGGGAC | 316 |
| 16771417 | 1234405 | OASL | CAGAAATGTACAGAGAAGTCTCCCA | 317 |
| 16771417 | 76037 | OASL | TCTTCGAGAGGATGAGAGTGTCACT | 318 |
| 16771417 | 872009 | OASL | TATTTGGCTAAGGAGCACCTGCTGC | 319 |
| 16771417 | 109865 | OASL | ACTGTCAAGTGGATGTCTCGTGCCC | 320 |
| 16771417 | 236353 | OASL | GAATTTGTCCAAGTTCACGGAGCCC | 321 |
| 16771417 | 642139 | OASL | TGCAGCTGGCCCTTAAACGGTGACT | 322 |
| 16771417 | 1229876 | OASL | CTTGACAGCCCAGAGAGGAGCCATT | 323 |
| 16771417 | 163043 | OASL | TGGGAGGCCCTCTGAGCAACGATGT | 324 |
| 16771417 | 644977 | OASL | TCTGTACCCTTCTGCCACGTTGAGG | 325 |
| 16771417 | 649352 | OASL | GGTGAAGCCTTCGTCCAACATGAAA | 326 |
| 16771417 | 137213 | OASL | GCTTAGTTGGCCGATGTTTCACGAA | 327 |
| 16771417 | 1272089 | OASL | TGGGCAGAAATTTCCAGGACCACCG | 328 |
| 16771417 | 135172 | OASL | TCTGTAGGCAGGCACAATGGTGACC | 329 |
| 16771417 | 785591 | OASL | CCCCTGGTCTGGATGGTGAAGACGA | 330 |
| 16771417 | 1112485 | OASL | TGGTGCTCCTGAGAACCGTGCCATT | 331 |
| 16771417 | 949899 | OASL | ACTGAGCCACGAAGGAGTCCAGCCT | 332 |
| 16771417 | 1295565 | OASL | GCTGGTGTGCTATACAGTTCCTGCA | 333 |
| 16771417 | 1297212 | OASL | TGGGCAGATATATAGCCAGGCTCCT | 334 |
| 16771417 | 603816 | OASL | AAACCAGGTGTGACGGGCTGACTCC | 335 |
| 16771417 | 174376 | OASL | CTTGGAGACACCCTTGCTGCAGTAG | 336 |
| 16772285 | 1126337 | LOC387895 | CATTCTGCTGCTATGAGCGAGGAGA | 337 |

APPENDIX 2-continued

PROBE SEQUENCES

| Probe Set ID | Probe ID | Gene Symbol | Probe Sequence | SEQ ID NO |
|---|---|---|---|---|
| 16772285 | 1397880 | LOC387895 | GCTTTAGCTCATGGTTGGCATCTGA | 338 |
| 16772285 | 12222 | LOC387895 | TAACTCAGGGTTTCCTAGCGAGAAG | 339 |
| 16772285 | 1019962 | LOC387895 | GGGCCATGAAGGTGTTCCCGCCATT | 340 |
| 16772285 | 419172 | LOC387895 | CATGAAGGTGTTCCCGCCATTGAGA | 341 |
| 16772285 | 545238 | LOC387895 | CAGCTCTGGAGAGTCATTCCATTCC | 342 |
| 16772285 | 1169029 | LOC387895 | TGCCACCATGACACGGAACAGCTTT | 343 |
| 16772285 | 1235905 | LOC387895 | GAACTTTCAGGCTCTCCTAATGGCT | 344 |
| 16772285 | 957489 | LOC387895 | GATACCTAGAAGGTTTGCCCCTCAG | 345 |
| 16772285 | 755179 | LOC387895 | TGTATCCAGGCTCCAGGTGCATAGA | 346 |
| 16772285 | 779644 | LOC387895 | TGAAGATTCCTGAAGGCCCTGGTCC | 347 |
| 16772285 | 667095 | LOC387895 | CCCTGGTCCTAGGTCATAGTTGTTC | 348 |
| 16772285 | 1219493 | LOC387895 | TTGAGTTACAGGGACCGAAGCAGCT | 349 |
| 16772285 | 791436 | LOC387895 | TGGATTCAGATCTGGGCGATACCGC | 350 |
| 16772285 | 359385 | LOC387895 | AACGTGGTTTTAGGATGTGAGTCTC | 351 |
| 16772285 | 858521 | LOC387895 | CTATGGTTCAAATGTGGGATCTCAC | 352 |
| 16772285 | 363506 | LOC387895 | GACGTGGTTTCATCTTGCAATTCGA | 353 |
| 16772285 | 156152 | LOC387895 | AGGTCCTGCCCGCTAACAGAGAGAG | 354 |
| 16772285 | 151154 | LOC387895 | TGGATGAAGCCCCTTAGTCCTCAAT | 355 |
| 16772285 | 544867 | LOC387895 | GCAGTGCTTCAGTCAAGGTGATCAA | 356 |
| 16772285 | 900280 | LOC387895 | CACCTGTGAAACTGTCCCTGTAAAC | 357 |
| 16772285 | 1180877 | LOC387895 | CGCTTAGCATTCACCATGAGGGAAG | 358 |
| 16772285 | 1096596 | LOC387895 | TCGATTAGAGAGTGTGCTGCGGCAA | 359 |
| 16778559 | 465915 | EPSTI1 | CAACTCCTGGTTGCATGCTGGAAAA | 360 |
| 16778559 | 202972 | EPSTI1 | AGTGAGGCACACCAAGCATAGACGC | 361 |
| 16778559 | 1069341 | EPSTI1 | GAAAGACAAGCCTGTAGCACCCATA | 362 |
| 16778559 | 1073179 | EPSTI1 | AACCTGAAAGCATCAAGTGACTCCC | 363 |
| 16778559 | 388855 | EPSTI1 | TAATGTAGCATTTCCCTGGCAGTAG | 364 |
| 16778559 | 66754 | EPSTI1 | GCATAAATGAGGACAAGGAGAAGCC | 365 |
| 16778559 | 321472 | EPSTI1 | TAGGTGCCTCGAAAAACTAATAGA | 366 |
| 16778559 | 948101 | EPSTI1 | GGTGCCTCGAAAAACTAATAGAGA | 367 |
| 16778559 | 123919 | EPSTI1 | CAGATTGCTCGAGGCCACCTGGTTG | 368 |
| 16778559 | 521358 | EPSTI1 | GGAGTCGGTCCAGAAAAGCATTATT | 369 |
| 16778559 | 367695 | EPSTI1 | GGTGGATTTTGGCTCTTTCTTGCTC | 370 |
| 16778559 | 1238287 | EPSTI1 | TGCCGTTTCAGTTCCAGTAATTCAC | 371 |
| 16778559 | 667159 | EPSTI1 | CAGCTGTGATCCCTAGGCAGGATAG | 372 |
| 16778559 | 1049850 | EPSTI1 | CTGTGATCCCTAGGCAGGATAGGAA | 373 |
| 16778559 | 1313170 | EPSTI1 | CCATGTTGAGGATTGTGGGCCACAA | 374 |

APPENDIX 2-continued

PROBE SEQUENCES

| Probe Set ID | Probe ID | Gene Symbol | Probe Sequence | SEQ ID NO |
|---|---|---|---|---|
| 16778559 | 1041627 | EPSTI1 | GTTTGCTCAAGAACTCAGCGGTTTT | 375 |
| 16778559 | 955415 | EPSTI1 | TTTGCTCAAGAACTCAGCGGTTTTG | 376 |
| 16778559 | 1202698 | EPSTI1 | CCGTCTGGGCACCAGGTGAACCGGT | 377 |
| 16778559 | 343646 | EPSTI1 | TAAGCCAGGCGAGAAATATCAAATC | 378 |
| 16778559 | 1232576 | EPSTI1 | CAAGAGTCAGCACAGAGGGTTCGAA | 379 |
| 16778559 | 102994 | EPSTI1 | TGCTACAGGTGGAGACCCTTGCTCT | 380 |
| 16778559 | 135779 | EPSTI1 | GGTTTCAGGCACTCCAGACCACTGT | 381 |
| 16778559 | 1399947 | EPSTI1 | TAGTCCCTGCATGGCTGTGATTGTC | 382 |
| 16778559 | 1091105 | EPSTI1 | CAAAAACGAGTAAGATGTGGTCCCT | 383 |
| 16778559 | 19416 | EPSTI1 | CATTTCTCCGGTTTATATTTGGTGC | 384 |
| 16778559 | 753527 | EPSTI1 | TATTTGGTGCTATCAAGGTGTATGC | 385 |
| 16778559 | 1055393 | EPSTI1 | TAAGAGGCTAGTTTATCTGCGAGTC | 386 |
| 16778559 | 983023 | EPSTI1 | TCTTGCTGGGACGTAGGCTTGCTCC | 387 |
| 16778559 | 168760 | EPSTI1 | TCTTGTTGACCCTTACCTGTTAGTG | 388 |
| 16778559 | 756146 | EPSTI1 | GTGCACGACGCTCTCCCGCGAAGGG | 389 |
| 16778559 | 202427 | EPSTI1 | GGAGTTCACCACTCTATTGCGGGTG | 390 |
| 16778559 | 327005 | EPSTI1 | CGGCTGGGACGCTTAGCGAGTCTCA | 391 |
| 16778559 | 1153908 | EPSTI1 | TAGCGAGTCTCAAGATGGGATTCCA | 392 |
| 16791436 | 1325372 | GZMH | TACACCAGAGATCCATTTATTACAG | 393 |
| 16791436 | 218334 | GZMH | TATTACAGTCCTGCAACCCCGACTG | 394 |
| 16791436 | 61216 | GZMH | CAGGCCCAGAGGAAGGTTAGTCTCA | 395 |
| 16791436 | 944542 | GZMH | GCCCAGAGGAAGGTTAGTCTCATGC | 396 |
| 16791436 | 460195 | GZMH | GAGGAAGGTTAGTCTCATGCCTGCT | 397 |
| 16791436 | 627288 | GZMH | GCAGGAAGTGTGAGACCTTGATGTA | 398 |
| 16791436 | 417994 | GZMH | TTTTGTTTCCATAGGAGAGAATACC | 399 |
| 16791436 | 68633 | GZMH | TTTCCATAGGAGAGAATACCTTGGG | 400 |
| 16791436 | 20954 | GZMH | GAAACCGGTCTGTGTCTTCTTTGGA | 401 |
| 16791436 | 299361 | GZMH | TGGAAGAGACGTTCACACTGGCAGT | 402 |
| 16791436 | 1000239 | GZMH | AGTGCTCATTGAGACATAACCCCAG | 403 |
| 16791436 | 603476 | GZMH | CAGAGCTGTTGGTGTTGACTCCTTC | 404 |
| 16791436 | 601589 | GZMH | GAGCTGTTGGTGTTGACTCCTTCCA | 405 |
| 16797490 | 639258 | IGHV3-20 | CTGCATAACCTGTGCTACCACCATT | 406 |
| 16797490 | 627535 | IGHV3-20 | TGCATAACCTGTGCTACCACCATTC | 407 |
| 16797490 | 751562 | IGHV3-20 | TAACCTGTGCTACCACCATTCCAAT | 408 |
| 16797490 | 1277561 | IGHV3-20 | CACCATTCCAATTAATACCAGAGAC | 409 |
| 16797490 | 1277858 | IGHV3-20 | ACCATTCCAATTAATACCAGAGACC | 410 |
| 16797490 | 408377 | IGHV3-20 | CCATTCCAATTAATACCAGAGACCC | 411 |

APPENDIX 2-continued

PROBE SEQUENCES

| Probe Set ID | Probe ID | Gene Symbol | Probe Sequence | SEQ ID NO |
|---|---|---|---|---|
| 16797490 | 1400985 | IGHV3-20 | GACCCAGCTCATGCCATAATCATCA | 412 |
| 16797490 | 884431 | IGHV3-20 | CCAGCTCATGCCATAATCATCAAAG | 413 |
| 16799289 | 1293117 | C15orf54 | GAAAGTTATATCTCTGTGTACATCC | 414 |
| 16799289 | 303340 | C15orf54 | GAATCCAGCACGTGTACTCCTAAGT | 415 |
| 16799289 | 1300540 | C15orf54 | TAATGAGAGAATCCAGCACGTGTAC | 416 |
| 16799289 | 1056754 | C15orf54 | TGATTCTGGATAGTTGACTCATGAA | 417 |
| 16799289 | 582631 | C15orf54 | CCACACCGCTTGAATAATAACTATG | 418 |
| 16799289 | 858759 | C15orf54 | GCCATGGCATCAAATCTCCTTTTAA | 419 |
| 16799289 | 1106899 | C15orf54 | CTAAGTCAGTGAGGTTTGCCATGGC | 420 |
| 16799289 | 537954 | C15orf54 | GAAGAACAGTCTAAGTCAGTGAGGT | 421 |
| 16799289 | 626193 | C15orf54 | GAAGCCATATGTGTTTCAGCCACTT | 422 |
| 16799289 | 624527 | C15orf54 | TGAAGCCATATGTGTTTCAGCCACT | 423 |
| 16799289 | 783180 | C15orf54 | TCTTGACACACTGAAGCCATATGTG | 424 |
| 16799289 | 682580 | C15orf54 | TCAGGTCTTCTTGACACACTGAAGC | 425 |
| 16799289 | 750014 | C15orf54 | GCCACCGTGCTTGCCAGTAATGAAT | 426 |
| 16799289 | 845595 | C15orf54 | TTCAAGATCAAACTAGGCCATGGAG | 427 |
| 16799289 | 1337167 | C15orf54 | CAAAGAGTAATGTCAATCCGCTGGA | 428 |
| 16799289 | 1139060 | C15orf54 | CAAGAGTCAGCCAATATAGTGCACA | 429 |
| 16799289 | 69435 | C15orf54 | CCAATACGAGGAGAGTGTCACTGAC | 430 |
| 16799289 | 563212 | C15orf54 | TGAACCTCTTGGTGACCCGGAATGA | 431 |
| 16799289 | 694060 | C15orf54 | TCCCAATGTCTAGCGTAGTGCCCAG | 432 |
| 16799289 | 1199154 | C15orf54 | TATTCTGATTGCAACAGTAGGCAGC | 433 |
| 16819539 | 536443 | GPR56 | CAGGCACCCAGTCTGAGCTTGTCTG | 434 |
| 16819539 | 884741 | GPR56 | AGAGGCTTAACCTGCCAGCCCTGGT | 435 |
| 16819539 | 982586 | GPR56 | GGCGGCTGGACCACCTTTCAGGATC | 436 |
| 16819539 | 162145 | GPR56 | TGCTGTCCAGCCCTTGTTTGGGTAC | 437 |
| 16819539 | 162573 | GPR56 | CTGCTGTCCAGCCCTTGTTTGGGTA | 438 |
| 16819539 | 579213 | GPR56 | ACAGAGACTTTGAAGCTGGGCCACC | 439 |
| 16819539 | 1183446 | GPR56 | GACGGAGTCACTCTTGGAAGTCACC | 440 |
| 16819539 | 982848 | GPR56 | TTCCTCCGACGGAGTCACTCTTGGA | 441 |
| 16819539 | 611067 | GPR56 | GCAGGAACAGTGTCGTCTGCAGCAG | 442 |
| 16819539 | 943048 | GPR56 | CAGACTCAGCAGGAACAGTGTCGTC | 443 |
| 16819539 | 1026664 | GPR56 | GAAGCGAAAGTCTTCCCTGTGGCCC | 444 |
| 16819539 | 838761 | GPR56 | TGCAGAAGCGAAAGTCTTCCCTGTG | 445 |
| 16819539 | 419729 | GPR56 | CAGCATGTCGGTTCCAGTAGAGGCA | 446 |
| 16819539 | 1254623 | GPR56 | TTTGTCACTCAGCAAGAAGTCACGC | 447 |
| 16819539 | 1382057 | GPR56 | CCACCGAGGCATTGTGAGCGGCCGT | 448 |

APPENDIX 2-continued

PROBE SEQUENCES

| Probe Set ID | Probe ID | Gene Symbol | Probe Sequence | SEQ ID NO |
|---|---|---|---|---|
| 16819539 | 136392 | GPR56 | TCCACCGAGGCATTGTGAGCGGCCG | 449 |
| 16819539 | 158915 | GPR56 | TGGAGGTCCCTTTTGAGCTCGCACA | 450 |
| 16819539 | 210893 | GPR56 | GCTGGAGGTCCCTTTTGAGCTCGCA | 451 |
| 16819539 | 364720 | GPR56 | CAGAGGTCAGTTTCGACTCCAGGCT | 452 |
| 16819539 | 516920 | GPR56 | GGTGTTCTGTACCACAATCCCCAAG | 453 |
| 16819539 | 726048 | GPR56 | GGGTTTCTCTCCTGACGGTCTCACA | 454 |
| 16819539 | 747815 | GPR56 | TCAGGTAGTGCTTGTGCACGGCGTC | 455 |
| 16819539 | 312055 | GPR56 | CACCACGAGTCGGTAGAGGTTGTAC | 456 |
| 16819539 | 997617 | GPR56 | TAGCCAGGGACATAGGTGCCAAAGA | 457 |
| 16819539 | 1177325 | GPR56 | ATAGTTGTCCACATCCACCAGGGCC | 458 |
| 16819539 | 1347949 | GPR56 | GGAGTCCTATGCACAGCCAAGATGA | 459 |
| 16819539 | 1062511 | GPR56 | AAAAGGTAGAGGACGACAAGCTGGA | 460 |
| 16819539 | 1111737 | GPR56 | GGCGCTGTCTGAGTTGCTCTTCAGA | 461 |
| 16819539 | 205618 | GPR56 | GAATTAACCATGATGGGCGGCCGAG | 462 |
| 16830214 | 31530 | FBXO39 | TGTTAGGCAGGGCTTCCAAAAATGA | 463 |
| 16830214 | 133248 | FBXO39 | TGTGTGTTAGGCAGGGCTTCCAAAA | 464 |
| 16830214 | 133301 | FBXO39 | CTGTGTGTTAGGCAGGGCTTCCAAA | 465 |
| 16830214 | 626079 | FBXO39 | TACAGTGCAGCTGTGTGTTAGGCAG | 466 |
| 16830214 | 1351048 | FBXO39 | GAACTGGGATGTACAGTGCAGCTGT | 467 |
| 16830214 | 1143600 | FBXO39 | TTTCTGCAGACAAGAGCAGCCCTGG | 468 |
| 16830214 | 765945 | FBXO39 | TGCATGTACCCTGGAAGGTCTCCCG | 469 |
| 16830214 | 701297 | FBXO39 | GATGCTGTTCCTCCATACCAGGCGG | 470 |
| 16830214 | 526507 | FBXO39 | TCAAGCAGCTCGTCGGAGATACAGT | 471 |
| 16830214 | 567848 | FBXO39 | GACTCATGGTTGTTGTTGAATTCAC | 472 |
| 16830214 | 259598 | FBXO39 | CAAGGAAAGCCCAGATTTTGAAGTA | 473 |
| 16830214 | 450954 | FBXO39 | TTCTGACTCTTCAGGATCCGCTCCA | 474 |
| 16830214 | 332602 | FBXO39 | TTGAATACACGCAGGGCACACTGCC | 475 |
| 16830214 | 222187 | FBXO39 | GGTCTTGTCCTCTTCATTCGTCTCA | 476 |
| 16830214 | 515051 | FBXO39 | TACTTCCTGTAAATTTCCTGCAGGG | 477 |
| 16830214 | 757468 | FBXO39 | AATAGCTAAGCTCTGATTCGATCAG | 478 |
| 16830214 | 495075 | FBXO39 | TACATCACAGAGTAAACGATGACAA | 479 |
| 16830214 | 1132892 | FBXO39 | CGGCAGTGCCCAAGTGTAGTTCTAA | 480 |
| 16830214 | 131382 | FBXO39 | TCAGGTCATGGGCAGTCTCAGCCTT | 481 |
| 16830214 | 860380 | FBXO39 | TAGCGCTTTAAAGCCACCTGGAGCC | 482 |
| 16844999 | 987467 | DHX58 | TAGGTCTGGACTAAGCTCTGGCCCT | 483 |
| 16844999 | 344650 | DHX58 | TTCCCATTGCGGGAGCCTAAGCCAG | 484 |
| 16844999 | 1090483 | DHX58 | TCCAGGGAGAGGTCCGACAAGTTCT | 485 |

APPENDIX 2-continued

PROBE SEQUENCES

| Probe Set ID | Probe ID | Gene Symbol | Probe Sequence | SEQ ID NO |
|---|---|---|---|---|
| 16844999 | 196639 | DHX58 | CACGCGGGACCACTTTTTGGCCTGG | 486 |
| 16844999 | 599401 | DHX58 | CACATTGACATGGTGGGTGCCCTCC | 487 |
| 16844999 | 242944 | DHX58 | GCTGCACGTGCTCCACTGGGAACTG | 488 |
| 16844999 | 765471 | DHX58 | TACTCGGCCTGGTCCATTTTCTGCA | 489 |
| 16844999 | 1291739 | DHX58 | CAAACGCGTATACACTCTGATCGGC | 490 |
| 16844999 | 201230 | DHX58 | TCGTGGCCACCAGAAGGTTCAGGGT | 491 |
| 16844999 | 810254 | DHX58 | CCAATCAGTAGCTGGGCCCGGATGT | 492 |
| 16844999 | 1137231 | DHX58 | CCATGAGTTGCCAAGTGGGCCAGCT | 493 |
| 16844999 | 360391 | DHX58 | GATCTGGGTTTTAGTGACGTGCTCC | 494 |
| 16844999 | 1299515 | DHX58 | TGTGATAGAAATCCTGCAGCGCAGC | 495 |
| 16844999 | 594494 | DHX58 | TGTACTGTTTGCAAGGCTGTTGGCT | 496 |
| 16844999 | 1356086 | DHX58 | GGGTGACATGATGCACCACGTGTCC | 497 |
| 16844999 | 805340 | DHX58 | CATCTGCAGAAGCTCTGCTGTGCAG | 498 |
| 16844999 | 1181367 | DHX58 | AGGGTTGTCACGGTCCAGCGTCCAT | 499 |
| 16844999 | 480340 | DHX58 | TCCCATTGGTAGGACCGAAGCTCCA | 500 |
| 16844999 | 484684 | DHX58 | TCTAGTAGGTAGGTCTGCCCAGGGC | 501 |
| 16844999 | 661479 | DHX58 | GCAGTCCCACTTAACTCAGCCTGGT | 502 |
| 16844999 | 1124342 | DHX58 | GGAGCCAGCTGAGCCGACTTAGGAA | 503 |
| 16844999 | 304493 | DHX58 | GCCAGCTGAGCCGACTTAGGAATCT | 504 |
| 16844999 | 865566 | DHX58 | TCCGGTTAAGTACTGCTGCTGCGCC | 505 |
| 16844999 | 1106892 | DHX58 | TGTGCTCAGCGCAGAGAGCAGAAAT | 506 |
| 16844999 | 1265420 | DHX58 | TCAGCGCAGAGAGCAGAAATCAGAA | 507 |
| 16870200 | 1323326 | BST2 | TCCAAGTTGATAGTCTGCATGCCGT | 508 |
| 16870200 | 1392622 | BST2 | TGTACCATTGCATGGCTTCCACGTG | 509 |
| 16870200 | 358859 | BST2 | CGTGAGTCGTTTACAAGGAGTTTGC | 510 |
| 16870200 | 370046 | BST2 | GCATTACGTTTGCAACTGTGCTTGT | 511 |
| 16870200 | 244386 | BST2 | GGCTTCGTCCATCTCAATCTTCAGT | 512 |
| 16870200 | 560227 | BST2 | TCGTTAGTTGGGTCTGAAGCCGGCT | 513 |
| 16870200 | 77722 | BST2 | CGTTAGTTGGGTCTGAAGCCGGCTC | 514 |
| 16870200 | 527497 | BST2 | TAGTTGGGTCTGAAGCCGGCTCTGA | 515 |
| 16870200 | 558474 | BST2 | TATTTTTGGAGCTCAAAGACCCCA | 516 |
| 16870200 | 286589 | BST2 | ACTCATTGTCCGGAGGGAGGCTCTG | 517 |
| 16870200 | 1245167 | BST2 | CATGACCCGCTCAGAACTGATGAGA | 518 |
| 16870200 | 499247 | BST2 | CAAGGGAATGTTCAAGCGAAAAGCC | 519 |
| 16870200 | 682132 | BST2 | TAGTACTTCTTGTCCGCGATTCTCA | 520 |
| 16870200 | 330209 | BST2 | GCGATTCTCACGCTTAAGACCTGGT | 521 |
| 16870200 | 737897 | BST2 | CGATTCTCACGCTTAAGACCTGGTT | 522 |

APPENDIX 2-continued

PROBE SEQUENCES

| Probe Set ID | Probe ID | Gene Symbol | Probe Sequence | SEQ ID NO |
|---|---|---|---|---|
| 16870200 | 734012 | BST2 | GATTCTCACGCTTAAGACCTGGTTT | 523 |
| 16870200 | 526625 | BST2 | TCTGCAGACGCGTCCTGAAGCTTAT | 524 |
| 16870200 | 223401 | BST2 | TGCAGACGCGTCCTGAAGCTTATGG | 525 |
| 16870200 | 223045 | BST2 | GCAGACGCGTCCTGAAGCTTATGGT | 526 |
| 16870200 | 777670 | BST2 | GACGCGTCCTGAAGCTTATGGTTTA | 527 |
| 16870200 | 884423 | BST2 | TGGTGAAGATAATCAAGGGCACCCC | 528 |
| 16870200 | 1263417 | BST2 | TATCCCCAGCAGAAGCTTACAGCGC | 529 |
| 16870200 | 1199398 | BST2 | TGGGCACTCTGCAATAGTCATACGA | 530 |
| 16870200 | 426260 | BST2 | TGCTGGAATCTTCTACGGGCCACCC | 531 |
| 16874828 | 79649 | NKG7 | GGGCAGATGTGGGACCAGACTTTCC | 532 |
| 16874828 | 199223 | NKG7 | CAGATGTGGGACCAGACTTTCCCGA | 533 |
| 16874828 | 1350139 | NKG7 | GAGGCTCCAGATGAGGCCTTTGGAA | 534 |
| 16874828 | 893884 | NKG7 | TGGAATACAACGCTCAAAACTCATC | 535 |
| 16874828 | 363812 | NKG7 | TCACAAGGTTTCATAGCCAGGACGG | 536 |
| 16874828 | 271287 | NKG7 | GTTTCATAGCCAGGACGGGGACCGC | 537 |
| 16874828 | 1211778 | NKG7 | TTTCATAGCCAGGACGGGGACCGCC | 538 |
| 16874828 | 190114 | NKG7 | ACAGTGAGCACCCAGGCTCAGGGCA | 539 |
| 16874828 | 1081558 | NKG7 | AGCAAGAGGATAGCTGAGACCCAGC | 540 |
| 16874828 | 1079855 | NKG7 | GCAAGAGGATAGCTGAGACCCAGCC | 541 |
| 16874828 | 811922 | NKG7 | CAAGAGGATAGCTGAGACCCAGCCC | 542 |
| 16874828 | 187240 | NKG7 | AGGCTGGTCCCACCGCTCGCTGGTG | 543 |
| 16874828 | 929847 | NKG7 | TCGCTGGTGTACACCGCCATGGCCA | 544 |
| 16874828 | 1232999 | NKG7 | CAGGGCCCACAGAACAGCCATAATG | 545 |
| 16874828 | 974917 | NKG7 | GCCATAATGCTGAAGGTCTGCGTCA | 546 |
| 16874828 | 151824 | NKG7 | CTGATATGATGTCCCCATGCCCTGT | 547 |
| 16874828 | 194244 | NKG7 | TATGATGTCCCCATGCCCTGTTGGC | 548 |
| 16874828 | 886735 | NKG7 | CACAGCCTCAAACCAGAAATCGGTG | 549 |
| 16874828 | 762848 | NKG7 | AAATCGGTGCTCAAAGCAATCAGGC | 550 |
| 16874828 | 1246090 | NKG7 | GAGGCTGCTGATCAGACTCTTGAAT | 551 |
| 16874828 | 1302484 | NKG7 | GACTCTTGAATCTCAGAGAGAAGGA | 552 |
| 16874828 | 639151 | NKG7 | AAGGAGGCTGTGCACCCAGACTCCT | 553 |
| 16874828 | 15055 | NKG7 | GACTCCTGGGTCCTTAGAGCCCAAG | 554 |
| 16876764 | 252747 | RSAD2 | GAGCGCCGGCCGTTTATCGCGCACA | 555 |
| 16876764 | 433855 | RSAD2 | GGGCCTCATTCGGTGTCAGCCCCGG | 556 |
| 16876764 | 1237059 | RSAD2 | TAAGTGTTCAGTTAGGGTTAGCTCC | 557 |
| 16876764 | 496709 | RSAD2 | GAGTCCTAGTAGCTGAACTTCCAGA | 558 |
| 16876764 | 646348 | RSAD2 | CAGGACACACCTTCTTTGACTAACA | 559 |

APPENDIX 2-continued

PROBE SEQUENCES

| Probe Set ID | Probe ID | Gene Symbol | Probe Sequence | SEQ ID NO |
|---|---|---|---|---|
| 16876764 | 111072 | RSAD2 | TATAGGGATGGAAATCAGCAGTCTC | 560 |
| 16876764 | 519804 | RSAD2 | AGAGCAGTCTCTGTATGCCAGGGAC | 561 |
| 16876764 | 972885 | RSAD2 | GGTTGCCTGAACACACTCAAGAGCT | 562 |
| 16876764 | 909053 | RSAD2 | TGTGTGGAAACAGAAGCCGCATTTG | 563 |
| 16876764 | 710283 | RSAD2 | GAAGGTACTCTAGGAAAGACAGGAA | 564 |
| 16876764 | 32738 | RSAD2 | AAATTCATCAGGGTGCACATCCAGA | 565 |
| 16876764 | 183607 | RSAD2 | GGCTCTCCACCTGAAAAGTTGATCT | 566 |
| 16876764 | 331047 | RSAD2 | GCTGGGCAGCCGCAACTCTACTTTG | 567 |
| 16876764 | 244919 | RSAD2 | GATCAGGCTTCCATTGCTCACGATG | 568 |
| 16876764 | 1208683 | RSAD2 | TAATGCCGTGCACAGCTTGAAAAGC | 569 |
| 16876764 | 570811 | RSAD2 | GCCAAACTTGTTTACTGAGAGCCCT | 570 |
| 16876764 | 1080752 | RSAD2 | TCACAGGAGATAGCGAGAATGTCCA | 571 |
| 16876764 | 115300 | RSAD2 | TTGGCCACGGCCAATAAGGACATTG | 572 |
| 16876764 | 54492 | RSAD2 | TTTCCAGCGGACAGGGTTTAGTGCT | 573 |
| 16876764 | 753408 | RSAD2 | TTTGTGGCGCTCCAAGAATCTTTCA | 574 |
| 16876764 | 1202471 | RSAD2 | TAGATTCAGGCACCAAGCAGGACAC | 575 |
| 16876764 | 35096 | RSAD2 | CCAGAATAAGGTAGGAGTCTTTCAT | 576 |
| 16876764 | 1281100 | RSAD2 | TTCATCCAGAATAAGGTAGGAGTCT | 577 |
| 16876764 | 159626 | RSAD2 | CTTCCGTCCCTTTCTACAGTTCAGA | 578 |
| 16876764 | 920230 | RSAD2 | GCTTCTTCTACACCAACATCCAGGA | 579 |
| 16876764 | 648841 | RSAD2 | TTCAGATCAGCCTTACTCCATATGT | 580 |
| 16876764 | 482437 | RSAD2 | TGACCACAGGTAATCAGATGCCACG | 581 |
| 16876764 | 910546 | RSAD2 | GCATTCATGGAACAGCCACCGTGGG | 582 |
| 16882332 | 986433 | GNLY | TTCCAGCTGGACTCCCTTAGGCTGA | 583 |
| 16882332 | 1246427 | GNLY | TTCCTTCCAGCTGGACTCCCTTAGG | 584 |
| 16882332 | 801372 | GNLY | GCAGGGAGCCTGCAGCTTAATCTTT | 585 |
| 16882332 | 497510 | GNLY | CAGTGTGGCCAGTAGAGTTAGGACC | 586 |
| 16882332 | 203465 | GNLY | TGGCCTTCACCACGCAGATGCGGAG | 587 |
| 16882332 | 330712 | GNLY | GAGGAAACGCAGATCCACCGATGAG | 588 |
| 16882332 | 421519 | GNLY | ACTCTCCCTTCCAGAAGTGTTCTTG | 589 |
| 16882332 | 421337 | GNLY | CACTCTCCCTTCCAGAAGTGTTCTT | 590 |
| 16882332 | 433702 | GNLY | CACGTTCCTTCTAGAAAGCCAGGAG | 591 |
| 16882332 | 845025 | GNLY | CACTCTCAGCACAAACACGTGTTCT | 592 |
| 16882332 | 937646 | GNLY | AGGAGAGGGAAAGCCCGTTCTCCTG | 593 |
| 16882332 | 493809 | GNLY | CAGGTCGTAGTACTCAGGGCTCAGA | 594 |
| 16882332 | 718254 | GNLY | GATTTCTCCTCATCACGCAGGTGGG | 595 |
| 16882332 | 504180 | GNLY | CCAGCTCCTGTGTTTTGGTCAACAG | 596 |

APPENDIX 2-continued

PROBE SEQUENCES

| Probe Set ID | Probe ID | Gene Symbol | Probe Sequence | SEQ ID NO |
|---|---|---|---|---|
| 16882332 | 1243055 | GNLY | GACTATCGTCAGACAGGTCCTGTAG | 597 |
| 16882332 | 640930 | GNLY | CCAGGATCACTGTGCAAGGTGCCCC | 598 |
| 16882332 | 743659 | GNLY | TATCCAGGGCTAAGTGCGAGCCTGC | 599 |
| 16882332 | 103754 | GNLY | CCTTCTGTGTGGAGAATGGTGCCCA | 600 |
| 16882332 | 803691 | GNLY | TGAAATTCTGCAGACGTCGCGCCA | 601 |
| 16882332 | 12671 | GNLY | GGCCCTGGGTAACTCTAGACTGATA | 602 |
| 16882332 | 264322 | GNLY | CCAGTCGGCAGCCTGAGCAGGTTGT | 603 |
| 16882332 | 1174988 | GNLY | GCTTCTTCCACAGGACAAGGTGAGA | 604 |
| 16889218 | 1393313 | SPATS2L | CAAGTTACACATGGGCATCGTGGGC | 605 |
| 16889218 | 898891 | SPATS2L | GAAAATGAACTTTGCTCCCTCAGCA | 606 |
| 16889218 | 302719 | SPATS2L | CACAATCCGCACGTGTTGCAAGAGA | 607 |
| 16889218 | 191246 | SPATS2L | GAAGAATCCCAGTACAGCTTCCGCA | 608 |
| 16889218 | 439558 | SPATS2L | GGACTGGATTCCTTCACTGACACAA | 609 |
| 16889218 | 798735 | SPATS2L | AATCAAAGACTGCAACGGTGTGGCC | 610 |
| 16889218 | 1199144 | SPATS2L | GAATCCACAGCAATGTTCCTGAAAG | 611 |
| 16889218 | 560507 | SPATS2L | CACTGAGATGTTTGGCACTCCCTCC | 612 |
| 16889218 | 155676 | SPATS2L | TCTTTTCCCGAGTTTCCCATGAGGC | 613 |
| 16889218 | 365969 | SPATS2L | TCCCTTTTTGTGAAACTGCCCAGTG | 614 |
| 16889218 | 703017 | SPATS2L | GGTTTCCTCGTGCTCCAAATCAGGG | 615 |
| 16889218 | 432615 | SPATS2L | CAAATCGCTTTCTGACTTGCTTGTC | 616 |
| 16889218 | 1288350 | SPATS2L | TTCACATGAGTATTGAGTTCAGCCA | 617 |
| 16889218 | 169890 | SPATS2L | GATTCTAACCGCGATCCCTTGGAGA | 618 |
| 16889218 | 323695 | SPATS2L | TGCCAATCCTCGATCAGCACCATGG | 619 |
| 16889218 | 102608 | SPATS2L | CAAACTGTTGGAGCACCAGGACTAT | 620 |
| 16889218 | 28661 | SPATS2L | TTCTCACGAGGGATAAGGGCTGGTT | 621 |
| 16889218 | 930149 | SPATS2L | CTTGGGTTACAAGGCTGCTCAGCTG | 622 |
| 16889218 | 1060912 | SPATS2L | TATCTAGTTAGAGAAACGGTGCAGC | 623 |
| 16889218 | 1364194 | SPATS2L | CCATTTCTGCCATTAATGAAACTTC | 624 |
| 16889218 | 864392 | SPATS2L | CGGTTTTAAGTTGGCAGGTGTCAGT | 625 |
| 16889218 | 775991 | SPATS2L | TCTTCTCAGCACTGGGTTAGGTGCC | 626 |
| 16889218 | 275751 | SPATS2L | TAATTTCTGCCCTGAGTTCGGCCAG | 627 |
| 16889218 | 150016 | SPATS2L | GCAGGAACCCCATGATTACAGAAAT | 628 |
| 16889218 | 286667 | SPATS2L | CTTGTTGGCCGGCATGGTCTGGTGA | 629 |
| 16889218 | 50480 | SPATS2L | TCACAGCCGGGACTGAGAGAACTGC | 630 |
| 16889218 | 830037 | SPATS2L | TTTAGGAAAAGAACTGCGCAGGCCC | 631 |
| 16894127 | 651726 | CMPK2 | CATTCCAGGCCTTGACTCGAGTGTG | 632 |
| 16894127 | 1200096 | CMPK2 | TCATGACGAGTGCAACCAGATGTGG | 633 |

APPENDIX 2-continued

PROBE SEQUENCES

| Probe Set ID | Probe ID | Gene Symbol | Probe Sequence | SEQ ID NO |
|---|---|---|---|---|
| 16894127 | 1355847 | CMPK2 | CACTGGAACATGATGAGAGGGACCT | 634 |
| 16894127 | 1060230 | CMPK2 | AATCTAGTTAGACGTGGCACCTGGC | 635 |
| 16894127 | 1183138 | CMPK2 | TACGGTTCACTAAAACTATTCTGGA | 636 |
| 16894127 | 874431 | CMPK2 | TTAGGCTTAATACCGTCTGCAGGAC | 637 |
| 16894127 | 1376609 | CMPK2 | CAGGATTCTCCATCCGCTGGTAGGA | 638 |
| 16894127 | 1072227 | CMPK2 | CACACGGGAAGCATCTAATAGGTAG | 639 |
| 16894127 | 820683 | CMPK2 | AGATAACAATGCTGCAGCCCTGTGG | 640 |
| 16894127 | 1067767 | CMPK2 | CAATCCTAAAGCCAGTGCCAGTGGT | 641 |
| 16894127 | 1258626 | CMPK2 | CAGGTTTGAGCAGGTCCTCTGGCCA | 642 |
| 16894127 | 1079429 | CMPK2 | GATTCTTTAGCTATTTCGGAGGCCA | 643 |
| 16894127 | 1139518 | CMPK2 | CTCCACTGGCCAATGCAAGAGGGTG | 644 |
| 16894127 | 648670 | CMPK2 | GAGGACAGCCTTAAGTGAATCTGCC | 645 |
| 16894127 | 1141248 | CMPK2 | TCGATGGCAACAACCTGGAACTTTC | 646 |
| 16894127 | 78630 | CMPK2 | TCTGTTTTGGGCACTGGTCGACCAG | 647 |
| 16894127 | 861555 | CMPK2 | TTGCGCTCTTAACTGCTCCACAACG | 648 |
| 16894127 | 154335 | CMPK2 | CAACGCTGTCCCGTAAGCTTGGAAA | 649 |
| 16894127 | 1291225 | CMPK2 | GGAAAATATTCCCAAGATCCATGGG | 650 |
| 16894127 | 81580 | CMPK2 | ACGGAACTGGGCAAGTCTGGCACCA | 651 |
| 16894127 | 17735 | CMPK2 | GCTTGCCGGGTGTCAGGGTCATCCA | 652 |
| 16894127 | 946306 | CMPK2 | TGCAGTCGGGAAGCTCCAGGACGAA | 653 |
| 16894127 | 900188 | CMPK2 | GACTCTCCAACTGGGAAGTGTCGCC | 654 |
| 16894127 | 1237108 | CMPK2 | GAAGTGTGTCAGGATAGCACCCTCT | 655 |
| 16894127 | 871388 | CMPK2 | TGTTGCTGCCTAACAGTGTAACTGC | 656 |
| 16895530 | 985145 | OTOF | CATGAAGAGTGGACGCTGGGCTCCT | 657 |
| 16895530 | 1071455 | OTOF | AACCAGATGAAGCTCGTGTCGGGCC | 658 |
| 16895530 | 1371858 | OTOF | TCATCGTTCTCATTGCGGGCCAGGA | 659 |
| 16895530 | 332052 | OTOF | AAGTGGTCCGCATCCCAGATCTGCA | 660 |
| 16895530 | 614928 | OTOF | CTTCCGAGGTGAGATGTCCAGAGGC | 661 |
| 16895530 | 623218 | OTOF | CACATGCTCGTCTGTGGGCTTCCTC | 662 |
| 16895530 | 269604 | OTOF | GGTCCCGCCAGATATTGTAGCCATG | 663 |
| 16895530 | 257075 | OTOF | GAAGGAGGCCTCGATGTCAAAGGAC | 664 |
| 16895530 | 588056 | OTOF | GATGTCAGTCTTGCCTAGCCGGATG | 665 |
| 16895530 | 930534 | OTOF | GCACTTTGTACACGCAGAGGGAGCC | 666 |
| 16895530 | 1191022 | OTOF | TCAATGGAGGCAAAGTACTTGGACC | 667 |
| 16895530 | 1177335 | OTOF | GTTTGGACACACAATCAAGCTCAGC | 668 |
| 16895530 | 95224 | OTOF | TTTCTTGATGGGTACCTCTGGCTCC | 669 |
| 16895530 | 1269120 | OTOF | ACAGCACACGGCAGCGCCGGAGAAG | 670 |

APPENDIX 2-continued

PROBE SEQUENCES

| Probe Set ID | Probe ID | Gene Symbol | Probe Sequence | SEQ ID NO |
|---|---|---|---|---|
| 16895530 | 296332 | OTOF | TCCACCACACGGATGTTCAAGGGCG | 671 |
| 16895530 | 1329786 | OTOF | TAATTGTGGATCAGGGACGACTGCA | 672 |
| 16895530 | 252133 | OTOF | GGTCCGGCCCATGAAGTCAGCTTTG | 673 |
| 16895530 | 42286 | OTOF | CATAGAGCTCCAGGTTGTCGAACAC | 674 |
| 16895530 | 638771 | OTOF | CCTGGTACATGTGCGCTCGGAGCTG | 675 |
| 16895530 | 1099671 | OTOF | TCCACGATGGAGAAGAGCAGGTCCT | 676 |
| 16895530 | 432062 | OTOF | TGCAGGAAGTTCTGGCACAGCCTCA | 677 |
| 16895530 | 165284 | OTOF | GATGAGTGGCCCTGGTCCTTGTCAG | 678 |
| 16895530 | 11640 | OTOF | GACGCTCAGGGTAGGACTTCTCCGT | 679 |
| 16895530 | 700679 | OTOF | CAAATGCCTCCTCCCTGTTGATCAG | 680 |
| 16895530 | 758065 | OTOF | TGATCTGGGAGCTCTCGCTAGGGCC | 681 |
| 16895530 | 1277770 | OTOF | GAAGTCATCAATTTCCCAGGTTCTG | 682 |
| 16895530 | 735376 | OTOF | TAGATGCAGGGCTTTCGCTCCAGGT | 683 |
| 16895530 | 1380804 | OTOF | GGCCTCGTCATCACTTGCGTTCTGA | 684 |
| 16895530 | 1330081 | OTOF | TCCGGTCGATCATTGAGGCCTCCAG | 685 |
| 16895530 | 488573 | OTOF | TGTGGAGCCGTACATGTTCACCCAG | 686 |
| 16895530 | 1065596 | OTOF | TTTTCACATAGAACCGGGCCCACTG | 687 |
| 16895530 | 1163802 | OTOF | CAGGATGGCCCACTTGTGATGGAAC | 688 |
| 16895530 | 1019728 | OTOF | CCATTTTGAAGGAGCCCACCAGGGT | 689 |
| 16895530 | 1099054 | OTOF | TGACATCCGGAGAGACATGGAAGTC | 690 |
| 16895530 | 1392179 | OTOF | ACAGGGTCCATGTTCAAGCCCACCA | 691 |
| 16895530 | 875570 | OTOF | GCTCCATCTTAATGTCTGGCTTAGA | 692 |
| 16895530 | 96637 | OTOF | AATGGCCAGATGGTCAAGGTCTTCC | 693 |
| 16895530 | 245286 | OTOF | TGGGAGCAGTCCATCCGTCTCTTGG | 694 |
| 16895530 | 779420 | OTOF | CGTCAGTGGCCTGATACCGGACCTC | 695 |
| 16895530 | 1401005 | OTOF | TTCTGCAGCACCATGCGGAAGGTCC | 696 |
| 16895530 | 323755 | OTOF | TCATTTCTGTCGATGCTGCTGGCCA | 697 |
| 16895530 | 155031 | OTOF | TCCAGGACCCGAGAGTAGAAGGATT | 698 |
| 16895530 | 661383 | OTOF | GAAAGTCACTTTGGCGATCCGGTCG | 699 |
| 16895530 | 598590 | OTOF | GCTAGCCGGTGGAGCACGGCTCACA | 700 |
| 16896442 | 1400964 | EIF2AK2 | TATGGATGCATCATGGAAGCCTCC | 701 |
| 16896442 | 1001489 | EIF2AK2 | GAAACTGCAGACATTGAGGCCTGGA | 702 |
| 16896442 | 866682 | EIF2AK2 | AAATTCTTAAGTCACATCAGGAGGG | 703 |
| 16896442 | 18257 | EIF2AK2 | CCACCTTGGGTGATGCTAAATTGAA | 704 |
| 16896442 | 875180 | EIF2AK2 | TGAATACATTAATGCCGTCCCTGGG | 705 |
| 16896442 | 944370 | EIF2AK2 | CATATAGTTGGAAGGCCCACTGGGC | 706 |
| 16896442 | 1226012 | EIF2AK2 | TCTTCCACACAGTCAAGGTCCTTAG | 707 |

APPENDIX 2-continued

PROBE SEQUENCES

| Probe Set ID | Probe ID | Gene Symbol | Probe Sequence | SEQ ID NO |
|---|---|---|---|---|
| 16896442 | 37256 | EIF2AK2 | CAGATGTGTTAGGTCGATCCTCAGG | 708 |
| 16896442 | 1358759 | EIF2AK2 | TATATCTGAGATGATGCCATCCCGT | 709 |
| 16896442 | 290468 | EIF2AK2 | GATGCCATCCCGTAGGTCTGTGAAA | 710 |
| 16896442 | 151298 | EIF2AK2 | GAATTAGCCCCAAAGCGTAGAGGTC | 711 |
| 16896442 | 952867 | EIF2AK2 | TACCGCCGAATAGCTGAATCCTCTG | 712 |
| 16896442 | 519028 | EIF2AK2 | TCTGGGCTCATGTATCGCAAAGTTC | 713 |
| 16896442 | 471910 | EIF2AK2 | TATCGCAAAGTTCCCTTACTCCTTG | 714 |
| 16896442 | 1351893 | EIF2AK2 | TCCATTTGGATGAAAAGGCACTTAG | 715 |
| 16896442 | 356414 | EIF2AK2 | GCCAATGCTTTTACTTCACGCTCCG | 716 |
| 16896442 | 363777 | EIF2AK2 | GTAAGTCTTTCCGTCAATTCTGTGT | 717 |
| 16896442 | 563634 | EIF2AK2 | GAAAACTTGGCCAAATCCACCTGAG | 718 |
| 16896442 | 538747 | EIF2AK2 | TCAGGAAGGTCAAATCTGGGTGCCA | 719 |
| 16896442 | 1372094 | EIF2AK2 | TGTAGCATGTGCACATAGTCAAAGA | 720 |
| 16896442 | 760509 | EIF2AK2 | GAAACTCTGCTCAAATAAGGGTGTA | 721 |
| 16896442 | 377741 | EIF2AK2 | GCCTTCCTTTGATTATTTCTGAGAC | 722 |
| 16896442 | 583956 | EIF2AK2 | CCTTCCTTTGATTATTTCTGAGACC | 723 |
| 16896442 | 506867 | EIF2AK2 | CGAAGAACTGTTTAAACTGTCACTG | 724 |
| 16896442 | 1115243 | EIF2AK2 | TGATGTATCTGCTGAGAAGTCACCT | 725 |
| 16896442 | 672138 | EIF2AK2 | TGTGCTGGTCACTAAAGAGTTGCTT | 726 |
| 16896442 | 1033233 | EIF2AK2 | GAAGATATGCAAGTTTAGCGGCCAA | 727 |
| 16896442 | 1051964 | EIF2AK2 | TCCTGTTTAGTAGAACCTGTACCAA | 728 |
| 16896442 | 669429 | EIF2AK2 | GATAAGGCCTATGTAATTCCCCATG | 729 |
| 16896442 | 965796 | EIF2AK2 | CCTTCTGAAGAATTCGTTGTTGTCA | 730 |
| 16896442 | 878182 | EIF2AK2 | TCTCAACAGCTAATTTGGCTGCGGC | 731 |
| 16896442 | 223252 | EIF2AK2 | CATGTGGAGGTCCTGAATTAGGCAG | 732 |
| 16896442 | 180144 | EIF2AK2 | TGAAGAAACCTGCTGAAAGATCACC | 733 |
| 16896442 | 1184747 | EIF2AK2 | CACGCAGATAATCACGGAAGTGTGG | 734 |
| 16896442 | 946814 | EIF2AK2 | CTGAGTCAGATGGAAGAACTGCTAA | 735 |
| 16896442 | 1146480 | EIF2AK2 | GGTCATTACAATTTACAAATCCAGG | 736 |
| 16896442 | 112252 | EIF2AK2 | TATTGGGATGGACCTCGATGCCTCG | 737 |
| 16896442 | 1164824 | EIF2AK2 | GAGCTGAATGCCACTGTGACCGCAA | 738 |
| 16896442 | 529487 | EIF2AK2 | CAAGCCCTCGTCTGCTACGGGATTG | 739 |
| 16896442 | 526633 | EIF2AK2 | AAGCCCTCGTCTGCTACGGGATTGG | 740 |
| 16900144 | 1225703 | IGKV6-21 | TACTCTGATGACAGTAATACGTTGC | 741 |
| 16900144 | 926107 | IGKV6-21 | TGACAGTAATACGTTGCAGCATCTT | 742 |
| 16900144 | 922424 | IGKV6-21 | GACAGTAATACGTTGCAGCATCTTC | 743 |
| 16900144 | 452143 | IGKV6-21 | CGTTGCAGCATCTTCAGCTTCCAGG | 744 |

APPENDIX 2-continued

PROBE SEQUENCES

| Probe Set ID | Probe ID | Gene Symbol | Probe Sequence | SEQ ID NO |
|---|---|---|---|---|
| 16900144 | 1114824 | IGKV6-21 | GACCCCTGAGAAGGACTGGGAAGCA | 745 |
| 16900144 | 1017431 | IGKV6-21 | ccCCTGAGAAGGACTGGGAAGCATA | 746 |
| 16900144 | 62322 | IGKV6-21 | CCCTGAGAAGGACTGGGAAGCATAC | 747 |
| 16900144 | 988328 | IGKV6-21 | cCTGAGAAGGACTGGGAAGCATACT | 748 |
| 16900144 | 947291 | IGKV6-21 | AGGACTGGGAAGCATACTTGATGAG | 749 |
| 16900144 | 1138092 | IGKV6-21 | AGAAACCCAATGAGTTGTGATGGCA | 750 |
| 16900144 | 1137101 | IGKV6-21 | GAAACCCAATGAGTTGTGATGGCAA | 751 |
| 16900144 | 1340087 | IGKV6-21 | AAACCCAATGAGTTGTGATGGCAAC | 752 |
| 16900144 | 1111225 | IGKV6-21 | AACCCAATGAGTTGTGATGGCAACA | 753 |
| 16900144 | 477094 | IGKV6-21 | ACCCAATGAGTTGTGATGGCAACAT | 754 |
| 16900152 | 148446 | IGKV1-27 | GATGGGACCCCTGATTGCAAAGTGG | 755 |
| 16900152 | 162942 | IGKV1-27 | ATGGGACCCCTGATTGCAAAGTGGA | 756 |
| 16900152 | 162623 | IGKV1-27 | TGGGACCCCTGATTGCAAAGTGGAT | 757 |
| 16900152 | 164887 | IGKV1-27 | GGGACCCCTGATTGCAAAGTGGATG | 758 |
| 16900152 | 784485 | IGKV1-27 | CTGTGTCCTGACTGAGAGAGACTTC | 759 |
| 16900152 | 1113945 | IGKV1-27 | TGTCCTGACTGAGAGAGACTTCTGC | 760 |
| 16900152 | 1114998 | IGKV1-27 | GTCCTGACTGAGAGAGACTTCTGCA | 761 |
| 16900152 | 1105784 | IGKV1-27 | TCCTGACTGAGAGAGACTTCTGCAC | 762 |
| 16916802 | 912473 | SIGLEC1 | TGAGACAAAACATGGCCTGCTGGTG | 763 |
| 16916802 | 563029 | SIGLEC1 | AAGTGTGACTTGGAGCCCTGGCCTA | 764 |
| 16916802 | 1376894 | SIGLEC1 | TGAAAAGCCATCTCCACCGAATTCT | 765 |
| 16916802 | 48205 | SIGLEC1 | CAAGAGCGTGGGAACCTCATGGAGA | 766 |
| 16916802 | 1060982 | SIGLEC1 | CAATCAGTTTAGAGTCGACAGGCAA | 767 |
| 16916802 | 367419 | SIGLEC1 | GCTGGGCTTTTGTGCAGAGTGGCCT | 768 |
| 16916802 | 1288882 | SIGLEC1 | GAACAGATGTATTCCCCTTGGTCGC | 769 |
| 16916802 | 599449 | SIGLEC1 | CCATGCAAAGGTGGAGTTGCCCACA | 770 |
| 16916802 | 633113 | SIGLEC1 | CGCCCGATGGTGCTGATTGAGCCCA | 771 |
| 16916802 | 465278 | SIGLEC1 | CAACGACCGTTGTGGTACCAAGTAT | 772 |
| 16916802 | 161456 | SIGLEC1 | TAGAAACCCTCATCCCTGGGCTGTG | 773 |
| 16916802 | 45183 | SIGLEC1 | CACACAAGGCAGGTCAGGTTCACCA | 774 |
| 16916802 | 949403 | SIGLEC1 | TTGAGCGTCGAAGTCAGCTGAGGCC | 775 |
| 16916802 | 191165 | SIGLEC1 | TGATAGGCCCCAGCTTGTGTCAAAG | 776 |
| 16916802 | 1269017 | SIGLEC1 | TAAAGGGCAGCATCAGTTCTGGCCA | 777 |
| 16916802 | 221211 | SIGLEC1 | CAACACGGTCCTTGTGGAGCAGCTG | 778 |
| 16916802 | 753668 | SIGLEC1 | GAAGCAGGGCTCCATTCAGGTACCA | 779 |
| 16916802 | 120918 | SIGLEC1 | GAAGCGTGGGCTGTGATCACTGTCC | 780 |
| 16916802 | 1055574 | SIGLEC1 | TATCAGCCCTAGTGGCCAAGTGCAG | 781 |

APPENDIX 2-continued

PROBE SEQUENCES

| Probe Set ID | Probe ID | Gene Symbol | Probe Sequence | SEQ ID NO |
|---|---|---|---|---|
| 16916802 | 1302626 | SIGLEC1 | TGGAGGTGAATCTCGCTCTGAGCCC | 782 |
| 16916802 | 54799 | SIGLEC1 | TCTCGAAGCGGAAGTTGTAGGAACC | 783 |
| 16920651 | 35350 | ZBP1 | CCATGATGGAAGGTAACTCCAGGCA | 784 |
| 16920651 | 269290 | ZBP1 | TACTCCTGGCCATCAAAAGACCTGG | 785 |
| 16920651 | 990513 | ZBP1 | TCAAACAAGACGCTAAGGAATGCAG | 786 |
| 16920651 | 150951 | ZBP1 | TGTCCAAGCCCCACGTGAGGCTGTG | 787 |
| 16920651 | 1041632 | ZBP1 | GTTTCCAAGAGTCATAGTTTCCAGC | 788 |
| 16920651 | 199506 | ZBP1 | GATGGGCTGACCAATGTCTCGAGGA | 789 |
| 16920651 | 1178579 | ZBP1 | CATAAGTGCAACACAGAGTGATTCC | 790 |
| 16920651 | 695218 | ZBP1 | GATCACCAATCTACATGCCGTTAAG | 791 |
| 16920651 | 526317 | ZBP1 | CGATGGTGGCGTCCTCGAGAAAGCA | 792 |
| 16920651 | 947685 | ZBP1 | TTCAAACGAAGCTTCTGGGCCGGCA | 793 |
| 16920651 | 639420 | ZBP1 | CTCGTGCTGTTGTGCTGTCTGGGAA | 794 |
| 16920651 | 529782 | ZBP1 | GCTGCACCCGTCTCAGTATGGACTG | 795 |
| 16920651 | 94594 | ZBP1 | GAATCACCTGGTGCCATTGAAGGGA | 796 |
| 16920651 | 48122 | ZBP1 | CAGAGTACAGGGAAATCAGGAGAGC | 797 |
| 16920651 | 250378 | ZBP1 | CTCAGGACGGCCGTAAAGGTGGACT | 798 |
| 16920651 | 23034 | ZBP1 | AGAGGATCCGGTGGCTCCCCACCGA | 799 |
| 16920651 | 599440 | ZBP1 | AGGATCCGGTGGCTCCCCACCGAGG | 800 |
| 16920651 | 594347 | ZBP1 | TCGGAGTTTGCAATGGAAATCCAGC | 801 |
| 16920651 | 2088 | ZBP1 | GGCGGTAAATCGTCCATGCTTTGGA | 802 |
| 16920651 | 240696 | ZBP1 | TGCTCATCCATGTCCAGAAGGTGCC | 803 |
| 16920651 | 1048231 | ZBP1 | AGTAGTCCTAGGGTTTGCATCTGCC | 804 |
| 16920651 | 26938 | ZBP1 | TAGTCCTAGGGTTTGCATCTGCCCC | 805 |
| 16920651 | 141723 | ZBP1 | CCGTTGTTGGCTGAACTGAGGGCCA | 806 |
| 16920651 | 105139 | ZBP1 | GGGTCTCTGGAATTGTAGCTGCATG | 807 |
| 16920651 | 167747 | ZBP1 | TGGGTGAACCCCAAAACAGTGCCTG | 808 |
| 16920651 | 1123059 | ZBP1 | AAACCTGTGAGCTCCCATGTGGCAG | 809 |
| 16920651 | 1081678 | ZBP1 | CATTCGGTAGAGGACTTGGTTGAGC | 810 |
| 16920651 | 129049 | ZBP1 | TCACCAGCTGGGCAAGTTTCACCGG | 811 |
| 16920651 | 619279 | ZBP1 | TAGGTACAGTGATAGGCTCCCCGTT | 812 |
| 16920651 | 985701 | ZBP1 | TTAATGAGGACTAAGCAGGACCCCA | 813 |
| 16920651 | 172883 | ZBP1 | CGGGAGCTACCGCTGGTCCTTGGAA | 814 |
| 16920651 | 807420 | ZBP1 | GAGCTACCGCTGGTCCTTGGAAGGA | 815 |
| 16920651 | 54699 | ZBP1 | TACAGCCCGGAAATAGATGCCTAGC | 816 |
| 16920651 | 312070 | ZBP1 | CGGCCAGATTCGGTTTCAGGAGAAA | 817 |
| 16926942 | 949377 | USP18 | TGGAAAGCGAAACTTACAGCGGCCT | 818 |

APPENDIX 2-continued

PROBE SEQUENCES

| Probe Set ID | Probe ID | Gene Symbol | Probe Sequence | SEQ ID NO |
|---|---|---|---|---|
| 16926942 | 474012 | USP18 | TCCGCTGCTGAGTTCCACGTCGGGA | 819 |
| 16926942 | 1203367 | USP18 | ATGTGAGCCAGGCACGATGGAATCT | 820 |
| 16926942 | 1344124 | USP18 | GAAGCGCTTATGTGAGCCAGGCACG | 821 |
| 16926942 | 325687 | USP18 | TGCCTGGCCCGCGTTCAGGACAGCA | 822 |
| 16926942 | 1127693 | USP18 | TCAGGAGCCCAAACGCCTTGCTCAT | 823 |
| 16926942 | 275128 | USP18 | GACAGATTTGCCTCAGGAGCCCAAA | 824 |
| 16926942 | 277161 | USP18 | TGACAGATTTGCCTCAGGAGCCCAA | 825 |
| 16926942 | 77123 | USP18 | GACTCAGCCAGGATGGACTGACAGA | 826 |
| 16927801 | 483233 | IGLV3-21 | TTGGACAGGTACAGGCCCCATTCCA | 827 |
| 16927801 | 1264944 | IGLV3-21 | GAGCCCAATGCAGGGACGCTTCTCA | 828 |
| 16927801 | 1332856 | IGLV3-21 | AAGAGCCCAATGCAGGGACGCTTCT | 829 |
| 16927801 | 1332612 | IGLV3-21 | CAAGAGCCCAATGCAGGGACGCTTC | 830 |
| 16927801 | 1135215 | IGLV3-21 | CCAAGAGCCCAATGCAGGGACGCTT | 831 |
| 16927801 | 989181 | IGLV3-21 | TCATGTCCAAGACGGGTCCCCAAGA | 832 |
| 16927801 | 1066279 | IGLV3-21 | TCGCTATCATCATAGACGACCAGCA | 833 |
| 16927801 | 745539 | IGLV3-21 | GCCGGTCGCTATCATCATAGACGAC | 834 |
| 16927801 | 325646 | IGLV3-21 | GGCCGGTCGCTATCATCATAGACGA | 835 |
| 16927801 | 525458 | IGLV3-21 | GGGCCGGTCGCTATCATCATAGACG | 836 |
| 16927801 | 525298 | IGLV3-21 | AGGGCCGGTCGCTATCATCATAGAC | 837 |
| 16927801 | 21195 | IGLV3-21 | GAGGGCCGGTCGCTATCATCATAGA | 838 |
| 16942367 | 32444 | RN5S134 | CTTCTGAGATCAGGGCGTGTTCAGG | 839 |
| 16942367 | 1242589 | RN5S134 | GCTTCTGAGATCAGGGCGTGTTCAG | 840 |
| 16942367 | 1242066 | RN5S134 | AGCTTCTGAGATCAGGGCGTGTTCA | 841 |
| 16942367 | 1331207 | RN5S134 | TAGCTTCTGAGATCAGGGCGTGTTC | 842 |
| 16949442 | 445288 | RTP4 | CAAACAGTTTCAGTTTCGGTGTTCG | 843 |
| 16949442 | 317505 | RTP4 | AGGTTTGCTCGTTTCTCAGGAAGAG | 844 |
| 16949442 | 813751 | RTP4 | CCCTCTGAAGCTGAGAGAGTAGCTT | 845 |
| 16949442 | 1073090 | RTP4 | TCCCTCTGAAGCTGAGAGAGTAGCT | 846 |
| 16949442 | 975179 | RTP4 | TTCCCTCTGAAGCTGAGAGAGTAGC | 847 |
| 16949442 | 761503 | RTP4 | TGAAATGTCTGCTCCCAAGTCCAGA | 848 |
| 16949442 | 803534 | RTP4 | TTGAAATGTCTGCTCCCAAGTCCAG | 849 |
| 16949442 | 526222 | RTP4 | AACTTCAGCGTCCATGTGGCCCGGG | 850 |
| 16949442 | 1019626 | RTP4 | CAGTCTAGCTGAAGGTTGCCATCCA | 851 |
| 16949442 | 234190 | RTP4 | GTATTGCTTCCACCCTTGAGCCAGG | 852 |
| 16949442 | 425776 | RTP4 | GGTATTGCTTCCACCCTTGAGCCAG | 853 |
| 16949442 | 728295 | RTP4 | CAGCCAAATGCTCTCTGTTGGTATT | 854 |
| 16949442 | 562698 | RTP4 | CAGAATCTGCACTTGGGCGGAAGCC | 855 |

APPENDIX 2-continued

PROBE SEQUENCES

| Probe Set ID | Probe ID | Gene Symbol | Probe Sequence | SEQ ID NO |
|---|---|---|---|---|
| 16949442 | 1292131 | RTP4 | TCAGGCATCTCATATTGGGACCAGG | 856 |
| 16949442 | 967436 | RTP4 | GGTTGCTCAGAATCCTCATGGTGCT | 857 |
| 16949442 | 1326098 | RTP4 | TGTGTCATGGGATCCTTCCAGGGAC | 858 |
| 16949442 | 85616 | RTP4 | TCTTGGCTTGGTTTGCGAGGTACAC | 859 |
| 16949442 | 722058 | RTP4 | GATCTGGGTCTCGACTGGGCCCTAA | 860 |
| 16949442 | 861067 | RTP4 | CAGTTATATTAAAGTGGCAGCCAGT | 861 |
| 16949442 | 142509 | RTP4 | TTCAGAGGATGGCTAGGAAACCAGT | 862 |
| 16949442 | 562159 | RTP4 | AGTCATGCATATGTTGGGAGACACC | 863 |
| 16949442 | 1306234 | RTP4 | GGTTCTTATCCACCCGGACAATATG | 864 |
| 16949442 | 277783 | RTP4 | GAGCTTGTTGCCTCCCTGTTACAAA | 865 |
| 16960186 | 1226928 | PLSCR1 | TATACAACCAGAGCTACAGGCCTTA | 866 |
| 16960186 | 1112370 | PLSCR1 | TACAGGTATGAGTTTAGATAGTCTC | 867 |
| 16960186 | 779067 | PLSCR1 | ACCACACTCCTGATTTTGTTCCTG | 868 |
| 16960186 | 632376 | PLSCR1 | CCTGGCTGCCAGTGCTTTCAAAAAA | 869 |
| 16960186 | 489426 | PLSCR1 | GAACTGAGGTATGGACTAGTCCTTG | 870 |
| 16960186 | 176872 | PLSCR1 | TCAGAATGAACCTAGAGAAAGCATC | 871 |
| 16960186 | 1281228 | PLSCR1 | TCAAGATTAATAAGAACAGACTTAC | 872 |
| 16960186 | 1368937 | PLSCR1 | AATTATGCACCATATGTAACCCTCA | 873 |
| 16960186 | 900501 | PLSCR1 | TCATTAGATAACTGGAGGCTCCTGT | 874 |
| 16960186 | 1260831 | PLSCR1 | CAATGACAGGGCAGAAATTCTTGCT | 875 |
| 16960186 | 766351 | PLSCR1 | CAAAGTGCCCTGGTAATTGATCACA | 876 |
| 16960186 | 1339350 | PLSCR1 | GGAGGTCAATGTGCCTTTATCTGCA | 877 |
| 16960186 | 277460 | PLSCR1 | GGTCAATGTGCCTTTATCTGCAAA | 878 |
| 16960186 | 870210 | PLSCR1 | TATTGAGACTAAAGAGCACTTCGCT | 879 |
| 16960186 | 1140706 | PLSCR1 | TATCAGGCATACAACAAAGGCAGGA | 880 |
| 16960186 | 813178 | PLSCR1 | TATACACTGGCTGATTTGGGACAGG | 881 |
| 16960186 | 1164527 | PLSCR1 | GGGTAGCCACTATATCCTGGAGGTC | 882 |
| 16960186 | 926530 | PLSCR1 | GAGGAGGATACCCAACTGGCAAGTT | 883 |
| 16960186 | 501111 | PLSCR1 | GCAAGTTTGTTTCCGGGTGAGAAGC | 884 |
| 16960186 | 552212 | PLSCR1 | TAACACACTGTCTACAAGGCCACAA | 885 |
| 16960186 | 1142371 | PLSCR1 | TGAATCGGGATACTCTAAAACTACA | 886 |
| 16960186 | 1354678 | PLSCR1 | GATACGGGATGAAACTGAGGTGACT | 887 |
| 16960186 | 1020497 | PLSCR1 | CTTGTAACAAGGAGCCATTCCATAA | 888 |
| 16960186 | 880842 | PLSCR1 | GCCATTCCATAAAAATCCTCTTGTG | 889 |
| 16960186 | 887263 | PLSCR1 | TGGGAGTAACCTTTGCGCCAACACC | 890 |
| 16965313 | 25440 | LAP3 | GGACTCAAGGGTGCGCCCGCATTCG | 891 |
| 16965313 | 84369 | LAP3 | CTGGACCGCTGGGATCAAACCGCGG | 892 |

APPENDIX 2-continued

PROBE SEQUENCES

| Probe Set ID | Probe ID | Gene Symbol | Probe Sequence | SEQ ID NO |
|---|---|---|---|---|
| 16965313 | 299056 | LAP3 | ACGGCCAGACGTCGGACGACTACTC | 893 |
| 16965313 | 598358 | LAP3 | TCATGTCTGCGGTGGAGAGACTCCG | 894 |
| 16965313 | 801254 | LAP3 | AATTCTCTCCTGCACTTGTGAACTG | 895 |
| 16965313 | 462247 | LAP3 | CATAAAAGGTTCGAGTCTTCCCTGC | 896 |
| 16965313 | 881525 | LAP3 | TGATGCAGACCATAAAAGGTTCGAG | 897 |
| 16965313 | 391166 | LAP3 | GAGGGTTTACCAAATGATCACGTTC | 898 |
| 16965313 | 1248717 | LAP3 | TATGACTAGACAGCCCCAATACTTG | 899 |
| 16965313 | 368163 | LAP3 | CAGCTGCCTTTTGCCGAGGCCAAC | 900 |
| 16965313 | 1037286 | LAP3 | TCATCAAAAGAGTGGATCCTCAGG | 901 |
| 16965313 | 1253755 | LAP3 | CAACCATATTCAGCAAGAGGAACTG | 902 |
| 16965313 | 343486 | LAP3 | TATGACAAGAGCAACAAATGGTAG | 903 |
| 16965313 | 906451 | LAP3 | TGGGAAAACACAGCTCTAATATGAC | 904 |
| 16965313 | 236708 | LAP3 | TGGAGTCAGTCCAAGACAACTCAAA | 905 |
| 16965313 | 826563 | LAP3 | GAATCAGAAAACTGGAGTCAGTCCA | 906 |
| 16965313 | 1301510 | LAP3 | AGGTCTTGAATCTGCCTGCACCCCG | 907 |
| 16965313 | 1104325 | LAP3 | GTATTCATAGAGACCAAGCACCGCT | 908 |
| 16965313 | 999025 | LAP3 | GCTTTGCCGACACAGCCATCTTCTT | 909 |
| 16965313 | 382397 | LAP3 | TCCATAGAGCTTTGCCGACACAGCC | 910 |
| 16965313 | 354740 | LAP3 | GATTCATTTTTGTGATCTGACCCA | 911 |
| 16965313 | 280572 | LAP3 | AATTGGCGTGCCAAGTTCTGCCCAG | 912 |
| 16965313 | 1378646 | LAP3 | GGCTGTAACATCTCGAGTCTGTGAC | 913 |
| 16965313 | 954990 | LAP3 | GATAGAAAGAACCTCAAACTCAGCT | 914 |
| 16965313 | 53473 | LAP3 | GACACCTGGGAGCACCAATGCTGGA | 915 |
| 16965313 | 1134024 | LAP3 | TGGAGATCCCAAGAGAGCGACGGAA | 916 |
| 16965313 | 1157620 | LAP3 | CCTGTTCCTCAATCCAAGACTTGGG | 917 |
| 16965313 | 596112 | LAP3 | GAGCATATAGTTGCAGCTCCTCCCA | 918 |
| 16965313 | 1002740 | LAP3 | GCTTTGCAGCAGACACGATGGCTGA | 919 |
| 16965313 | 1382944 | LAP3 | GCCGCTGGGCATATTTTCACAAAGA | 920 |
| 16965313 | 208550 | LAP3 | GATGGTCTTCCCGTTTTTGGCTCTA | 921 |
| 16965313 | 1234480 | LAP3 | TGTGCGTAACAGAGCGCATCAGCCA | 922 |
| 16965313 | 1343385 | LAP3 | CGGCATTGAGGATGACCTTCGGGTT | 923 |
| 16965313 | 419684 | LAP3 | GAGTTTGTTCCAGAGCCAGGATGAA | 924 |
| 16965313 | 947699 | LAP3 | TAATGTTCGAAGAGAGGCATCCTCC | 925 |
| 16965313 | 913976 | LAP3 | TGTTGTTAACATCAGCAAGCTGGCA | 926 |
| 16965313 | 692930 | LAP3 | CGCCTGCTATGTCTAAATGTGCCCA | 927 |
| 16965313 | 1365544 | LAP3 | CAGAGTGAAGACATTTTGAGTATC | 928 |
| 16965313 | 1389553 | LAP3 | GTTCCTAGCATCACAAATCTGAGTT | 929 |

APPENDIX 2-continued

PROBE SEQUENCES

| Probe Set ID | Probe ID | Gene Symbol | Probe Sequence | SEQ ID NO |
|---|---|---|---|---|
| 16968735 | 351119 | HERC6 | GACTGGGTGCGCGATGATTTCCTGA | 930 |
| 16968735 | 150241 | HERC6 | AGTCGGCGCCCCAACAGAAGTACAT | 931 |
| 16968735 | 645105 | HERC6 | GAAGACCCTTCCTTTGTGGCACACA | 932 |
| 16968735 | 52065 | HERC6 | TAATGCCAGGGAGTGGTAGTGTCCA | 933 |
| 16968735 | 949382 | HERC6 | AGCCAAACGAAGTCCCACAGAGAGA | 934 |
| 16968735 | 983358 | HERC6 | CAAGTTGTGGACCTCTCTTCTCAGG | 935 |
| 16968735 | 605187 | HERC6 | GACCAGTGGTGTGCACATATGCCAG | 936 |
| 16968735 | 853644 | HERC6 | AAAGTCATAAATCCATGCTTAGAGT | 937 |
| 16968735 | 1388903 | HERC6 | CAAAGTTGGCATATGTTCCAGCAAA | 938 |
| 16968735 | 1338352 | HERC6 | TACATATTTATGGTCCGGCCCTGCC | 939 |
| 16968735 | 1121181 | HERC6 | TCCCGGGAGCACGTGTGGAACTAGT | 940 |
| 16968735 | 406283 | HERC6 | CTTATAATTTATCAGACAGAGCCAC | 941 |
| 16968735 | 725945 | HERC6 | GAAGGTATCTCTTGCCATTTCTAAG | 942 |
| 16968735 | 323767 | HERC6 | GCAGATCATCCTCGAGACACGTAGT | 943 |
| 16968735 | 1330174 | HERC6 | TAAGCATCTGGATCAGCGGATTCAG | 944 |
| 16968735 | 1306917 | HERC6 | GGTGGTTATCCCGAAAGAGCTGTCT | 945 |
| 16968735 | 596414 | HERC6 | TGTGAATCAGCTTGCAATAATTTAA | 946 |
| 16968735 | 861388 | HERC6 | GAGCATCTTTAACCAGGCGACTTCG | 947 |
| 16968735 | 193573 | HERC6 | CATGCAGGAACCCATTTCAGGATAC | 948 |
| 16968735 | 1254131 | HERC6 | GAGTCCACACAGCATTCCAAAGAGG | 949 |
| 16968735 | 1267837 | HERC6 | AAAGCGTATGCAGAGCGCATCTCCA | 950 |
| 16968735 | 1174541 | HERC6 | TTTGGTCCACAGGTATGGAGATCCC | 951 |
| 16968735 | 471952 | HERC6 | GCTGTCATTAGTTCTTCAGGGTAGA | 952 |
| 16968735 | 397479 | HERC6 | CATCCAAGGTTAGTTTGTGGAAAGC | 953 |
| 16968735 | 631458 | HERC6 | CCAGAGATTCGTGCCCTATGCGGAT | 954 |
| 16968735 | 1114466 | HERC6 | TGAGCATGGGTGAGACAAATCCTCT | 955 |
| 16968765 | 342217 | HERC5 | TTGCGCTGCAGAGCGGGAACCAGCT | 956 |
| 16968765 | 561150 | HERC5 | GAGCAGCAGAGTTGGCGCGTCACCT | 957 |
| 16968765 | 1020981 | HERC5 | GAAGGCCAAGGTAAAATCCCATCAC | 958 |
| 16968765 | 640599 | HERC5 | GAGAATCAGCATGTGCTCTGCTCCT | 959 |
| 16968765 | 96289 | HERC5 | GCAAGAGAATGGTAATCTCCACATG | 960 |
| 16968765 | 946359 | HERC5 | TCCAGCACCGAAAGTAAACAGCAGC | 961 |
| 16968765 | 445459 | HERC5 | GATGATACTTTCACTGGAAGCGGCA | 962 |
| 16968765 | 1107067 | HERC5 | TGTTACTTGAGGTCACCACTAAGCT | 963 |
| 16968765 | 644093 | HERC5 | TTAACTCCTTTTCTGAGGTATGGCT | 964 |
| 16968765 | 1096136 | HERC5 | CCTTCATTCAGAGTAGGAATTGTCC | 965 |
| 16968765 | 1296716 | HERC5 | CATGTTAGTAATCCAGTCCTTTTGG | 966 |

APPENDIX 2-continued

PROBE SEQUENCES

| Probe Set ID | Probe ID | Gene Symbol | Probe Sequence | SEQ ID NO |
|---|---|---|---|---|
| 16968765 | 1199559 | HERC5 | TGGAGCACCTGCAAAAAGAAAACCT | 967 |
| 16968765 | 505399 | HERC5 | CAGCACTAAGTGTTGTAGGGTCCCA | 968 |
| 16968765 | 379912 | HERC5 | GCAGATTATCTTTGAGGCAGGTGGT | 969 |
| 16968765 | 140349 | HERC5 | AATCCAACTGGCATATGACGGCTGT | 970 |
| 16968765 | 783389 | HERC5 | GAAAGTGACTGAATATGACGCAGCA | 971 |
| 16968765 | 299143 | HERC5 | TAGATCAAACGTGGGCCTCAAAGCG | 972 |
| 16968765 | 1368318 | HERC5 | TGAACATCCCATATTCCGGCTGGAT | 973 |
| 16968765 | 1307358 | HERC5 | TCAAAGTTATCACCTTCATCATCCA | 974 |
| 16968765 | 623558 | HERC5 | TAAGTTTGTGTCGTTTCTGTCCCAG | 975 |
| 16968765 | 938699 | HERC5 | TAGGAAGGAAAACTGAATTTAATCA | 976 |
| 16968765 | 461360 | HERC5 | CAGTCACGGGTTCTAACCGGCCAGT | 977 |
| 16974529 | 393930 | FGFBP2 | TAGCTGCTATTTACTGAACACTGGA | 978 |
| 16974529 | 759568 | FGFBP2 | TCATAGAAGGCTCAGATCAACAAAG | 979 |
| 16974529 | 554854 | FGFBP2 | TGTGTATGCTTGTCACTCTTGGGCC | 980 |
| 16974529 | 419440 | FGFBP2 | TCAGCACCTGTTCCCTATCATATTG | 981 |
| 16974529 | 114371 | FGFBP2 | GAATTTGGGCCGTTGCATCTGATTA | 982 |
| 16974529 | 560939 | FGFBP2 | TGAGAACGTTGGATTGAAAGCGGCA | 983 |
| 16974529 | 96300 | FGFBP2 | AAAAGAGATGGTTGTCTGTCAGGGA | 984 |
| 16974529 | 775691 | FGFBP2 | TGAGTTTCACTGTGGCCTTGGGCCT | 985 |
| 16974529 | 1028519 | FGFBP2 | GAGGCTGGAAGTCACCTGCTGCATA | 986 |
| 16974529 | 734406 | FGFBP2 | TCCTGCAGGGCTTGATTCCAGTAAG | 987 |
| 16974529 | 1068525 | FGFBP2 | TCAGCAGCGAAAGCCTGGCACATGC | 988 |
| 16974529 | 1258608 | FGFBP2 | TGTGTTGCGGCAGTCGACACGAAGC | 989 |
| 16974529 | 1264146 | FGFBP2 | GACGCATAGTGCAGGAATCTCTCCC | 990 |
| 16974529 | 607141 | FGFBP2 | GAACACAAGTGGGACGAGTCACCCT | 991 |
| 16974529 | 80353 | FGFBP2 | AACACAAGTGGGACGAGTCACCCTT | 992 |
| 16974529 | 980143 | FGFBP2 | CACAAGTGGGACGAGTCACCCTTTA | 993 |
| 16974529 | 19329 | FGFBP2 | TTAAAGGGTGCTGCACAAAAGACTC | 994 |
| 16974529 | 633804 | FGFBP2 | TAAAGGGTGCTGCACAAAAGACTCT | 995 |
| 16974529 | 1146980 | FGFBP2 | AGGGTGCTGCACAAAAGACTCTTTC | 996 |
| 16974529 | 1145079 | FGFBP2 | GGGTGCTGCACAAAAGACTCTTTCT | 997 |
| 16974529 | 843274 | FGFBP2 | GGTGCTGCACAAAAGACTCTTTCTC | 998 |
| 16981219 | 828232 | DDX60 | CGTGACCTGAAAAACTACTATGGAA | 999 |
| 16981219 | 734517 | DDX60 | TGTACCTGGCTTATAGTAACAGCTC | 1000 |
| 16981219 | 1120817 | DDX60 | TGGAGCCTGAGAGCGATTGACACCG | 1001 |
| 16981219 | 419033 | DDX60 | CATCATCAAAGTTCCCAGACAGACA | 1002 |
| 16981219 | 532945 | DDX60 | GTGATACAAGTCCAGCAAACCCCAT | 1003 |

APPENDIX 2-continued

PROBE SEQUENCES

| Probe Set ID | Probe ID | Gene Symbol | Probe Sequence | SEQ ID NO |
|---|---|---|---|---|
| 16981219 | 881361 | DDX60 | AGTCACCACATAATAAGTAACTTAT | 1004 |
| 16981219 | 465117 | DDX60 | CATGACTCTGGGTTGCTTGAAGGAC | 1005 |
| 16981219 | 1168120 | DDX60 | GGCATGTTGACACCTAAAGCAAGTG | 1006 |
| 16981219 | 719240 | DDX60 | CTTTGAAACTCATAGCACTGTGATG | 1007 |
| 16981219 | 1267882 | DDX60 | GATCAGCATATGTGCAGTCCTGTGG | 1008 |
| 16981219 | 500454 | DDX60 | CGAAGTTTGTTAGCCATGACATGGG | 1009 |
| 16981219 | 1300959 | DDX60 | GGACTCAAATCTGCTTCAGGACTAA | 1010 |
| 16981219 | 1191178 | DDX60 | TATCTGGAGGCAAATCCTCTGGGAG | 1011 |
| 16981219 | 1175050 | DDX60 | TGCATTCCTGCCACAAAAGTCTAGA | 1012 |
| 16981219 | 78125 | DDX60 | TAGTCTTTGGGAAAGCCGGCCTGAC | 1013 |
| 16981219 | 509098 | DDX60 | TCGGTGAGATGTTCAGGATTACTTA | 1014 |
| 16981219 | 848987 | DDX60 | AGAATTTCAAAGCAGGCAGGCACTG | 1015 |
| 16981219 | 928515 | DDX60 | GCATCATGACGATACTCCCTGGTGA | 1016 |
| 16981219 | 1378530 | DDX60 | TATCCACAACATCAAGGAGCTCTCG | 1017 |
| 16981219 | 519692 | DDX60 | CTGGGCTGGATGTAAAGAACTTGCC | 1018 |
| 16981219 | 1034849 | DDX60 | TGCACAGATCTAAGAACACGAGGGT | 1019 |
| 16981219 | 1362300 | DDX60 | TTGGGCACCATTTCATTGGAGCTGT | 1020 |
| 16981219 | 378069 | DDX60 | GACCAACTTTGATACGGTATTCCAG | 1021 |
| 16981219 | 865966 | DDX60 | GCTCATCATTTAAGTCAGAAAGGTG | 1022 |
| 16981219 | 201523 | DDX60 | TTTCCTGACCAGAGGAGGGCTCTCT | 1023 |
| 16981219 | 735745 | DDX60 | TCTGCCCAGGCTTAAATGATATCTC | 1024 |
| 16981219 | 829197 | DDX60 | TTCCTGTGAAAATGTTGTAAGAACA | 1025 |
| 16981219 | 241267 | DDX60 | TGCCTGTGCCTCCAACCTGAACTGG | 1026 |
| 16981219 | 1232487 | DDX60 | GAGTGAAACAGAGACCTAGCGCAGA | 1027 |
| 16981219 | 1343892 | DDX60 | CAGTCTTTTATGCATCCGGCGGGAG | 1028 |
| 16984783 | 1328787 | GZMK | AAATGTGTTGATCCTGTGATGAAGG | 1029 |
| 16984783 | 1355472 | GZMK | GAAGCCCAGATGAAATGTGTTGATC | 1030 |
| 16984783 | 384171 | GZMK | GATTTAGATTTAAGAAGCCCAGATG | 1031 |
| 16984783 | 184991 | GZMK | CATATAAGCCCCAACTATTAGGAAA | 1032 |
| 16984783 | 881796 | GZMK | CACATGAGTCATATAAGCCCCAACT | 1033 |
| 16984783 | 1295602 | GZMK | ACACATGAGTCATATAAGCCCCAAC | 1034 |
| 16984783 | 768535 | GZMK | TAAATGGCCTGGAATGAGGTGACAC | 1035 |
| 16984783 | 553147 | GZMK | CAAACGTGATGTCCGCCATACTGGA | 1036 |
| 16984783 | 621231 | GZMK | GCACCCACTGTGGATCAATCAGAAC | 1037 |
| 16984783 | 1338165 | GZMK | AAAGCAGCAGAATGATTTCCAAATC | 1038 |
| 16984783 | 239601 | GZMK | CATTTGGTTCCAGATCTAAGAGAGG | 1039 |
| 16984783 | 657893 | GZMK | TAACAGTGACTTCTCGCAGGGTGTC | 1040 |

APPENDIX 2-continued

PROBE SEQUENCES

| Probe Set ID | Probe ID | Gene Symbol | Probe Sequence | SEQ ID NO |
|---|---|---|---|---|
| 16984783 | 230219 | GZMK | TACAGGAATCCTTCTGGCCTTTGGC | 1041 |
| 16984783 | 342630 | GZMK | GAGACTATAGCGTGGAAGACACCTT | 1042 |
| 16984783 | 734667 | GZMK | GATTCCAGGCTTTGTGGCAACACCA | 1043 |
| 16984783 | 1122679 | GZMK | TAACCTGCGAGCATATTAGGAAAAA | 1044 |
| 16984783 | 1367971 | GZMK | GGACCCCATATGTGCTCTGCTTTAC | 1045 |
| 16984783 | 1030703 | GZMK | GACTTACAAGTGCAAAAATGGACCC | 1046 |
| 16984783 | 1287598 | GZMK | CAGTGACCTTATTGCCCTTTGGCGA | 1047 |
| 16984783 | 1027161 | GZMK | TGATCCAGCAGAAGTTACACCTAGT | 1048 |
| 16984783 | 566215 | GZMK | TAAACATTTGTTGCAAGGGCCTATC | 1049 |
| 16997041 | 362379 | LOC647859 | AATTTGCTGTTTAACTGCTTGCAAT | 1050 |
| 16997041 | 391494 | LOC647859 | TTTGCTGTTTAACTGCTTGCAATGA | 1051 |
| 16997041 | 861511 | LOC647859 | TTGCTGTTTAACTGCTTGCAATGAT | 1052 |
| 16997041 | 710794 | LOC647859 | TCATCACAGGACTCGCCACCAGTTG | 1053 |
| 16997041 | 268508 | LOC647859 | CACAGGACTCGCCACCAGTTGTGTA | 1054 |
| 16997041 | 257902 | LOC647859 | ACAGGACTCGCCACCAGTTGTGTAG | 1055 |
| 16997041 | 1160561 | LOC647859 | CAGGACTCGCCACCAGTTGTGTAGT | 1056 |
| 16997041 | 199082 | LOC647859 | GACTCGCCACCAGTTGTGTAGTCTG | 1057 |
| 16997041 | 515607 | LOC647859 | CACCAGTTGTGTAGTCTGTCTCATA | 1058 |
| 17025697 | 1377244 | MIR3939 | CCAGTGTGGACATCCTGTGGTCTGC | 1059 |
| 17025697 | 232433 | MIR3939 | CAGTGTGGACATCCTGTGGTCTGCG | 1060 |
| 17025697 | 231902 | MIR3939 | AGTGTGGACATCCTGTGGTCTGCGC | 1061 |
| 17025697 | 771814 | MIR3939 | TGTGGACATCCTGTGGTCTGCGCGT | 1062 |
| 17025697 | 771240 | MIR3939 | GTGGACATCCTGTGGTCTGCGCGTA | 1063 |
| 17025697 | 622277 | MIR3939 | TGGACATCCTGTGGTCTGCGCGTAC | 1064 |
| 17025697 | 622771 | MIR3939 | GGACATCCTGTGGTCTGCGCGTACA | 1065 |
| 17025697 | 89321 | MIR3939 | GACATCCTGTGGTCTGCGCGTACAC | 1066 |
| 17025697 | 530265 | MIR3939 | ACATCCTGTGGTCTGCGCGTACACA | 1067 |
| 17025697 | 802563 | MIR3939 | CATCCTGTGGTCTGCGCGTACACAT | 1068 |
| 17025697 | 489218 | MIR3939 | TGGTCTGCGCGTACACATGTGACAG | 1069 |
| 17025697 | 489102 | MIR3939 | GGTCTGCGCGTACACATGTGACAGG | 1070 |
| 17025697 | 931146 | MIR3939 | GTCTGCGCGTACACATGTGACAGGT | 1071 |
| 17025697 | 1179503 | MIR3939 | TCTGCGCGTACACATGTGACAGGTA | 1072 |
| 17025697 | 1221923 | MIR3939 | TACACATGTGACAGGTACGTGCACG | 1073 |
| 17025697 | 43428 | MIR3939 | ACACATGTGACAGGTACGTGCACGC | 1074 |
| 17025697 | 483528 | MIR3939 | CACATGTGACAGGTACGTGCACGCC | 1075 |
| 17025697 | 482555 | MIR3939 | ACATGTGACAGGTACGTGCACGCCC | 1076 |
| 17025697 | 917600 | MIR3939 | ATGTGACAGGTACGTGCACGCCCAC | 1077 |

APPENDIX 2-continued

PROBE SEQUENCES

| Probe Set ID | Probe ID | Gene Symbol | Probe Sequence | SEQ ID NO |
|---|---|---|---|---|
| 17056807 | 380060 | TRGC2 | CATTTGCATCCTTTGAATAATTGTA | 1078 |
| 17056807 | 975041 | TRGC2 | GCATCCTTTGAATAATTGTATTTGG | 1079 |
| 17056807 | 1282314 | TRGC2 | CATCCTTTGAATAATTGTATTTGGG | 1080 |
| 17056807 | 881781 | TRGC2 | CCTTTGAATAATTGTATTTGGGATC | 1081 |
| 17056807 | 1273803 | TRGC2 | CTTTGAATAATTGTATTTGGGATCC | 1082 |
| 17056807 | 576608 | TRGC2 | TTGAATAATTGTATTTGGGATCCAC | 1083 |
| 17056807 | 517357 | TRGC2 | TGAATAATTGTATTTGGGATCCACT | 1084 |
| 17056807 | 516996 | TRGC2 | GAATAATTGTATTTGGGATCCACTG | 1085 |
| 17056823 | 1032399 | TARP | CTGTGACAACAAGTGTTGTTCCACT | 1086 |
| 17056823 | 1028040 | TARP | TGTGACAACAAGTGTTGTTCCACTG | 1087 |
| 17056823 | 1029567 | TARP | GTGACAACAAGTGTTGTTCCACTGC | 1088 |
| 17056823 | 610118 | TARP | TGACAACAAGTGTTGTTCCACTGCC | 1089 |
| 17056823 | 609102 | TARP | GACAACAAGTGTTGTTCCACTGCCA | 1090 |
| 17056823 | 489622 | TARP | ACAACAAGTGTTGTTCCACTGCCAA | 1091 |
| 17056823 | 569123 | TARP | CAACAAGTGTTGTTCCACTGCCAAA | 1092 |
| 17056823 | 567714 | TARP | AACAAGTGTTGTTCCACTGCCAAAG | 1093 |
| 17056823 | 500979 | TARP | ACAAGTGTTGTTCCACTGCCAAAGA | 1094 |
| 17056823 | 419171 | TARP | CAAGTGTTGTTCCACTGCCAAAGAG | 1095 |
| 17056823 | 419065 | TARP | AAGTGTTGTTCCACTGCCAAAGAGT | 1096 |
| 17056823 | 236716 | TARP | AGTGTTGTTCCACTGCCAAAGAGTT | 1097 |
| 17056823 | 236294 | TARP | GTGTTGTTCCACTGCCAAAGAGTTT | 1098 |
| 17056823 | 1167136 | TARP | TGTTGTTCCACTGCCAAAGAGTTTC | 1099 |
| 17056853 | 1256547 | TRGV2 | TAGATTTCGCAGTATCAATCTCAAG | 1100 |
| 17056853 | 218037 | TRGV2 | AAGTTGTTCCTTGTGCTTGCGTAAG | 1101 |
| 17056853 | 207652 | TRGV2 | TAATACTTCCCTGGACTGACTCCTG | 1102 |
| 17056853 | 1176615 | TRGV2 | TGATTCCAACACAACCTTGGAGTTG | 1103 |
| 17056853 | 923772 | TRGV2 | GAGTCATAGTACTGAAGACGCTGTG | 1104 |
| 17056853 | 465924 | TRGV2 | GATGTAGCCGTTACTTCCTTCAGCA | 1105 |
| 17056853 | 1166024 | TRGV2 | TCAGGTTCCACTCAACAAGGAAGTG | 1106 |
| 17056853 | 88884 | TRGV2 | GAGGAGGTGGTCTTCCTGAGACACA | 1107 |
| 17056853 | 1114141 | TRGV2 | GTCTTCCTGAGACACAAGCAGAGGG | 1108 |
| 17056853 | 1146518 | TRGV2 | TCCTGAGACACAAGCAGAGGGAAGT | 1109 |
| 17059776 | 1114478 | SAMD9L | GAATGCTGCTTGAGACTGTTCTGGC | 1110 |
| 17059776 | 219409 | SAMD9L | GGATGGCATTCCTTGACACTGAAAA | 1111 |
| 17059776 | 162908 | SAMD9L | TGAGGAAGCCCTCTAATCAGGCAGG | 1112 |
| 17059776 | 477417 | SAMD9L | CAGCCTGACCAGTTAGACGACGCAG | 1113 |
| 17059776 | 750277 | SAMD9L | AAAGTGTGCTTGCCTGCTTGGACC | 1114 |

APPENDIX 2-continued

PROBE SEQUENCES

| Probe Set ID | Probe ID | Gene Symbol | Probe Sequence | SEQ ID NO |
|---|---|---|---|---|
| 17059776 | 237966 | SAMD9L | GAGGATTTCCAGTGCAGTCAAGACA | 1115 |
| 17059776 | 960024 | SAMD9L | ATAACTGAAGAAGATCCACGGGCGG | 1116 |
| 17059776 | 285994 | SAMD9L | AATTGTCCCGGATCATGATTGTCAC | 1117 |
| 17059776 | 1029533 | SAMD9L | TTATCAAAAGTGCTGGACCCCATGG | 1118 |
| 17059776 | 1263848 | SAMD9L | TCTTCACTGAGCAGAATTTGCCCGT | 1119 |
| 17059776 | 257665 | SAMD9L | CTTTCCGTGCCTCCGGGAAAGGATG | 1120 |
| 17059776 | 1300296 | SAMD9L | GGATGCTCAGAATCCCAGCTGCAGC | 1121 |
| 17059776 | 1331936 | SAMD9L | GGCTGTTTGATCTGGATCCCTTAGA | 1122 |
| 17059776 | 158061 | SAMD9L | TAGTTCCCCTTTCTTGATAATTTGC | 1123 |
| 17059776 | 1320021 | SAMD9L | GCCGGAGGATATACTTGTTGAGAAC | 1124 |
| 17059776 | 1121758 | SAMD9L | TTCAATGTGGAGCAAATCCTATGGG | 1125 |
| 17059776 | 263306 | SAMD9L | TGGTCCAAGCCTTCCTCATCTCTTT | 1126 |
| 17059776 | 219175 | SAMD9L | GAATAGCTTCCTTGCCAGGTTCCCT | 1127 |
| 17059776 | 1363664 | SAMD9L | GAATGAGGCCATTTCTCACACAGCG | 1128 |
| 17059776 | 36184 | SAMD9L | CCTGGAGGAGGTCCCTTTTGACTCT | 1129 |
| 17059776 | 803906 | SAMD9L | ACAGACACAGTCTGCTCGGGTGAGA | 1130 |
| 17059776 | 392669 | SAMD9L | TCAGAAATTTAACCAGCCAGTCTCT | 1131 |
| 17059776 | 861192 | SAMD9L | AGAAATTTAACCAGCCAGTCTCTCT | 1132 |
| 17059776 | 582339 | SAMD9L | TCAGAAACTTGAAACAGGCCATTTG | 1133 |
| 17059776 | 745105 | SAMD9L | TCTTCTGATGGCTAGGAGACATGAA | 1134 |
| 17059776 | 436825 | SAMD9L | TGTGAAGTCTTCTGTTCTCCCAGTA | 1135 |
| 17063828 | 1198758 | TRBV7-3 | CAGGCCTGACTGCAAAGAACCGATC | 1136 |
| 17063828 | 1196695 | TRBV7-3 | GGCCTGACTGCAAAGAACCGATCGT | 1137 |
| 17063828 | 846398 | TRBV7-3 | GCCTGACTGCAAAGAACCGATCGTT | 1138 |
| 17063828 | 1034759 | TRBV7-3 | CCTGACTGCAAAGAACCGATCGTTG | 1139 |
| 17063828 | 954914 | TRBV7-3 | TGACTGCAAAGAACCGATCGTTGGG | 1140 |
| 17063828 | 953223 | TRBV7-3 | GACTGCAAAGAACCGATCGTTGGGC | 1141 |
| 17063828 | 262571 | TRBV7-3 | CGTTGGGCAGCCCTGAGTCATCTGC | 1142 |
| 17063828 | 289067 | TRBV7-3 | TGCCGCACCCGTGCCTTGGAAGTAA | 1143 |
| 17063828 | 781503 | TRBV7-3 | TGGATCACACCTGAGCTCTACATAT | 1144 |
| 17063828 | 1003051 | TRBV7-3 | CCTTCTCTGTGACCTTGTTACTGGG | 1145 |
| 17063828 | 392847 | TRBV7-3 | GGGAGCTTTACCAGATCAGGGTCAC | 1146 |
| 17077826 | 353745 | MYBL1 | TGCAGACTGTTTTAGGGACCAAGG | 1147 |
| 17077826 | 493109 | MYBL1 | TAGCCTAAGTAAATCAGCACATGGG | 1148 |
| 17077826 | 582930 | MYBL1 | TATGAGAGCTCTTGAAGTACTACTG | 1149 |
| 17077826 | 592621 | MYBL1 | CAGATATCTTCTTGCTTGTTCAGTC | 1150 |
| 17077826 | 403686 | MYBL1 | TACATGGCTCTTAGAAAGCAGTGGC | 1151 |

APPENDIX 2-continued

PROBE SEQUENCES

| Probe Set ID | Probe ID | Gene Symbol | Probe Sequence | SEQ ID NO |
|---|---|---|---|---|
| 17077826 | 299284 | MYBL1 | TGCCAAAGACGTTTTCAAGGTATGC | 1152 |
| 17077826 | 594132 | MYBL1 | GAATCAAGTTGCACCTATTGTCATG | 1153 |
| 17077826 | 581438 | MYBL1 | CAGTCAACAGTTGAGTGCCTGATTC | 1154 |
| 17077826 | 672624 | MYBL1 | TATCTAAGACTAGTGATTTTCTGAC | 1155 |
| 17077826 | 955300 | MYBL1 | TCTTCCAAGAAAGCAAGTGGCTGGG | 1156 |
| 17077826 | 1196733 | MYBL1 | TCTCCTGAGCAGCAAGCGCATTCTT | 1157 |
| 17077826 | 915880 | MYBL1 | GGTGTGGTACCCAGTATAGATCTTC | 1158 |
| 17077826 | 802542 | MYBL1 | TGAGAGCTTTCTGCCCACAAATAGG | 1159 |
| 17077826 | 199499 | MYBL1 | TGTTCATTACCAGGACATGTGTTGA | 1160 |
| 17077826 | 265123 | MYBL1 | TTTTAGCGCCATATTACCACCATCG | 1161 |
| 17077826 | 631682 | MYBL1 | GCTGGTGGAGTGCTAAACTTGGCTA | 1162 |
| 17077826 | 540956 | MYBL1 | GGTAACGTCACTCCATGCTACAGGA | 1163 |
| 17077826 | 341469 | MYBL1 | GATAACACAGCGTTTGCCTCCACGG | 1164 |
| 17077826 | 883760 | MYBL1 | TCTCAGCTGACATAAGAAGCATCTC | 1165 |
| 17077826 | 1147322 | MYBL1 | TGTTCTATACAATTGCCTTCAGGTG | 1166 |
| 17077826 | 1210684 | MYBL1 | GATCCATAGCTGCACAAGGTTTGTG | 1167 |
| 17077826 | 1282838 | MYBL1 | CATCTTGTAAATAGCCCTCCTGTTC | 1168 |
| 17077826 | 208296 | MYBL1 | AACGATTTCCCAACCGCTTATGTGC | 1169 |
| 17077826 | 1313157 | MYBL1 | TACCTCAGGATTCAGATGATTATGC | 1170 |
| 17077826 | 641198 | MYBL1 | CAAGGACCCTTTATCAATTCAGGAT | 1171 |
| 17077826 | 973712 | MYBL1 | GATGCTGGCACTGAAAATCAGAGCG | 1172 |
| 17077826 | 1079453 | MYBL1 | TGAAGATGACTAGCAATTAGAGTCC | 1173 |
| 17077826 | 365913 | MYBL1 | CAGTCCTTTTGTTGTGGTACTTCA | 1174 |
| 17077826 | 783281 | MYBL1 | CATGATCGGCATACTGAAGGTCATC | 1175 |
| 17077826 | 829815 | MYBL1 | CGTCATTCAGAAAAGAGTCGCCCGA | 1176 |
| 17077826 | 426864 | MYBL1 | CAGTCAGTTTTCTCTGCGTAGCGGA | 1177 |
| 17077826 | 797530 | MYBL1 | CAAGAAACCTGCCTCGAAGAAGTGG | 1178 |
| 17077826 | 103496 | MYBL1 | TCAGAAATCTGGACGCGCATTACGG | 1179 |
| 17077826 | 76412 | MYBL1 | CACTAGTTAGGATGCGCGGTCTTCA | 1180 |
| 17077826 | 107207 | MYBL1 | CCCTGTCCTGGAGAATAACGCGTGA | 1181 |
| 17082012 | 883210 | LOC100133669 | AAATCTATCATAACCTGGTAGCAGG | 1182 |
| 17082012 | 1326974 | LOC100133669 | GGTAGCAGGATCCAAAAATTCAATC | 1183 |
| 17082012 | 412155 | LOC100133669 | GCAGGTGCCATTACTGTGAGGCCAG | 1184 |
| 17082012 | 1193825 | LOC100133669 | CAATGTTTTCAGCTACTAACCCAGC | 1185 |
| 17082012 | 190256 | LOC100133669 | TACTAACCCAGCCATGTGTGACCAC | 1186 |
| 17082012 | 1398121 | LOC100133669 | CCAGTGGCCCATGATGATCTAGTGA | 1187 |
| 17082012 | 739001 | LOC100133669 | GAGAGGACGCTTCGGTCTCTGTACG | 1188 |

APPENDIX 2-continued

PROBE SEQUENCES

| Probe Set ID | Probe ID | Gene Symbol | Probe Sequence | SEQ ID NO |
|---|---|---|---|---|
| 17082012 | 817455 | LOC100133669 | GGTACCAGCTGCAGCCGACAGGTAA | 1189 |
| 17082012 | 900622 | LOC100133669 | GACAGGTAACTGTTTCTTTCACTCT | 1190 |
| 17082012 | 130228 | LOC100133669 | TAAATTGGGCAATGTCCTCTCCTCA | 1191 |
| 17082012 | 56499 | LOC100133669 | TGGCTCCCGGAGGTTAGGAATCAAC | 1192 |
| 17082012 | 1057734 | LOC100133669 | TACACTCTGATAGGTGGTGCCAGCC | 1193 |
| 17082012 | 42916 | LOC100133669 | AAACACACAGGTACACTGGCGGGCA | 1194 |
| 17082012 | 863461 | LOC100133669 | GGACCAGTAACGAGTCCCAGTGCGC | 1195 |
| 17082012 | 533328 | LOC100133669 | AGTAACGAGTCCCAGTGCGCAGTGG | 1196 |
| 17082012 | 83766 | LOC100133669 | AGTCCACTCTGGGTGTCCCGCAGTC | 1197 |
| 17082012 | 330796 | LOC100133669 | GGTGTCCCGCAGTCCACTCCTGGTG | 1198 |
| 17082012 | 523273 | LOC100133669 | AAGCCGGGTCCAGCTGTCACGGAAT | 1199 |
| 17082012 | 809278 | LOC100133669 | CGGGTCCAGCTGTCACGGAATCCAA | 1200 |
| 17082012 | 809659 | LOC100133669 | GGGTCCAGCTGTCACGGAATCCAAA | 1201 |
| 17082012 | 1297731 | LOC100133669 | TGTCACGGAATCCAAAACCAAGCGG | 1202 |
| 17082012 | 418226 | LOC100133669 | GAGCAAGCGTTCCTCTAACAGTGGG | 1203 |
| 17082012 | 533163 | LOC100133669 | TCGGGCCAGTCGGTAAGAAGTTCCA | 1204 |
| 17082012 | 1265181 | LOC100133669 | GACGCTATCTGCAGGTACCGGAATG | 1205 |
| 17082012 | 738158 | LOC100133669 | CAGAACTGATGGCTTGCTCGGTGGC | 1206 |
| 17082012 | 889666 | LOC100133669 | CCGAACACAACGAGGACTGTCCAGG | 1207 |
| 17082012 | 308150 | LOC100133669 | CGAACACAACGAGGACTGTCCAGGT | 1208 |
| 17082012 | 604235 | LOC100133669 | ACTGTCCAGGTGTCAGTGACGGTCA | 1209 |
| 17082012 | 521094 | LOC100133669 | TCAGTGACGGTCACCCCGACCTGGT | 1210 |
| 17093090 | 265563 | DDX58 | TCAACAGGGCCAAATGCGCAGAGGT | 1211 |
| 17093090 | 625725 | DDX58 | TACGTCAGCTGTGTAACATGCCAAG | 1212 |
| 17093090 | 316546 | DDX58 | AATACTGCTTCGTCCCATGTCTGAA | 1213 |
| 17093090 | 1200656 | DDX58 | GAAGGAAGCACTTGCTACCTCTTGC | 1214 |
| 17093090 | 661171 | DDX58 | CCAATATACACTTCTGTGCCGGGAG | 1215 |
| 17093090 | 1217677 | DDX58 | TGCCACGTCCAGTCAATATGCCAGG | 1216 |
| 17093090 | 999011 | DDX58 | CCTGCTGCTCGGACATTGCTGAAGA | 1217 |
| 17093090 | 332322 | DDX58 | AAATTTGTCGCTAATCCGTGATTCC | 1218 |
| 17093090 | 974265 | DDX58 | CAGTGGGCCTGAAGATCCTCCAAGT | 1219 |
| 17093090 | 1325449 | DDX58 | CATACACTGGGATCTGATTCGCAAA | 1220 |
| 17093090 | 1192298 | DDX58 | TTCATAGCAGGCAAAGCAAGCTCTA | 1221 |
| 17093090 | 808620 | DDX58 | TAAATGGGCTGTACAAGTTTGTATC | 1222 |
| 17093090 | 999859 | DDX58 | GAAGGTGGACATGAATTCTCACTAA | 1223 |
| 17093090 | 1020355 | DDX58 | TCTGATCTGAGAAGGCATTCCACCA | 1224 |
| 17093090 | 1341894 | DDX58 | GCCCAGGTGCATGCTTCTACTTTCA | 1225 |

APPENDIX 2-continued

PROBE SEQUENCES

| Probe Set ID | Probe ID | Gene Symbol | Probe Sequence | SEQ ID NO |
|---|---|---|---|---|
| 17093090 | 206898 | DDX58 | AAATGGCCACCATGCAGACTGCAAC | 1226 |
| 17093090 | 132105 | DDX58 | GGTCTAGGGCATCCAAAAAGCCACG | 1227 |
| 17093090 | 1077658 | DDX58 | TGTGCCTCACTAGCTTTAAAGCCGG | 1228 |

What is claimed:

1. A method for selecting and treating patients with active Systemic Lupus Erythematosus (SLE) that are predicted to have an increased likelihood of having a positive response to a treatment with an anti-interleukin-12/interleukin-23p40 antibody (anti-IL-12/IL-23p40 antibody), the method comprising:
   a) determining levels of one or more cytotoxic cell markers in biological samples from the patients, wherein the one or more cytotoxic cell markers is selected from the group consisting of: expression level of one or more cytotoxic cell-associated transcriptional genes and percentage of natural killer cells;
   b) determining levels of one or more Interferon I (IFN-I) markers in biological samples from the patients, wherein the one or more IFN-I markers is selected from the group consisting of: expression level of one or more Interferon I (IFN-I) inducible genes and expression level of Interferon alpha;
   c) calculating mean levels of the one or more cytotoxic cell markers and the one or more IFN-I markers in the biological samples from the patients;
   d) comparing the calculated mean levels to the levels in individual patients for the one or more cytotoxic cell markers and the one or more IFN-I markers;
   e) determining if individual patients have higher levels or lower levels compared to the calculated mean levels of the one or more cytotoxic cell markers and the one or more IFN-I markers;
   f) selecting the individual patients from the group consisting of: individual patients with higher levels of the one or more cytotoxic cell markers and higher levels of the one or more IFN-I markers, individual patients with higher levels of the one or more cytotoxic cell markers and lower levels of the one or more IFN-I markers, and individual patients with lower levels of the one or more cytotoxic cell markers and lower levels of the one or more IFN-I markers, wherein the selected patients are predicted to have an increased likelihood of having a positive response to the treatment with an anti-IL-12/IL-23p40 antibody; and,
   g) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6;
   wherein the one or more cytotoxic cell-associated transcriptional genes is selected from the group consisting of: FCRL6, FGFBP2, GNLY, GPR56, GZMH, GZMK, KLRC3, KLRD1, KLRG1, LOC387895, MYBL1, NKG7, PRF1, TARP, TRGC2, XRRA1, GSTM4, CXCR3, GZMA, and TRGV2; and wherein the one or more IFN-I inducible genes is selected from the group consisting of: BST2, CARD17, CMPK2, DDX58, DDX60, DHX58, EIF2AK2, EPSTI1, FBXO39, HERC5, HERC6, IFIT1, IFIT2, IFIT3, IRF7, LAP3, LOC100133669, OAS3, OASL, OTOF, PLSCR1, RSAD2, RTP4, SAMD9L, SIGLEC1, SPATS2L, TIMM10, USP18, ISG15, IFI27, IFI44, IFI44L, and ZBP1.

2. The method of claim 1, wherein the positive response is selected from the group consisting of: a significant improvement in disease activity as determined by a decrease from baseline in the Systemic Lupus Erythematosus Disease Activity Index 2000 (SLEDAI-2K) score of ≥4 (SLE Responder Index-4 (SRI-4 response) at 24 weeks of treatment with the anti-IL-12/IL-23p40 antibody; a statistically significant reduction in the risk of a new British Isles Lupus Assessment Group (BILAG) flare, defined as ≥1 new BILAG A domain score or ≥2 new BILAG B domain score, by week 24 of treatment with the anti-IL-12/IL-23p40 antibody; a statistically significant increase in the proportion of patients with a 50% improvement from baseline in Cutaneous Lupus Erythematosus Disease Area and Severity Index (CLASI) score; and a statistically significant improvement in disease activity as determined by a 50% improvement from baseline joint disease activity by week 24 of treatment with the anti-IL-12/IL-23p40 antibody.

3. The method of claim 2, wherein the positive response comprises a significant improvement in disease activity as determined by a decrease from baseline in the Systemic Lupus Erythematosus Disease Activity Index 2000 (SLE-DAI-2K) score of ≥4 (SRI-4 response) at 24 weeks of treatment with the anti-IL-12/IL-23p40 antibody.

4. The method of claim 1, wherein the one or more cytotoxic cell-associated transcriptional genes is selected from the group consisting of: FCRL6, FGFBP2, GNLY, GZMH, GZMK, NKG7 and PRF1; and wherein the one or more IFN-I inducible genes is selected from the group consisting of: BST2, CMPK2, DDX58, DDX60, DHX58, EIF2AK2, EPSTI1, HERC5, IFIT1, IFIT2, IFIT3, IRF7, ISG15, LAP3, OAS3, OASL, PLSCR1, RSAD2, RTP4, SAMD9L, SIGLEC1, TIMM10, USP18 and ZBP1.

5. The method of claim 1, wherein the one or more cytotoxic cell-associated transcriptional genes comprise FCRL6, FGFBP2, GNLY, GZMH, NKG7, and PRF1; and the one or more IFN-I inducible genes comprise IFIT3 and RSAD2.

6. The method of claim 1, wherein the levels of the one or more cytotoxic cell markers and the one or more IFN-I markers are determined by quantifying RNA transcripts in the biological samples or quantifying protein expression levels in the biological samples.

7. The method of claim 1, wherein the biological sample is selected from the group consisting of: skin biopsies, kidney biopsies, whole blood, serum, and urine.

8. The method of claim 7, wherein the biological sample is whole blood.

9. The method of claim 1, wherein the one or more cytotoxic cell markers comprises the percentage of natural killer cells.

10. The method of claim 1, wherein one or more cytotoxic cell markers comprises the expression level of the one or more cytotoxic cell-associated transcriptional genes.

11. The method of claim 1, wherein the one or more IFN-I markers comprises the expression level of Interferon alpha.

12. The method of claim 1, wherein the one or more IFN-I markers comprises the expression level of one or more IFN-I inducible genes.

13. The method of claim 1, wherein the one or more cytotoxic cell marker comprises percentage of natural killer cells and the one or more IFN-I markers comprises the expression level of Interferon alpha.

14. The method of claim 1, wherein the anti-IL-12/IL-23p40 antibody comprises a heavy chain variable region comprising the amino acid sequence of SEQ ID NO:7 and a light chain variable region comprising the amino acid sequence of SEQ ID NO:8.

15. The method of claim 1, wherein the anti-IL-12/IL-23p40 antibody comprises a heavy chain comprising the amino acid sequence of SEQ ID NO:10 and a light chain comprising the amino acid sequence of SEQ ID NO:11.

16. The method of claim 1, wherein the patients are treated by administering the anti-IL-12/IL-23p40 antibody and an IFN-I inhibitor.

17. The method of claim 16, wherein the IFN-I inhibitor is selected from the group consisting of: an anti-IFN alpha antibody, an anti IFN-I receptor antibody, inhibitors of Toll-Like Receptors (TLRs) 7, 8, and 9, agents that deplete or inhibit plasmacytoid dendritic cell function, and agents that inhibit Janus Kinase 1 (JAK1).

18. The method of claim 17, wherein the IFN-I inhibitor is selected from the group consisting of: the anti-IFN alpha antibody sifalimumab, the anti-IFN alpha antibody JNJ-55920839 (CNTO 6358) and the anti IFN-I receptor antibody anifrolumab.

19. The method of any of claims 1-3 or 4-18, wherein the anti-IL-12/IL-23p40 antibody is administered with an initial intravenous (IV) dose at week 0, followed by administrations of a subcutaneous (SC) dose every 8 weeks (q8w) or wherein the antibody is administered as an initial subcutaneous (SC) dose, followed by administrations of a SC dose every 8 weeks (q8w).

20. The method of claim 19, wherein the initial IV dose is 6.0 mg/kg ±1.5 mg/kg and the SC dose is 90 mg.

21. The method of claim 20, wherein the initial IV dose is 260 mg for patients with body weight ≥35 kg and ≤55 kg, 390 mg for patients with body weight >55 kg and ≤85 kg, and 520 mg for patients with body weight >85 kg.

22. A method for selecting and treating patients with active Systemic Lupus Erythematosus (SLE) that are predicted to have an increased likelihood of having a positive response to a treatment with an anti-IL-12/IL-23p40 antibody, the method comprising:

a) determining the expression level of one or more cytotoxic cell-associated transcriptional genes or one or more IFN-1 inducible genes in biological samples from the patients; wherein the one or more cytotoxic cell-associated transcriptional genes is selected from the group consisting of: FCRL6, FGFBP2, GNLY, GPR56, GZMH, GZMK, KLRC3, KLRD1, KLRG1, LOC387895, MYBL1, NKG7, PRF1, TARP, TRGC2, XRRA1, GSTM4, CXCR3, GZMA, and TRGV2; and wherein the one or more IFN-I inducible genes is selected from the group consisting of: BST2, CARD17, CMPK2, DDX58, DDX60, DHX58, EIF2AK2, EPSTI1, FBXO39, HERC5, HERC6, IFIT1, IFIT2, IFIT3, IRF7, LAP3, LOC100133669, OAS3, OASL, OTOF, PLSCR1, RSAD2, RTP4, SAMD9L, SIGLEC1, SPATS2L, TIMM10, USP18, ISG15, IFI27, IFI44, IFI44L, and ZBP1;

b) selecting the individual patients who are predicted to have an increased likelihood of having a positive response to the treatment with the anti-IL-12/IL-23p40 antibody, wherein the predicted increased likelihood of having a positive response to the treatment with the anti-IL-12/IL-23p40 antibody is determined with a logistic regression model of the formula:

$$\min_{\beta_0,\beta} - \left[\frac{1}{N}\sum_{i=1}^{N} y_i(\beta_0 + \beta^T x_i) - \log(1 + e^{(\beta_0 + \beta^T x_i)})\right] + \lambda\left[\frac{(1-\alpha)}{2}\|\beta\|_2^2 + \alpha\|\beta\|_1\right]$$

wherein N is the number of patients used to learn the model, $x_i$ is a vector of the centered gene expression data of patient i, $y_i$ is the response outcome for patient i (responder/non-responder), λ, controls the total penalty weight, α controls the elastic-net penalty weight: form lasso (α=1) to ridge (α=0), and α, λ, are optimized using grid search based on best training accuracy; and, wherein after $\beta_0$, $\beta$ parameters are determined a response probability is determined by the formula:

$$P(x_{new}) = \frac{1}{1 + e^{-(\beta_0 + \beta^T x_{new})}}$$

and response prediction is determined with a threshold of 0.5 using the formula:

$$\text{Response}(x_{new}) = \begin{cases} \text{responder,} & \text{if } P(x) \geq threshlod \\ \text{non-responder,} & \text{else} \end{cases};$$

and c) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

23. A method for selecting and treating patients with active Systemic Lupus Erythematosus (SLE) that are predicted to have an increased likelihood of having a positive response to a treatment with an anti-IL-12/IL-23p40 antibody, the method comprising:
  a) determining the expression level of one or more cytotoxic cell-associated transcriptional genes in biological samples from the patients;
  b) calculating the mean expression levels of the one or more cytotoxic cell-associated transcriptional genes in the biological samples from the patients;
  c) comparing the calculated mean expression levels to the expression levels in individual patients for the one or more cytotoxic cell-associated transcriptional genes;
  d) determining if the individual patients have higher expression levels or lower expression levels compared to the mean expression levels of the one or more cytotoxic cell-associated transcriptional genes;
  e) selecting the individual patients from the group consisting of: individual patients with higher expression levels of the one or more cytotoxic cell-associated transcriptional genes, wherein the selected patients are predicted to have an increased likelihood of having a positive response to the treatment with an anti-IL-12/IL-23p40 antibody; and
  f) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6;
  wherein the one or more cytotoxic cell-associated transcriptional genes is selected from the group consisting of: FCRL6, FGFBP2, GNLY, GPR56, GZMH, GZMK, XRRA1, GSTM4, KLRC3, KLRD1, KLRG1, LOC387895, MYBL1, NKG7, PRF1, TARP, TRGC2, CXCR3, GZMA, and TRGV2.

24. The method of claim 23, wherein the one or more cytotoxic cell-associated transcriptional genes is selected from the group consisting of: FCRL6, FGFBP2, GNLY, GZMH, GZMK, NKG7 and PRF1.

25. The method of claim 23, wherein the anti-IL-12/IL-23p40 antibody comprises a heavy chain variable region comprising the amino acid sequence of SEQ ID NO:7 and a light chain variable region comprising the amino acid sequence of SEQ ID NO:8.

26. The method of claim 23, wherein the anti-IL-12/IL-23p40 antibody comprises a heavy chain comprising the amino acid sequence of SEQ ID NO:10 and a light chain comprising the amino acid sequence of SEQ ID NO:11.

27. A method for selecting and treating patients with active Systemic Lupus Erythematosus (SLE) that are predicted to have an increased likelihood of having a positive response to a treatment with an anti-IL-12/IL-23p40 antibody, the method comprising:
  a) determining the expression level of one or more cytotoxic cell-associated transcriptional genes in biological samples from the patients;
  b) comparing the expression levels in individual patients to the average expression levels in healthy controls for the one or more cytotoxic cell-associated transcriptional genes;
  c) determining if the individual patients have lower expression levels compared to the average expression levels in healthy controls for the one or more cytotoxic cell-associated transcriptional genes;
  d) selecting the individual patients that do not have lower expression levels compared to the average expression levels in healthy controls for the one or more cytotoxic cell-associated transcriptional genes, wherein the selected patients are predicted to have an increased likelihood of having a positive response to the treatment with an anti-IL-12/IL-23p40 antibody; and
  e) treating the selected patients by administering the anti-IL-12/IL-23p40 antibody, wherein the anti-IL-12/IL-23p40 antibody comprises a heavy chain variable region and a light chain variable region, said heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and said light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6;
  wherein the one or more cytotoxic cell-associated transcriptional genes is selected from the group consisting of: FCRL6, FGFBP2, GNLY, GPR56, GZMH, GZMK, XRRA1, GSTM4, KLRC3, KLRD1, KLRG1, LOC387895, MYBL1, NKG7, PRF1, TARP, TRGC2, CXCR3, GZMA, and TRGV2.

28. The method of claim 27, wherein the lower expression levels of the one or more cytotoxic cell-associated transcriptional genes compared to the average expression levels in healthy controls is a Gene Set Variation Analysis (GSVA) Enrichment Score (ES) of the one or more cytotoxic cell-associated transcriptional genes 0.4 below the median of the healthy controls.

29. The method of claim 28, wherein the anti-IL-12/IL-23p40 antibody comprises a heavy chain variable region comprising the amino acid sequence of SEQ ID NO:7 and a light chain variable region comprising the amino acid sequence of SEQ ID NO:8.

30. The method of claim 28, wherein the anti-IL-12/IL-23p40 antibody comprises a heavy chain comprising the amino acid sequence of SEQ ID NO:10 and a light chain comprising the amino acid sequence of SEQ ID NO:11.

* * * * *